United States Patent
James et al.

(10) Patent No.: US 11,248,219 B2
(45) Date of Patent: *Feb. 15, 2022

(54) FUSION PROTEINS COMPRISING A NON-CYTOTOXIC PROTEASE, A TRANSLOCATION DOMAIN, AND A TARGETING MOIETY THAT BINDS A GALANIN RECEPTOR AND METHODS FOR TREATING, PREVENTING OR AMELIORATING PAIN USING SUCH FUSION PROTEINS

(71) Applicants: IPSEN BIOINNOVATION LIMITED, Abingdon (GB); ALLERGAN, INC., Irvine, CA (US)

(72) Inventors: Peter James, Abingdon (GB); Keith Foster, Abingdon (GB); John Chaddock, Abingdon (GB); Roger Aoki, Irvine, CA (US); Lance Steward, Irvine, CA (US); Joseph Francis, Irvine, CA (US)

(73) Assignees: Ipsen Bioinnovation Limited, Abingdon (GB); Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/416,435

(22) Filed: May 20, 2019

(65) Prior Publication Data
US 2019/0309277 A1    Oct. 10, 2019

Related U.S. Application Data

(63) Continuation of application No. 15/661,433, filed on Jul. 27, 2017, now abandoned, which is a continuation of application No. 14/422,574, filed as application No. PCT/GB2013/052243 on Aug. 27, 2013, now abandoned, which is a continuation-in-part of application No. 13/595,927, filed on Aug. 27, 2012, now abandoned.

(51) Int. Cl.
| | |
|---|---|
| *C12N 9/52* | (2006.01) |
| *A61K 47/65* | (2017.01) |
| *A61K 38/00* | (2006.01) |
| *C07K 14/575* | (2006.01) |
| *A61K 47/64* | (2017.01) |
| *C12N 15/62* | (2006.01) |

(52) U.S. Cl.
CPC .............. *C12N 9/52* (2013.01); *A61K 47/64* (2017.08); *A61K 47/65* (2017.08); *C07K 14/575* (2013.01); *C12N 15/625* (2013.01); *C12Y 304/21072* (2013.01); *C12Y 304/24068* (2013.01); *C12Y 304/24069* (2013.01); *A61K 38/00* (2013.01); *C07K 2319/01* (2013.01); *C07K 2319/50* (2013.01); *C07K 2319/55* (2013.01); *C07K 2319/74* (2013.01); *C12Y 304/24013* (2013.01)

(58) Field of Classification Search
CPC ........ C12Y 304/24069; C07K 2319/55; C07K 2319/50; C07K 2319/74
USPC ...................................................... 424/236.1
See application file for complete search history.

(56) References Cited

U.S. PATENT DOCUMENTS

| | | |
|---|---|---|
| 5,989,545 A | 11/1999 | Foster et al. |
| 6,136,564 A | 10/2000 | Kopetzki |
| 6,395,513 B1 | 5/2002 | Foster et al. |
| 6,461,617 B1 | 10/2002 | Shone et al. |
| 6,776,990 B2 | 8/2004 | Sachs et al. |
| 6,843,998 B1 | 1/2005 | Steward et al. |
| 7,056,729 B2 | 6/2006 | Donovan |
| 7,132,259 B1 | 11/2006 | Dolly et al. |
| 7,244,436 B2 | 7/2007 | Donovan |
| 7,244,437 B2 | 7/2007 | Donovan |
| 7,262,291 B2 | 8/2007 | Donovan |
| 7,276,473 B2 | 10/2007 | Sachs et al. |
| 7,413,742 B2 | 8/2008 | Donovan |
| 7,419,676 B2 | 9/2008 | Dolly et al. |
| 7,422,877 B2 | 9/2008 | Dolly et al. |
| 7,494,661 B2 | 2/2009 | Sanders |
| 7,514,088 B2 | 4/2009 | Steward et al. |
| 7,658,933 B2 | 2/2010 | Foster et al. |
| 7,659,092 B2 | 2/2010 | Foster et al. |
| 7,709,228 B2 | 5/2010 | Dolly et al. |

(Continued)

FOREIGN PATENT DOCUMENTS

| | | |
|---|---|---|
| EP | 1422240 | 1/2005 |
| JP | H11504006 | 4/1999 |

(Continued)

OTHER PUBLICATIONS

J.P. Blanc, et al., "Examination of the Requirement for an Amphiphilic Helical Structure in Beta-Endorphin Through the Design, Synthesis, and Study of Model Peptides," Journal of Biological Chemistry 258(13):8277-8284, Jul. 1983.

(Continued)

*Primary Examiner* — Sheridan Swope
(74) *Attorney, Agent, or Firm* — Gene J. Yao; Barnes & Thornburg LLP

(57) ABSTRACT

Single chain polypeptide fusion protein, comprising: a non-cytotoxic protease capable of cleaving a protein of the exocytic fusion apparatus of a nociceptive sensory afferent; a galanin targeting moiety; a protease cleavage site; a translocation domain; a first spacer located between the non-cytotoxic protease and the protease cleavage site; and a second spacer located between the galanin targeting moiety and the translocation domain.

9 Claims, 13 Drawing Sheets

Figure 1:
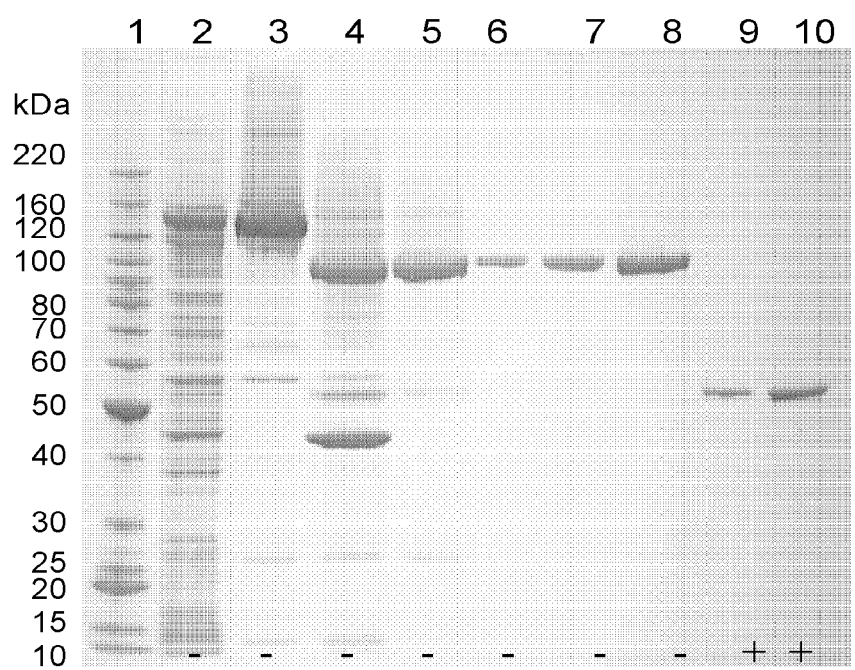
Figure 1:
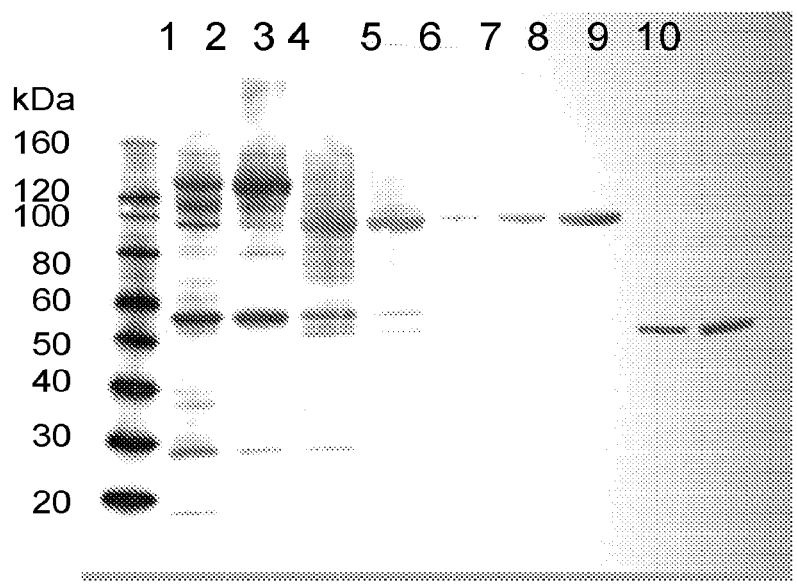
Figure 1:
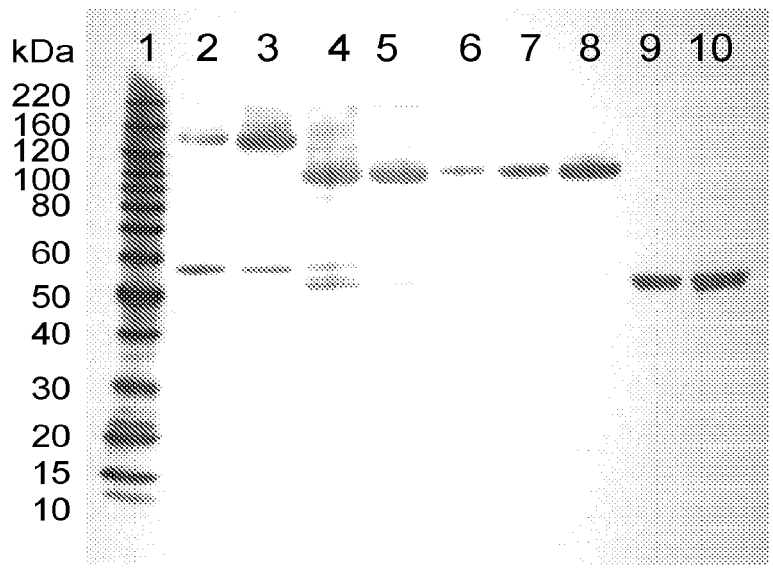

Specification includes a Sequence Listing.

(56) References Cited

U.S. PATENT DOCUMENTS

| | | |
|---|---|---|
| 7,736,659 B2 | 6/2010 | Donovan |
| 7,740,868 B2 | 6/2010 | Steward et al. |
| 7,749,514 B2 | 7/2010 | Steward et al. |
| 7,780,968 B2 | 8/2010 | Donovan |
| 7,785,606 B2 | 8/2010 | Ichtchenko et al. |
| 7,833,535 B2 | 11/2010 | Donovan |
| 7,887,810 B2 | 2/2011 | Foster et al. |
| 7,892,560 B2 | 2/2011 | Foster et al. |
| 7,897,157 B2 | 3/2011 | Steward et al. |
| 8,067,200 B2 | 11/2011 | Foster et al. |
| 8,187,834 B2 | 5/2012 | Foster et al. |
| 8,399,400 B2 | 3/2013 | Foster et al. |
| 8,399,401 B2 | 3/2013 | Foster et al. |
| 8,512,984 B2 | 8/2013 | Foster et al. |
| 8,603,779 B2 | 12/2013 | Foster et al. |
| 8,778,634 B2 | 7/2014 | Foster et al. |
| 8,940,870 B2 | 1/2015 | Foster et al. |
| 9,012,195 B2 | 4/2015 | Foster et al. |
| 2003/0166571 A1 | 9/2003 | Judd |
| 2004/0115727 A1 | 6/2004 | Steward et al. |
| 2005/0095251 A1 | 5/2005 | Steward et al. |
| 2006/0051356 A1 | 3/2006 | Foster et al. |
| 2007/0010475 A1 | 1/2007 | Richardson |
| 2007/0066559 A1 | 3/2007 | Richardson et al. |
| 2008/0025994 A1 | 1/2008 | Steward et al. |
| 2008/0032931 A1 | 2/2008 | Steward et al. |
| 2008/0182294 A1 | 7/2008 | Dolly et al. |
| 2008/0311622 A1 | 12/2008 | Dolly et al. |
| 2009/0004224 A1 | 1/2009 | Steward et al. |
| 2009/0005313 A1 | 1/2009 | Steward et al. |
| 2009/0018081 A1 | 1/2009 | Steward et al. |
| 2009/0030182 A1 | 1/2009 | Dolly et al. |
| 2009/0030188 A1 | 1/2009 | Dolly et al. |
| 2009/0042270 A1 | 2/2009 | Dolly et al. |
| 2009/0069238 A1 | 3/2009 | Steward et al. |
| 2009/0081730 A1 | 3/2009 | Dolly et al. |
| 2009/0087458 A1 | 4/2009 | Dolly et al. |
| 2009/0104234 A1 | 4/2009 | Francis et al. |
| 2009/0117157 A1 | 5/2009 | Brin et al. |
| 2009/0162341 A1 | 6/2009 | Foster et al. |
| 2010/0034802 A1 | 2/2010 | Foster et al. |
| 2010/0055761 A1 | 3/2010 | Seed et al. |
| 2010/0196421 A1 | 8/2010 | Ichtchenko et al. |
| 2010/0209955 A1 | 8/2010 | Oyler et al. |
| 2010/0233741 A1* | 9/2010 | Wang ............... C12Q 1/37 435/7.94 |
| 2010/0247509 A1 | 9/2010 | Foster et al. |
| 2010/0303757 A1 | 12/2010 | Francis et al. |
| 2010/0303789 A1 | 12/2010 | Francis et al. |
| 2010/0303791 A1 | 12/2010 | Francis et al. |
| 2011/0027256 A1 | 2/2011 | Foster et al. |
| 2011/0091437 A1 | 4/2011 | Foster et al. |
| 2011/0177053 A1 | 7/2011 | Foster et al. |
| 2012/0058098 A1 | 3/2012 | Foster et al. |
| 2012/0064059 A1 | 3/2012 | Foster et al. |
| 2012/0156186 A1 | 6/2012 | Foster et al. |
| 2012/0189610 A1 | 7/2012 | Foster et al. |
| 2012/0207735 A1 | 8/2012 | Foster et al. |
| 2012/0230975 A1 | 9/2012 | Foster et al. |
| 2013/0189238 A1 | 7/2013 | Foster et al. |
| 2014/0056870 A1 | 2/2014 | James et al. |
| 2014/0294797 A1 | 10/2014 | Foster et al. |

FOREIGN PATENT DOCUMENTS

| | | |
|---|---|---|
| JP | 2003522199 | 7/2003 |
| WO | 9633273 | 10/1996 |
| WO | 9807864 | 2/1998 |
| WO | 9917806 | 4/1999 |
| WO | 0158936 | 8/2001 |
| WO | 2004024909 | 3/2004 |
| WO | 2006026780 | 3/2006 |
| WO | 2006059093 | 6/2006 |
| WO | 2006059105 | 6/2006 |
| WO | 2006059113 | 6/2006 |
| WO | 2007138339 | 12/2007 |
| WO | 2012156743 | 11/2012 |

OTHER PUBLICATIONS

J.A. Chaddock, et al., "Manipulation of Signal Transduction by Botulinum Neurotoxins and Their Derivatives," Current Signal Transduction Therapy 2(3):221-225, Jan. 2007.

J.A. Chaddock, et al., "A Conjugate Composed of Nerve Growth Factor Coupled to an Non-Toxic Derivative of Clostridium botulinum Neurotoxin Type A Can Inhibit Neurotransmitter Release in Vitro," Growth Factors 18 (2):147-155, Jan. 2000.

J.A. Chaddock, et al., "Expression and Purification of Catalytically Active, Non-Toxic Endopeptidase Derivatives of Clostridium botulinum Toxin Type A," Protein Expression and Purification 25(2):219-228, Jul. 2002.

J.A. Chaddock, et al., "Inhibition of Vesicular Secretion in Both Neuronal and nonneuronal Cells by a Retargeted Endopeptidase Derivative of Clostridium botulinum Toxin Type A," Infection and Immunity 68(5)2587-2593, May 2000.

J.A. Chaddock, et al., "Retargeted Clostridial Endopeptidases:Inhibition or Nociceptive Neurotransmitter Release In Vitro, and Antinociceptive Activity in In Vivo Models of Pain," Movement Disorders 19(Suppl 8):S42-S47, March 20041 and un Naynyn-Schnuedeberg;s Archives of Pharmacology 365(Suppl 2):R15, Jun. 2002.

C. Crasto, et al., "LINKER: a Program to Generate Linker Sequences for Fusion Proteins," Protein Engineering 13 (5):309-312, May 2000.

M. Cui, et al., "Retargeted Clostridial Endopeptidase: Antinociceptive Activity in Preclinicai Models of Pain," Naunyn-Schmiedeberg's Archives of Pharmacology:R16, Jun. 2002.

C.T. Dooley, et al., "Binding and In Vitro Activities of Peptides With High Affinity for the Nociceptin/Orphanin FQ Receptor, ORL 1 ," Journal of Pharmacology and Experimental Therapy 283(2)735-741, Nov. 1997.

M.J. Duggan, et al., "Inhibition of Release of Neurotransmitters From Rat Forsal Root Ganglia by a Novel Conjugate of a Clostridium botulinum Toxin A Endopeptidase Fragment and Erythrina cristagalli Lectin," Journal of Biological Chemistry 277(38):34846-34852, Sep. 2002.

KA Foster, et al., "Re-Engineering the Target Specificity of Clostridial Neurotoxins: A Route to Novel Therapeutics," Neurotoxicity Research 9{2, 3}:1 01-107, Apr. 2006.

R. Guerrini, et al., "Address and Message Sequences for the Nociceptin Receptor: A Structure-Activity Study of Nociceptin-(1-13)-Peptide Amide," Journal of Medicinal Chemistry 40( 12): 1789-1793, Jun. 1997.

M. Inoue, "Nociceptin/Orphanin FQ-Induced Nociceptive Responses Through Substance P Release From Peripheral Nerve Endings in Mice," Proceedings of the National Academy of Sciences of the United States of America (PNAS) 95 (18):10949-10953, Sep. 1998.

R. Maile, et al., "Effects of Nociceptin and Analogues of Nociceptin Upon Spontaneous Dorsal Root Activity Recorded From an In Vitro Preparation of Rat Spinal Cord," Neuroscience Letters 350(3): 190-192, Oct. 2003.

J.S. Mogil, et al., "The Molecular and Behavioural Pharmacology of the Orphan in FQ/Nociceptin Peptide and Receptor Family," Pharmacological Review 53(3):381-415, Sep. 2001.

K. Okada, et al., "Highly Potent Nociceptin Analog Containing the Arg-Lys Triple Repeat," Biochemical and Biophysical Research Communications 278(2):493-498, Nov. 2000.

C. Plank, et al., "The Influence of Endosome-Disruptive Peptides on Gene Transfer Using Synthetic Virus-Like Gene Transfer Systems," Journal of Biological Chemistry 269(17):12918-12924, Apr. 1994.

D. Rizzi, et al., "[Arg(14),Lys(15)]Nociceptin, A Highly Potent Agonist of the Nociceptin/Orphanin FQ Receptor: In Vitro and In Vivo Studies," Journal of Pharmacology and Experimental Therapy 300(1):57-63, Jan. 2002.

G. Schiavo, et al., "Neurotoxins Affecting Neuroexocytosis," Physiological Reviews 80(2):717-766, Apr. 2000.

(56) References Cited

OTHER PUBLICATIONS

C.C. Shone, et al., "A 50-kDa Fragment From the NH2-Terminus of the Heavy Subunit of Clostridium botulinum Type A Neurotoxin Forms Channels in Lipids Vesicles." European Journal of Biochemistry 167(1):175-180. Aug. 1987.
J.M. Sutton, et al., "Preparation of Specifically Activatable Endopeptidase Derivatives of Clostridium botulinum Toxins Type A, B, and C and Their Applications," Protein Expression and Purification 40(1):31-41, Mar. 2005.
K. Turton, et al., "Botulinum and Tetanus Neurotoxins: Structure, Function and Therapeutic Utility," Trends in Biochemical Science 27(11):552-558, Nov. 2002.
N. Vergnolle, et al., "Proteinase-Activated Receptor-2 and Hyperalgesia: A Novel Pain Pathway," Nature Medicine 7(7):821-826, Jul. 2001.
E. Wagner, et al., "Influenza Virus Hemagglutinin HA-2 N-Terminal Fusogenic Peptides Augment Gene Transfer by Transferrin-Polylysine-DNA Complexes: Toward a Synthetic Virus-Like Gene-Transfer Vehicle," Proceedings of the National Academy of Sciences of the United States of America (PNAS) 89(17)7934-7938, Sep. 1992.
X.J. Xu, et al., "Galan In and Spinal Nociceptive Mechanisms: Recent Advances and Therapeutic Implications," Neuropeptides 34(3-4): 137-147, Jun.-Aug. 2000.
S.R. Blanke, et al., "Fused Poiycationic Peptide Mediates Delivery of Diphtheria Toxin A Chain to the Cytosol in the Presence of Anthrax Protective Antigen," Proceedings of the National Academy of Sciences of the United States of America (PNAS) 93(16):8437-8442, Aug. 1996.
R.O. Blaustein, et al., "TheN-Terminal Half of the Heavy Chain of Botulinum Tape A Neurotoxin Forms Channels in Planar Phospholipids Bilayers," FEBS(Federatuin of European Biochemical Societies) Letters 226(1):115-120, Dec. 1987.
M. Kielian, et al., "Mechanisms of mutations Inhibiting Fusion and Infection by Semliki Forest Virus," Journal of Cell Biologoy 134(4):863-872, Aug. 1996.
A. Kihara, et al., "Analysis of Sequences Required for the Cytotoxic Action of a Chimeric Toxin Composed of Pseudomonas Exotoxins and Transforming Growth Factor a," Bioconjugate Chemistry 5(6):532-538, Nov. 1994.

H.-X. Liu, et al., "The Participation of Galanin in Pain Processing at the Spinas Level," Trends in Pharmacological Sciences 23(10):468-474, Oct. 2002.
E. London. "Diphtheria Toxin: Membrane interaction and Membrane Translocation," Biochimica et Biophysics Acta (BBA)—Reviews of Biomembranes 1113(1):25-51, Mar. 1992.
M. Murata, et al., "pH-Dependent Membrane Fusion and Vesiculation of Phospholipid Large Unilamellar Vesicles Induced by Amphiphilic Anionic and Cationic Peptides," Biochemisty 31(7):1986-1992, Feb. 1992.
D.O. O'Keefe, et al., "pH-Dependent Insertion of Proteins into Membranes: B-Chain Mutation of Diphtheria Toxin Tha Inhibits Membrane Translocation, Glue-349-->Lys," Proceedings of the National Academy of Sciences of the United States of America (PNAS) 89(13):6202-6206, Jul. 1992.
M. Picard=Maureau, et al., "Foamy Virus Envelope Glycoprotein-Mediated Entry Involves a pH-Dependent Fusion Process," Journal of Virology 77(8):4722-4730, Apr. 2003.
J. Pohlner, et al., "Gene Structure and Extracellular Secretion of Neisseria Gonorrhoeae IgA Protease," Nature 325:458-462, Jan. 1987.
T.I. Prior, et al., "Translocation Mediated by Domain II of Pseudomonas Extoxin A: Transport of Barnase Into the Cytosol," Biochemistry 31(14) 3555-3559, Apr. 14, 1992.
S. Seth, et al., "Activation of Fusion by the SER Virus F Protein: A Low-pH-Dependent Paramyxovirus Entry Process," Journal of Virology 77(11):6520-6527, Jun. 2003.
J.A. Silverman, et al., "Mutational Analysis of the Helical Hairpin Region of Diphtheria Toxin Transmembrane Domain," Journal of Biological Chemistry 269(36):22524-22532, Sep. 1994.
O.K. Smith, et al., "Improved Amino Acid Flexibility Parameters, "Protein Science 12(5):1060-1072, May 2003.
Y. Yao, et al., "Membrane Fusion Activity of Vesicular Stomatitis Virus Glycoprotein G Is Induced by Low pH but Not by Heat or Denaturant," Virology 310(2):319-332, Jun. 2003.
S. TachiBana et al., "Design and Synthesis of Metabolically Stable Analogue of Dynorphin-A", Journal of Synthetic Organic Chemistry, Japan, 1991 vol. 49, No. 1, p. 16-25.
Published_ApplicatiorIs_AA_Main database from Wang et al, US201 00233741, SEQ ID No. Alignment with SEQ ID No. 13.

* cited by examiner

A

B

B

A

B

Figure 5

| Fusion protein | EC50 n=1 | EC50 n=2 | EC50 n=3 | EC50 n=4 | Mean EC50 |
|---|---|---|---|---|---|
| LC-GS5-EN-CPGA30-GS20-H$_N$-HT | 82 nM | 44 nM | 60 nM | - | 62 nM |
| LC-GS10-EN-CPGA30-GS20-H$_N$-HT | 83 nM | 49 nM | 48.7 nM | 41 nM | 55 nM |
| LC-GS5-EN-CPGA16-GS20-H$_N$-HT | 10 nM | 11.7 nM | 17.5 nM | ND | 13 nM |
| LC-GS10-EN-CPGA16-GS20-H$_N$-HT | 6.14 nM | 1.2 nM | 9.47 nM | 11 nM | 7 nM |
| LC-GS18-EN-CPGA16-GS20-H$_N$-HT | 4 nM | 15.6 nM | 11.7 nM | 21.7 nM | 13 nM |

Figure 6

| | Maximum % effect | | |
|---|---|---|---|
| Fusion protein | 25ng | 2.5ng | 0.25ng |
| LC-GS5-EN-CPGA16-GS20-H$_N$-HT | 25.3± 3.35 | 20.84± 6.38 | 17.19± 7.94 |
| LC-GS18-EN-CPGA16-GS20-H$_N$-HT | 22.07± 7.86 | 19.98± 7.42 | |

Figure 8

| Fusion protein | Backbone serotype | MPE % |
|---|---|---|
| LC-GS5-EN-CPGA16-GS20-$H_N$-HT | A | 40.4± 8.9 |
| LC-GS5-EN-CPGA16-GS20-$H_N$-HT | B | 27.5± 4.6 |
| LC-GS5-EN-CPGA16-GS20-$H_N$-HT | C | 46.2± 7.0 |
| LC-GS5-EN-CPGA16-GS20-$H_N$-HT | D | 30.5± 6.6 |

A

B

C

SEQUENCE LISTING

```
<160> NUMBER OF SEQ ID NOS: 89

<210> SEQ ID NO 1
<211> LENGTH: 1302
<212> TYPE: DNA
```

<213> ORGANISM: Artificial Sequence
<220> FEATURE:
<223> OTHER INFORMATION: Synthetic sequence

<400> SEQUENCE: 1

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gatacctta ctaacccgga agaaggtgac      180
ctgaacccgc caccggaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc cacccgaac     900
aaagcgaaat ccatcgtggg taccactgct tctctccagt acatgaagaa cgttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttctt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg ac                       1302
```

<210> SEQ ID NO 2
<211> LENGTH: 1257
<212> TYPE: DNA
<213> ORGANISM: Artificial Sequence
<220> FEATURE:
<223> OTHER INFORMATION: Synthetic

<400> SEQUENCE: 2

```
ctgcagtgta tcaaggttaa caactgggat ttattcttca gcccgagtga agacaacttc      60
accaacgacc tgaacaaagg tgaagaaatc acctcagata ctaacatcga agcagccgaa     120
gaaaacatct cgctggacct gatccagcag tactacctga ctttaatttt cgacaacgag     180
ccggaaaaca tttctatcga aaacctgagc tctgatatca tcggccagct ggaactgatg     240
ccgaacatcg aacgtttccc aaacggtaaa agtacgagc tggacaaata ccatgttc       300
cactacctgc gcgcgcagga atttgaacac ggcaaatccc gtatcgcact gactaactcc     360
gttaacgaag ctctgctcaa cccgtcccgt gtatacacct tcttctctag cgactacgtg     420
aaaaaggtca acaaagcgac tgaagctgca atgttcttgg ttgggttgag acagcttgtt     480
tatgatttta ccgacgagac gtccgaagta tctactaccg acaaaattgc ggatatcact     540
atcatcatcc cgtacatcgg tccggctctg aacattggca acatgctgta caaagacgac     600
```

-continued

| | |
|---|---|
| ttcgttggcg cactgatctt ctccggtgcg gtgatcctgc tggagttcat cccggaaatc | 660 |
| gccatcccgg tactgggcac ctttgctctg gtttcttaca ttgcaaacaa ggttctgact | 720 |
| gtacaaacca tcgacaacgc gctgagcaaa cgtaacgaaa aatgggatga agtttacaaa | 780 |
| tatatcgtga ccaactggct ggctaaggtt aatactcaga tcgacctcat ccgcaaaaaa | 840 |
| atgaaagaag cactggaaaa ccaggcggaa gctaccaagg caatcattaa ctaccagtac | 900 |
| aaccagtaca ccgaggaaga aaaaacaac atcaacttca acatcgacga tctgtcctct | 960 |
| aaactgaacg aatccatcaa caaagctatg atcaacatca caagttcct gaaccagtgc | 1020 |
| tctgtaagct atctgatgaa ctccatgatc ccgtacggtg ttaaacgtct ggaggacttc | 1080 |
| gatgcgtctc tgaaagacgc cctgctgaaa tacatttacg acaaccgtgg cactctgatc | 1140 |
| ggtcaggttg atcgtctgaa ggacaaagtg aacaatacct tatcgaccga catcccttt | 1200 |
| cagctcagta aatatgtcga taaccaacgc cttttgtcca ctctagacta gaagctt | 1257 |

<210> SEQ ID NO 3
<211> LENGTH: 1323
<212> TYPE: DNA
<213> ORGANISM: Artificial Sequence
<220> FEATURE:
<223> OTHER INFORMATION: Synthetic

<400> SEQUENCE: 3

| | |
|---|---|
| ggatccatgc cggttaccat caacaacttc aactacaacg acccgatcga caacaacaac | 60 |
| atcattatga tggaaccgcc gttcgcacgt ggtaccggac gttactacaa ggcttttaag | 120 |
| atcaccgacc gtatctggat catcccggaa cgttacacct tcggttacaa acctgaggac | 180 |
| ttcaacaaga gtagcgggat tttcaatcgt gacgtctgcg agtactatga tccagattat | 240 |
| ctgaatacca acgataagaa gaacatattc cttcagacta tgattaaact cttcaaccgt | 300 |
| atcaaaagca aaccgctcgg tgaaaaactc ctcgaaatga ttatcaacgg tatcccgtac | 360 |
| ctcggtgacc gtcgtgtccc gcttgaagag ttcaacacca acatcgcaag cgtcaccgtc | 420 |
| aacaaactca tcagcaaccc aggtgaagtc gaacgtaaaa aaggtatctt cgcaaacctc | 480 |
| atcatcttcg gtccgggtcc ggtcctcaac gaaaacgaaa ccatcgacat cggtatccag | 540 |
| aaccacttcg caagccgtga aggtttcggt ggtatcatgc agatgaaatt ctgcccggaa | 600 |
| tacgtcagtg tcttcaacaa cgtccaggaa acaaaggtg caagcatctt caaccgtcgt | 660 |
| ggttacttca gcgacccggc actcatcctc atgcatgaac tcatccacgt cctccacggt | 720 |
| ctctacggta tcaaagttga cgacctcccg atcgtcccga acgagaagaa attcttcatg | 780 |
| cagagcaccg acgcaatcca ggctgaggaa ctctacacct tcggtggcca agacccaagt | 840 |
| atcataaccc cgtccaccga caaaagcatc tacgacaaag tcctccagaa cttcaggggt | 900 |
| atcgtggaca gactcaacaa agtcctcgtc tgcatcagcg acccgaacat caatatcaac | 960 |
| atatacaaga caagttcaa agacaagtac aaattcgtcg aggacagcga aggcaaatac | 1020 |
| agcatcgacg tagaaagttt cgacaagctc tacaaaagcc tcatgttcgg tttcaccgaa | 1080 |
| accaacatcg ccgagaacta caagatcaag acaagggcaa gttacttcag cgacagcctc | 1140 |
| ccgcctgtca aaatcaagaa cctcttagac aacgagattt acacaattga gagggcttc | 1200 |
| aacatcagtg acaaagacat ggagaaggaa tacagaggtc agaacaaggc tatcaacaaa | 1260 |
| caggcatacg aggagatcag caaagaacac ctcgcagtct acaagatcca gatgtgcgtc | 1320 |
| gac | 1323 |

<210> SEQ ID NO 4
<211> LENGTH: 1260
<212> TYPE: DNA
<213> ORGANISM: Artificial Sequence
<220> FEATURE:
<223> OTHER INFORMATION: Synthetic

<400> SEQUENCE: 4

```
ctgcagtgca tcgacgttga caacgaagac ctgttcttca tcgctgacaa aaacagcttc    60
agtgacgacc tgagcaaaaa cgaacgtatc gaatacaaca cccagagcaa ctacatcgaa   120
aacgacttcc cgatcaacga actgatcctg acaccgacc tgataagtaa aatcgaactg    180
ccgagcgaaa acaccgaaag tctgaccgac ttcaacgttg acgttccggt ttacgaaaaa   240
cagccggcta tcaagaaaat cttcaccgac gaaaacacca tcttccagta cctgtacagc   300
cagaccttcc cgctggacat ccgtgacatc agtctgacca gcagtttcga cgacgctctg   360
ctgttcagca acaaagtttta cagtttcttc agcatggact acatcaaaac cgctaacaaa   420
gttgttgaag cagggctgtt cgctggttgg gttaaacaga tcgttaacga cttcgttatc   480
gaagctaaca aaagcaacac tatggacaaa atcgctgaca tcagtctgat cgttccgtac   540
atcggtctgg ctctgaacgt tggtaacgaa accgctaaag gtaactttga aaacgctttc   600
gagatcgctg gtgcaagcat cctgctggag ttcatcccgg aactgctgat cccggttgtt   660
ggtgctttcc tgctggaaag ttacatcgac aacaaaaaca gatcatcaa aaccatcgac   720 aacgctctga ccaaacgtaa cgaaaaatgg agtgatatgt acggtctgat cgttgctcag   780
tggctgagca ccgtcaacac ccagttctac accatcaaag aaggtatgta caaagctctg   840
aactaccagg ctcaggctct ggaagagatc atcaaatacc gttacaacat ctacagtgag   900
aaggaaaaga gtaacatcaa catcgacttc aacgacatca cagcaaact gaacgaaggt   960 atcaaccagg ctatcgacaa catcaacaac ttcatcaacg gttgcagtgt tagctacctg  1020
atgaagaaga tgatcccgct ggctgttgaa aaactgctgg acttcgacaa caccctgaaa  1080
aagaacctgc tgaactacat cgacgaaaac aagctgtacc tgatcggtag tgctgaatac  1140 gaaaaagta agtgaacaa atacctgaag accatcatgc cgttcgacct gagtatctac  1200
accaacgaca ccatcctgat cgaaatgttc aacaaataca actctctaga ctagaagctt  1260
```

<210> SEQ ID NO 5
<211> LENGTH: 1329
<212> TYPE: DNA
<213> ORGANISM: Artificial Sequence
<220> FEATURE:
<223> OTHER INFORMATION: Synthetic

<400> SEQUENCE: 5

```
ggatccgaat tcatgccgat caccatcaac aacttcaact acagcgatcc ggtggataac    60
aaaaacatcc tgtacctgga tacccatctg aatacactgg cgaacgaacc ggaaaaagcg   120
tttcgtatca ccggcaacat ttgggttatt ccggatcgtt ttagccgtaa cagcaacccg   180
aatctgaata aaccgccgcg tgttaccagc ccgaaaagcg gttattacga tccgaactat   240
ctgagcaccg atagcgataa agataccttc ctgaaagaaa tcatcaaact gttcaaacgc   300
atcaacagcc gtgaaattgg cgaagaactg atctatcgcc tgagcaccga tattccgttt   360
ccgggcaaca caacacccc gatcaacacc tttgatttcg atgtggattt caacagcgtt   420
gatgttaaaa cccgccaggg taacaattgg gtgaaaaccg gcagcattaa cccgagcgtg   480
attattaccg gtccgcgcga aaacattatt gatccggaaa ccagcaccctt taaactgacc   540
```

```
aacaacacct tgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat tccgaacgat cagaccatta gcagcgtgac cagcaacatc    780
ttttacagcc agtacaacgt gaaactggaa tatgcggaaa tctatgcgtt ggcggtccg     840 accattgatc tgattccgaa agcgcgcgc aaatacttcg aagaaaaagc gctggattac     900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc   1020
agcggcgaag ttaccgttaa ccgcaataaa ttcgtggaac tgtacaacga actgacccag   1080
atcttcaccg aatttaacta tgcgaaaatc tataacgtgc agaaccgtaa aatctacctg   1140
agcaacgtgt ataccccggt gaccgcgaat attctggatg ataacgtgta cgatatccag   1200
aacggcttta acatcccgaa aagcaacctg aacgttctgt ttatgggcca gaacctgagc   1260
cgtaatccgg cgctgcgtaa agtgaacccg gaaaacatgc tgtacctgtt caccaaattt   1320
tgcgtcgac                                                            1329

<210> SEQ ID NO 6
<211> LENGTH: 1263
<212> TYPE: DNA
<213> ORGANISM: Artificial Sequence
<220> FEATURE:
<223> OTHER INFORMATION: Synthetic

<400> SEQUENCE: 6
ctgcagtgtc gtgaactgct ggtgaaaaac accgatctgc cgtttattgg cgatatcagc     60
gatgtgaaaa ccgatatctt cctgcgcaaa gatatcaacg aagaaaccga agtgatctac    120
tacccggata acgtgagcgt tgatcaggtg atcctgagca aaaacaccag cgaacatggt    180
cagctggatc tgctgtatcc gagcattgat agcgaaagcg aaattctgcc gggcgaaaac    240
caggtgtttt acgataaccg tacccagaac gtggattacc tgaacagcta ttactacctg    300
gaaagccaga aactgagcga taacgtggaa gattttacct ttacccgcag cattgaagaa    360
gcgctggata cagcgcgaa agtttacacc tattttccga ccctggcgaa caaagttaat    420
gcgggtgttc agggcggtct gtttctgatg tgggcgaacg atgtggtgga agatttcacc    480
accaacatcc tgcgtaaaga taccctggat aaaatcagcg atgttagcgc gattattccg    540
tatattggtc cggcgctgaa cattagcaat agcgtgcgtc gtggcaattt taccgaagcg    600
tttgcggtta ccggtgtgac cattctgctg gaagcgtttc cggaatttac cattccggcg    660
ctgggtgcgt ttgtgatcta tagcaaagtg caggaacgca acgaaatcat caaaaccatc    720
gataactgcc tggaacagcg tattaaacgc tggaaagata gctatgaatg gatgatgggc    780
acctggctga gccgtattat cacccagttc aacaacatca gctaccagat gtacgatagc    840
ctgaactatc aggcgggtgc gattaaagcg aaaatcgatc tggaatacaa aaaatacagc    900
ggcagcgata aagaaaacat caaaagccag gttgaaaacc tgaaaaacag cctggatgtg    960
aaaattagcg aagcgatgaa taacatcaac aaattcatcc gcaatgcag cgtgacctac   1020 ctgttcaaaa acatgctgcc gaaagtgatc gatgaactga cgaatttga tcgcaacacc   1080 aaagcgaaac tgatcaacct gatcgatagc cacaacatta ttctggtggg cgaagtggat   1140
aaactgaaag cgaaagttaa caacagcttc cagaacacca tcccgtttaa catcttcagc   1200
```

-continued

| tataccaaca acagcctgct gaaagatatc atcaacgaat acttcaatct agactagaag | 1260 |
| ctt | 1263 |

<210> SEQ ID NO 7
<211> LENGTH: 30
<212> TYPE: PRT
<213> ORGANISM: Artificial Sequence
<220> FEATURE:
<223> OTHER INFORMATION: Synthetic sequence

<400> SEQUENCE: 7

Gly Trp Thr Leu Asn Ser Ala Gly Tyr Leu Leu Gly Pro His Ala Val
1               5                   10                  15

Gly Asn His Arg Ser Phe Ser Asp Leu Asn Gly Leu Thr Ser
            20                  25                  30

<210> SEQ ID NO 8
<211> LENGTH: 16
<212> TYPE: PRT
<213> ORGANISM: Artificial Sequence
<220> FEATURE:
<223> OTHER INFORMATION: Synthetic sequence

<400> SEQUENCE: 8

Gly Trp Thr Leu Asn Ser Ala Gly Tyr Leu Leu Gly Pro His Ala Val
1               5                   10                  15

<210> SEQ ID NO 9
<211> LENGTH: 2781
<212> TYPE: DNA
<213> ORGANISM: Artificial Sequence
<220> FEATURE:
<223> OTHER INFORMATION: Synthetic sequence

<400> SEQUENCE: 9

| atttcagaat tcggatccat ggagttcgtt aacaaacagt tcaactataa agacccagtt | 60 |
| aacggtgttg acattgctta catcaaaatc ccgaacgctg ccagatgca gccggtaaag | 120 |
| gcattcaaaa tccacaacaa aatctgggtt atcccggaac gtgataccct tactaacccg | 180 |
| gaagaaggtg acctgaaccc gccaccggaa gcgaaacagg tgccggtatc ttactatgac | 240 |
| tccacctacc tgtctaccga taacgaaaag acaactacc tgaaaggtgt tactaaactg | 300 |
| ttcgagcgta tttactccac cgacctgggc cgtatgctgc tgactagcat cgttcgcggt | 360 |
| atcccgttct ggggcggttc taccatcgat accgaactga agtaatcga cactaactgc | 420 |
| atcaacgtta ttcagccgga cggttcctat cgttccgaag aactgaaccct ggtgatcatc | 480 |
| ggcccgtctg ctgatatcat ccagttcgag tgtaagagct ttggtcacga agttctgaac | 540 |
| ctcacccgta acggctacgg ttccactcag tacatccgtt tctctccgga cttcaccttc | 600 |
| ggttttgaag aatccctgga agtagacacg aacccactgc tgggcgctgg taaattcgca | 660 |
| actgatcctg cggttaccct ggctcacgaa ctgattcatg caggccaccg cctgtacggt | 720 |
| atcgccatca atccgaaccg tgtcttcaaa gttaacacca acgcgtatta cgagatgtcc | 780 |
| ggtctggaag ttagcttcga agaactgcgt acttttggcg tcacgacgc taaattcatc | 840 |
| gactctctgc aagaaaacga gttccgtctg tactactata caagttcaa agatatcgca | 900 |
| tccaccctga acaaagcgaa atccatcgtg gtaccactg cttctctcca gtacatgaag | 960 |
| aacgtttta agaaaaaata cctgctcagc gaagacaccct ccggcaaatt ctctgtagac | 1020 |
| aagttgaaat cgataaaact ttacaaaatg ctgactgaaa tttacaccga agacaacttc | 1080 |

```
gttaagttct ttaaagttct gaaccgcaaa acctatctga acttcgacaa ggcagtattc    1140
aaaatcaaca tcgtgccgaa agttaactac actatctacg atggtttcaa cctgcgtaac    1200
accaacctgg ctgctaattt taacggccag aacacggaaa tcaacaacat gaacttcaca    1260
aaactgaaaa acttcactgg tctgttcgag ttttacaagc tgctgtgcgt cgacggcggt    1320
ggcggtagcg gcggtggcgg tagcggcggt ggcggtagcg cagacgatga cgataaggt     1380 tggaccctga actctgctgg ttacctgctg gtccgcacg ctgttgcgct agcgggcggt     1440
ggcggtagcg gcggtggcgg tagcggcggt ggcggtagcg cactagtgct gcagtgtatc    1500
aaggttaaca actgggattt attcttcagc ccgagtgaag acaacttcac caacgacctg    1560
aacaaaggtg aagaaatcac ctcagatact aacatcgaag cagccgaaga aaacatctcg    1620
ctggacctga tccagcagta ctacctgacc tttaatttcg acaacgagcc ggaaaacatt    1680
tctatcgaaa acctgagctc tgatatcatc ggccagctgg aactgatgcc gaacatcgaa    1740
cgtttcccaa acggtaaaaa gtacgagctg acaaatata ccatgttcca ctacctgcgc     1800
gcgcaggaat ttgaacacgg caaatcccgt atcgcactga ctaactccgt taacgaagct    1860
ctgctcaacc cgtcccgtgt atacaccttc ttctctagcg actacgtgaa aaaggtcaac    1920
aaagcgactg aagctgcaat gttcttgggt tgggttgaac agcttgttta tgattttacc    1980
gacgagacgt ccgaagtatc tactaccgac aaaattgcgg atatcactat catcatcccg    2040
tacatcggtc cggctctgaa cattggcaac atgctgtaca agacgacttc gttggcgca    2100 ctgatcttct ccggtgcggt gatcctgctg gagttcatcc cggaaatcgc catcccggta    2160
ctgggcacct ttgctctggt ttcttacatt gcaacaagg ttctgactgt acaaaccatc     2220
gacaacgcgc tgagcaaacg taacgaaaaa tgggatgaag tttacaaata tatcgtgacc    2280
aactggctgg ctaaggttaa tactcagatc gacctcatcc gcaaaaaaat gaagaagca     2340 ctggaaaacc aggcggaagc taccaaggca atcattaact accagtacaa ccagtacacc    2400
gaggaagaaa aaacaacat caacttcaac atcgacgatc tgtcctctaa actgaacgaa     2460
tccatcaaca agctatgat caacatcaac aagttcctga accagtgctc tgtaagctat      2520
ctgatgaact ccatgatccc gtacggtgtt aaacgtctgg aggacttcga tgcgtctctg    2580
aaagacgccc tgctgaaata catttacgac aaccgtggca ctctgatcgg tcaggttgat    2640
cgtctgaagg acaaagtgaa caataccta tcgaccgaca tccctttca gctcagtaaa     2700 tatgtcgata ccaacgcct tttgtccact ctagaagcac tagcgagtgg gcaccatcac     2760
catcaccatt aatgaaagct t                                             2781
```

<210> SEQ ID NO 10
<211> LENGTH: 923
<212> TYPE: PRT
<213> ORGANISM: Artificial Sequence
<220> FEATURE:
<223> OTHER INFORMATION: Synthetic sequence

<400> SEQUENCE: 10

```
Ile Ser Glu Phe Gly Ser Met Glu Phe Val Asn Lys Gln Phe Asn Tyr
1               5                   10                  15

Lys Asp Pro Val Asn Gly Val Asp Ile Ala Tyr Ile Lys Ile Pro Asn
            20                  25                  30

Ala Gly Gln Met Gln Pro Val Lys Ala Phe Lys Ile His Asn Lys Ile
        35                  40                  45

Trp Val Ile Pro Glu Arg Asp Thr Phe Thr Asn Pro Glu Glu Gly Asp
    50                  55                  60
```

```
Leu Asn Pro Pro Glu Ala Lys Gln Val Pro Val Ser Tyr Tyr Asp
 65                  70                  75                  80

Ser Thr Tyr Leu Ser Thr Asp Asn Glu Lys Asp Asn Tyr Leu Lys Gly
                 85                  90                  95

Val Thr Lys Leu Phe Glu Arg Ile Tyr Ser Thr Asp Leu Gly Arg Met
            100                 105                 110

Leu Leu Thr Ser Ile Val Arg Gly Ile Pro Phe Trp Gly Gly Ser Thr
            115                 120                 125

Ile Asp Thr Glu Leu Lys Val Ile Asp Thr Asn Cys Ile Asn Val Ile
130                 135                 140

Gln Pro Asp Gly Ser Tyr Arg Ser Glu Glu Leu Asn Leu Val Ile Ile
145                 150                 155                 160

Gly Pro Ser Ala Asp Ile Ile Gln Phe Glu Cys Lys Ser Phe Gly His
                165                 170                 175

Glu Val Leu Asn Leu Thr Arg Asn Gly Tyr Gly Ser Thr Gln Tyr Ile
            180                 185                 190

Arg Phe Ser Pro Asp Phe Thr Phe Gly Phe Glu Glu Ser Leu Glu Val
            195                 200                 205

Asp Thr Asn Pro Leu Leu Gly Ala Gly Lys Phe Ala Thr Asp Pro Ala
210                 215                 220

Val Thr Leu Ala His Glu Leu Ile His Ala Gly His Arg Leu Tyr Gly
225                 230                 235                 240

Ile Ala Ile Asn Pro Asn Arg Val Phe Lys Val Asn Thr Asn Ala Tyr
                245                 250                 255

Tyr Glu Met Ser Gly Leu Glu Val Ser Phe Glu Glu Leu Arg Thr Phe
            260                 265                 270

Gly Gly His Asp Ala Lys Phe Ile Asp Ser Leu Gln Glu Asn Glu Phe
            275                 280                 285

Arg Leu Tyr Tyr Tyr Asn Lys Phe Lys Asp Ile Ala Ser Thr Leu Asn
            290                 295                 300

Lys Ala Lys Ser Ile Val Gly Thr Thr Ala Ser Leu Gln Tyr Met Lys
305                 310                 315                 320

Asn Val Phe Lys Glu Lys Tyr Leu Leu Ser Glu Asp Thr Ser Gly Lys
                325                 330                 335

Phe Ser Val Asp Lys Leu Lys Phe Asp Lys Leu Tyr Lys Met Leu Thr
            340                 345                 350

Glu Ile Tyr Thr Glu Asp Asn Phe Val Lys Phe Phe Lys Val Leu Asn
            355                 360                 365

Arg Lys Thr Tyr Leu Asn Phe Asp Lys Ala Val Phe Lys Ile Asn Ile
            370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
                405                 410                 415

Met Asn Phe Thr Lys Leu Lys Asn Phe Thr Gly Leu Phe Glu Phe Tyr
            420                 425                 430

Lys Leu Leu Cys Val Asp Gly Gly Gly Ser Gly Gly Gly Gly Ser
            435                 440                 445

Gly Gly Gly Gly Ser Ala Asp Asp Asp Lys Gly Trp Thr Leu Asn
            450                 455                 460

Ser Ala Gly Tyr Leu Leu Gly Pro His Ala Val Ala Leu Ala Gly Gly
465                 470                 475                 480
```

-continued

Gly Gly Ser Gly Gly Gly Gly Ser Gly Gly Gly Ser Ala Leu Val
                485                 490                 495

Leu Gln Cys Ile Lys Val Asn Asn Trp Asp Leu Phe Phe Ser Pro Ser
            500                 505                 510

Glu Asp Asn Phe Thr Asn Asp Leu Asn Lys Gly Glu Glu Ile Thr Ser
            515                 520                 525

Asp Thr Asn Ile Glu Ala Ala Glu Glu Asn Ile Ser Leu Asp Leu Ile
            530                 535                 540

Gln Gln Tyr Tyr Leu Thr Phe Asn Phe Asp Asn Glu Pro Glu Asn Ile
545                 550                 555                 560

Ser Ile Glu Asn Leu Ser Ser Asp Ile Ile Gly Gln Leu Glu Leu Met
                565                 570                 575

Pro Asn Ile Glu Arg Phe Pro Asn Gly Lys Lys Tyr Glu Leu Asp Lys
                580                 585                 590

Tyr Thr Met Phe His Tyr Leu Arg Ala Gln Glu Phe Glu His Gly Lys
                595                 600                 605

Ser Arg Ile Ala Leu Thr Asn Ser Val Asn Glu Ala Leu Leu Asn Pro
            610                 615                 620

Ser Arg Val Tyr Thr Phe Phe Ser Ser Asp Tyr Val Lys Lys Val Asn
625                 630                 635                 640

Lys Ala Thr Glu Ala Ala Met Phe Leu Gly Trp Val Glu Gln Leu Val
                645                 650                 655

Tyr Asp Phe Thr Asp Glu Thr Ser Glu Val Ser Thr Thr Asp Lys Ile
                660                 665                 670

Ala Asp Ile Thr Ile Ile Pro Tyr Ile Gly Pro Ala Leu Asn Ile
            675                 680                 685

Gly Asn Met Leu Tyr Lys Asp Asp Phe Val Gly Ala Leu Ile Phe Ser
            690                 695                 700

Gly Ala Val Ile Leu Leu Glu Phe Ile Pro Glu Ile Ala Ile Pro Val
705                 710                 715                 720

Leu Gly Thr Phe Ala Leu Val Ser Tyr Ile Ala Asn Lys Val Leu Thr
                725                 730                 735

Val Gln Thr Ile Asp Asn Ala Leu Ser Lys Arg Asn Glu Lys Trp Asp
                740                 745                 750

Glu Val Tyr Lys Tyr Ile Val Thr Asn Trp Leu Ala Lys Val Asn Thr
            755                 760                 765

Gln Ile Asp Leu Ile Arg Lys Lys Met Lys Glu Ala Leu Glu Asn Gln
            770                 775                 780

Ala Glu Ala Thr Lys Ala Ile Ile Asn Tyr Gln Tyr Asn Gln Tyr Thr
785                 790                 795                 800

Glu Glu Glu Lys Asn Asn Ile Asn Phe Asn Ile Asp Asp Leu Ser Ser
                805                 810                 815

Lys Leu Asn Glu Ser Ile Asn Lys Ala Met Ile Asn Ile Asn Lys Phe
            820                 825                 830

Leu Asn Gln Cys Ser Val Ser Tyr Leu Met Asn Ser Met Ile Pro Tyr
            835                 840                 845

Gly Val Lys Arg Leu Glu Asp Phe Asp Ala Ser Leu Lys Asp Ala Leu
            850                 855                 860

Leu Lys Tyr Ile Tyr Asp Asn Arg Gly Thr Leu Ile Gly Gln Val Asp
865                 870                 875                 880

Arg Leu Lys Asp Lys Val Asn Asn Thr Leu Ser Thr Asp Ile Pro Phe
                885                 890                 895

Gln Leu Ser Lys Tyr Val Asp Asn Gln Arg Leu Leu Ser Thr Leu Glu

```
                   900                 905                 910
Ala Leu Ala Ser Gly His His His His His
            915                 920

<210> SEQ ID NO 11
<211> LENGTH: 912
<212> TYPE: PRT
<213> ORGANISM: Artificial Sequence
<220> FEATURE:
<223> OTHER INFORMATION: Synthetic sequence

<400> SEQUENCE: 11

Ile Ser Glu Phe Gly Ser Met Glu Phe Val Asn Lys Gln Phe Asn Tyr
1               5                   10                  15

Lys Asp Pro Val Asn Gly Val Asp Ile Ala Tyr Ile Lys Ile Pro Asn
            20                  25                  30

Ala Gly Gln Met Gln Pro Val Lys Ala Phe Lys Ile His Asn Lys Ile
        35                  40                  45

Trp Val Ile Pro Glu Arg Asp Thr Phe Thr Asn Pro Glu Glu Gly Asp
    50                  55                  60

Leu Asn Pro Pro Glu Ala Lys Gln Val Pro Val Ser Tyr Tyr Asp
65                  70                  75                  80

Ser Thr Tyr Leu Ser Thr Asp Asn Glu Lys Asp Asn Tyr Leu Lys Gly
                85                  90                  95

Val Thr Lys Leu Phe Glu Arg Ile Tyr Ser Thr Asp Leu Gly Arg Met
            100                 105                 110

Leu Leu Thr Ser Ile Val Arg Gly Ile Pro Phe Trp Gly Gly Ser Thr
        115                 120                 125

Ile Asp Thr Glu Leu Lys Val Ile Asp Thr Asn Cys Ile Asn Val Ile
    130                 135                 140

Gln Pro Asp Gly Ser Tyr Arg Ser Glu Glu Leu Asn Leu Val Ile Ile
145                 150                 155                 160

Gly Pro Ser Ala Asp Ile Ile Gln Phe Glu Cys Lys Ser Phe Gly His
                165                 170                 175

Glu Val Leu Asn Leu Thr Arg Asn Gly Tyr Gly Ser Thr Gln Tyr Ile
            180                 185                 190

Arg Phe Ser Pro Asp Phe Thr Phe Gly Phe Glu Glu Ser Leu Glu Val
        195                 200                 205

Asp Thr Asn Pro Leu Leu Gly Ala Gly Lys Phe Ala Thr Asp Pro Ala
    210                 215                 220

Val Thr Leu Ala His Glu Leu Ile His Ala Gly His Arg Leu Tyr Gly
225                 230                 235                 240

Ile Ala Ile Asn Pro Asn Arg Val Phe Lys Val Asn Thr Asn Ala Tyr
                245                 250                 255

Tyr Glu Met Ser Gly Leu Glu Val Ser Phe Glu Glu Leu Arg Thr Phe
            260                 265                 270

Gly Gly His Asp Ala Lys Phe Ile Asp Ser Leu Gln Glu Asn Glu Phe
        275                 280                 285

Arg Leu Tyr Tyr Tyr Asn Lys Phe Lys Asp Ile Ala Ser Thr Leu Asn
    290                 295                 300

Lys Ala Lys Ser Ile Val Gly Thr Thr Ala Ser Leu Gln Tyr Met Lys
305                 310                 315                 320

Asn Val Phe Lys Glu Lys Tyr Leu Leu Ser Glu Asp Thr Ser Gly Lys
                325                 330                 335

Phe Ser Val Asp Lys Leu Lys Phe Asp Lys Leu Tyr Lys Met Leu Thr
```

```
                    340             345             350
Glu Ile Tyr Thr Glu Asp Asn Phe Val Lys Phe Lys Val Leu Asn
                355                 360             365

Arg Lys Thr Tyr Leu Asn Phe Asp Lys Ala Val Phe Lys Ile Asn Ile
        370                 375                 380

Val Pro Lys Val Asn Tyr Thr Ile Tyr Asp Gly Phe Asn Leu Arg Asn
385                 390                 395                 400

Thr Asn Leu Ala Ala Asn Phe Asn Gly Gln Asn Thr Glu Ile Asn Asn
                405                 410                 415

Met Asn Phe Thr Lys Leu Lys Asn Phe Thr Gly Leu Phe Glu Phe Tyr
                420                 425                 430

Lys Leu Leu Cys Val Asp Gly Gly Gly Ser Gly Gly Gly Gly Ser
            435                 440                 445

Gly Gly Gly Gly Ser Ala Asp Asp Asp Lys Gly Trp Thr Leu Asn
450                 455                 460

Ser Ala Gly Tyr Leu Leu Gly Pro His Ala Val Ala Leu Ala Gly Gly
465                 470                 475                 480

Gly Gly Ser Gly Gly Gly Ser Gly Gly Gly Ser Ala Leu Val
            485                 490                 495

Leu Gln Cys Ile Lys Val Asn Asn Trp Asp Leu Phe Phe Ser Pro Ser
            500                 505                 510

Glu Asp Asn Phe Thr Asn Asp Leu Asn Lys Gly Glu Glu Ile Thr Ser
            515                 520                 525

Asp Thr Asn Ile Glu Ala Ala Glu Glu Asn Ile Ser Leu Asp Leu Ile
530                 535                 540

Gln Gln Tyr Tyr Leu Thr Phe Asn Phe Asp Asn Glu Pro Glu Asn Ile
545                 550                 555                 560

Ser Ile Glu Asn Leu Ser Ser Asp Ile Ile Gly Gln Leu Glu Leu Met
                565                 570                 575

Pro Asn Ile Glu Arg Phe Pro Asn Gly Lys Lys Tyr Glu Leu Asp Lys
            580                 585                 590

Tyr Thr Met Phe His Tyr Leu Arg Ala Gln Glu Phe Glu His Gly Lys
            595                 600                 605

Ser Arg Ile Ala Leu Thr Asn Ser Val Asn Glu Ala Leu Leu Asn Pro
        610                 615                 620

Ser Arg Val Tyr Thr Phe Phe Ser Ser Asp Tyr Val Lys Lys Val Asn
625                 630                 635                 640

Lys Ala Thr Glu Ala Ala Met Phe Leu Gly Trp Val Glu Gln Leu Val
                645                 650                 655

Tyr Asp Phe Thr Asp Glu Thr Ser Glu Val Ser Thr Thr Asp Lys Ile
                660                 665                 670

Ala Asp Ile Thr Ile Ile Pro Tyr Ile Gly Pro Ala Leu Asn Ile
            675                 680                 685

Gly Asn Met Leu Tyr Lys Asp Asp Phe Val Gly Ala Leu Ile Phe Ser
            690                 695                 700

Gly Ala Val Ile Leu Leu Glu Phe Ile Pro Glu Ile Ala Ile Pro Val
705                 710                 715                 720

Leu Gly Thr Phe Ala Leu Val Ser Tyr Ile Ala Asn Lys Val Leu Thr
                725                 730                 735

Val Gln Thr Ile Asp Asn Ala Leu Ser Lys Arg Asn Glu Lys Trp Asp
            740                 745                 750

Glu Val Tyr Lys Tyr Ile Val Thr Asn Trp Leu Ala Lys Val Asn Thr
            755                 760                 765
```

```
Gln Ile Asp Leu Ile Arg Lys Met Lys Glu Ala Leu Glu Asn Gln
        770                 775                 780

Ala Glu Ala Thr Lys Ala Ile Ile Asn Tyr Gln Tyr Asn Gln Tyr Thr
785                 790                 795                 800

Glu Glu Glu Lys Asn Asn Ile Asn Phe Asn Ile Asp Asp Leu Ser Ser
                805                 810                 815

Lys Leu Asn Glu Ser Ile Asn Lys Ala Met Ile Asn Ile Asn Lys Phe
                820                 825                 830

Leu Asn Gln Cys Ser Val Ser Tyr Leu Met Asn Ser Met Ile Pro Tyr
                835                 840                 845

Gly Val Lys Arg Leu Glu Asp Phe Asp Ala Ser Leu Lys Asp Ala Leu
        850                 855                 860

Leu Lys Tyr Ile Tyr Asp Asn Arg Gly Thr Leu Ile Gly Gln Val Asp
865                 870                 875                 880

Arg Leu Lys Asp Lys Val Asn Asn Thr Leu Ser Thr Asp Ile Pro Phe
                885                 890                 895

Gln Leu Ser Lys Tyr Val Asp Asn Gln Arg Leu Leu Ser Thr Leu Asp
                900                 905                 910

<210> SEQ ID NO 12
<211> LENGTH: 2745
<212> TYPE: DNA
<213> ORGANISM: Artificial Sequence
<220> FEATURE:
<223> OTHER INFORMATION: Synthetic sequence

<400> SEQUENCE: 12
catatgggat ccatggagtt cgttaacaaa cagttcaact ataaagaccc agttaacggt      60
gttgacattg cttacatcaa atcccgaac gctggccaga tgcagccggt aaaggcattc     120
aaaatccaca acaaaatctg ggttatcccg aacgtgata cctttactaa cccggaagaa     180
ggtgacctga cccgccacc ggaagcgaaa caggtgccgg tatcttacta tgactccacc     240
tacctgtcta ccgataacga aaaggacaac tacctgaaag gtgttactaa actgttcgag     300
cgtatttact ccaccgacct gggccgtatg ctgctgacta gcatcgttcg cggtatcccg     360
ttctggggcg gttctaccat cgataccgaa ctgaaagtaa tcgacactaa ctgcatcaac     420
gttattcagc cggacggttc ctatcgttcc gaagaactga acctggtgat catcggcccg     480
tctgctgata tcatccagtt cgagtgtaag agctttggtc acgaagttct gaacctcacc     540
cgtaacggct acggttccac tcagtacatc cgtttctctc cggacttcac cttcggtttt     600
gaagaatccc tggaagtaga cacgaaccca ctgctgggcg ctggtaaatt cgcaactgat     660
cctgcggtta ccctggctca cgaactgatt catgcaggcc accgcctgta cggtatcgcc     720
atcaatccga accgtgtctt caaagttaac accaacgcgt attacgagat gtccggtctg     780
gaagttagct tcgaagaact gcgtactttt ggcggtcacg acgctaaatt catcgactct     840
ctgcaagaaa acgagttccg tctgtactac tataacaagt tcaaagatat cgcatccacc     900
ctgaacaaag cgaaatccat cgtgggtacc actgcttctc tccagtacat gaagaacgtt     960
tttaaagaaa ataccctgct cagcgaagac acctccggca aattctctgt agacaagttg    1020
aaattcgata acttttacaa atgctgact gaaatttaca ccgaagacaa cttcgttaag    1080
ttctttaaag ttctgaaccg caaacctat ctgaacttcg acaaggcagt attcaaaatc    1140
aacatcgtgc cgaaagttaa ctacactatc tacgatggtt caacctgcg taacaccaac    1200 ctggctgcta attttaacgg ccagaacacg gaaatcaaca acatgaactt cacaaaactg    1260
```

```
aaaaacttca ctggtctgtt cgagttttac aagctgctgt gcgtcgacgg cggtggcggt    1320
agcgcagacg atgacgataa aggttggacc ctgaactctg ctggttacct gctgggtccg    1380
cacgctgttg cgctagcggg cggtggcggt agcggcggtg gcggtagcgg cggtggcggt    1440
agcgcactag tgctgcagtg tatcaaggtt aacaactggg atttattctt cagcccgagt    1500
gaagacaact tcaccaacga cctgaacaaa ggtgaagaaa tcacctcaga tactaacatc    1560
gaagcagccg aagaaaacat ctcgctggac ctgatccagc agtactacct gacctttaat    1620
ttcgacaacg agccggaaaa catttctatc gaaaacctga gctctgatat catcggccag    1680
ctggaactga tgccgaacat cgaacgtttc ccaaacggta aaagtacga gctggacaaa    1740 tataccatgt tccactacct gcgcgcgcag gaatttgaac acggcaaatc ccgtatcgca    1800
ctgactaact ccgttaacga agctctgctc aacccgtccc gtgtatacac cttcttctct    1860
agcgactacg tgaaaaaggt caacaaagcg actgaagctg caatgttctt gggttgggtt    1920
gaacagcttg tttatgattt taccgacgag acgtccgaag tatctactac cgacaaaatt    1980
gcggatatca ctatcatcat cccgtacatc ggtccggctc tgaacattgg caacatgctg    2040
tacaaagacg acttcgttgg cgcactgatc ttctccggtg cggtgatcct gctggagttc    2100
atcccggaaa tcgccatccc ggtactgggc acctttgctc tggtttctta cattgcaaac    2160
aaggttctga ctgtacaaac catcgacaac gcgctgagca acgtaacga aaaatgggat    2220 gaagtttaca atatatcgt gaccaactgg ctggctaagg ttaatactca gatcgacctc    2280
atccgcaaaa aaatgaaaga agcactgaa aaccaggcgg aagctaccaa ggcaatcatt    2340
aactaccagt acaaccagta caccgaggaa gaaaaaaaca acatcaactt caacatcgac    2400
gatctgtcct ctaaactgaa cgaatccatc aacaaagcta tgatcaacat caacaagttc    2460
ctgaaccagt gctctgtaag ctatctgatg aactccatga tcccgtacgg tgttaaacgt    2520
ctggaggact cgatgcgtc tctgaaagac gccctgctga atacattta cgacaaccgt    2580 ggcactctga tcggtcaggt tgatcgtctg aaggacaaag tgaacaatac cttatcgacc    2640
gacatcccct ttcagctcag taaatatgtc gataaccaac gccttttgtc cactctagaa    2700
gcactagcga gtgggcacca tcaccatcac cattaatgaa agctt               2745
```

<210> SEQ ID NO 13
<211> LENGTH: 910
<212> TYPE: PRT
<213> ORGANISM: Artificial Sequence
<220> FEATURE:
<223> OTHER INFORMATION: Synthetic sequence

<400> SEQUENCE: 13

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95
```

-continued

```
Leu Phe Glu Arg Ile Tyr Ser Thr Asp Leu Gly Arg Met Leu Leu Thr
            100                 105                 110

Ser Ile Val Arg Gly Ile Pro Phe Trp Gly Ser Thr Ile Asp Thr
        115                 120                 125

Glu Leu Lys Val Ile Asp Thr Asn Cys Ile Asn Val Ile Gln Pro Asp
            130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
        210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
        290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
        370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Ala Asp Asp Asp Lys Gly Trp
        435                 440                 445

Thr Leu Asn Ser Ala Gly Tyr Leu Leu Gly Pro His Ala Val Ala Leu
        450                 455                 460

Ala Gly Gly Gly Ser Gly Gly Gly Ser Gly Gly Gly Ser
465                 470                 475                 480

Ala Leu Val Leu Gln Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
```

```
            515                 520                 525
Asp Leu Ile Gln Gln Tyr Tyr Leu Thr Phe Asn Phe Asp Asn Glu Pro
        530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
        595                 600                 605

Leu Asn Pro Ser Arg Val Tyr Thr Phe Phe Ser Ser Asp Tyr Val Lys
610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
    690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
            740                 745                 750

Val Asn Thr Gln Ile Asp Leu Ile Arg Lys Lys Met Lys Glu Ala Leu
        755                 760                 765

Glu Asn Gln Ala Glu Ala Thr Lys Ala Ile Ile Asn Tyr Gln Tyr Asn
770                 775                 780

Gln Tyr Thr Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
            820                 825                 830

Ile Pro Tyr Gly Val Lys Arg Leu Glu Asp Phe Asp Ala Ser Leu Lys
        835                 840                 845

Asp Ala Leu Leu Lys Tyr Ile Tyr Asp Asn Arg Gly Thr Leu Ile Gly
    850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Glu Ala Leu Ala Ser Gly His His His His His
            900                 905                 910

<210> SEQ ID NO 14
<211> LENGTH: 899
<212> TYPE: PRT
<213> ORGANISM: Artificial Sequence
```

<220> FEATURE:
<223> OTHER INFORMATION: Synthetic sequence

<400> SEQUENCE: 14

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400
```

```
Ala Ala Asn Phe Asn Gly Gln Asn Thr Glu Ile Asn Met Asn Phe
            405                 410                 415

Thr Lys Leu Lys Asn Phe Thr Gly Leu Phe Glu Phe Tyr Lys Leu Leu
        420                 425                 430

Cys Val Asp Gly Gly Gly Ser Ala Asp Asp Asp Lys Gly Trp
        435                 440                 445

Thr Leu Asn Ser Ala Gly Tyr Leu Leu Gly Pro His Ala Val Ala Leu
    450                 455                 460

Ala Gly Gly Gly Ser Gly Gly Gly Ser Gly Gly Gly Ser
465                 470                 475                 480

Ala Leu Val Leu Gln Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
            500                 505                 510

Ile Thr Ser Asp Thr Asn Ile Glu Ala Ala Glu Glu Asn Ile Ser Leu
        515                 520                 525

Asp Leu Ile Gln Gln Tyr Tyr Leu Thr Phe Asn Phe Asp Asn Glu Pro
    530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
            580                 585                 590

His Gly Lys Ser Arg Ile Ala Leu Thr Asn Ser Val Asn Glu Ala Leu
        595                 600                 605

Leu Asn Pro Ser Arg Val Tyr Thr Phe Phe Ser Ser Asp Tyr Val Lys
    610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
    690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
            740                 745                 750

Val Asn Thr Gln Ile Asp Leu Ile Arg Lys Lys Met Lys Glu Ala Leu
        755                 760                 765

Glu Asn Gln Ala Glu Ala Thr Lys Ala Ile Ile Asn Tyr Gln Tyr Asn
    770                 775                 780

Gln Tyr Thr Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815
```

| | | | | | | | | | | | | |
|---|---|---|---|---|---|---|---|---|---|---|---|---|
|Asn|Lys|Phe|Leu|Asn|Gln|Cys|Ser|Val|Ser|Tyr|Leu|Met|Asn|Ser|Met|
| | | |820| | | | |825| | | | |830| | |

Ile Pro Tyr Gly Val Lys Arg Leu Glu Asp Phe Asp Ala Ser Leu Lys
                835                 840                 845

Asp Ala Leu Leu Lys Tyr Ile Tyr Asp Asn Arg Gly Thr Leu Ile Gly
    850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Asp

<210> SEQ ID NO 15
<211> LENGTH: 2787
<212> TYPE: DNA
<213> ORGANISM: Artificial Sequence
<220> FEATURE:
<223> OTHER INFORMATION: Synthetic sequence

<400> SEQUENCE: 15

```
catatgggat ccatggagtt cgttaacaaa cagttcaact ataaagaccc agttaacggt      60
gttgacattg cttacatcaa atcccgaac gctggccaga tgcagccggt aaaggcattc     120
aaaatccaca acaaaatctg ggttatcccg aacgtgata cctttactaa cccgaagaa      180
ggtgacctga acccgccacc ggaagcgaaa caggtgccgg tatcttacta tgactccacc    240
tacctgtcta ccgataacga aaggacaac tacctgaaag gtgttactaa actgttcgag    300
cgtatttact ccaccgacct gggccgtatg ctgctgacta gcatcgttcg cggtatcccg    360
ttctggggcg gttctaccat cgataccgaa ctgaaagtaa tcgacactaa ctgcatcaac    420
gttattcagc cggacggttc ctatcgttcc gaagaactga acctggtgat catcggcccg    480
tctgctgata tcatccagtt cgagtgtaag agctttggtc acgaagttct gaacctcacc    540
cgtaacggct acggttccac tcagtacatc cgtttctctc cggacttcac cttcggtttt    600
gaagaatccc tggaagtaga cacgaaccca ctgctgggcg ctggtaaatt cgcaactgat    660
cctgcggtta ccctggctca cgaactgatt catgcaggcc accgctgta cggtatcgcc    720
atcaatccga accgtgtctt caaagttaac accaacgcgt attacgagat gtccggtctg    780
gaagttagct tcgaagaact gcgtactttt ggcggtcacg acgctaaatt catcgactct    840
ctgcaagaaa cgagttccg tctgtactac tataacaagt tcaaagatat cgcatccacc    900
ctgaacaaag cgaaatccat cgtgggtacc actgcttctc tccagtacat gaagaacgtt    960
tttaagaaa ataccctgct cagcgaagac acctccggca aattctctgt agacaagttg     1020
aaattcgata acttttacaa aatgctgact gaaatttaca ccgaagacaa cttcgttaag    1080
ttctttaaag ttctgaaccg caaaacctat ctgaacttcg acaaggcagt attcaaaatc    1140
aacatcgtgc cgaaagttaa ctacactatc tacgatggtt tcaacctgcg taacaccaac    1200
ctggctgcta ttttaacgg ccagaacacg gaaatcaaca acatgaactt cacaaaactg    1260
aaaaacttca ctggtctgtt cgagttttac aagctgctgt gcgtcgacgg cggtggcggt    1320
agcgcagacg atgacgataa aggttggacc ctgaactctg ctggttacct gctgggtccg    1380
cacgctgttg gtaaccaccg ttctttctct gacctgaacg tctgacctc tgcgctagcg    1440
ggcggtggcg gtagcggcgg tggcggtagc ggcggtggcg gtagcgcact agtgctgcag    1500
tgtatcaagg ttaacaactg ggatttattc ttcagcccga gtgaagacaa cttcaccaac    1560
```

```
gacctgaaca aaggtgaaga aatcacctca gatactaaca tcgaagcagc cgaagaaaac   1620
atctcgctgg aacctgatcca gcagtactac ctgaccttta atttcgacaa cgagccggaa   1680
aacatttcta tcgaaaacct gagctctgat atcatcggcc agctggaact gatgccgaac   1740
atcgaacgtt tcccaaacgg taaaaagtac gagctggaca atataccat gttccactac   1800 ctgcgcgcgc aggaatttga acacggcaaa tcccgtatcg cactgactaa ctccgttaac   1860
gaagctctgc tcaacccgtc ccgtgtatac accttcttct ctagcgacta cgtgaaaaag   1920
gtcaacaaag cgactgaagc tgcaatgttc ttgggttggg ttgaacagct tgtttatgat   1980
tttaccgacg agacgtccga agtatctact accgacaaaa ttgcggatat cactatcatc   2040
atcccgtaca tcggtccggc tctgaacatt ggcaacatgc tgtacaaaga cgacttcgtt   2100
ggcgcactga tcttctccgg tgcggtgatc ctgctggagt tcatcccgga aatcgccatc   2160
ccggtactgg gcacctttgc tctggttcct tacattgcaa acaaggttct gactgtacaa   2220
accatcgaca acgcgctgag caaacgtaac gaaaaatggg atgaagttta caaatatatc   2280
gtgaccaact ggctggctaa ggttaatact cagatcgacc tcatccgcaa aaaaatgaaa   2340
gaagcactgg aaaaccaggc ggaagctacc aaggcaatca ttaactacca gtacaaccag   2400
tacaccgagg aagaaaaaaa caacatcaac ttcaacatcg acgatctgtc ctctaaactg   2460
aacgaatcca tcaacaaagc tatgatcaac atcaacaagt cctgaaacca gtgctctgta   2520
agctatctga tgaactccat gatcccgtac ggtgttaaac gtctggagga cttcgatgcg   2580
tctctgaaag acgccctgct gaaatacatt tacgacaacc gtggcactct gatcggtcag   2640
gttgatcgtc tgaaggacaa agtgaacaat accttatcga ccgacatccc ttttcagctc   2700
agtaaatatg tcgataacca acgccttttg tccactctag aagcactagc gagtgggcac   2760
catcaccatc accattaatg aaagctt                                         2787
```

<210> SEQ ID NO 16
<211> LENGTH: 924
<212> TYPE: PRT
<213> ORGANISM: Artificial Sequence
<220> FEATURE:
<223> OTHER INFORMATION: Synthetic sequence

<400> SEQUENCE: 16

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140
```

```
Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
            165                 170                 175

Asn Leu Thr Arg Asn Gly Tyr Gly Ser Thr Gln Tyr Ile Arg Phe Ser
        180                 185                 190

Pro Asp Phe Thr Phe Gly Phe Glu Glu Ser Leu Glu Val Asp Thr Asn
    195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
            245                 250                 255

Ser Gly Leu Glu Val Ser Phe Glu Glu Leu Arg Thr Phe Gly Gly His
        260                 265                 270

Asp Ala Lys Phe Ile Asp Ser Leu Gln Glu Asn Glu Phe Arg Leu Tyr
    275                 280                 285

Tyr Tyr Asn Lys Phe Lys Asp Ile Ala Ser Thr Leu Asn Lys Ala Lys
290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
            325                 330                 335

Asp Lys Leu Lys Phe Asp Lys Leu Tyr Lys Met Leu Thr Glu Ile Tyr
        340                 345                 350

Thr Glu Asp Asn Phe Val Lys Phe Phe Lys Val Leu Asn Arg Lys Thr
    355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
            405                 410                 415

Thr Lys Leu Lys Asn Phe Thr Gly Leu Phe Glu Phe Tyr Lys Leu Leu
        420                 425                 430

Cys Val Asp Gly Gly Gly Ser Ala Asp Asp Asp Lys Gly Trp
    435                 440                 445

Thr Leu Asn Ser Ala Gly Tyr Leu Leu Gly Pro His Ala Val Gly Asn
    450                 455                 460

His Arg Ser Phe Ser Asp Leu Asn Gly Leu Thr Ser Ala Leu Ala Gly
465                 470                 475                 480

Gly Gly Gly Ser Gly Gly Gly Ser Gly Gly Gly Ser Ala Leu
            485                 490                 495

Val Leu Gln Cys Ile Lys Val Asn Asn Trp Asp Leu Phe Phe Ser Pro
        500                 505                 510

Ser Glu Asp Asn Phe Thr Asn Asp Leu Asn Lys Gly Glu Glu Ile Thr
    515                 520                 525

Ser Asp Thr Asn Ile Glu Ala Ala Glu Glu Asn Ile Ser Leu Asp Leu
    530                 535                 540

Ile Gln Gln Tyr Tyr Leu Thr Phe Asn Phe Asp Asn Glu Pro Glu Asn
545                 550                 555                 560

Ile Ser Ile Glu Asn Leu Ser Ser Asp Ile Ile Gly Gln Leu Glu Leu
```

```
                565                 570                 575
Met Pro Asn Ile Glu Arg Phe Pro Asn Gly Lys Lys Tyr Glu Leu Asp
                580                 585                 590
Lys Tyr Thr Met Phe His Tyr Leu Arg Ala Gln Glu Phe Glu His Gly
            595                 600                 605
Lys Ser Arg Ile Ala Leu Thr Asn Ser Val Asn Glu Ala Leu Leu Asn
        610                 615                 620
Pro Ser Arg Val Tyr Thr Phe Phe Ser Ser Asp Tyr Val Lys Lys Val
625                 630                 635                 640
Asn Lys Ala Thr Glu Ala Ala Met Phe Leu Gly Trp Val Glu Gln Leu
                645                 650                 655
Val Tyr Asp Phe Thr Asp Glu Thr Ser Glu Val Ser Thr Thr Asp Lys
                660                 665                 670
Ile Ala Asp Ile Thr Ile Ile Pro Tyr Ile Gly Pro Ala Leu Asn
                675                 680                 685
Ile Gly Asn Met Leu Tyr Lys Asp Asp Phe Val Gly Ala Leu Ile Phe
            690                 695                 700
Ser Gly Ala Val Ile Leu Leu Glu Phe Ile Pro Glu Ile Ala Ile Pro
705                 710                 715                 720
Val Leu Gly Thr Phe Ala Leu Val Ser Tyr Ile Ala Asn Lys Val Leu
                725                 730                 735
Thr Val Gln Thr Ile Asp Asn Ala Leu Ser Lys Arg Asn Glu Lys Trp
                740                 745                 750
Asp Glu Val Tyr Lys Tyr Ile Val Thr Asn Trp Leu Ala Lys Val Asn
            755                 760                 765
Thr Gln Ile Asp Leu Ile Arg Lys Lys Met Lys Glu Ala Leu Glu Asn
        770                 775                 780
Gln Ala Glu Ala Thr Lys Ala Ile Ile Asn Tyr Gln Tyr Asn Gln Tyr
785                 790                 795                 800
Thr Glu Glu Glu Lys Asn Asn Ile Asn Phe Asn Ile Asp Asp Leu Ser
                805                 810                 815
Ser Lys Leu Asn Glu Ser Ile Asn Lys Ala Met Ile Asn Ile Asn Lys
                820                 825                 830
Phe Leu Asn Gln Cys Ser Val Ser Tyr Leu Met Asn Ser Met Ile Pro
            835                 840                 845
Tyr Gly Val Lys Arg Leu Glu Asp Phe Asp Ala Ser Leu Lys Asp Ala
            850                 855                 860
Leu Leu Lys Tyr Ile Tyr Asp Asn Arg Gly Thr Leu Ile Gly Gln Val
865                 870                 875                 880
Asp Arg Leu Lys Asp Lys Val Asn Asn Thr Leu Ser Thr Asp Ile Pro
                885                 890                 895
Phe Gln Leu Ser Lys Tyr Val Asp Asn Gln Arg Leu Leu Ser Thr Leu
            900                 905                 910
Glu Ala Leu Ala Ser Gly His His His His His
            915                 920

<210> SEQ ID NO 17
<211> LENGTH: 913
<212> TYPE: PRT
<213> ORGANISM: Artificial Sequence
<220> FEATURE:
<223> OTHER INFORMATION: Synthetic sequence

<400> SEQUENCE: 17

Met Gly Ser Met Glu Phe Val Asn Lys Gln Phe Asn Tyr Lys Asp Pro
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Val | Asn | Gly | Val | Asp | Ile | Ala | Tyr | Ile | Lys | Ile | Pro | Asn | Ala | Gly | Gln |
|   |   |   | 20 |   |   |   |   | 25 |   |   |   |   | 30 |   |
| Met | Gln | Pro | Val | Lys | Ala | Phe | Lys | Ile | His | Asn | Lys | Ile | Trp | Val | Ile |
|   |   |   | 35 |   |   |   |   | 40 |   |   |   |   | 45 |   |
| Pro | Glu | Arg | Asp | Thr | Phe | Thr | Asn | Pro | Glu | Gly | Asp | Leu | Asn | Pro |
|   |   | 50 |   |   |   |   | 55 |   |   |   |   | 60 |   |   |
| Pro | Pro | Glu | Ala | Lys | Gln | Val | Pro | Val | Ser | Tyr | Tyr | Asp | Ser | Thr | Tyr |
| 65 |   |   |   |   | 70 |   |   |   |   | 75 |   |   |   |   | 80 |
| Leu | Ser | Thr | Asp | Asn | Glu | Lys | Asp | Asn | Tyr | Leu | Lys | Gly | Val | Thr | Lys |
|   |   |   |   | 85 |   |   |   |   | 90 |   |   |   |   | 95 |   |
| Leu | Phe | Glu | Arg | Ile | Tyr | Ser | Thr | Asp | Leu | Gly | Arg | Met | Leu | Leu | Thr |
|   |   |   |   | 100 |   |   |   |   | 105 |   |   |   |   | 110 |   |
| Ser | Ile | Val | Arg | Gly | Ile | Pro | Phe | Trp | Gly | Gly | Ser | Thr | Ile | Asp | Thr |
|   |   |   |   | 115 |   |   |   |   | 120 |   |   |   |   | 125 |   |
| Glu | Leu | Lys | Val | Ile | Asp | Thr | Asn | Cys | Ile | Asn | Val | Ile | Gln | Pro | Asp |
|   |   |   | 130 |   |   |   |   | 135 |   |   |   |   | 140 |   |
| Gly | Ser | Tyr | Arg | Ser | Glu | Glu | Leu | Asn | Leu | Val | Ile | Ile | Gly | Pro | Ser |
| 145 |   |   |   |   | 150 |   |   |   |   | 155 |   |   |   |   | 160 |
| Ala | Asp | Ile | Ile | Gln | Phe | Glu | Cys | Lys | Ser | Phe | Gly | His | Glu | Val | Leu |
|   |   |   |   | 165 |   |   |   |   | 170 |   |   |   |   | 175 |   |
| Asn | Leu | Thr | Arg | Asn | Gly | Tyr | Gly | Ser | Thr | Gln | Tyr | Ile | Arg | Phe | Ser |
|   |   |   | 180 |   |   |   |   | 185 |   |   |   |   | 190 |   |
| Pro | Asp | Phe | Thr | Phe | Gly | Phe | Glu | Glu | Ser | Leu | Glu | Val | Asp | Thr | Asn |
|   |   |   | 195 |   |   |   |   | 200 |   |   |   |   | 205 |   |
| Pro | Leu | Leu | Gly | Ala | Gly | Lys | Phe | Ala | Thr | Asp | Pro | Ala | Val | Thr | Leu |
|   | 210 |   |   |   |   | 215 |   |   |   |   | 220 |   |   |   |   |
| Ala | His | Glu | Leu | Ile | His | Ala | Gly | His | Arg | Leu | Tyr | Gly | Ile | Ala | Ile |
| 225 |   |   |   |   | 230 |   |   |   |   | 235 |   |   |   |   | 240 |
| Asn | Pro | Asn | Arg | Val | Phe | Lys | Val | Asn | Thr | Asn | Ala | Tyr | Tyr | Glu | Met |
|   |   |   | 245 |   |   |   |   | 250 |   |   |   |   | 255 |   |
| Ser | Gly | Leu | Glu | Val | Ser | Phe | Glu | Glu | Leu | Arg | Thr | Phe | Gly | Gly | His |
|   |   |   | 260 |   |   |   |   | 265 |   |   |   |   | 270 |   |
| Asp | Ala | Lys | Phe | Ile | Asp | Ser | Leu | Gln | Glu | Asn | Glu | Phe | Arg | Leu | Tyr |
|   |   | 275 |   |   |   |   | 280 |   |   |   |   | 285 |   |   |   |
| Tyr | Tyr | Asn | Lys | Phe | Lys | Asp | Ile | Ala | Ser | Thr | Leu | Asn | Lys | Ala | Lys |
|   | 290 |   |   |   |   | 295 |   |   |   |   | 300 |   |   |   |   |
| Ser | Ile | Val | Gly | Thr | Thr | Ala | Ser | Leu | Gln | Tyr | Met | Lys | Asn | Val | Phe |
| 305 |   |   |   |   | 310 |   |   |   |   | 315 |   |   |   |   | 320 |
| Lys | Glu | Lys | Tyr | Leu | Leu | Ser | Glu | Asp | Thr | Ser | Gly | Lys | Phe | Ser | Val |
|   |   |   |   | 325 |   |   |   |   | 330 |   |   |   |   | 335 |   |
| Asp | Lys | Leu | Lys | Phe | Asp | Lys | Leu | Tyr | Lys | Met | Leu | Thr | Glu | Ile | Tyr |
|   |   |   | 340 |   |   |   |   | 345 |   |   |   |   | 350 |   |
| Thr | Glu | Asp | Asn | Phe | Val | Lys | Phe | Phe | Lys | Val | Leu | Asn | Arg | Lys | Thr |
|   |   |   | 355 |   |   |   |   | 360 |   |   |   |   | 365 |   |
| Tyr | Leu | Asn | Phe | Asp | Lys | Ala | Val | Phe | Lys | Ile | Asn | Ile | Val | Pro | Lys |
|   | 370 |   |   |   |   | 375 |   |   |   |   | 380 |   |   |   |   |
| Val | Asn | Tyr | Thr | Ile | Tyr | Asp | Gly | Phe | Asn | Leu | Arg | Asn | Thr | Asn | Leu |
| 385 |   |   |   |   | 390 |   |   |   |   | 395 |   |   |   |   | 400 |
| Ala | Ala | Asn | Phe | Asn | Gly | Gln | Asn | Thr | Glu | Ile | Asn | Asn | Met | Asn | Phe |
|   |   |   |   | 405 |   |   |   |   | 410 |   |   |   |   | 415 |   |
| Thr | Lys | Leu | Lys | Asn | Phe | Thr | Gly | Leu | Phe | Glu | Phe | Tyr | Lys | Leu | Leu |
|   |   |   | 420 |   |   |   |   | 425 |   |   |   |   | 430 |   |

```
Cys Val Asp Gly Gly Gly Ser Ala Asp Asp Asp Lys Gly Trp
        435             440             445

Thr Leu Asn Ser Ala Gly Tyr Leu Leu Gly Pro His Ala Val Gly Asn
450             455                 460

His Arg Ser Phe Ser Asp Leu Asn Gly Leu Thr Ser Ala Leu Ala Gly
465             470             475                 480

Gly Gly Gly Ser Gly Gly Gly Gly Ser Gly Gly Gly Ser Ala Leu
            485             490             495

Val Leu Gln Cys Ile Lys Val Asn Asn Trp Asp Leu Phe Phe Ser Pro
            500             505             510

Ser Glu Asp Asn Phe Thr Asn Asp Leu Asn Lys Gly Glu Glu Ile Thr
            515             520             525

Ser Asp Thr Asn Ile Glu Ala Ala Glu Glu Asn Ile Ser Leu Asp Leu
            530             535             540

Ile Gln Gln Tyr Tyr Leu Thr Phe Asn Phe Asp Asn Glu Pro Glu Asn
545             550             555             560

Ile Ser Ile Glu Asn Leu Ser Ser Asp Ile Ile Gly Gln Leu Glu Leu
                565             570             575

Met Pro Asn Ile Glu Arg Phe Pro Asn Gly Lys Lys Tyr Glu Leu Asp
            580             585             590

Lys Tyr Thr Met Phe His Tyr Leu Arg Ala Gln Glu Phe Glu His Gly
            595             600             605

Lys Ser Arg Ile Ala Leu Thr Asn Ser Val Asn Glu Ala Leu Leu Asn
610             615             620

Pro Ser Arg Val Tyr Thr Phe Phe Ser Ser Asp Tyr Val Lys Lys Val
625             630             635             640

Asn Lys Ala Thr Glu Ala Ala Met Phe Leu Gly Trp Val Glu Gln Leu
            645             650             655

Val Tyr Asp Phe Thr Asp Glu Thr Ser Glu Val Ser Thr Thr Asp Lys
            660             665             670

Ile Ala Asp Ile Thr Ile Ile Pro Tyr Ile Gly Pro Ala Leu Asn
            675             680             685

Ile Gly Asn Met Leu Tyr Lys Asp Asp Phe Val Gly Ala Leu Ile Phe
            690             695             700

Ser Gly Ala Val Ile Leu Leu Glu Phe Ile Pro Glu Ile Ala Ile Pro
705             710             715             720

Val Leu Gly Thr Phe Ala Leu Val Ser Tyr Ile Ala Asn Lys Val Leu
                725             730             735

Thr Val Gln Thr Ile Asp Asn Ala Leu Ser Lys Arg Asn Glu Lys Trp
            740             745             750

Asp Glu Val Tyr Lys Tyr Ile Val Thr Asn Trp Leu Ala Lys Val Asn
            755             760             765

Thr Gln Ile Asp Leu Ile Arg Lys Lys Met Lys Glu Ala Leu Glu Asn
770             775             780

Gln Ala Glu Ala Thr Lys Ala Ile Ile Asn Tyr Gln Tyr Asn Gln Tyr
785             790             795             800

Thr Glu Glu Glu Lys Asn Asn Ile Asn Phe Asn Ile Asp Asp Leu Ser
            805             810             815

Ser Lys Leu Asn Glu Ser Ile Asn Lys Ala Met Ile Asn Ile Asn Lys
            820             825             830

Phe Leu Asn Gln Cys Ser Val Ser Tyr Leu Met Asn Ser Met Ile Pro
            835             840             845
```

```
Tyr Gly Val Lys Arg Leu Glu Asp Phe Asp Ala Ser Leu Lys Asp Ala
    850                 855                 860

Leu Leu Lys Tyr Ile Tyr Asp Asn Arg Gly Thr Leu Ile Gly Gln Val
865                 870                 875                 880

Asp Arg Leu Lys Asp Lys Val Asn Asn Thr Leu Ser Thr Asp Ile Pro
                885                 890                 895

Phe Gln Leu Ser Lys Tyr Val Asp Asn Gln Arg Leu Leu Ser Thr Leu
            900                 905                 910

Asp

<210> SEQ ID NO 18
<211> LENGTH: 2769
<212> TYPE: DNA
<213> ORGANISM: Artificial Sequence
<220> FEATURE:
<223> OTHER INFORMATION: Synthetic sequence

<400> SEQUENCE: 18
```

| | | | | | |
|---|---|---|---|---|---|
| catatgggat | ccatgccggt | taccatcaac | aacttcaact | acaacgaccc | gatcgacaac | 60 |
| aacaacatca | ttatgatgga | accgccgttc | gcacgtggta | ccggacgtta | ctacaaggct | 120 |
| tttaagatca | ccgaccgtat | ctggatcatc | ccggaacgtt | acaccttcgg | ttacaaacct | 180 |
| gaggacttca | caagagtag | cgggattttc | aatcgtgacg | tctgcgagta | ctatgatcca | 240 |
| gattatctga | taccaacga | taagaagaac | atattccttc | agactatgat | taaactcttc | 300 |
| aaccgtatca | aaagcaaacc | gctcggtgaa | aaactcctcg | aaatgattat | caacggtatc | 360 |
| ccgtacctcg | gtgaccgtcg | tgtcccgctt | gaagagttca | caccaacat | cgcaagcgtc | 420 |
| accgtcaaca | aactcatcag | caacccaggt | gaagtcgaac | gtaaaaaagg | tatcttcgca | 480 |
| aacctcatca | tcttcggtcc | gggtccggtc | ctcaacgaaa | acgaaaccat | cgacatcggt | 540 |
| atccagaacc | acttcgcaag | ccgtgaaggt | ttcggtggta | tcatgcagat | gaaattctgc | 600 |
| ccggaatacg | tcagtgtctt | caacaacgtc | aggaaaaca | aaggtgcaag | catcttcaac | 660 |
| cgtcgtggtt | acttcagcga | cccggcactc | atcctcatgc | atgaactcat | ccacgtcctc | 720 |
| cacggtctct | acggtatcaa | agttgacgac | ctcccgatcg | tcccgaacga | gaagaaattc | 780 |
| ttcatgcaga | gcaccgacgc | aatccaggct | gaggaactct | acaccttcgg | tggccaagac | 840 |
| ccaagtatca | taccccgtc | caccgacaaa | agcatctacg | acaaagtcct | ccagaacttc | 900 |
| agggggtatcg | tggacagact | caacaaagtc | ctcgtctgca | tcagcgaccc | gaacatcaat | 960 |
| atcaacatat | acaagaacaa | gttcaaagac | aagtacaaat | cgtcgaggga | cagcgaaggc | 1020 |
| aaatacagca | tcgacgtaga | aagtttcgac | aagctctaca | aaagcctcat | gttcggtttc | 1080 |
| accgaaacca | acatcgccga | gaactacaag | atcaagacaa | gggcaagtta | cttcagcgac | 1140 |
| agcctcccgc | ctgtcaaaat | caagaacctc | ttagacaacg | agatttacac | aattgaagag | 1200 |
| ggcttcaaca | tcagtgacaa | agacatggag | aaggaataca | gaggtcagaa | caaggctatc | 1260 |
| aacaaacagg | catacgagga | gatcagcaaa | gaacacctcg | cagtctacaa | gatccagatg | 1320 |
| tgcgtcgacg | gcggtggcgg | tagcgcagac | gatgacgata | aaggttggac | cctgaactct | 1380 |
| gctggttacc | tgctgggtcc | gcacgctgtt | gcgctagcgg | gcggtggcgg | tagcggcggt | 1440 |
| ggcggtagcg | gcggtggcgg | tagcgcacta | gtgctgcagt | gcatcgacgt | tgacaacgaa | 1500 |
| gacctgttct | tcatcgctga | caaaaacagc | ttcagtgacg | acctgagcaa | aaacgaacgt | 1560 |
| atcgaataca | cacccagag | caactacatc | gaaaacgact | tcccgatcaa | cgaactgatc | 1620 |
| ctggacaccg | acctgataag | taaaatcgaa | ctgccgagcg | aaaacaccga | agtctgacc | 1680 |

```
gacttcaacg ttgacgttcc ggtttacgaa aaacagccgg ctatcaagaa aatcttcacc    1740
gacgaaaaca ccatcttcca gtacctgtac agccagacct cccgctggca catccgtgac    1800
atcagtctga ccagcagttt cgacgacgct ctgctgttca gcaacaaagt ttacagtttc    1860
ttcagcatgg actacatcaa aaccgctaac aaagttgttg aagcagggct gttcgctggt    1920
tgggttaaac agatcgttaa cgacttcgtt atcgaagcta acaaaagcaa cactatggac    1980
gcaatcgctg acatcagtct gatcgttccg tacatcggtc tggctctgaa cgttggtaac    2040
gaaccgctaa aggtaacttt gaaaacgct tcgagatcg ctggtgcaag catcctgctg    2100
```

-continued

```
Leu Ile Ile Phe Gly Pro Gly Pro Val Leu Asn Glu Asn Glu Thr Ile
                165                 170                 175
Asp Ile Gly Ile Gln Asn His Phe Ala Ser Arg Glu Gly Phe Gly Gly
            180                 185                 190
Ile Met Gln Met Lys Phe Cys Pro Glu Tyr Val Ser Val Phe Asn Asn
        195                 200                 205
Val Gln Glu Asn Lys Gly Ala Ser Ile Phe Asn Arg Arg Gly Tyr Phe
    210                 215                 220
Ser Asp Pro Ala Leu Ile Leu Met His Glu Leu Ile His Val Leu His
225                 230                 235                 240
Gly Leu Tyr Gly Ile Lys Val Asp Asp Leu Pro Ile Val Pro Asn Glu
                245                 250                 255
Lys Lys Phe Phe Met Gln Ser Thr Asp Ala Ile Gln Ala Glu Glu Leu
            260                 265                 270
Tyr Thr Phe Gly Gly Gln Asp Pro Ser Ile Ile Thr Pro Ser Thr Asp
        275                 280                 285
Lys Ser Ile Tyr Asp Lys Val Leu Gln Asn Phe Arg Gly Ile Val Asp
    290                 295                 300
Arg Leu Asn Lys Val Leu Val Cys Ile Ser Asp Pro Asn Ile Asn Ile
305                 310                 315                 320
Asn Ile Tyr Lys Asn Lys Phe Lys Asp Lys Tyr Lys Phe Val Glu Asp
                325                 330                 335
Ser Glu Gly Lys Tyr Ser Ile Asp Val Glu Ser Phe Asp Lys Leu Tyr
            340                 345                 350
Lys Ser Leu Met Phe Gly Phe Thr Glu Thr Asn Ile Ala Glu Asn Tyr
        355                 360                 365
Lys Ile Lys Thr Arg Ala Ser Tyr Phe Ser Asp Ser Leu Pro Pro Val
    370                 375                 380
Lys Ile Lys Asn Leu Leu Asp Asn Glu Ile Tyr Thr Ile Glu Glu Gly
385                 390                 395                 400
Phe Asn Ile Ser Asp Lys Asp Met Glu Lys Glu Tyr Arg Gly Gln Asn
                405                 410                 415
Lys Ala Ile Asn Lys Gln Ala Tyr Glu Glu Ile Ser Lys Glu His Leu
            420                 425                 430
Ala Val Tyr Lys Ile Gln Met Cys Val Asp Gly Gly Gly Ser Ala
        435                 440                 445
Asp Asp Asp Asp Lys Gly Trp Thr Leu Asn Ser Ala Gly Tyr Leu Leu
    450                 455                 460
Gly Pro His Ala Val Ala Leu Ala Gly Gly Gly Ser Gly Gly Gly
465                 470                 475                 480
Gly Ser Gly Gly Gly Gly Ser Ala Leu Val Leu Gln Cys Ile Asp Val
                485                 490                 495
Asp Asn Glu Asp Leu Phe Phe Ile Ala Asp Lys Asn Ser Phe Ser Asp
            500                 505                 510
Asp Leu Ser Lys Asn Glu Arg Ile Glu Tyr Asn Thr Gln Ser Asn Tyr
        515                 520                 525
Ile Glu Asn Asp Phe Pro Ile Asn Glu Leu Ile Leu Asp Thr Asp Leu
    530                 535                 540
Ile Ser Lys Ile Glu Leu Pro Ser Glu Asn Thr Glu Ser Leu Thr Asp
545                 550                 555                 560
Phe Asn Val Asp Val Pro Val Tyr Glu Lys Gln Pro Ala Ile Lys Lys
                565                 570                 575
Ile Phe Thr Asp Glu Asn Thr Ile Phe Gln Tyr Leu Tyr Ser Gln Thr
```

```
                580             585             590
        Phe Pro Leu Asp Ile Arg Asp Ile Ser Leu Thr Ser Ser Phe Asp Asp
                    595                 600                 605
        Ala Leu Leu Phe Ser Asn Lys Val Tyr Ser Phe Phe Ser Met Asp Tyr
                    610                 615                 620
        Ile Lys Thr Ala Asn Lys Val Val Glu Ala Gly Leu Phe Ala Gly Trp
        625                 630                 635                 640
        Val Lys Gln Ile Val Asn Asp Phe Val Ile Glu Ala Asn Lys Ser Asn
                        645                 650                 655
        Thr Met Asp Ala Ile Ala Asp Ile Ser Leu Ile Val Pro Tyr Ile Gly
                    660                 665                 670
        Leu Ala Leu Asn Val Gly Asn Glu Thr Ala Lys Gly Asn Phe Glu Asn
                    675                 680                 685
        Ala Phe Glu Ile Ala Gly Ala Ser Ile Leu Leu Glu Phe Ile Pro Glu
                    690                 695                 700
        Leu Leu Ile Pro Val Val Gly Ala Phe Leu Leu Glu Ser Tyr Ile Asp
        705                 710                 715                 720
        Asn Lys Asn Lys Ile Ile Lys Thr Ile Asp Asn Ala Leu Thr Lys Arg
                        725                 730                 735
        Asn Glu Lys Trp Ser Asp Met Tyr Gly Leu Ile Val Ala Gln Trp Leu
                    740                 745                 750
        Ser Thr Val Asn Thr Gln Phe Tyr Thr Ile Lys Glu Gly Met Tyr Lys
                    755                 760                 765
        Ala Leu Asn Tyr Gln Ala Gln Ala Leu Glu Glu Ile Ile Lys Tyr Arg
                    770                 775                 780
        Tyr Asn Ile Tyr Ser Glu Lys Glu Lys Ser Asn Ile Asn Ile Asp Phe
        785                 790                 795                 800
        Asn Asp Ile Asn Ser Lys Leu Asn Glu Gly Ile Asn Gln Ala Ile Asp
                        805                 810                 815
        Asn Ile Asn Asn Phe Ile Asn Gly Cys Ser Val Ser Tyr Leu Met Lys
                    820                 825                 830
        Lys Met Ile Pro Leu Ala Val Glu Lys Leu Leu Asp Phe Asp Asn Thr
                    835                 840                 845
        Leu Lys Lys Asn Leu Leu Asn Tyr Ile Asp Glu Asn Lys Leu Tyr Leu
                    850                 855                 860
        Ile Gly Ser Ala Glu Tyr Glu Lys Ser Lys Val Asn Lys Tyr Leu Lys
        865                 870                 875                 880
        Thr Ile Met Pro Phe Asp Leu Ser Ile Tyr Thr Asn Asp Thr Ile Leu
                        885                 890                 895
        Ile Glu Met Phe Asn Lys Tyr Asn Ser Leu Glu Ala Leu Ala Ser Gly
                    900                 905                 910
        His His His His His His
                915

<210> SEQ ID NO 20
<211> LENGTH: 908
<212> TYPE: PRT
<213> ORGANISM: Artificial Sequence
<220> FEATURE:
<223> OTHER INFORMATION: Synthetic sequence

<400> SEQUENCE: 20

Met Gly Ser Met Pro Val Thr Ile Asn Asn Phe Asn Tyr Asn Asp Pro
1               5                   10                  15

Ile Asp Asn Asn Asn Ile Ile Met Met Glu Pro Pro Phe Ala Arg Gly
```

```
                20                  25                  30
Thr Gly Arg Tyr Tyr Lys Ala Phe Lys Ile Thr Asp Arg Ile Trp Ile
             35                  40                  45

Ile Pro Glu Arg Tyr Thr Phe Gly Tyr Lys Pro Glu Asp Phe Asn Lys
 50                  55                  60

Ser Ser Gly Ile Phe Asn Arg Asp Val Cys Glu Tyr Tyr Asp Pro Asp
 65                  70                  75                  80

Tyr Leu Asn Thr Asn Asp Lys Lys Asn Ile Phe Leu Gln Thr Met Ile
             85                  90                  95

Lys Leu Phe Asn Arg Ile Lys Ser Lys Pro Leu Gly Glu Lys Leu Leu
            100                 105                 110

Glu Met Ile Ile Asn Gly Ile Pro Tyr Leu Gly Asp Arg Arg Val Pro
            115                 120                 125

Leu Glu Glu Phe Asn Thr Asn Ile Ala Ser Val Thr Val Asn Lys Leu
            130                 135                 140

Ile Ser Asn Pro Gly Glu Val Glu Arg Lys Lys Gly Ile Phe Ala Asn
145                 150                 155                 160

Leu Ile Ile Phe Gly Pro Gly Pro Val Leu Asn Glu Asn Glu Thr Ile
                165                 170                 175

Asp Ile Gly Ile Gln Asn His Phe Ala Ser Arg Glu Gly Phe Gly Gly
                180                 185                 190

Ile Met Gln Met Lys Phe Cys Pro Glu Tyr Val Ser Val Phe Asn Asn
                195                 200                 205

Val Gln Glu Asn Lys Gly Ala Ser Ile Phe Asn Arg Arg Gly Tyr Phe
            210                 215                 220

Ser Asp Pro Ala Leu Ile Leu Met His Glu Leu Ile His Val Leu His
225                 230                 235                 240

Gly Leu Tyr Gly Ile Lys Val Asp Asp Leu Pro Ile Val Pro Asn Glu
                245                 250                 255

Lys Lys Phe Phe Met Gln Ser Thr Asp Ala Ile Gln Ala Glu Glu Leu
                260                 265                 270

Tyr Thr Phe Gly Gly Gln Asp Pro Ser Ile Ile Thr Pro Ser Thr Asp
            275                 280                 285

Lys Ser Ile Tyr Asp Lys Val Leu Gln Asn Phe Arg Gly Ile Val Asp
            290                 295                 300

Arg Leu Asn Lys Val Leu Val Cys Ile Ser Asp Pro Asn Ile Asn Ile
305                 310                 315                 320

Asn Ile Tyr Lys Asn Lys Phe Lys Asp Lys Tyr Lys Phe Val Glu Asp
                325                 330                 335

Ser Glu Gly Lys Tyr Ser Ile Asp Val Glu Ser Phe Asp Lys Leu Tyr
            340                 345                 350

Lys Ser Leu Met Phe Gly Phe Thr Glu Thr Asn Ile Ala Glu Asn Tyr
            355                 360                 365

Lys Ile Lys Thr Arg Ala Ser Tyr Phe Ser Asp Ser Leu Pro Pro Val
            370                 375                 380

Lys Ile Lys Asn Leu Leu Asp Asn Glu Ile Tyr Thr Ile Glu Glu Gly
385                 390                 395                 400

Phe Asn Ile Ser Asp Lys Asp Met Glu Lys Glu Tyr Arg Gly Gln Asn
                405                 410                 415

Lys Ala Ile Asn Lys Gln Ala Tyr Glu Glu Ile Ser Lys Glu His Leu
            420                 425                 430

Ala Val Tyr Lys Ile Gln Met Cys Val Asp Gly Gly Gly Gly Ser Ala
            435                 440                 445
```

Asp Asp Asp Asp Lys Gly Trp Thr Leu Asn Ser Ala Gly Tyr Leu Leu
450                 455                 460

Gly Pro His Ala Val Ala Leu Ala Gly Gly Gly Ser Gly Gly Gly
465                 470                 475                 480

Gly Ser Gly Gly Gly Ser Ala Leu Val Leu Gln Cys Ile Asp Val
            485                 490                 495

Asp Asn Glu Asp Leu Phe Phe Ile Ala Asp Lys Asn Ser Phe Ser Asp
            500                 505                 510

Asp Leu Ser Lys Asn Glu Arg Ile Glu Tyr Asn Thr Gln Ser Asn Tyr
            515                 520                 525

Ile Glu Asn Asp Phe Pro Ile Asn Glu Leu Ile Leu Asp Thr Asp Leu
530                 535                 540

Ile Ser Lys Ile Glu Leu Pro Ser Glu Asn Thr Glu Ser Leu Thr Asp
545                 550                 555                 560

Phe Asn Val Asp Val Pro Val Tyr Glu Lys Gln Pro Ala Ile Lys Lys
            565                 570                 575

Ile Phe Thr Asp Glu Asn Thr Ile Phe Gln Tyr Leu Tyr Ser Gln Thr
            580                 585                 590

Phe Pro Leu Asp Ile Arg Asp Ile Ser Leu Thr Ser Ser Phe Asp Asp
            595                 600                 605

Ala Leu Leu Phe Ser Asn Lys Val Tyr Ser Phe Phe Ser Met Asp Tyr
            610                 615                 620

Ile Lys Thr Ala Asn Lys Val Val Glu Ala Gly Leu Phe Ala Gly Trp
625                 630                 635                 640

Val Lys Gln Ile Val Asn Asp Phe Val Ile Glu Ala Asn Lys Ser Asn
            645                 650                 655

Thr Met Asp Ala Ile Ala Asp Ile Ser Leu Ile Val Pro Tyr Ile Gly
            660                 665                 670

Leu Ala Leu Asn Val Gly Asn Glu Thr Ala Lys Gly Asn Phe Glu Asn
            675                 680                 685

Ala Phe Glu Ile Ala Gly Ala Ser Ile Leu Leu Glu Phe Ile Pro Glu
            690                 695                 700

Leu Leu Ile Pro Val Val Gly Ala Phe Leu Leu Glu Ser Tyr Ile Asp
705                 710                 715                 720

Asn Lys Asn Lys Ile Ile Lys Thr Ile Asp Asn Ala Leu Thr Lys Arg
            725                 730                 735

Asn Glu Lys Trp Ser Asp Met Tyr Gly Leu Ile Val Ala Gln Trp Leu
            740                 745                 750

Ser Thr Val Asn Thr Gln Phe Tyr Thr Ile Lys Glu Gly Met Tyr Lys
            755                 760                 765

Ala Leu Asn Tyr Gln Ala Gln Ala Leu Glu Glu Ile Ile Lys Tyr Arg
770                 775                 780

Tyr Asn Ile Tyr Ser Glu Lys Glu Lys Ser Asn Ile Asn Ile Asp Phe
785                 790                 795                 800

Asn Asp Ile Asn Ser Lys Leu Asn Glu Gly Ile Asn Gln Ala Ile Asp
            805                 810                 815

Asn Ile Asn Asn Phe Ile Asn Gly Cys Ser Val Ser Tyr Leu Met Lys
            820                 825                 830

Lys Met Ile Pro Leu Ala Val Glu Lys Leu Leu Asp Phe Asp Asn Thr
            835                 840                 845

Leu Lys Lys Asn Leu Leu Asn Tyr Ile Asp Glu Asn Lys Leu Tyr Leu
            850                 855                 860

```
Ile Gly Ser Ala Glu Tyr Glu Lys Ser Lys Val Asn Lys Tyr Leu Lys
865                 870                 875                 880

Thr Ile Met Pro Phe Asp Leu Ser Ile Tyr Thr Asn Asp Thr Ile Leu
                885                 890                 895

Ile Glu Met Phe Asn Lys Tyr Asn Ser Leu Glu Asp
                900                 905

<210> SEQ ID NO 21
<211> LENGTH: 2769
<212> TYPE: DNA
<213> ORGANISM: Artificial Sequence
<220> FEATURE:
<223> OTHER INFORMATION: Synthetic sequence

<400> SEQUENCE: 21
catatgggat ccatgccggt taccatcaac aacttcaact acaacgaccc gatcgacaac      60
aacaacatca ttatgatgga accgccgttc gcacgtggta ccggacgtta ctacaaggct     120
tttaagatca ccgaccgtat ctggatcatc ccggaacgtt acaccttcgg ttacaaacct     180
gaggacttca acaagagtag cgggattttc aatcgtgacg tctgcgagta ctatgatcca     240
gattatctga ataccaacga taagaagaac atattccttc agactatgat taaactcttc     300
aaccgtatca aaagcaaacc gctcggtgaa aaactcctcg aaatgattat caacggtatc     360
ccgtacctcg gtgaccgtcg tgtcccgctt gaagagttca caccaacat cgcaagcgtc     420 accgtcaaca aactcatcag caacccaggt gaagtcgaac gtaaaaaagg tatcttcgca     480
aacctcatca tcttcggtcc gggtccggtc ctcaacgaaa acgaaaccat cgacatcggt     540
atccagaacc acttcgcaag ccgtgaaggt ttcggtggta tcatgcagat gaaattctgc     600
ccggaatacg tcagtgtctt caacaacgtc caggaaaaca aggtgcaag catcttcaac     660 cgtcgtggtt acttcagcga cccggcactc atcctcatgc atgaactcat ccacgtcctc     720
cacggtctct acggtatcaa agttgacgac ctcccgatcg tcccgaacga aagaaattc     780 ttcatgcaga gcaccgacgc aatccaggct gaggaactct acaccttcgg tggccaagac     840
ccaagtatca taaccccgtc caccgacaaa agcatctacg acaaagtcct ccagaacttc     900 agggggtatcg tggacagact caacaaagtc ctcgtctgca tcagcgaccc gaacatcaat     960
atcaacatat acaagaacaa gttcaaagac aagtacaaat cgtcgaggaa cagcgaaggc    1020
aaatacagca tcgacgtaga aagtttcgac aagctctaca aaagcctcat gttcggtttc    1080
accgaaacca acatcgccga gaactacaag atcaagacaa gggcaagtta cttcagcgac    1140
agcctcccgc tgtcaaaat caagaacctc ttagacaacg agatttacac aattgaagag    1200
ggcttcaaca tcagtgacaa agacatggag aaggaataca gaggtcagaa caaggctatc    1260
aacaaacagg catacgagga gatcagcaaa gaacaccctcg cagtctacaa gatccagatg    1320
tgcgtcgacg gcggtggcgg tagcgcagac gatgacgata aaggttggac cctgaactct    1380
gctggttacc tgctgggtcc gcacgctgtt gcgctagcgg gcggtggcgg tagcggcggt    1440
ggcggtagcg gcggtggcgg tagcgcacta gtgctgcagt gcatcgacgt tgacaacgaa    1500
gacctgttct tcatcgctga caaaacagc ttcagtgacg acctgagcaa aaacgaacgt    1560
atcgaataca cacccagag caactacatc gaaaacgact cccgatcaa cgaactgatc    1620 ctggacaccg acctgataag taaaatcgaa ctgccgagcg aaaacaccga agtctgacc    1680 gacttcaacg ttgacgttcc ggtttacgaa aaacagccgg ctatcaagaa atcttcacc    1740 gacgaaaaca ccatcttcca gtacctgtac agccagacct tcccgctgga catccgtgac    1800
```

```
atcagtctga ccagcagttt cgacgacgct ctgctgttca gcaacaaagt ttacagtttc   1860
ttcagcatgg actacatcaa aaccgctaac aaagttgttg aagcagggct gttcgctggt   1920
tgggttaaac agatcgttaa cgacttcgtt atcgaagcta acaaaagcaa cactatggac   1980
aaaatcgctg acatcagtct gatcgttccg tacatcggtc tggctctgaa cgttggtaac   2040
gaaaccgcta aggtaacttt gaaaacgct ttcgagatcg ctggtgcaag catcctgctg   2100
gagttcatcc cggaactgct gatcccggtt gttggtgctt cctgctggaa agttacatc   2160 gacaacaaaa acaagatcat caaaaccatc gacaacgctc tgaccaaacg taacgaaaaa   2220
tggagtgata tgtacggtct gatcgttgct cagtggctga gcaccgtcaa cacccagttc   2280
tacaccatca agaaggtat gtacaaagct ctgaactacc aggctcaggc tctggaagag   2340
atcatcaaat accgttacaa catctacagt gagaaggaaa agagtaacat caacatcgac   2400
ttcaacgaca tcaacagcaa actgaacgaa ggtatcaacc aggctatcga caacatcaac   2460
aacttcatca acggttgcag tgttagctac ctgatgaaga agatgatccc gctggctgtt   2520
gaaaaactgc tggacttcga caacaccctg aaaaagaacc tgctgaacta catcgacgaa   2580
aacaagctgt acctgatcgg tagtgctgaa tacgaaaaaa gtaaagtgaa caaatacctg   2640
aagaccatca tgccgttcga cctgagtatc tacaccaacg acaccatcct gatcgaaatg   2700
ttcaacaaat acaactctct agaagcacta gcgagtgggc accatcacca tcaccattaa   2760
tgaaagctt                                                           2769
```

<210> SEQ ID NO 22
<211> LENGTH: 918
<212> TYPE: PRT
<213> ORGANISM: Artificial Sequence
<220> FEATURE:
<223> OTHER INFORMATION: Synthetic sequence

<400> SEQUENCE: 22

```
Met Gly Ser Met Pro Val Thr Ile Asn Asn Phe Asn Tyr Asn Asp Pro
1               5                   10                  15

Ile Asp Asn Asn Asn Ile Ile Met Met Glu Pro Pro Phe Ala Arg Gly
            20                  25                  30

Thr Gly Arg Tyr Tyr Lys Ala Phe Lys Ile Thr Asp Arg Ile Trp Ile
        35                  40                  45

Ile Pro Glu Arg Tyr Thr Phe Gly Tyr Lys Pro Glu Asp Phe Asn Lys
    50                  55                  60

Ser Ser Gly Ile Phe Asn Arg Asp Val Cys Glu Tyr Tyr Asp Pro Asp
65                  70                  75                  80

Tyr Leu Asn Thr Asn Asp Lys Lys Asn Ile Phe Leu Gln Thr Met Ile
                85                  90                  95

Lys Leu Phe Asn Arg Ile Lys Ser Lys Pro Leu Gly Glu Lys Leu Leu
            100                 105                 110

Glu Met Ile Ile Asn Gly Ile Pro Tyr Leu Gly Asp Arg Arg Val Pro
        115                 120                 125

Leu Glu Glu Phe Asn Thr Asn Ile Ala Ser Val Thr Val Asn Lys Leu
    130                 135                 140

Ile Ser Asn Pro Gly Glu Val Glu Arg Lys Lys Gly Ile Phe Ala Asn
145                 150                 155                 160

Leu Ile Ile Phe Gly Pro Gly Pro Val Leu Asn Glu Asn Glu Thr Ile
                165                 170                 175

Asp Ile Gly Ile Gln Asn His Phe Ala Ser Arg Glu Gly Phe Gly Gly
            180                 185                 190
```

```
Ile Met Gln Met Lys Phe Cys Pro Glu Tyr Val Ser Val Phe Asn Asn
            195                 200                 205

Val Gln Glu Asn Lys Gly Ala Ser Ile Phe Asn Arg Arg Gly Tyr Phe
        210                 215                 220

Ser Asp Pro Ala Leu Ile Leu Met His Glu Leu Ile His Val Leu His
225                 230                 235                 240

Gly Leu Tyr Gly Ile Lys Val Asp Asp Leu Pro Ile Val Pro Asn Glu
                245                 250                 255

Lys Lys Phe Phe Met Gln Ser Thr Asp Ala Ile Gln Ala Glu Glu Leu
            260                 265                 270

Tyr Thr Phe Gly Gly Gln Asp Pro Ser Ile Ile Thr Pro Ser Thr Asp
        275                 280                 285

Lys Ser Ile Tyr Asp Lys Val Leu Gln Asn Phe Arg Gly Ile Val Asp
    290                 295                 300

Arg Leu Asn Lys Val Leu Val Cys Ile Ser Asp Pro Asn Ile Asn Ile
305                 310                 315                 320

Asn Ile Tyr Lys Asn Lys Phe Lys Asp Lys Tyr Lys Phe Val Glu Asp
                325                 330                 335

Ser Glu Gly Lys Tyr Ser Ile Asp Val Glu Ser Phe Lys Leu Tyr
            340                 345                 350

Lys Ser Leu Met Phe Gly Phe Thr Glu Thr Asn Ile Ala Glu Asn Tyr
        355                 360                 365

Lys Ile Lys Thr Arg Ala Ser Tyr Phe Ser Asp Ser Leu Pro Pro Val
    370                 375                 380

Lys Ile Lys Asn Leu Leu Asp Asn Glu Ile Tyr Thr Ile Glu Glu Gly
385                 390                 395                 400

Phe Asn Ile Ser Asp Lys Asp Met Glu Lys Glu Tyr Arg Gly Gln Asn
                405                 410                 415

Lys Ala Ile Asn Lys Gln Ala Tyr Glu Glu Ile Ser Lys Glu His Leu
            420                 425                 430

Ala Val Tyr Lys Ile Gln Met Cys Val Asp Gly Gly Gly Ser Ala
        435                 440                 445

Asp Asp Asp Asp Lys Gly Trp Thr Leu Asn Ser Ala Gly Tyr Leu Leu
    450                 455                 460

Gly Pro His Ala Val Ala Leu Ala Gly Gly Gly Ser Gly Gly Gly
465                 470                 475                 480

Gly Ser Gly Gly Gly Gly Ser Ala Leu Val Leu Gln Cys Ile Asp Val
                485                 490                 495

Asp Asn Glu Asp Leu Phe Phe Ile Ala Asp Lys Asn Ser Phe Ser Asp
            500                 505                 510

Asp Leu Ser Lys Asn Glu Arg Ile Glu Tyr Asn Thr Gln Ser Asn Tyr
        515                 520                 525

Ile Glu Asn Asp Phe Pro Ile Asn Glu Leu Ile Leu Asp Thr Asp Leu
    530                 535                 540

Ile Ser Lys Ile Glu Leu Pro Ser Glu Asn Thr Glu Ser Leu Thr Asp
545                 550                 555                 560

Phe Asn Val Asp Val Pro Val Tyr Glu Lys Gln Pro Ala Ile Lys Lys
                565                 570                 575

Ile Phe Thr Asp Glu Asn Thr Ile Phe Gln Tyr Leu Tyr Ser Gln Thr
            580                 585                 590

Phe Pro Leu Asp Ile Arg Asp Ile Ser Leu Thr Ser Ser Phe Asp Asp
        595                 600                 605
```

```
Ala Leu Leu Phe Ser Asn Lys Val Tyr Ser Phe Phe Ser Met Asp Tyr
610                 615                 620

Ile Lys Thr Ala Asn Lys Val Glu Ala Gly Leu Phe Ala Gly Trp
625                 630                 635                 640

Val Lys Gln Ile Val Asn Asp Phe Val Ile Glu Ala Asn Lys Ser Asn
                645                 650                 655

Thr Met Asp Lys Ile Ala Asp Ile Ser Leu Ile Val Pro Tyr Ile Gly
            660                 665                 670

Leu Ala Leu Asn Val Gly Asn Glu Thr Ala Lys Gly Asn Phe Glu Asn
        675                 680                 685

Ala Phe Glu Ile Ala Gly Ala Ser Ile Leu Leu Glu Phe Ile Pro Glu
    690                 695                 700

Leu Leu Ile Pro Val Val Gly Ala Phe Leu Leu Glu Ser Tyr Ile Asp
705                 710                 715                 720

Asn Lys Asn Lys Ile Ile Lys Thr Ile Asp Asn Ala Leu Thr Lys Arg
                725                 730                 735

Asn Glu Lys Trp Ser Asp Met Tyr Gly Leu Ile Val Ala Gln Trp Leu
            740                 745                 750

Ser Thr Val Asn Thr Gln Phe Tyr Thr Ile Lys Glu Gly Met Tyr Lys
        755                 760                 765

Ala Leu Asn Tyr Gln Ala Gln Ala Leu Glu Glu Ile Ile Lys Tyr Arg
    770                 775                 780

Tyr Asn Ile Tyr Ser Glu Lys Glu Lys Ser Asn Ile Asn Ile Asp Phe
785                 790                 795                 800

Asn Asp Ile Asn Ser Lys Leu Asn Glu Gly Ile Asn Gln Ala Ile Asp
                805                 810                 815

Asn Ile Asn Asn Phe Ile Asn Gly Cys Ser Val Ser Tyr Leu Met Lys
            820                 825                 830

Lys Met Ile Pro Leu Ala Val Glu Lys Leu Leu Asp Phe Asp Asn Thr
        835                 840                 845

Leu Lys Lys Asn Leu Leu Asn Tyr Ile Asp Glu Asn Lys Leu Tyr Leu
    850                 855                 860

Ile Gly Ser Ala Glu Tyr Glu Lys Ser Lys Val Asn Lys Tyr Leu Lys
865                 870                 875                 880

Thr Ile Met Pro Phe Asp Leu Ser Ile Tyr Thr Asn Asp Thr Ile Leu
                885                 890                 895

Ile Glu Met Phe Asn Lys Tyr Asn Ser Leu Glu Ala Leu Ala Ser Gly
            900                 905                 910

His His His His His His
        915

<210> SEQ ID NO 23
<211> LENGTH: 907
<212> TYPE: PRT
<213> ORGANISM: Artificial Sequence
<220> FEATURE:
<223> OTHER INFORMATION: Synthetic sequence

<400> SEQUENCE: 23

Met Gly Ser Met Pro Val Thr Ile Asn Asn Phe Asn Tyr Asn Asp Pro
1               5                   10                  15

Ile Asp Asn Asn Asn Ile Ile Met Met Glu Pro Pro Phe Ala Arg Gly
                20                  25                  30

Thr Gly Arg Tyr Tyr Lys Ala Phe Lys Ile Thr Asp Arg Ile Trp Ile
            35                  40                  45
```

-continued

```
Ile Pro Glu Arg Tyr Thr Phe Gly Tyr Lys Pro Glu Asp Phe Asn Lys
    50                  55                  60

Ser Ser Gly Ile Phe Asn Arg Asp Val Cys Glu Tyr Tyr Asp Pro Asp
 65                  70                  75                  80

Tyr Leu Asn Thr Asn Asp Lys Lys Asn Ile Phe Leu Gln Thr Met Ile
                85                  90                  95

Lys Leu Phe Asn Arg Ile Lys Ser Lys Pro Leu Gly Glu Lys Leu Leu
            100                 105                 110

Glu Met Ile Ile Asn Gly Ile Pro Tyr Leu Gly Asp Arg Arg Val Pro
            115                 120                 125

Leu Glu Glu Phe Asn Thr Asn Ile Ala Ser Val Thr Val Asn Lys Leu
130                 135                 140

Ile Ser Asn Pro Gly Glu Val Glu Arg Lys Lys Gly Ile Phe Ala Asn
145                 150                 155                 160

Leu Ile Ile Phe Gly Pro Gly Pro Val Leu Asn Glu Asn Glu Thr Ile
                165                 170                 175

Asp Ile Gly Ile Gln Asn His Phe Ala Ser Arg Glu Gly Phe Gly Gly
            180                 185                 190

Ile Met Gln Met Lys Phe Cys Pro Glu Tyr Val Ser Val Phe Asn Asn
            195                 200                 205

Val Gln Glu Asn Lys Gly Ala Ser Ile Phe Asn Arg Arg Gly Tyr Phe
        210                 215                 220

Ser Asp Pro Ala Leu Ile Leu Met His Glu Leu Ile His Val Leu His
225                 230                 235                 240

Gly Leu Tyr Gly Ile Lys Val Asp Asp Leu Pro Ile Val Pro Asn Glu
                245                 250                 255

Lys Lys Phe Phe Met Gln Ser Thr Asp Ala Ile Gln Ala Glu Glu Leu
            260                 265                 270

Tyr Thr Phe Gly Gly Gln Asp Pro Ser Ile Ile Thr Pro Ser Thr Asp
            275                 280                 285

Lys Ser Ile Tyr Asp Lys Val Leu Gln Asn Phe Arg Gly Ile Val Asp
        290                 295                 300

Arg Leu Asn Lys Val Leu Val Cys Ile Ser Asp Pro Asn Ile Asn Ile
305                 310                 315                 320

Asn Ile Tyr Lys Asn Lys Phe Lys Asp Lys Tyr Lys Phe Val Glu Asp
                325                 330                 335

Ser Glu Gly Lys Tyr Ser Ile Asp Val Glu Ser Phe Asp Lys Leu Tyr
            340                 345                 350

Lys Ser Leu Met Phe Gly Phe Thr Glu Thr Asn Ile Ala Glu Asn Tyr
            355                 360                 365

Lys Ile Lys Thr Arg Ala Ser Tyr Phe Ser Asp Ser Leu Pro Pro Val
        370                 375                 380

Lys Ile Lys Asn Leu Leu Asp Asn Glu Ile Tyr Thr Ile Glu Glu Gly
385                 390                 395                 400

Phe Asn Ile Ser Asp Lys Asp Met Glu Lys Glu Tyr Arg Gly Gln Asn
                405                 410                 415

Lys Ala Ile Asn Lys Gln Ala Tyr Glu Glu Ile Ser Lys Glu His Leu
            420                 425                 430

Ala Val Tyr Lys Ile Gln Met Cys Val Asp Gly Gly Gly Ser Ala
            435                 440                 445

Asp Asp Asp Asp Lys Gly Trp Thr Leu Asn Ser Ala Gly Tyr Leu Leu
450                 455                 460

Gly Pro His Ala Val Ala Leu Ala Gly Gly Gly Gly Ser Gly Gly Gly
```

```
            465                 470                 475                 480
        Gly Ser Gly Gly Gly Ser Ala Leu Val Leu Gln Cys Ile Asp Val
                        485                 490                 495

Asp Asn Glu Asp Leu Phe Phe Ile Ala Asp Lys Asn Ser Phe Ser Asp
                    500                 505                 510

Asp Leu Ser Lys Asn Glu Arg Ile Glu Tyr Asn Thr Gln Ser Asn Tyr
                    515                 520                 525

Ile Glu Asn Asp Phe Pro Ile Asn Glu Leu Ile Leu Asp Thr Asp Leu
                530                 535                 540

Ile Ser Lys Ile Glu Leu Pro Ser Glu Asn Thr Glu Ser Leu Thr Asp
        545                 550                 555                 560

Phe Asn Val Asp Val Pro Val Tyr Glu Lys Gln Pro Ala Ile Lys Lys
                        565                 570                 575

Ile Phe Thr Asp Glu Asn Thr Ile Phe Gln Tyr Leu Tyr Ser Gln Thr
                    580                 585                 590

Phe Pro Leu Asp Ile Arg Asp Ile Ser Leu Thr Ser Ser Phe Asp Asp
                    595                 600                 605

Ala Leu Leu Phe Ser Asn Lys Val Tyr Ser Phe Phe Ser Met Asp Tyr
                610                 615                 620

Ile Lys Thr Ala Asn Lys Val Val Glu Ala Gly Leu Phe Ala Gly Trp
        625                 630                 635                 640

Val Lys Gln Ile Val Asn Asp Phe Val Ile Glu Ala Asn Lys Ser Asn
                        645                 650                 655

Thr Met Asp Lys Ile Ala Asp Ile Ser Leu Ile Val Pro Tyr Ile Gly
                    660                 665                 670

Leu Ala Leu Asn Val Gly Asn Glu Thr Ala Lys Gly Asn Phe Glu Asn
                    675                 680                 685

Ala Phe Glu Ile Ala Gly Ala Ser Ile Leu Leu Glu Phe Ile Pro Glu
                690                 695                 700

Leu Leu Ile Pro Val Val Gly Ala Phe Leu Leu Glu Ser Tyr Ile Asp
        705                 710                 715                 720

Asn Lys Asn Lys Ile Ile Lys Thr Ile Asp Asn Ala Leu Thr Lys Arg
                        725                 730                 735

Asn Glu Lys Trp Ser Asp Met Tyr Gly Leu Ile Val Ala Gln Trp Leu
                    740                 745                 750

Ser Thr Val Asn Thr Gln Phe Tyr Thr Ile Lys Glu Gly Met Tyr Lys
                    755                 760                 765

Ala Leu Asn Tyr Gln Ala Gln Ala Leu Glu Glu Ile Ile Lys Tyr Arg
                770                 775                 780

Tyr Asn Ile Tyr Ser Glu Lys Glu Lys Ser Asn Ile Asn Ile Asp Phe
        785                 790                 795                 800

Asn Asp Ile Asn Ser Lys Leu Asn Glu Gly Ile Asn Gln Ala Ile Asp
                        805                 810                 815

Asn Ile Asn Asn Phe Ile Asn Gly Cys Ser Val Ser Tyr Leu Met Lys
                    820                 825                 830

Lys Met Ile Pro Leu Ala Val Glu Lys Leu Leu Asp Phe Asp Asn Thr
                    835                 840                 845

Leu Lys Lys Asn Leu Leu Asn Tyr Ile Asp Glu Asn Lys Leu Tyr Leu
                850                 855                 860

Ile Gly Ser Ala Glu Tyr Glu Lys Ser Lys Val Asn Lys Tyr Leu Lys
        865                 870                 875                 880

Thr Ile Met Pro Phe Asp Leu Ser Ile Tyr Thr Asn Asp Thr Ile Leu
                        885                 890                 895
```

Ile Glu Met Phe Asn Lys Tyr Asn Ser Leu Asp
        900                 905

<210> SEQ ID NO 24
<211> LENGTH: 2778
<212> TYPE: DNA
<213> ORGANISM: Artificial Sequence
<220> FEATURE:
<223> OTHER INFORMATION: Synthetic sequence

<400> SEQUENCE: 24

| | | | | |
|---|---|---|---|---|
| catatgggat ccgaattcat gccgatcacc atcaacaact tcaactacag cgatccggtg | 60 |
| gataacaaaa acatcctgta cctggatacc catctgaata ccctggcgaa cgaaccggaa | 120 |
| aaagcgtttc gtatcaccgg caacatttgg gttattccgg atcgttttag ccgtaacagc | 180 |
| aaccccgaatc tgaataaacc gccgcgtgtt accagcccga aaagcggtta ttacgatccg | 240 |
| aactatctga gcaccgatag cgataaagat accttcctga agaaatcat caaactgttc | 300 |
| aaacgcatca acagccgtga attggcgaa gaactgatct atcgcctgag caccgatatt | 360 |
| ccgtttccgg caacaacaa caccccgatc aacacctttg atttcgatgt ggatttcaac | 420 |
| agcgttgatg ttaaaacccg ccagggtaac aattgggtga aaaccggcag cattaacccg | 480 |
| agcgtgatta ttaccggtcc gcgcgaaaac attattgatc cggaaaccag cacctttaaa | 540 |
| ctgaccaaca caccctttgc ggcgcaggaa ggttttggcg cgctgagcat tattagcatt | 600 |
| agcccgcgct ttatgctgac ctatagcaac gcgaccaacg atgttggtga aggccgtttc | 660 |
| agcaaaagcg aattttgcat ggacccgatc ctgatcctga tgcatgaact gaaccatgcg | 720 |
| atgcataacc tgtatggcat cgcgattccg aacgatcaga ccattagcag cgtgaccagc | 780 |
| aacatctttt acagccagta caacgtgaaa ctggaatatg cggaaatcta tgcgtttggc | 840 |
| ggtccgacca ttgatctgat tccgaaaagc gcgcgcaaat acttcgaaga aaaagcgctg | 900 |
| gattactatc gcagcattgc gaaacgtctg aacagcatta ccaccgcgaa tccgagcagc | 960 |
| ttcaacaaat atatcggcga atataaacag aaactgatcc gcaaatatcg ctttgtggtg | 1020 |
| gaaagcagcg gcgaagttac cgttaaccgc aataaaattcg tggaactgta caacgaactg | 1080 |
| acccagatct tcaccgaatt taactatgcg aaaatctata cgtgcagaa ccgtaaaatc | 1140 |
| tacctgagca cgtgtatac cccggtgacc gcgaatattc tggatgataa cgtgtacgat | 1200 |
| atccagaacg gctttaacat cccgaaaagc aacctgaacg ttctgtttat gggccagaac | 1260 |
| ctgagccgta tccggcgct gcgtaaagtg aacccggaaa acatgctgta cctgttcacc | 1320 |
| aaattttgcg tcgacggcgg tggcggtagc gcagacgatg acgataaagg ttggaccctg | 1380 |
| aactctgctg gttacctgct gggtccgcac gctgttgcgc tagcgggcgg tggcggtagc | 1440 |
| ggcggtggcg gtagcggcgg tggcggtagc gcactagtgc tgcagtgtcg tgaactgctg | 1500 |
| gtgaaaaaca ccgatctgcc gtttattggc gatatcagcg atgtgaaaac cgatatcttc | 1560 |
| ctgcgcaaag atatcaacga agaaaccgaa gtgatctact acccggataa cgtgagcgtt | 1620 |
| gatcaggtga tcctgagcaa aaacaccagc gaacatggtc agctggatct gctgtatccg | 1680 |
| agcattgata cgaaagcga attctgccg ggcgaaaacc aggtgtttta cgataaccgt | 1740 |
| acccagaacg tggattacct gaacagctat tactacctgg aaagccagaa actgagcgat | 1800 |
| aacgtggaag attttacctt acccgcagc attgaagaag cgctggataa cagcgcgaaa | 1860 |
| gtttacacct attttccgac cctggcgaac aaagttaatg cgggtgttca gggcggtctg | 1920 |
| tttctgatgt gggcgaacga tgtggtggaa gatttcacca ccaacatcct gcgtaaagat | 1980 |

-continued

```
acctggata     aaatcagcga   tgttagcgcg   attattccgt   atattggtcc   ggcgctgaac   2040
attagcaata    gcgtgcgtcg   tggcaatttt   accgaagcgt   ttgcggttac   cggtgtgacc   2100
attctgctgg    aagcgtttcc   ggaatttacc   attccggcgc   tgggtgcgtt   tgtgatctat   2160
agcaaagtgc    aggaacgcaa   cgaaatcatc   aaaaccatcg   ataactgcct   ggaacagcgt   2220
attaaacgct    ggaaagatag   ctatgaatgg   atgatgggca   cctggctgag   ccgtattatc   2280
acccagttca    acaacatcag   ctaccagatg   tacgatagcc   tgaactatca   ggcgggtgcg   2340
attaaagcga    aaatcgatct   ggaatacaaa   aaatacagcg   gcagcgataa   agaaaacatc   2400
aaaagccagg    ttgaaaacct   gaaaaacagc   ctggatgtga   aaattagcga   agcgatgaat   2460
aacatcaaca    aattcatccg   gaatgcagc    gtgacctacc   tgttcaaaaa   catgctgccg   2520
aaagtgatcg    atgaactgaa   cgaatttgat   cgcaacacca   aagcgaaact   gatcaacctg   2580
atcgatagcc    acaacattat   tctggtgggc   gaagtggata   aactgaaagc   gaaagttaac   2640
aacagcttcc    agaacaccat   cccgtttaac   atcttcagct   ataccaacaa   cagcctgctg   2700
aaagatatca    tcaacgaata   cttcaatcta   gaagcactag   cgagtgggca   ccatcaccat   2760
caccattaat    gaaagctt                                                        2778
```

```
<210> SEQ ID NO 25
<211> LENGTH: 921
<212> TYPE: PRT
<213> ORGANISM: Artificial Sequence
<220> FEATURE:
<223> OTHER INFORMATION: Synthetic sequence

<400> SEQUENCE: 25
```

| | | | | | | | | | | | | | | |
|---|---|---|---|---|---|---|---|---|---|---|---|---|---|---|
| Met | Gly | Ser | Glu | Phe | Met | Pro | Ile | Thr | Ile | Asn | Asn | Phe | Asn | Tyr | Ser |
| 1 | | | | 5 | | | | | 10 | | | | | 15 | |
| Asp | Pro | Val | Asp | Asn | Lys | Asn | Ile | Leu | Tyr | Leu | Asp | Thr | His | Leu | Asn |
| | | 20 | | | | | 25 | | | | | 30 | | | |
| Thr | Leu | Ala | Asn | Glu | Pro | Glu | Lys | Ala | Phe | Arg | Ile | Thr | Gly | Asn | Ile |
| | | | 35 | | | | | 40 | | | | | 45 | | |
| Trp | Val | Ile | Pro | Asp | Arg | Phe | Ser | Arg | Asn | Ser | Asn | Pro | Asn | Leu | Asn |
| 50 | | | | | 55 | | | | | 60 | | | | | |
| Lys | Pro | Pro | Arg | Val | Thr | Ser | Pro | Lys | Ser | Gly | Tyr | Tyr | Asp | Pro | Asn |
| 65 | | | | | 70 | | | | | 75 | | | | | 80 |
| Tyr | Leu | Ser | Thr | Asp | Ser | Asp | Lys | Asp | Thr | Phe | Leu | Lys | Glu | Ile | Ile |
| | | | | 85 | | | | | 90 | | | | | 95 | |
| Lys | Leu | Phe | Lys | Arg | Ile | Asn | Ser | Arg | Glu | Ile | Gly | Glu | Glu | Leu | Ile |
| | | | 100 | | | | | 105 | | | | | 110 | | |
| Tyr | Arg | Leu | Ser | Thr | Asp | Ile | Pro | Phe | Pro | Gly | Asn | Asn | Asn | Thr | Pro |
| | | | 115 | | | | | 120 | | | | | 125 | | |
| Ile | Asn | Thr | Phe | Asp | Phe | Asp | Val | Asp | Phe | Asn | Ser | Val | Asp | Val | Lys |
| | 130 | | | | | 135 | | | | | 140 | | | | |
| Thr | Arg | Gln | Gly | Asn | Asn | Trp | Val | Lys | Thr | Gly | Ser | Ile | Asn | Pro | Ser |
| 145 | | | | | 150 | | | | | 155 | | | | | 160 |
| Val | Ile | Ile | Thr | Gly | Pro | Arg | Glu | Asn | Ile | Ile | Asp | Pro | Glu | Thr | Ser |
| | | | | 165 | | | | | 170 | | | | | 175 | |
| Thr | Phe | Lys | Leu | Thr | Asn | Asn | Thr | Phe | Ala | Ala | Gln | Glu | Gly | Phe | Gly |
| | | | 180 | | | | | 185 | | | | | 190 | | |
| Ala | Leu | Ser | Ile | Ile | Ser | Ile | Ser | Pro | Arg | Phe | Met | Leu | Thr | Tyr | Ser |
| | | | 195 | | | | | 200 | | | | | 205 | | |
| Asn | Ala | Thr | Asn | Asp | Val | Gly | Glu | Gly | Arg | Phe | Ser | Lys | Ser | Glu | Phe |

```
            210                 215                 220
Cys Met Asp Pro Ile Leu Ile Leu Met His Glu Leu Asn His Ala Met
225                 230                 235                 240

His Asn Leu Tyr Gly Ile Ala Ile Pro Asn Asp Gln Thr Ile Ser Ser
                245                 250                 255

Val Thr Ser Asn Ile Phe Tyr Ser Gln Tyr Asn Val Lys Leu Glu Tyr
                260                 265                 270

Ala Glu Ile Tyr Ala Phe Gly Gly Pro Thr Ile Asp Leu Ile Pro Lys
            275                 280                 285

Ser Ala Arg Lys Tyr Phe Glu Glu Lys Ala Leu Asp Tyr Tyr Arg Ser
        290                 295                 300

Ile Ala Lys Arg Leu Asn Ser Ile Thr Thr Ala Asn Pro Ser Ser Phe
305                 310                 315                 320

Asn Lys Tyr Ile Gly Glu Tyr Lys Gln Lys Leu Ile Arg Lys Tyr Arg
                325                 330                 335

Phe Val Val Glu Ser Ser Gly Glu Val Thr Val Asn Arg Asn Lys Phe
                340                 345                 350

Val Glu Leu Tyr Asn Glu Leu Thr Gln Ile Phe Thr Glu Phe Asn Tyr
            355                 360                 365

Ala Lys Ile Tyr Asn Val Gln Asn Arg Lys Ile Tyr Leu Ser Asn Val
        370                 375                 380

Tyr Thr Pro Val Thr Ala Asn Ile Leu Asp Asp Asn Val Tyr Asp Ile
385                 390                 395                 400

Gln Asn Gly Phe Asn Ile Pro Lys Ser Asn Leu Asn Val Leu Phe Met
                405                 410                 415

Gly Gln Asn Leu Ser Arg Asn Pro Ala Leu Arg Lys Val Asn Pro Glu
                420                 425                 430

Asn Met Leu Tyr Leu Phe Thr Lys Phe Cys Val Asp Gly Gly Gly Gly
            435                 440                 445

Ser Ala Asp Asp Asp Lys Gly Trp Thr Leu Asn Ser Ala Gly Tyr
        450                 455                 460

Leu Leu Gly Pro His Ala Val Ala Leu Ala Gly Gly Gly Ser Gly
465                 470                 475                 480

Gly Gly Gly Ser Gly Gly Gly Ser Ala Leu Val Leu Gln Cys Arg
                485                 490                 495

Glu Leu Leu Val Lys Asn Thr Asp Leu Pro Phe Ile Gly Asp Ile Ser
                500                 505                 510

Asp Val Lys Thr Asp Ile Phe Leu Arg Lys Asp Ile Asn Glu Glu Thr
            515                 520                 525

Glu Val Ile Tyr Tyr Pro Asp Asn Val Ser Val Asp Gln Val Ile Leu
        530                 535                 540

Ser Lys Asn Thr Ser Glu His Gly Gln Leu Asp Leu Tyr Pro Ser
545                 550                 555                 560

Ile Asp Ser Glu Ser Glu Ile Leu Pro Gly Glu Asn Gln Val Phe Tyr
                565                 570                 575

Asp Asn Arg Thr Gln Asn Val Asp Tyr Leu Asn Ser Tyr Tyr Tyr Leu
                580                 585                 590

Glu Ser Gln Lys Leu Ser Asp Asn Val Glu Asp Phe Thr Phe Thr Arg
            595                 600                 605

Ser Ile Glu Glu Ala Leu Asp Asn Ser Ala Lys Val Tyr Thr Tyr Phe
        610                 615                 620

Pro Thr Leu Ala Asn Lys Val Asn Ala Gly Val Gln Gly Gly Leu Phe
625                 630                 635                 640
```

-continued

```
Leu Met Trp Ala Asn Asp Val Val Glu Asp Phe Thr Thr Asn Ile Leu
            645                 650                 655

Arg Lys Asp Thr Leu Asp Lys Ile Ser Asp Val Ser Ala Ile Ile Pro
            660                 665                 670

Tyr Ile Gly Pro Ala Leu Asn Ile Ser Asn Ser Val Arg Arg Gly Asn
            675                 680                 685

Phe Thr Glu Ala Phe Ala Val Thr Gly Val Thr Ile Leu Leu Glu Ala
            690                 695                 700

Phe Pro Glu Phe Thr Ile Pro Ala Leu Gly Ala Phe Val Ile Tyr Ser
705                 710                 715                 720

Lys Val Gln Glu Arg Asn Glu Ile Ile Lys Thr Ile Asp Asn Cys Leu
            725                 730                 735

Glu Gln Arg Ile Lys Arg Trp Lys Asp Ser Tyr Glu Trp Met Met Gly
            740                 745                 750

Thr Trp Leu Ser Arg Ile Ile Thr Gln Phe Asn Asn Ile Ser Tyr Gln
            755                 760                 765

Met Tyr Asp Ser Leu Asn Tyr Gln Ala Gly Ala Ile Lys Ala Lys Ile
            770                 775                 780

Asp Leu Glu Tyr Lys Lys Tyr Ser Gly Ser Asp Lys Glu Asn Ile Lys
785                 790                 795                 800

Ser Gln Val Glu Asn Leu Lys Asn Ser Leu Asp Val Lys Ile Ser Glu
            805                 810                 815

Ala Met Asn Asn Ile Asn Lys Phe Ile Arg Glu Cys Ser Val Thr Tyr
            820                 825                 830

Leu Phe Lys Asn Met Leu Pro Lys Val Ile Asp Glu Leu Asn Glu Phe
            835                 840                 845

Asp Arg Asn Thr Lys Ala Lys Leu Ile Asn Leu Ile Asp Ser His Asn
            850                 855                 860

Ile Ile Leu Val Gly Glu Val Asp Lys Leu Lys Ala Lys Val Asn Asn
865                 870                 875                 880

Ser Phe Gln Asn Thr Ile Pro Phe Asn Ile Phe Ser Tyr Thr Asn Asn
            885                 890                 895

Ser Leu Leu Lys Asp Ile Ile Asn Glu Tyr Phe Asn Leu Glu Ala Leu
            900                 905                 910

Ala Ser Gly His His His His His His
            915                 920

<210> SEQ ID NO 26
<211> LENGTH: 910
<212> TYPE: PRT
<213> ORGANISM: Artificial Sequence
<220> FEATURE:
<223> OTHER INFORMATION: Synthetic sequence

<400> SEQUENCE: 26

Met Gly Ser Glu Phe Met Pro Ile Thr Ile Asn Asn Phe Asn Tyr Ser
1               5                   10                  15

Asp Pro Val Asp Asn Lys Asn Ile Leu Tyr Leu Asp Thr His Leu Asn
            20                  25                  30

Thr Leu Ala Asn Glu Pro Glu Lys Ala Phe Arg Ile Thr Gly Asn Ile
            35                  40                  45

Trp Val Ile Pro Asp Arg Phe Ser Arg Asn Ser Asn Pro Asn Leu Asn
        50                  55                  60

Lys Pro Pro Arg Val Thr Ser Pro Lys Ser Gly Tyr Tyr Asp Pro Asn
65                  70                  75                  80
```

```
Tyr Leu Ser Thr Asp Ser Asp Lys Asp Thr Phe Leu Lys Glu Ile Ile
                85                  90                  95

Lys Leu Phe Lys Arg Ile Asn Ser Arg Glu Ile Gly Glu Glu Leu Ile
            100                 105                 110

Tyr Arg Leu Ser Thr Asp Ile Pro Phe Pro Gly Asn Asn Asn Thr Pro
        115                 120                 125

Ile Asn Thr Phe Asp Phe Asp Val Asp Phe Asn Ser Val Asp Val Lys
    130                 135                 140

Thr Arg Gln Gly Asn Asn Trp Val Lys Thr Gly Ser Ile Asn Pro Ser
145                 150                 155                 160

Val Ile Ile Thr Gly Pro Arg Glu Asn Ile Ile Asp Pro Glu Thr Ser
                165                 170                 175

Thr Phe Lys Leu Thr Asn Asn Thr Phe Ala Ala Gln Glu Gly Phe Gly
            180                 185                 190

Ala Leu Ser Ile Ile Ser Ile Ser Pro Arg Phe Met Leu Thr Tyr Ser
        195                 200                 205

Asn Ala Thr Asn Asp Val Gly Glu Gly Arg Phe Ser Lys Ser Glu Phe
    210                 215                 220

Cys Met Asp Pro Ile Leu Ile Leu Met His Glu Leu Asn His Ala Met
225                 230                 235                 240

His Asn Leu Tyr Gly Ile Ala Ile Pro Asn Asp Gln Thr Ile Ser Ser
                245                 250                 255

Val Thr Ser Asn Ile Phe Tyr Ser Gln Tyr Asn Val Lys Leu Glu Tyr
            260                 265                 270

Ala Glu Ile Tyr Ala Phe Gly Gly Pro Thr Ile Asp Leu Ile Pro Lys
        275                 280                 285

Ser Ala Arg Lys Tyr Phe Glu Glu Lys Ala Leu Asp Tyr Tyr Arg Ser
    290                 295                 300

Ile Ala Lys Arg Leu Asn Ser Ile Thr Thr Ala Asn Pro Ser Ser Phe
305                 310                 315                 320

Asn Lys Tyr Ile Gly Glu Tyr Lys Gln Lys Leu Ile Arg Lys Tyr Arg
                325                 330                 335

Phe Val Val Glu Ser Ser Gly Glu Val Thr Val Asn Arg Asn Lys Phe
            340                 345                 350

Val Glu Leu Tyr Asn Glu Leu Thr Gln Ile Phe Thr Glu Phe Asn Tyr
        355                 360                 365

Ala Lys Ile Tyr Asn Val Gln Asn Arg Lys Ile Tyr Leu Ser Asn Val
    370                 375                 380

Tyr Thr Pro Val Thr Ala Asn Ile Leu Asp Asp Asn Val Tyr Asp Ile
385                 390                 395                 400

Gln Asn Gly Phe Asn Ile Pro Lys Ser Asn Leu Asn Val Leu Phe Met
                405                 410                 415

Gly Gln Asn Leu Ser Arg Asn Pro Ala Leu Arg Lys Val Asn Pro Glu
            420                 425                 430

Asn Met Leu Tyr Leu Phe Thr Lys Phe Cys Val Asp Gly Gly Gly Gly
        435                 440                 445

Ser Ala Asp Asp Asp Asp Lys Gly Trp Thr Leu Asn Ser Ala Gly Tyr
    450                 455                 460

Leu Leu Gly Pro His Ala Val Ala Leu Ala Gly Gly Gly Ser Gly
465                 470                 475                 480

Gly Gly Gly Ser Gly Gly Gly Ser Ala Leu Val Leu Gln Cys Arg
                485                 490                 495
```

```
Glu Leu Leu Val Lys Asn Thr Asp Leu Pro Phe Ile Gly Asp Ile Ser
            500                 505                 510

Asp Val Lys Thr Asp Ile Phe Leu Arg Lys Asp Ile Asn Glu Glu Thr
            515                 520                 525

Glu Val Ile Tyr Tyr Pro Asp Asn Val Ser Val Asp Gln Val Ile Leu
            530                 535                 540

Ser Lys Asn Thr Ser Glu His Gly Gln Leu Asp Leu Leu Tyr Pro Ser
545                 550                 555                 560

Ile Asp Ser Glu Ser Glu Ile Leu Pro Gly Glu Asn Gln Val Phe Tyr
            565                 570                 575

Asp Asn Arg Thr Gln Asn Val Asp Tyr Leu Asn Ser Tyr Tyr Tyr Leu
            580                 585                 590

Glu Ser Gln Lys Leu Ser Asp Asn Val Glu Asp Phe Thr Phe Thr Arg
            595                 600                 605

Ser Ile Glu Glu Ala Leu Asp Asn Ser Ala Lys Val Tyr Thr Tyr Phe
            610                 615                 620

Pro Thr Leu Ala Asn Lys Val Asn Ala Gly Val Gln Gly Gly Leu Phe
625                 630                 635                 640

Leu Met Trp Ala Asn Asp Val Val Glu Asp Phe Thr Thr Asn Ile Leu
            645                 650                 655

Arg Lys Asp Thr Leu Asp Lys Ile Ser Asp Val Ser Ala Ile Ile Pro
            660                 665                 670

Tyr Ile Gly Pro Ala Leu Asn Ile Ser Asn Ser Val Arg Arg Gly Asn
            675                 680                 685

Phe Thr Glu Ala Phe Ala Val Thr Gly Val Thr Ile Leu Leu Glu Ala
            690                 695                 700

Phe Pro Glu Phe Thr Ile Pro Ala Leu Gly Ala Phe Val Ile Tyr Ser
705                 710                 715                 720

Lys Val Gln Glu Arg Asn Glu Ile Ile Lys Thr Ile Asp Asn Cys Leu
            725                 730                 735

Glu Gln Arg Ile Lys Arg Trp Lys Asp Ser Tyr Glu Trp Met Met Gly
            740                 745                 750

Thr Trp Leu Ser Arg Ile Ile Thr Gln Phe Asn Asn Ile Ser Tyr Gln
            755                 760                 765

Met Tyr Asp Ser Leu Asn Tyr Gln Ala Gly Ala Ile Lys Ala Lys Ile
770                 775                 780

Asp Leu Glu Tyr Lys Lys Tyr Ser Gly Ser Asp Lys Glu Asn Ile Lys
785                 790                 795                 800

Ser Gln Val Glu Asn Leu Lys Asn Ser Leu Asp Val Lys Ile Ser Glu
            805                 810                 815

Ala Met Asn Asn Ile Asn Lys Phe Ile Arg Glu Cys Ser Val Thr Tyr
            820                 825                 830

Leu Phe Lys Asn Met Leu Pro Lys Val Ile Asp Glu Leu Asn Glu Phe
            835                 840                 845

Asp Arg Asn Thr Lys Ala Lys Leu Ile Asn Leu Ile Asp Ser His Asn
            850                 855                 860

Ile Ile Leu Val Gly Glu Val Asp Lys Leu Lys Ala Lys Val Asn Asn
865                 870                 875                 880

Ser Phe Gln Asn Thr Ile Pro Phe Asn Ile Phe Ser Tyr Thr Asn Asn
            885                 890                 895

Ser Leu Leu Lys Asp Ile Ile Asn Glu Tyr Phe Asn Leu Asp
            900                 905                 910
```

-continued

<210> SEQ ID NO 27
<211> LENGTH: 2769
<212> TYPE: DNA
<213> ORGANISM: Artificial Sequence
<220> FEATURE:
<223> OTHER INFORMATION: Synthetic sequence

<400> SEQUENCE: 27

| | | | | | |
|---|---|---|---|---|---|
| catatgggat | ccatgacgtg | gccagttaag | gatttcaact | actcagatcc | tgtaaatgac | 60 |
| aacgatattc | tgtaccttcg | cattccacaa | aataaactga | tcaccacacc | agtcaaagca | 120 |
| ttcatgatta | ctcaaaacat | ttgggtcatt | ccagaacgct | tttctagtga | cacaaatccg | 180 |
| agtttatcta | aacctccgcg | tccgacgtcc | aaatatcaga | gctattacga | tccctcatat | 240 |
| ctcagtacgg | acgaacaaaa | agatactttc | cttaaaggta | tcattaaact | gtttaagcgt | 300 |
| attaatgagc | gcgatatcgg | gaaaaagttg | attaattatc | ttgttgtggg | ttccccgttc | 360 |
| atgggcgata | gctctacccc | cgaagacact | tttgatttta | cccgtcatac | gacaaacatc | 420 |
| gcggtagaga | agtttgagaa | cggatcgtgg | aaagtcacaa | acatcattac | acctagcgtc | 480 |
| ttaatttttg | gtccgctgcc | aaacatctta | gattatacag | ccagcctgac | tttgcagggg | 540 |
| caacagtcga | atccgagttt | cgaaggtttt | ggtaccctga | gcattctgaa | agttgccccg | 600 |
| gaatttctgc | tcactttttc | agatgtcacc | agcaaccaga | gctcagcagt | attaggaaag | 660 |
| tcaattttt | gcatggaccc | ggttattgca | ctgatgcacg | aactgacgca | ctctctgcat | 720 |
| caactgtatg | ggatcaacat | ccccagtgac | aaacgtattc | gtccccaggt | gtctgaagga | 780 |
| tttttctcac | aggatgggcc | gaacgtccag | ttcgaagagt | tgtatacttt | cggaggcctg | 840 |
| gacgtagaga | tcattcccca | gattgagcgc | agtcagctgc | gtgagaaggc | attgggccat | 900 |
| tataaggata | ttgcaaaacg | cctgaataac | attaacaaaa | cgattccatc | ttcgtggatc | 960 |
| tcgaatattg | ataaatataa | gaaaattttt | agcgagaaat | ataattttga | taaagataat | 1020 |
| acaggtaact | ttgtggttaa | cattgacaaa | ttcaactccc | tttacagtga | tttgacgaat | 1080 |
| gtaatgagcg | aagttgtgta | tagttcccaa | tacaacgtta | agaatcgtac | ccattacttc | 1140 |
| tctcgtcact | acctgccggt | tttcgcgaac | atccttgacg | ataatattta | cactattcgt | 1200 |
| gacggcttta | acttgaccaa | caagggcttc | aatattgaaa | attcaggcca | gaacattgaa | 1260 |
| cgcaacccgg | ccttgcagaa | actgtcgagt | gaatccgtgg | ttgacctgtt | taccaaagtc | 1320 |
| tgcgtcgacg | gcggtggcgg | tagcgcagac | gatgacgata | aaggttggac | cctgaactct | 1380 |
| gctggttacc | tgctgggtcc | gcacgctgtt | gcgctagcgg | gcggtggcgg | tagcggcggt | 1440 |
| ggcggtagcg | gcggtggcgg | tagcgcacta | gtgctgcagt | gtattaaagt | gaaaacaat | 1500 |
| cggctgcctt | atgtagcaga | taaagatagc | attagtcagg | agattttcga | aaataaaatt | 1560 |
| atcactgacg | aaaccaatgt | tcagaattat | tcagataaat | tttcactgga | cgaaagcatc | 1620 |
| ttagatggcc | aagttccgat | taacccggaa | attgttgatc | cgttactgcc | gaacgtgaat | 1680 |
| atggaaccgt | taaacctccc | tggcgaagag | atcgtatttt | atgatgacat | tacgaaatat | 1740 |
| gtggactacc | ttaattctta | ttactatttg | gaaagccaga | aactgtccaa | taacgtggaa | 1800 |
| aacattactc | tgaccacaag | cgtggaagag | gctttaggct | actcaaataa | gatttatacc | 1860 |
| ttcctcccgt | cgctggcgga | aaaagtaaat | aaaggtgtgc | aggctggtct | gttcctcaac | 1920 |
| tgggcgaatg | aagttgtcga | agactttacc | acgaatatta | tgaaaaagga | taccctggat | 1980 |
| aaaatctccg | acgtctcggt | tattatccca | tatattggcc | ctgcgttaaa | tatcggtaat | 2040 |
| agtgcgctgc | gggggaattt | taaccaggcc | tttgctaccg | cgggcgtcgc | gttcctcctg | 2100 |

```
gagggctttc ctgaatttac tatcccggcg ctcggtgttt ttacatttta ctcttccatc    2160
caggagcgtg agaaaattat caaaaccatc gaaaactgcc tggagcagcg ggtgaaacgc    2220
tggaaagatt cttatcaatg gatggtgtca aactggttat ctcgcatcac gacccaattc    2280
aaccatatta attaccagat gtatgatagt ctgtcgtacc aagctgacgc cattaaagcc    2340
aaaattgatc tggaatataa aaagtactct ggtagcgata aggagaacat caaaagccag    2400
gtggagaacc ttaagaatag tctggatgtg aaaatctctg aagctatgaa taacattaac    2460
aaattcattc gtgaatgttc ggtgacgtac ctgttcaaga atatgctgcc aaaagttatt    2520
gatgaactga ataaatttga tctgcgtacc aaaaccgaac ttatcaacct catcgactcc    2580
cacaacatta tccttgtggg cgaagtggat cgtctgaagg ccaaagtaaa cgagagcttt    2640
gaaaatacga tgccgtttaa tattttttca tataccaata actccttgct gaaagatatc    2700
atcaatgaat atttcaatct agaagcacta gcgagtgggc accatcacca tcaccattaa    2760
tgaaagctt                                                             2769
```

<210> SEQ ID NO 28
<211> LENGTH: 918
<212> TYPE: PRT
<213> ORGANISM: Artificial Sequence
<220> FEATURE:
<223> OTHER INFORMATION: Synthetic sequence

<400> SEQUENCE: 28

```
Met Gly Ser Met Thr Trp Pro Val Lys Asp Phe Asn Tyr Ser Asp Pro
1               5                   10                  15

Val Asn Asp Asn Asp Ile Leu Tyr Leu Arg Ile Pro Gln Asn Lys Leu
            20                  25                  30

Ile Thr Thr Pro Val Lys Ala Phe Met Ile Thr Gln Asn Ile Trp Val
        35                  40                  45

Ile Pro Glu Arg Phe Ser Ser Asp Thr Asn Pro Ser Leu Ser Lys Pro
    50                  55                  60

Pro Arg Pro Thr Ser Lys Tyr Gln Ser Tyr Tyr Asp Pro Ser Tyr Leu
65                  70                  75                  80

Ser Thr Asp Glu Gln Lys Asp Thr Phe Leu Lys Gly Ile Ile Lys Leu
                85                  90                  95

Phe Lys Arg Ile Asn Glu Arg Asp Ile Gly Lys Lys Leu Ile Asn Tyr
            100                 105                 110

Leu Val Val Gly Ser Pro Phe Met Gly Asp Ser Ser Thr Pro Glu Asp
        115                 120                 125

Thr Phe Asp Phe Thr Arg His Thr Thr Asn Ile Ala Val Glu Lys Phe
    130                 135                 140

Glu Asn Gly Ser Trp Lys Val Thr Asn Ile Ile Thr Pro Ser Val Leu
145                 150                 155                 160

Ile Phe Gly Pro Leu Pro Asn Ile Leu Asp Tyr Thr Ala Ser Leu Thr
                165                 170                 175

Leu Gln Gly Gln Gln Ser Asn Pro Ser Phe Glu Gly Phe Gly Thr Leu
            180                 185                 190

Ser Ile Leu Lys Val Ala Pro Glu Phe Leu Leu Thr Phe Ser Asp Val
        195                 200                 205

Thr Ser Asn Gln Ser Ser Ala Val Leu Gly Lys Ser Ile Phe Cys Met
    210                 215                 220

Asp Pro Val Ile Ala Leu Met His Glu Leu Thr His Ser Leu His Gln
225                 230                 235                 240
```

-continued

```
Leu Tyr Gly Ile Asn Ile Pro Ser Asp Lys Arg Ile Arg Pro Gln Val
            245                 250                 255

Ser Glu Gly Phe Phe Ser Gln Asp Gly Pro Asn Val Gln Phe Glu Glu
        260                 265                 270

Leu Tyr Thr Phe Gly Leu Asp Val Glu Ile Ile Pro Gln Ile Glu
        275                 280                 285

Arg Ser Gln Leu Arg Glu Lys Ala Leu Gly His Tyr Lys Asp Ile Ala
    290                 295                 300

Lys Arg Leu Asn Asn Ile Asn Lys Thr Ile Pro Ser Ser Trp Ile Ser
305                 310                 315                 320

Asn Ile Asp Lys Tyr Lys Lys Ile Phe Ser Glu Lys Tyr Asn Phe Asp
                325                 330                 335

Lys Asp Asn Thr Gly Asn Phe Val Val Asn Ile Asp Lys Phe Asn Ser
            340                 345                 350

Leu Tyr Ser Asp Leu Thr Asn Val Met Ser Glu Val Val Tyr Ser Ser
        355                 360                 365

Gln Tyr Asn Val Lys Asn Arg Thr His Tyr Phe Ser Arg His Tyr Leu
    370                 375                 380

Pro Val Phe Ala Asn Ile Leu Asp Asp Asn Ile Tyr Thr Ile Arg Asp
385                 390                 395                 400

Gly Phe Asn Leu Thr Asn Lys Gly Phe Asn Ile Glu Asn Ser Gly Gln
                405                 410                 415

Asn Ile Glu Arg Asn Pro Ala Leu Gln Lys Leu Ser Ser Glu Ser Val
            420                 425                 430

Val Asp Leu Phe Thr Lys Val Cys Val Asp Gly Gly Gly Ser Ala
        435                 440                 445

Asp Asp Asp Asp Lys Gly Trp Thr Leu Asn Ser Ala Gly Tyr Leu Leu
450                 455                 460

Gly Pro His Ala Val Ala Leu Ala Gly Gly Gly Ser Gly Gly Gly
465                 470                 475                 480

Gly Ser Gly Gly Gly Ser Ala Leu Val Leu Gln Cys Ile Lys Val
                485                 490                 495

Lys Asn Asn Arg Leu Pro Tyr Val Ala Asp Lys Asp Ser Ile Ser Gln
            500                 505                 510

Glu Ile Phe Glu Asn Lys Ile Ile Thr Asp Glu Thr Asn Val Gln Asn
        515                 520                 525

Tyr Ser Asp Lys Phe Ser Leu Asp Glu Ser Ile Leu Asp Gly Gln Val
    530                 535                 540

Pro Ile Asn Pro Glu Ile Val Asp Pro Leu Leu Pro Asn Val Asn Met
545                 550                 555                 560

Glu Pro Leu Asn Leu Pro Gly Glu Glu Ile Val Phe Tyr Asp Asp Ile
                565                 570                 575

Thr Lys Tyr Val Asp Tyr Leu Asn Ser Tyr Tyr Leu Glu Ser Gln
            580                 585                 590

Lys Leu Ser Asn Asn Val Glu Asn Ile Thr Leu Thr Thr Ser Val Glu
        595                 600                 605

Glu Ala Leu Gly Tyr Ser Asn Lys Ile Tyr Thr Phe Leu Pro Ser Leu
    610                 615                 620

Ala Glu Lys Val Asn Lys Gly Val Gln Ala Gly Leu Phe Leu Asn Trp
625                 630                 635                 640

Ala Asn Glu Val Val Glu Asp Phe Thr Thr Asn Ile Met Lys Lys Asp
                645                 650                 655

Thr Leu Asp Lys Ile Ser Asp Val Ser Val Ile Ile Pro Tyr Ile Gly
```

```
                660                 665                 670
Pro Ala Leu Asn Ile Gly Asn Ser Ala Leu Arg Gly Asn Phe Asn Gln
            675                 680                 685
Ala Phe Ala Thr Ala Gly Val Ala Phe Leu Glu Gly Phe Pro Glu
        690                 695                 700
Phe Thr Ile Pro Ala Leu Gly Val Phe Thr Phe Tyr Ser Ser Ile Gln
705                 710                 715                 720
Glu Arg Glu Lys Ile Ile Lys Thr Ile Glu Asn Cys Leu Glu Gln Arg
                725                 730                 735
Val Lys Arg Trp Lys Asp Ser Tyr Gln Trp Met Val Ser Asn Trp Leu
            740                 745                 750
Ser Arg Ile Thr Thr Gln Phe Asn His Ile Asn Tyr Gln Met Tyr Asp
        755                 760                 765
Ser Leu Ser Tyr Gln Ala Asp Ala Ile Lys Ala Lys Ile Asp Leu Glu
            770                 775                 780
Tyr Lys Lys Tyr Ser Gly Ser Asp Lys Glu Asn Ile Lys Ser Gln Val
785                 790                 795                 800
Glu Asn Leu Lys Asn Ser Leu Asp Val Lys Ile Ser Glu Ala Met Asn
                805                 810                 815
Asn Ile Asn Lys Phe Ile Arg Glu Cys Ser Val Thr Tyr Leu Phe Lys
            820                 825                 830
Asn Met Leu Pro Lys Val Ile Asp Glu Leu Asn Lys Phe Asp Leu Arg
        835                 840                 845
Thr Lys Thr Glu Leu Ile Asn Leu Ile Asp Ser His Asn Ile Ile Leu
850                 855                 860
Val Gly Glu Val Asp Arg Leu Lys Ala Lys Val Asn Glu Ser Phe Glu
865                 870                 875                 880
Asn Thr Met Pro Phe Asn Ile Phe Ser Tyr Thr Asn Asn Ser Leu Leu
                885                 890                 895
Lys Asp Ile Ile Asn Glu Tyr Phe Asn Leu Glu Ala Leu Ala Ser Gly
            900                 905                 910
His His His His His His
        915

<210> SEQ ID NO 29
<211> LENGTH: 907
<212> TYPE: PRT
<213> ORGANISM: Artificial Sequence
<220> FEATURE:
<223> OTHER INFORMATION: Synthetic sequence

<400> SEQUENCE: 29

Met Gly Ser Met Thr Trp Pro Val Lys Asp Phe Asn Tyr Ser Asp Pro
1               5                   10                  15
Val Asn Asp Asn Asp Ile Leu Tyr Leu Arg Ile Pro Gln Asn Lys Leu
            20                  25                  30
Ile Thr Thr Pro Val Lys Ala Phe Met Ile Thr Gln Asn Ile Trp Val
        35                  40                  45
Ile Pro Glu Arg Phe Ser Ser Asp Thr Asn Pro Ser Leu Ser Lys Pro
    50                  55                  60
Pro Arg Pro Thr Ser Lys Tyr Gln Ser Tyr Tyr Asp Pro Ser Tyr Leu
65                  70                  75                  80
Ser Thr Asp Glu Gln Lys Asp Thr Phe Leu Lys Gly Ile Ile Lys Leu
                85                  90                  95
Phe Lys Arg Ile Asn Glu Arg Asp Ile Gly Lys Lys Leu Ile Asn Tyr
```

```
                    100                 105                 110
Leu Val Val Gly Ser Pro Phe Met Gly Asp Ser Ser Thr Pro Glu Asp
                115                 120                 125

Thr Phe Asp Phe Thr Arg His Thr Thr Asn Ile Ala Val Glu Lys Phe
130                 135                 140

Glu Asn Gly Ser Trp Lys Val Thr Asn Ile Ile Thr Pro Ser Val Leu
145                 150                 155                 160

Ile Phe Gly Pro Leu Pro Asn Ile Leu Asp Tyr Thr Ala Ser Leu Thr
                165                 170                 175

Leu Gln Gly Gln Gln Ser Asn Pro Ser Phe Glu Gly Phe Gly Thr Leu
                180                 185                 190

Ser Ile Leu Lys Val Ala Pro Glu Phe Leu Leu Thr Phe Ser Asp Val
                195                 200                 205

Thr Ser Asn Gln Ser Ser Ala Val Leu Gly Lys Ser Ile Phe Cys Met
                210                 215                 220

Asp Pro Val Ile Ala Leu Met His Glu Leu Thr His Ser Leu His Gln
225                 230                 235                 240

Leu Tyr Gly Ile Asn Ile Pro Ser Asp Lys Arg Ile Arg Pro Gln Val
                245                 250                 255

Ser Glu Gly Phe Phe Ser Gln Asp Gly Pro Asn Val Gln Phe Glu Glu
                260                 265                 270

Leu Tyr Thr Phe Gly Gly Leu Asp Val Glu Ile Ile Pro Gln Ile Glu
                275                 280                 285

Arg Ser Gln Leu Arg Glu Lys Ala Leu Gly His Tyr Lys Asp Ile Ala
                290                 295                 300

Lys Arg Leu Asn Asn Ile Asn Lys Thr Ile Pro Ser Ser Trp Ile Ser
305                 310                 315                 320

Asn Ile Asp Lys Tyr Lys Lys Ile Phe Ser Glu Lys Tyr Asn Phe Asp
                325                 330                 335

Lys Asp Asn Thr Gly Asn Phe Val Val Asn Ile Asp Lys Phe Asn Ser
                340                 345                 350

Leu Tyr Ser Asp Leu Thr Asn Val Met Ser Glu Val Val Tyr Ser Ser
                355                 360                 365

Gln Tyr Asn Val Lys Asn Arg Thr His Tyr Phe Ser Arg His Tyr Leu
                370                 375                 380

Pro Val Phe Ala Asn Ile Leu Asp Asp Asn Ile Tyr Thr Ile Arg Asp
385                 390                 395                 400

Gly Phe Asn Leu Thr Asn Lys Gly Phe Asn Ile Glu Asn Ser Gly Gln
                405                 410                 415

Asn Ile Glu Arg Asn Pro Ala Leu Gln Lys Leu Ser Ser Glu Ser Val
                420                 425                 430

Val Asp Leu Phe Thr Lys Val Cys Val Asp Gly Gly Gly Ser Ala
                435                 440                 445

Asp Asp Asp Asp Lys Gly Trp Thr Leu Asn Ser Ala Gly Tyr Leu Leu
450                 455                 460

Gly Pro His Ala Val Ala Leu Ala Gly Gly Gly Ser Gly Gly
465                 470                 475                 480

Gly Ser Gly Gly Gly Ser Ala Leu Val Leu Gln Cys Ile Lys Val
                485                 490                 495

Lys Asn Asn Arg Leu Pro Tyr Val Ala Asp Lys Asp Ser Ile Ser Gln
                500                 505                 510

Glu Ile Phe Glu Asn Lys Ile Ile Thr Asp Glu Thr Asn Val Gln Asn
                515                 520                 525
```

Tyr Ser Asp Lys Phe Ser Leu Asp Glu Ser Ile Leu Asp Gly Gln Val
530                 535                 540

Pro Ile Asn Pro Glu Ile Val Asp Pro Leu Leu Pro Asn Val Asn Met
545                 550                 555                 560

Glu Pro Leu Asn Leu Pro Gly Glu Glu Ile Val Phe Tyr Asp Asp Ile
                565                 570                 575

Thr Lys Tyr Val Asp Tyr Leu Asn Ser Tyr Tyr Leu Glu Ser Gln
            580                 585                 590

Lys Leu Ser Asn Asn Val Glu Asn Ile Thr Leu Thr Thr Ser Val Glu
        595                 600                 605

Glu Ala Leu Gly Tyr Ser Asn Lys Ile Tyr Thr Phe Leu Pro Ser Leu
    610                 615                 620

Ala Glu Lys Val Asn Lys Gly Val Gln Ala Gly Leu Phe Leu Asn Trp
625                 630                 635                 640

Ala Asn Glu Val Val Glu Asp Phe Thr Thr Asn Ile Met Lys Lys Asp
                645                 650                 655

Thr Leu Asp Lys Ile Ser Asp Val Ser Val Ile Pro Tyr Ile Gly
            660                 665                 670

Pro Ala Leu Asn Ile Gly Asn Ser Ala Leu Arg Gly Asn Phe Asn Gln
        675                 680                 685

Ala Phe Ala Thr Ala Gly Val Ala Phe Leu Leu Glu Gly Phe Pro Glu
    690                 695                 700

Phe Thr Ile Pro Ala Leu Gly Val Phe Thr Phe Tyr Ser Ser Ile Gln
705                 710                 715                 720

Glu Arg Glu Lys Ile Ile Lys Thr Ile Glu Asn Cys Leu Glu Gln Arg
                725                 730                 735

Val Lys Arg Trp Lys Asp Ser Tyr Gln Trp Met Val Ser Asn Trp Leu
            740                 745                 750

Ser Arg Ile Thr Thr Gln Phe Asn His Ile Asn Tyr Gln Met Tyr Asp
        755                 760                 765

Ser Leu Ser Tyr Gln Ala Asp Ala Ile Lys Ala Lys Ile Asp Leu Glu
    770                 775                 780

Tyr Lys Lys Tyr Ser Gly Ser Asp Lys Glu Asn Ile Lys Ser Gln Val
785                 790                 795                 800

Glu Asn Leu Lys Asn Ser Leu Asp Val Lys Ile Ser Glu Ala Met Asn
                805                 810                 815

Asn Ile Asn Lys Phe Ile Arg Glu Cys Ser Val Thr Tyr Leu Phe Lys
            820                 825                 830

Asn Met Leu Pro Lys Val Ile Asp Glu Leu Asn Lys Phe Asp Leu Arg
        835                 840                 845

Thr Lys Thr Glu Leu Ile Asn Leu Ile Asp Ser His Asn Ile Ile Leu
    850                 855                 860

Val Gly Glu Val Asp Arg Leu Lys Ala Lys Val Asn Glu Ser Phe Glu
865                 870                 875                 880

Asn Thr Met Pro Phe Asn Ile Phe Ser Tyr Thr Asn Asn Ser Leu Leu
                885                 890                 895

Lys Asp Ile Ile Asn Glu Tyr Phe Asn Leu Asp
            900                 905

<210> SEQ ID NO 30
<211> LENGTH: 2766
<212> TYPE: DNA
<213> ORGANISM: Artificial Sequence
<220> FEATURE:

<223> OTHER INFORMATION: Synthetic sequence

<400> SEQUENCE: 30

```
catatgggat ccatggagtt cgttaacaaa cagttcaact ataaagaccc agttaacggt      60
gttgacattg cttacatcaa atcccgaac gctggccaga tgcagccggt aaaggcattc      120
aaaatccaca acaaaatctg ggttatcccg aacgtgata cctttactaa cccggaagaa      180
ggtgacctga acccgccacc ggaagcgaaa caggtgccgg tatcttacta tgactccacc      240
tacctgtcta ccgataacga aaaggacaac tacctgaaag gtgttactaa actgttcgag      300
cgtatttact ccaccgacct gggccgtatg ctgctgacta gcatcgttcg cggtatcccg      360
ttctggggcg gttctaccat cgataccgaa ctgaaagtaa tcgacactaa ctgcatcaac      420
gttattcagc cggacggttc ctatcgttcc gaagaactga acctggtgat catcggcccg      480
tctgctgata tcatccagtt cgagtgtaag agctttggtc acgaagttct gaacctcacc      540
cgtaacggct acggttccac tcagtacatc cgtttctctc cggacttcac cttcggtttt      600
gaagaatccc tggaagtaga cacgaaccca ctgctgggcg ctggtaaatt cgcaactgat      660
cctgcggtta ccctggctca cgaactgatt catgcaggcc accgctgta cggtatcgcc      720
atcaatccga accgtgtctt caaagttaac accaacgcgt attacgagat gtccggtctg      780
gaagttagct tcgaagaact gcgtactttt ggcggtcacg acgctaaatt catcgactct      840
ctgcaagaaa acgagttccg tctgtactac tataacaagt caaagatat cgcatccacc      900
ctgaacaaag cgaaatccat cgtgggtacc actgcttctc tccagtacat gaagaacgtt      960
tttaaagaaa ataccctgct cagcgaagac acctccggca aattctctgt agacaagttg     1020
aaattcgata aactttacaa aatgctgact gaaatttaca ccgaagacaa cttcgttaag     1080
ttctttaaag ttctgaaccg caaaacctat ctgaacttcg acaaggcagt attcaaaatc     1140
aacatcgtgc cgaaagttaa ctacactatc tacgatggtt caacctgcg taacaccaac     1200
ctggctgcta attttaacgg ccagaacacg gaaatcaaca acatgaactt cacaaaactg     1260
aaaaacttca ctggtctgtt cgagttttac aagctgctgt gcgtcgacgg cggtggcggt     1320
agcgcagacg atgacgataa aggttggacc ctgaactctg ctggttacct gctgggtccg     1380
cacgctgttg cgctagcggc tgaagctgct gctaaagaag ctgctgctaa agaagctgct     1440
gctaaagctg gtggcggtgg ttccgcacta gtgctgcagt gtatcaaggt taacaactgg     1500
gatttattct tcagcccgag tgaagacaac ttcaccaacg acctgaacaa aggtgaagaa     1560
atccacctcag atactaacat cgaagcagcc gaagaaaaca tctcgctgga cctgatccag     1620
cagtactacc tgaccttaa tttcgacaac gagccggaaa acatttctat cgaaaacctg     1680
agctctgata tcatcggcca gctggaactg atgccgaaca tcgaacgttt cccaaacggt     1740
aaaaagtacg agctggacaa atataccatg ttccactacc tgcgcgcgca ggaatttgaa     1800
cacggcaaat cccgtatcgc actgactaac tccgttaacg aagctctgct caacccgtcc     1860
cgtgtataca ccttcttctc tagcgactac gtgaaaaagg tcaacaaagc gactgaagct     1920
gcaatgttct gggttgggt tgaacagctt gtttatgatt ttaccgacga cgtccgaa     1980
gtatctacta ccgacaaaat tgcggatatc actatcatca tcccgtacat cggtccggct     2040
ctgaacattg gcaacatgct gtacaaagac gacttcgttg gcgcactgat cttctccggt     2100
gcggtgatcc tgctggagtt catccccggaa atcgccatcc cggtactggg cacctttgct     2160
ctggtttctt acattgcaaa caaggttctg actgtacaaa ccatcgacaa cgcgctgagc     2220
aaacgtaacg aaaaatggga tgaagtttac aaatatatcg tgaccaactg gctggctaag     2280
```

```
gttaatactc agatcgacct catccgcaaa aaaatgaaag aagcactgga aaaccaggcg    2340
gaagctacca aggcaatcat taactaccag tacaaccagt acaccgagga agaaaaaaac    2400
aacatcaact tcaacatcga cgatctgtcc tctaaactga acgaatccat caacaaagct    2460
atgatcaaca tcaacaagtt cctgaaccag tgctctgtaa gctatctgat gaactccatg    2520
atcccgtacg gtgttaaacg tctggaggac ttcgatgcgt ctctgaaaga cgccctgctg    2580
aaatacattt acgacaaccg tggcactctg atcggtcagg ttgatcgtct gaaggacaaa    2640
gtgaacaata ccttatcgac cgacatccct tttcagctca gtaaatatgt cgataaccaa    2700
cgccttttgt ccactctaga agcactagcg agtgggcacc atcaccatca ccattaatga    2760
aagctt                                                             2766
```

<210> SEQ ID NO 31
<211> LENGTH: 917
<212> TYPE: PRT
<213> ORGANISM: Artificial Sequence
<220> FEATURE:
<223> OTHER INFORMATION: Synthetic sequence

<400> SEQUENCE: 31

```
Met Gly Ser Met Glu Phe Val Asn Lys Gln Phe Asn Tyr Lys Asp Pro
1               5                  10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270
```

```
Asp Ala Lys Phe Ile Asp Ser Leu Gln Glu Asn Glu Phe Arg Leu Tyr
            275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
        370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Gly Ser Ala Asp Asp Asp Lys Gly Trp
            435                 440                 445

Thr Leu Asn Ser Ala Gly Tyr Leu Leu Gly Pro His Ala Val Ala Leu
        450                 455                 460

Ala Ala Glu Ala Ala Ala Lys Glu Ala Ala Lys Glu Ala Ala Ala
465                 470                 475                 480

Lys Ala Gly Gly Gly Gly Ser Ala Leu Val Leu Gln Cys Ile Lys Val
                485                 490                 495

Asn Asn Trp Asp Leu Phe Phe Ser Pro Ser Glu Asp Asn Phe Thr Asn
            500                 505                 510

Asp Leu Asn Lys Gly Glu Glu Ile Thr Ser Asp Thr Asn Ile Glu Ala
        515                 520                 525

Ala Glu Glu Asn Ile Ser Leu Asp Leu Ile Gln Gln Tyr Tyr Leu Thr
        530                 535                 540

Phe Asn Phe Asp Asn Glu Pro Glu Asn Ile Ser Ile Glu Asn Leu Ser
545                 550                 555                 560

Ser Asp Ile Ile Gly Gln Leu Glu Leu Met Pro Asn Ile Glu Arg Phe
                565                 570                 575

Pro Asn Gly Lys Lys Tyr Glu Leu Asp Lys Tyr Thr Met Phe His Tyr
            580                 585                 590

Leu Arg Ala Gln Glu Phe Glu His Gly Lys Ser Arg Ile Ala Leu Thr
        595                 600                 605

Asn Ser Val Asn Glu Ala Leu Leu Asn Pro Ser Arg Val Tyr Thr Phe
        610                 615                 620

Phe Ser Ser Asp Tyr Val Lys Lys Val Asn Lys Ala Thr Glu Ala Ala
625                 630                 635                 640

Met Phe Leu Gly Trp Val Glu Gln Leu Val Tyr Asp Phe Thr Asp Glu
                645                 650                 655

Thr Ser Glu Val Ser Thr Thr Asp Lys Ile Ala Asp Ile Thr Ile Ile
            660                 665                 670

Ile Pro Tyr Ile Gly Pro Ala Leu Asn Ile Gly Asn Met Leu Tyr Lys
        675                 680                 685
```

-continued

```
Asp Asp Phe Val Gly Ala Leu Ile Phe Ser Gly Ala Val Ile Leu Leu
    690                 695                 700

Glu Phe Ile Pro Glu Ile Ala Ile Pro Val Leu Gly Thr Phe Ala Leu
705                 710                 715                 720

Val Ser Tyr Ile Ala Asn Lys Val Leu Thr Val Gln Thr Ile Asp Asn
                725                 730                 735

Ala Leu Ser Lys Arg Asn Glu Lys Trp Asp Glu Val Tyr Lys Tyr Ile
            740                 745                 750

Val Thr Asn Trp Leu Ala Lys Val Asn Thr Gln Ile Asp Leu Ile Arg
        755                 760                 765

Lys Lys Met Lys Glu Ala Leu Glu Asn Gln Ala Glu Ala Thr Lys Ala
770                 775                 780

Ile Ile Asn Tyr Gln Tyr Asn Gln Tyr Thr Glu Glu Lys Asn Asn
785                 790                 795                 800

Ile Asn Phe Asn Ile Asp Asp Leu Ser Ser Lys Leu Asn Glu Ser Ile
                805                 810                 815

Asn Lys Ala Met Ile Asn Ile Asn Lys Phe Leu Asn Gln Cys Ser Val
            820                 825                 830

Ser Tyr Leu Met Asn Ser Met Ile Pro Tyr Gly Val Lys Arg Leu Glu
        835                 840                 845

Asp Phe Asp Ala Ser Leu Lys Asp Ala Leu Leu Lys Tyr Ile Tyr Asp
850                 855                 860

Asn Arg Gly Thr Leu Ile Gly Gln Val Asp Arg Leu Lys Asp Lys Val
865                 870                 875                 880

Asn Asn Thr Leu Ser Thr Asp Ile Pro Phe Gln Leu Ser Lys Tyr Val
                885                 890                 895

Asp Asn Gln Arg Leu Leu Ser Thr Leu Glu Ala Leu Ala Ser Gly His
            900                 905                 910

His His His His His
        915

<210> SEQ ID NO 32
<211> LENGTH: 906
<212> TYPE: PRT
<213> ORGANISM: Artificial Sequence
<220> FEATURE:
<223> OTHER INFORMATION: Synthetic sequence

<400> SEQUENCE: 32

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
                20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
        50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125
```

```
Glu Leu Lys Val Ile Asp Thr Asn Cys Ile Asn Val Ile Gln Pro Asp
130                 135                 140

Gly Ser Tyr Arg Ser Glu Leu Asn Leu Val Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Ser Leu Glu Val Asp Thr Asn
                195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
            275                 280                 285

Tyr Tyr Asn Lys Phe Lys Asp Ile Ala Ser Thr Leu Asn Lys Ala Lys
290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
            355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Ala Asp Asp Asp Lys Gly Trp
            435                 440                 445

Thr Leu Asn Ser Ala Gly Tyr Leu Leu Gly Pro His Ala Val Ala Leu
450                 455                 460

Ala Ala Glu Ala Ala Lys Glu Ala Ala Lys Glu Ala Ala
465                 470                 475                 480

Lys Ala Gly Gly Gly Ser Ala Leu Val Leu Gln Cys Ile Lys Val
                485                 490                 495

Asn Asn Trp Asp Leu Phe Phe Ser Pro Ser Glu Asp Asn Phe Thr Asn
            500                 505                 510

Asp Leu Asn Lys Gly Glu Glu Ile Thr Ser Asp Thr Asn Ile Glu Ala
            515                 520                 525

Ala Glu Glu Asn Ile Ser Leu Asp Leu Ile Gln Gln Tyr Tyr Leu Thr
530                 535                 540

Phe Asn Phe Asp Asn Glu Pro Glu Asn Ile Ser Ile Glu Asn Leu Ser
```

```
            545                 550                 555                 560
Ser Asp Ile Ile Gly Gln Leu Glu Leu Met Pro Asn Ile Glu Arg Phe
                565                 570                 575

Pro Asn Gly Lys Lys Tyr Glu Leu Asp Lys Tyr Thr Met Phe His Tyr
                580                 585                 590

Leu Arg Ala Gln Glu Phe Glu His Gly Lys Ser Arg Ile Ala Leu Thr
                595                 600                 605

Asn Ser Val Asn Glu Ala Leu Leu Asn Pro Ser Arg Val Tyr Thr Phe
610                 615                 620

Phe Ser Ser Asp Tyr Val Lys Lys Val Asn Lys Ala Thr Glu Ala Ala
625                 630                 635                 640

Met Phe Leu Gly Trp Val Gln Leu Val Tyr Asp Phe Thr Asp Glu
                645                 650                 655

Thr Ser Glu Val Ser Thr Thr Asp Lys Ile Ala Asp Ile Thr Ile Ile
                660                 665                 670

Ile Pro Tyr Ile Gly Pro Ala Leu Asn Ile Gly Asn Met Leu Tyr Lys
                675                 680                 685

Asp Asp Phe Val Gly Ala Leu Ile Phe Ser Gly Ala Val Ile Leu Leu
                690                 695                 700

Glu Phe Ile Pro Glu Ile Ala Ile Pro Val Leu Gly Thr Phe Ala Leu
705                 710                 715                 720

Val Ser Tyr Ile Ala Asn Lys Val Leu Thr Val Gln Thr Ile Asp Asn
                725                 730                 735

Ala Leu Ser Lys Arg Asn Glu Lys Trp Asp Glu Val Tyr Lys Tyr Ile
                740                 745                 750

Val Thr Asn Trp Leu Ala Lys Val Asn Thr Gln Ile Asp Leu Ile Arg
                755                 760                 765

Lys Lys Met Lys Glu Ala Leu Glu Asn Gln Ala Glu Ala Thr Lys Ala
                770                 775                 780

Ile Ile Asn Tyr Gln Tyr Asn Gln Tyr Thr Glu Glu Lys Asn Asn
785                 790                 795                 800

Ile Asn Phe Asn Ile Asp Asp Leu Ser Ser Lys Leu Asn Glu Ser Ile
                805                 810                 815

Asn Lys Ala Met Ile Asn Ile Asn Lys Phe Leu Asn Gln Cys Ser Val
                820                 825                 830

Ser Tyr Leu Met Asn Ser Met Ile Pro Tyr Gly Val Lys Arg Leu Glu
                835                 840                 845

Asp Phe Asp Ala Ser Leu Lys Asp Ala Leu Leu Lys Tyr Ile Tyr Asp
                850                 855                 860

Asn Arg Gly Thr Leu Ile Gly Gln Val Asp Arg Leu Lys Asp Lys Val
865                 870                 875                 880

Asn Asn Thr Leu Ser Thr Asp Ile Pro Phe Gln Leu Ser Lys Tyr Val
                885                 890                 895

Asp Asn Gln Arg Leu Leu Ser Thr Leu Asp
                900                 905

<210> SEQ ID NO 33
<211> LENGTH: 915
<212> TYPE: PRT
<213> ORGANISM: Artificial Sequence
<220> FEATURE:
<223> OTHER INFORMATION: Synthetic sequence

<400> SEQUENCE: 33

Met Gly Ser Met Glu Phe Val Asn Lys Gln Phe Asn Tyr Lys Asp Pro
```

-continued

```
1               5                   10                  15
Val Asn Gly Val Asp Ile Ala Tyr Ile Lys Ile Pro Asn Ala Gly Gln
                20                  25                  30
Met Gln Pro Val Lys Ala Phe Lys Ile His Asn Lys Ile Trp Val Ile
                35                  40                  45
Pro Glu Arg Asp Thr Phe Thr Asn Pro Glu Gly Asp Leu Asn Pro
    50                  55                  60
Pro Pro Glu Ala Lys Gln Val Pro Val Ser Tyr Tyr Asp Ser Thr Tyr
65                  70                  75                  80
Leu Ser Thr Asp Asn Glu Lys Asp Asn Tyr Leu Lys Gly Val Thr Lys
                85                  90                  95
Leu Phe Glu Arg Ile Tyr Ser Thr Asp Leu Gly Arg Met Leu Leu Thr
                100                 105                 110
Ser Ile Val Arg Gly Ile Pro Phe Trp Gly Gly Ser Thr Ile Asp Thr
                115                 120                 125
Glu Leu Lys Val Ile Asp Thr Asn Cys Ile Asn Val Ile Gln Pro Asp
                130                 135                 140
Gly Ser Tyr Arg Ser Glu Glu Leu Asn Leu Val Ile Ile Gly Pro Ser
145                 150                 155                 160
Ala Asp Ile Ile Gln Phe Glu Cys Lys Ser Phe Gly His Glu Val Leu
                165                 170                 175
Asn Leu Thr Arg Asn Gly Tyr Gly Ser Thr Gln Tyr Ile Arg Phe Ser
                180                 185                 190
Pro Asp Phe Thr Phe Gly Phe Glu Glu Ser Leu Glu Val Asp Thr Asn
                195                 200                 205
Pro Leu Leu Gly Ala Gly Lys Phe Ala Thr Asp Pro Ala Val Thr Leu
    210                 215                 220
Ala His Glu Leu Ile His Ala Gly His Arg Leu Tyr Gly Ile Ala Ile
225                 230                 235                 240
Asn Pro Asn Arg Val Phe Lys Val Asn Thr Asn Ala Tyr Tyr Glu Met
                245                 250                 255
Ser Gly Leu Glu Val Ser Phe Glu Glu Leu Arg Thr Phe Gly Gly His
                260                 265                 270
Asp Ala Lys Phe Ile Asp Ser Leu Gln Glu Asn Glu Phe Arg Leu Tyr
                275                 280                 285
Tyr Tyr Asn Lys Phe Lys Asp Ile Ala Ser Thr Leu Asn Lys Ala Lys
                290                 295                 300
Ser Ile Val Gly Thr Thr Ala Ser Leu Gln Tyr Met Lys Asn Val Phe
305                 310                 315                 320
Lys Glu Lys Tyr Leu Leu Ser Glu Asp Thr Ser Gly Lys Phe Ser Val
                325                 330                 335
Asp Lys Leu Lys Phe Asp Lys Leu Tyr Lys Met Leu Thr Glu Ile Tyr
                340                 345                 350
Thr Glu Asp Asn Phe Val Lys Phe Phe Lys Val Leu Asn Arg Lys Thr
                355                 360                 365
Tyr Leu Asn Phe Asp Lys Ala Val Phe Lys Ile Asn Ile Val Pro Lys
                370                 375                 380
Val Asn Tyr Thr Ile Tyr Asp Gly Phe Asn Leu Arg Asn Thr Asn Leu
385                 390                 395                 400
Ala Ala Asn Phe Asn Gly Gln Asn Thr Glu Ile Asn Asn Met Asn Phe
                405                 410                 415
Thr Lys Leu Lys Asn Phe Thr Gly Leu Phe Glu Phe Tyr Lys Leu Leu
                420                 425                 430
```

```
Cys Val Asp Gly Gly Gly Ser Gly Gly Gly Ser Ala Asp Asp
        435                 440                 445

Asp Asp Lys Gly Trp Thr Leu Asn Ser Ala Gly Tyr Leu Leu Gly Pro
    450                 455                 460

His Ala Val Ala Leu Ala Gly Gly Gly Ser Gly Gly Gly Gly Ser
465                 470                 475                 480

Gly Gly Gly Gly Ser Ala Leu Val Leu Gln Cys Ile Lys Val Asn Asn
                485                 490                 495

Trp Asp Leu Phe Phe Ser Pro Ser Glu Asp Asn Phe Thr Asn Asp Leu
                500                 505                 510

Asn Lys Gly Glu Glu Ile Thr Ser Asp Thr Asn Ile Glu Ala Ala Glu
            515                 520                 525

Glu Asn Ile Ser Leu Asp Leu Ile Gln Gln Tyr Tyr Leu Thr Phe Asn
        530                 535                 540

Phe Asp Asn Glu Pro Glu Asn Ile Ser Ile Glu Asn Leu Ser Ser Asp
545                 550                 555                 560

Ile Ile Gly Gln Leu Glu Leu Met Pro Asn Ile Glu Arg Phe Pro Asn
                565                 570                 575

Gly Lys Lys Tyr Glu Leu Asp Lys Tyr Thr Met Phe His Tyr Leu Arg
                580                 585                 590

Ala Gln Glu Phe Glu His Gly Lys Ser Arg Ile Ala Leu Thr Asn Ser
        595                 600                 605

Val Asn Glu Ala Leu Leu Asn Pro Ser Arg Val Tyr Thr Phe Phe Ser
        610                 615                 620

Ser Asp Tyr Val Lys Lys Val Asn Lys Ala Thr Glu Ala Ala Met Phe
625                 630                 635                 640

Leu Gly Trp Val Glu Gln Leu Val Tyr Asp Phe Thr Asp Glu Thr Ser
                645                 650                 655

Glu Val Ser Thr Thr Asp Lys Ile Ala Asp Ile Thr Ile Ile Pro
                660                 665                 670

Tyr Ile Gly Pro Ala Leu Asn Ile Gly Asn Met Leu Tyr Lys Asp Asp
                675                 680                 685

Phe Val Gly Ala Leu Ile Phe Ser Gly Ala Val Ile Leu Leu Glu Phe
                690                 695                 700

Ile Pro Glu Ile Ala Ile Pro Val Leu Gly Thr Phe Ala Leu Val Ser
705                 710                 715                 720

Tyr Ile Ala Asn Lys Val Leu Thr Val Gln Thr Ile Asp Asn Ala Leu
                725                 730                 735

Ser Lys Arg Asn Glu Lys Trp Asp Glu Val Tyr Lys Tyr Ile Val Thr
                740                 745                 750

Asn Trp Leu Ala Lys Val Asn Thr Gln Ile Asp Leu Ile Arg Lys Lys
                755                 760                 765

Met Lys Glu Ala Leu Glu Asn Gln Ala Glu Ala Thr Lys Ala Ile Ile
    770                 775                 780

Asn Tyr Gln Tyr Asn Gln Tyr Thr Glu Glu Lys Asn Asn Ile Asn
785                 790                 795                 800

Phe Asn Ile Asp Asp Leu Ser Ser Lys Leu Asn Glu Ser Ile Asn Lys
                805                 810                 815

Ala Met Ile Asn Ile Asn Lys Phe Leu Asn Gln Cys Ser Val Ser Tyr
                820                 825                 830

Leu Met Asn Ser Met Ile Pro Tyr Gly Val Lys Arg Leu Glu Asp Phe
                835                 840                 845
```

```
Asp Ala Ser Leu Lys Asp Ala Leu Leu Lys Tyr Ile Tyr Asp Asn Arg
    850                 855                 860

Gly Thr Leu Ile Gly Gln Val Asp Arg Leu Lys Asp Lys Val Asn Asn
865                 870                 875                 880

Thr Leu Ser Thr Asp Ile Pro Phe Gln Leu Ser Lys Tyr Val Asp Asn
                885                 890                 895

Gln Arg Leu Leu Ser Thr Leu Glu Ala Leu Ala Ser Gly His His His
                900                 905                 910

His His His
        915

<210> SEQ ID NO 34
<211> LENGTH: 904
<212> TYPE: PRT
<213> ORGANISM: Artificial Sequence
<220> FEATURE:
<223> OTHER INFORMATION: Synthetic sequence

<400> SEQUENCE: 34

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285
```

```
Tyr Tyr Asn Lys Phe Lys Asp Ile Ala Ser Thr Leu Asn Lys Ala Lys
        290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                    325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Lys Val Leu Asn Arg Lys Thr
        355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Ala Asp Asp
            435                 440                 445

Asp Asp Lys Gly Trp Thr Leu Asn Ser Ala Gly Tyr Leu Leu Gly Pro
450                 455                 460

His Ala Val Ala Leu Ala Gly Gly Gly Gly Ser Gly Gly Gly Gly Ser
465                 470                 475                 480

Gly Gly Gly Gly Ser Ala Leu Val Leu Gln Cys Ile Lys Val Asn Asn
                485                 490                 495

Trp Asp Leu Phe Phe Ser Pro Ser Glu Asp Asn Phe Thr Asn Asp Leu
            500                 505                 510

Asn Lys Gly Glu Glu Ile Thr Ser Asp Thr Asn Ile Glu Ala Ala Glu
            515                 520                 525

Glu Asn Ile Ser Leu Asp Leu Ile Gln Gln Tyr Leu Thr Phe Asn
        530                 535                 540

Phe Asp Asn Glu Pro Glu Asn Ile Ser Ile Glu Asn Leu Ser Ser Asp
545                 550                 555                 560

Ile Ile Gly Gln Leu Glu Leu Met Pro Asn Ile Glu Arg Phe Pro Asn
                565                 570                 575

Gly Lys Lys Tyr Glu Leu Asp Lys Tyr Thr Met Phe His Tyr Leu Arg
            580                 585                 590

Ala Gln Glu Phe Glu His Gly Lys Ser Arg Ile Ala Leu Thr Asn Ser
        595                 600                 605

Val Asn Glu Ala Leu Leu Asn Pro Ser Arg Val Tyr Thr Phe Phe Ser
610                 615                 620

Ser Asp Tyr Val Lys Lys Val Asn Lys Ala Thr Glu Ala Ala Met Phe
625                 630                 635                 640

Leu Gly Trp Val Glu Gln Leu Val Tyr Asp Phe Thr Asp Glu Thr Ser
                645                 650                 655

Glu Val Ser Thr Thr Asp Lys Ile Ala Asp Ile Thr Ile Ile Pro
            660                 665                 670

Tyr Ile Gly Pro Ala Leu Asn Ile Gly Asn Met Leu Tyr Lys Asp Asp
            675                 680                 685

Phe Val Gly Ala Leu Ile Phe Ser Gly Ala Val Ile Leu Leu Glu Phe
690                 695                 700

Ile Pro Glu Ile Ala Ile Pro Val Leu Gly Thr Phe Ala Leu Val Ser
```

```
                705                 710                 715                 720

Tyr Ile Ala Asn Lys Val Leu Thr Val Gln Thr Ile Asp Asn Ala Leu
                        725                 730                 735

Ser Lys Arg Asn Glu Lys Trp Asp Glu Val Tyr Lys Tyr Ile Val Thr
                        740                 745                 750

Asn Trp Leu Ala Lys Val Asn Thr Gln Ile Asp Leu Ile Arg Lys Lys
                        755                 760                 765

Met Lys Glu Ala Leu Glu Asn Gln Ala Glu Ala Thr Lys Ala Ile Ile
                        770                 775                 780

Asn Tyr Gln Tyr Asn Gln Tyr Thr Glu Glu Lys Asn Asn Ile Asn
        785                 790                 795                 800

Phe Asn Ile Asp Asp Leu Ser Ser Lys Leu Asn Glu Ser Ile Asn Lys
                        805                 810                 815

Ala Met Ile Asn Ile Asn Lys Phe Leu Asn Gln Cys Ser Val Ser Tyr
                        820                 825                 830

Leu Met Asn Ser Met Ile Pro Tyr Gly Val Lys Arg Leu Glu Asp Phe
                        835                 840                 845

Asp Ala Ser Leu Lys Asp Ala Leu Leu Lys Tyr Ile Tyr Asp Asn Arg
                        850                 855                 860

Gly Thr Leu Ile Gly Gln Val Asp Arg Leu Lys Asp Lys Val Asn Asn
        865                 870                 875                 880

Thr Leu Ser Thr Asp Ile Pro Phe Gln Leu Ser Lys Tyr Val Asp Asn
                        885                 890                 895

Gln Arg Leu Leu Ser Thr Leu Asp
                        900

<210> SEQ ID NO 35
<211> LENGTH: 905
<212> TYPE: PRT
<213> ORGANISM: Artificial Sequence
<220> FEATURE:
<223> OTHER INFORMATION: Synthetic sequence

<400> SEQUENCE: 35

Met Gly Ser Met Glu Phe Val Asn Lys Gln Phe Asn Tyr Lys Asp Pro
        1               5                   10                  15

Val Asn Gly Val Asp Ile Ala Tyr Ile Lys Ile Pro Asn Ala Gly Gln
                        20                  25                  30

Met Gln Pro Val Lys Ala Phe Lys Ile His Asn Lys Ile Trp Val Ile
                        35                  40                  45

Pro Glu Arg Asp Thr Phe Thr Asn Pro Glu Glu Gly Asp Leu Asn Pro
                        50                  55                  60

Pro Pro Glu Ala Lys Gln Val Pro Val Ser Tyr Tyr Asp Ser Thr Tyr
        65                  70                  75                  80

Leu Ser Thr Asp Asn Glu Lys Asp Asn Tyr Leu Lys Gly Val Thr Lys
                        85                  90                  95

Leu Phe Glu Arg Ile Tyr Ser Thr Asp Leu Gly Arg Met Leu Leu Thr
                        100                 105                 110

Ser Ile Val Arg Gly Ile Pro Phe Trp Gly Gly Ser Thr Ile Asp Thr
                        115                 120                 125

Glu Leu Lys Val Ile Asp Thr Asn Cys Ile Asn Val Ile Gln Pro Asp
                        130                 135                 140

Gly Ser Tyr Arg Ser Glu Glu Leu Asn Leu Val Ile Ile Gly Pro Ser
        145                 150                 155                 160

Ala Asp Ile Ile Gln Phe Glu Cys Lys Ser Phe Gly His Glu Val Leu
```

```
              165                 170                 175
Asn Leu Thr Arg Asn Gly Tyr Gly Ser Thr Gln Tyr Ile Arg Phe Ser
            180                 185                 190
Pro Asp Phe Thr Phe Gly Phe Glu Glu Ser Leu Glu Val Asp Thr Asn
            195                 200                 205
Pro Leu Leu Gly Ala Gly Lys Phe Ala Thr Asp Pro Ala Val Thr Leu
210                 215                 220
Ala His Glu Leu Ile His Ala Gly His Arg Leu Tyr Gly Ile Ala Ile
225                 230                 235                 240
Asn Pro Asn Arg Val Phe Lys Val Asn Thr Asn Ala Tyr Tyr Glu Met
                245                 250                 255
Ser Gly Leu Glu Val Ser Phe Glu Glu Leu Arg Thr Phe Gly Gly His
                260                 265                 270
Asp Ala Lys Phe Ile Asp Ser Leu Gln Glu Asn Glu Phe Arg Leu Tyr
                275                 280                 285
Tyr Tyr Asn Lys Phe Lys Asp Ile Ala Ser Thr Leu Asn Lys Ala Lys
            290                 295                 300
Ser Ile Val Gly Thr Thr Ala Ser Leu Gln Tyr Met Lys Asn Val Phe
305                 310                 315                 320
Lys Glu Lys Tyr Leu Leu Ser Glu Asp Thr Ser Gly Lys Phe Ser Val
                325                 330                 335
Asp Lys Leu Lys Phe Asp Lys Leu Tyr Lys Met Leu Thr Glu Ile Tyr
                340                 345                 350
Thr Glu Asp Asn Phe Val Lys Phe Phe Lys Val Leu Asn Arg Lys Thr
            355                 360                 365
Tyr Leu Asn Phe Asp Lys Ala Val Phe Lys Ile Asn Ile Val Pro Lys
            370                 375                 380
Val Asn Tyr Thr Ile Tyr Asp Gly Phe Asn Leu Arg Asn Thr Asn Leu
385                 390                 395                 400
Ala Ala Asn Phe Asn Gly Gln Asn Thr Glu Ile Asn Asn Met Asn Phe
                405                 410                 415
Thr Lys Leu Lys Asn Phe Thr Gly Leu Phe Glu Phe Tyr Lys Leu Leu
                420                 425                 430
Cys Val Asp Gly Gly Gly Ser Ala Asp Asp Asp Lys Gly Trp
                435                 440                 445
Thr Leu Asn Ser Ala Gly Tyr Leu Leu Gly Pro His Ala Val Ala Leu
            450                 455                 460
Ala Gly Gly Gly Ser Gly Gly Gly Ser Ala Leu Val Leu Gln
465                 470                 475                 480
Cys Ile Lys Val Asn Asn Trp Asp Leu Phe Phe Ser Pro Ser Glu Asp
                485                 490                 495
Asn Phe Thr Asn Asp Leu Asn Lys Gly Glu Glu Ile Thr Ser Asp Thr
                500                 505                 510
Asn Ile Glu Ala Ala Glu Glu Asn Ile Ser Leu Asp Leu Ile Gln Gln
            515                 520                 525
Tyr Tyr Leu Thr Phe Asn Phe Asp Asn Glu Pro Glu Asn Ile Ser Ile
            530                 535                 540
Glu Asn Leu Ser Ser Asp Ile Ile Gly Gln Leu Glu Leu Met Pro Asn
545                 550                 555                 560
Ile Glu Arg Phe Pro Asn Gly Lys Lys Tyr Glu Leu Asp Lys Tyr Thr
                565                 570                 575
Met Phe His Tyr Leu Arg Ala Gln Glu Phe Glu His Gly Lys Ser Arg
                580                 585                 590
```

Ile Ala Leu Thr Asn Ser Val Asn Glu Ala Leu Leu Asn Pro Ser Arg
                595                 600                 605

Val Tyr Thr Phe Phe Ser Ser Asp Tyr Val Lys Lys Val Asn Lys Ala
            610                 615                 620

Thr Glu Ala Ala Met Phe Leu Gly Trp Val Glu Gln Leu Val Tyr Asp
625                 630                 635                 640

Phe Thr Asp Glu Thr Ser Glu Val Ser Thr Thr Asp Lys Ile Ala Asp
                645                 650                 655

Ile Thr Ile Ile Ile Pro Tyr Ile Gly Pro Ala Leu Asn Ile Gly Asn
            660                 665                 670

Met Leu Tyr Lys Asp Asp Phe Val Gly Ala Leu Ile Phe Ser Gly Ala
            675                 680                 685

Val Ile Leu Leu Glu Phe Ile Pro Glu Ile Ala Ile Pro Val Leu Gly
            690                 695                 700

Thr Phe Ala Leu Val Ser Tyr Ile Ala Asn Lys Val Leu Thr Val Gln
705                 710                 715                 720

Thr Ile Asp Asn Ala Leu Ser Lys Arg Asn Glu Lys Trp Asp Glu Val
                725                 730                 735

Tyr Lys Tyr Ile Val Thr Asn Trp Leu Ala Lys Val Asn Thr Gln Ile
            740                 745                 750

Asp Leu Ile Arg Lys Lys Met Lys Glu Ala Leu Glu Asn Gln Ala Glu
            755                 760                 765

Ala Thr Lys Ala Ile Ile Asn Tyr Gln Tyr Asn Gln Tyr Thr Glu Glu
770                 775                 780

Glu Lys Asn Asn Ile Asn Phe Asn Ile Asp Asp Leu Ser Ser Lys Leu
785                 790                 795                 800

Asn Glu Ser Ile Asn Lys Ala Met Ile Asn Ile Asn Lys Phe Leu Asn
                805                 810                 815

Gln Cys Ser Val Ser Tyr Leu Met Asn Ser Met Ile Pro Tyr Gly Val
            820                 825                 830

Lys Arg Leu Glu Asp Phe Asp Ala Ser Leu Lys Asp Ala Leu Leu Lys
            835                 840                 845

Tyr Ile Tyr Asp Asn Arg Gly Thr Leu Ile Gly Gln Val Asp Arg Leu
850                 855                 860

Lys Asp Lys Val Asn Asn Thr Leu Ser Thr Asp Ile Pro Phe Gln Leu
865                 870                 875                 880

Ser Lys Tyr Val Asp Asn Gln Arg Leu Leu Ser Thr Leu Glu Ala Leu
                885                 890                 895

Ala Ser Gly His His His His His
            900                 905

<210> SEQ ID NO 36
<211> LENGTH: 894
<212> TYPE: PRT
<213> ORGANISM: Artificial Sequence
<220> FEATURE:
<223> OTHER INFORMATION: Synthetic sequence

<400> SEQUENCE: 36

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

```
Pro Glu Arg Asp Thr Phe Thr Asn Pro Glu Glu Gly Asp Leu Asn Pro
 50                  55                  60

Pro Pro Glu Ala Lys Gln Val Pro Val Ser Tyr Tyr Asp Ser Thr Tyr
 65                  70                  75                  80

Leu Ser Thr Asp Asn Glu Lys Asp Asn Tyr Leu Lys Gly Val Thr Lys
                     85                  90                  95

Leu Phe Glu Arg Ile Tyr Ser Thr Asp Leu Gly Arg Met Leu Leu Thr
                100                 105                 110

Ser Ile Val Arg Gly Ile Pro Phe Trp Gly Ser Thr Ile Asp Thr
            115                 120                 125

Glu Leu Lys Val Ile Asp Thr Asn Cys Ile Asn Val Ile Gln Pro Asp
        130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Ala Asp Asp Asp Lys Gly Trp
        435                 440                 445

Thr Leu Asn Ser Ala Gly Tyr Leu Leu Gly Pro His Ala Val Ala Leu
    450                 455                 460
```

```
Ala Gly Gly Gly Gly Ser Gly Gly Gly Ser Ala Leu Val Leu Gln
465                 470                 475                 480

Cys Ile Lys Val Asn Asn Trp Asp Leu Phe Phe Ser Pro Ser Glu Asp
            485                 490                 495

Asn Phe Thr Asn Asp Leu Asn Lys Gly Glu Glu Ile Thr Ser Asp Thr
                500                 505                 510

Asn Ile Glu Ala Ala Glu Asn Ile Ser Leu Asp Leu Ile Gln Gln
            515                 520                 525

Tyr Tyr Leu Thr Phe Asn Phe Asp Asn Glu Pro Asn Ile Ser Ile
530                 535                 540

Glu Asn Leu Ser Ser Asp Ile Ile Gly Gln Leu Glu Leu Met Pro Asn
545                 550                 555                 560

Ile Glu Arg Phe Pro Asn Gly Lys Lys Tyr Glu Leu Asp Lys Tyr Thr
                565                 570                 575

Met Phe His Tyr Leu Arg Ala Gln Glu Phe Glu His Gly Lys Ser Arg
                580                 585                 590

Ile Ala Leu Thr Asn Ser Val Asn Glu Ala Leu Leu Asn Pro Ser Arg
            595                 600                 605

Val Tyr Thr Phe Phe Ser Ser Asp Tyr Val Lys Lys Val Asn Lys Ala
        610                 615                 620

Thr Glu Ala Ala Met Phe Leu Gly Trp Val Glu Gln Leu Val Tyr Asp
625                 630                 635                 640

Phe Thr Asp Glu Thr Ser Glu Val Ser Thr Asp Lys Ile Ala Asp
                645                 650                 655

Ile Thr Ile Ile Ile Pro Tyr Ile Gly Pro Ala Leu Asn Ile Gly Asn
            660                 665                 670

Met Leu Tyr Lys Asp Asp Phe Val Gly Ala Leu Ile Phe Ser Gly Ala
            675                 680                 685

Val Ile Leu Leu Glu Phe Ile Pro Glu Ile Ala Ile Pro Val Leu Gly
        690                 695                 700

Thr Phe Ala Leu Val Ser Tyr Ile Ala Asn Lys Val Leu Thr Val Gln
705                 710                 715                 720

Thr Ile Asp Asn Ala Leu Ser Lys Arg Asn Glu Lys Trp Asp Glu Val
            725                 730                 735

Tyr Lys Tyr Ile Val Thr Asn Trp Leu Ala Lys Val Asn Thr Gln Ile
            740                 745                 750

Asp Leu Ile Arg Lys Lys Met Lys Glu Ala Leu Glu Asn Gln Ala Glu
            755                 760                 765

Ala Thr Lys Ala Ile Ile Asn Tyr Gln Tyr Asn Gln Tyr Thr Glu Glu
770                 775                 780

Glu Lys Asn Asn Ile Asn Phe Asn Ile Asp Asp Leu Ser Ser Lys Leu
785                 790                 795                 800

Asn Glu Ser Ile Asn Lys Ala Met Ile Asn Ile Asn Lys Phe Leu Asn
                805                 810                 815

Gln Cys Ser Val Ser Tyr Leu Met Asn Ser Met Ile Pro Tyr Gly Val
                820                 825                 830

Lys Arg Leu Glu Asp Phe Asp Ala Ser Leu Lys Asp Ala Leu Leu Lys
                835                 840                 845

Tyr Ile Tyr Asp Asn Arg Gly Thr Leu Ile Gly Gln Val Asp Arg Leu
            850                 855                 860

Lys Asp Lys Val Asn Asn Thr Leu Ser Thr Asp Ile Pro Phe Gln Leu
865                 870                 875                 880

Ser Lys Tyr Val Asp Asn Gln Arg Leu Leu Ser Thr Leu Asp
```

885                 890

<210> SEQ ID NO 37
<211> LENGTH: 900
<212> TYPE: PRT
<213> ORGANISM: Artificial Sequence
<220> FEATURE:
<223> OTHER INFORMATION: Synthetic sequence

<400> SEQUENCE: 37

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr

```
            355                 360                 365
Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
                420                 425                 430

Cys Val Asp Gly Gly Gly Ser Ala Asp Asp Asp Lys Gly Trp
                435                 440                 445

Thr Leu Asn Ser Ala Gly Tyr Leu Leu Gly Pro His Ala Val Ala Leu
                450                 455                 460

Ala Gly Gly Gly Ser Ala Leu Val Leu Gln Cys Ile Lys Val Asn
465                 470                 475                 480

Asn Trp Asp Leu Phe Phe Ser Pro Ser Glu Asp Asn Phe Thr Asn Asp
                485                 490                 495

Leu Asn Lys Gly Glu Glu Ile Thr Ser Asp Thr Asn Ile Glu Ala Ala
                500                 505                 510

Glu Glu Asn Ile Ser Leu Asp Leu Ile Gln Gln Tyr Tyr Leu Thr Phe
                515                 520                 525

Asn Phe Asp Asn Glu Pro Glu Asn Ile Ser Ile Glu Asn Leu Ser Ser
530                 535                 540

Asp Ile Ile Gly Gln Leu Glu Leu Met Pro Asn Ile Glu Arg Phe Pro
545                 550                 555                 560

Asn Gly Lys Lys Tyr Glu Leu Asp Lys Tyr Thr Met Phe His Tyr Leu
                565                 570                 575

Arg Ala Gln Glu Phe Glu His Gly Lys Ser Arg Ile Ala Leu Thr Asn
                580                 585                 590

Ser Val Asn Glu Ala Leu Leu Asn Pro Ser Arg Val Tyr Thr Phe Phe
                595                 600                 605

Ser Ser Asp Tyr Val Lys Lys Val Asn Lys Ala Thr Glu Ala Ala Met
610                 615                 620

Phe Leu Gly Trp Val Glu Gln Leu Val Tyr Asp Phe Thr Asp Glu Thr
625                 630                 635                 640

Ser Glu Val Ser Thr Thr Asp Lys Ile Ala Asp Ile Thr Ile Ile Ile
                645                 650                 655

Pro Tyr Ile Gly Pro Ala Leu Asn Ile Gly Asn Met Leu Tyr Lys Asp
                660                 665                 670

Asp Phe Val Gly Ala Leu Ile Phe Ser Gly Ala Val Ile Leu Leu Glu
                675                 680                 685

Phe Ile Pro Glu Ile Ala Ile Pro Val Leu Gly Thr Phe Ala Leu Val
                690                 695                 700

Ser Tyr Ile Ala Asn Lys Val Leu Thr Val Gln Thr Ile Asp Asn Ala
705                 710                 715                 720

Leu Ser Lys Arg Asn Glu Lys Trp Asp Glu Val Tyr Lys Tyr Ile Val
                725                 730                 735

Thr Asn Trp Leu Ala Lys Val Asn Thr Gln Ile Asp Leu Ile Arg Lys
                740                 745                 750

Lys Met Lys Glu Ala Leu Glu Asn Gln Ala Glu Ala Thr Lys Ala Ile
                755                 760                 765

Ile Asn Tyr Gln Tyr Asn Gln Tyr Thr Glu Glu Lys Asn Asn Ile
                770                 775                 780
```

```
Asn Phe Asn Ile Asp Asp Leu Ser Ser Lys Leu Asn Glu Ser Ile Asn
785                 790                 795                 800

Lys Ala Met Ile Asn Ile Asn Lys Phe Leu Asn Gln Cys Ser Val Ser
            805                 810                 815

Tyr Leu Met Asn Ser Met Ile Pro Tyr Gly Val Lys Arg Leu Glu Asp
        820                 825                 830

Phe Asp Ala Ser Leu Lys Asp Ala Leu Leu Lys Tyr Ile Tyr Asp Asn
                835                 840                 845

Arg Gly Thr Leu Ile Gly Gln Val Asp Arg Leu Lys Asp Lys Val Asn
    850                 855                 860

Asn Thr Leu Ser Thr Asp Ile Pro Phe Gln Leu Ser Lys Tyr Val Asp
865                 870                 875                 880

Asn Gln Arg Leu Leu Ser Thr Leu Glu Ala Leu Ala Ser Gly His His
                885                 890                 895

His His His His
            900

<210> SEQ ID NO 38
<211> LENGTH: 889
<212> TYPE: PRT
<213> ORGANISM: Artificial Sequence
<220> FEATURE:
<223> OTHER INFORMATION: Synthetic sequence

<400> SEQUENCE: 38

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240
```

-continued

Asn Pro Asn Arg Val Phe Lys Val Asn Thr Asn Ala Tyr Tyr Glu Met
            245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
            275                 280                 285

Tyr Tyr Asn Lys Phe Lys Asp Ile Ala Ser Thr Leu Asn Lys Ala Lys
            290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
            325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
            355                 360                 365

Tyr Leu Asn Phe Asp Lys Ala Val Phe Lys Ile Asn Ile Val Pro Lys
            370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
            405                 410                 415

Thr Lys Leu Lys Asn Phe Thr Gly Leu Phe Glu Phe Tyr Lys Leu Leu
            420                 425                 430

Cys Val Asp Gly Gly Gly Ser Ala Asp Asp Asp Lys Gly Trp
            435                 440                 445

Thr Leu Asn Ser Ala Gly Tyr Leu Leu Gly Pro His Ala Val Ala Leu
            450                 455                 460

Ala Gly Gly Gly Gly Ser Ala Leu Val Leu Gln Cys Ile Lys Val Asn
465                 470                 475                 480

Asn Trp Asp Leu Phe Phe Ser Pro Ser Glu Asp Asn Phe Thr Asn Asp
            485                 490                 495

Leu Asn Lys Gly Glu Glu Ile Thr Ser Asp Thr Asn Ile Glu Ala Ala
            500                 505                 510

Glu Glu Asn Ile Ser Leu Asp Leu Ile Gln Gln Tyr Tyr Leu Thr Phe
            515                 520                 525

Asn Phe Asp Asn Glu Pro Glu Asn Ile Ser Ile Glu Asn Leu Ser Ser
            530                 535                 540

Asp Ile Ile Gly Gln Leu Glu Leu Met Pro Asn Ile Glu Arg Phe Pro
545                 550                 555                 560

Asn Gly Lys Lys Tyr Glu Leu Asp Lys Tyr Thr Met Phe His Tyr Leu
            565                 570                 575

Arg Ala Gln Glu Phe Glu His Gly Lys Ser Arg Ile Ala Leu Thr Asn
            580                 585                 590

Ser Val Asn Glu Ala Leu Leu Asn Pro Ser Arg Val Tyr Thr Phe Phe
            595                 600                 605

Ser Ser Asp Tyr Val Lys Lys Val Asn Lys Ala Thr Glu Ala Ala Met
            610                 615                 620

Phe Leu Gly Trp Val Glu Gln Leu Val Tyr Asp Phe Thr Asp Glu Thr
625                 630                 635                 640

Ser Glu Val Ser Thr Thr Asp Lys Ile Ala Asp Ile Thr Ile Ile Ile
            645                 650                 655

Pro Tyr Ile Gly Pro Ala Leu Asn Ile Gly Asn Met Leu Tyr Lys Asp
            660                 665                 670

Asp Phe Val Gly Ala Leu Ile Phe Ser Gly Ala Val Ile Leu Leu Glu
        675                 680                 685

Phe Ile Pro Glu Ile Ala Ile Pro Val Leu Gly Thr Phe Ala Leu Val
    690                 695                 700

Ser Tyr Ile Ala Asn Lys Val Leu Thr Val Gln Thr Ile Asp Asn Ala
705                 710                 715                 720

Leu Ser Lys Arg Asn Glu Lys Trp Asp Glu Val Tyr Lys Tyr Ile Val
                725                 730                 735

Thr Asn Trp Leu Ala Lys Val Asn Thr Gln Ile Asp Leu Ile Arg Lys
            740                 745                 750

Lys Met Lys Glu Ala Leu Glu Asn Gln Ala Glu Ala Thr Lys Ala Ile
        755                 760                 765

Ile Asn Tyr Gln Tyr Asn Gln Tyr Thr Glu Glu Lys Asn Asn Ile
    770                 775                 780

Asn Phe Asn Ile Asp Asp Leu Ser Ser Lys Leu Asn Glu Ser Ile Asn
785                 790                 795                 800

Lys Ala Met Ile Asn Ile Asn Lys Phe Leu Asn Gln Cys Ser Val Ser
                805                 810                 815

Tyr Leu Met Asn Ser Met Ile Pro Tyr Gly Val Lys Arg Leu Glu Asp
            820                 825                 830

Phe Asp Ala Ser Leu Lys Asp Ala Leu Leu Lys Tyr Ile Tyr Asp Asn
        835                 840                 845

Arg Gly Thr Leu Ile Gly Gln Val Asp Arg Leu Lys Asp Lys Val Asn
    850                 855                 860

Asn Thr Leu Ser Thr Asp Ile Pro Phe Gln Leu Ser Lys Tyr Val Asp
865                 870                 875                 880

Asn Gln Arg Leu Leu Ser Thr Leu Asp
                885

<210> SEQ ID NO 39
<211> LENGTH: 927
<212> TYPE: PRT
<213> ORGANISM: Artificial Sequence
<220> FEATURE:
<223> OTHER INFORMATION: Synthetic sequence

<400> SEQUENCE: 39

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
                20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
        50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

```
Glu Leu Lys Val Ile Asp Thr Asn Cys Ile Asn Val Ile Gln Pro Asp
130                 135                 140

Gly Ser Tyr Arg Ser Glu Leu Asn Leu Val Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Ser Leu Glu Val Asp Thr Asn
        195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
            275                 280                 285

Tyr Tyr Asn Lys Phe Lys Asp Ile Ala Ser Thr Leu Asn Lys Ala Lys
290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Gly Gly Gly
            435                 440                 445

Gly Ser Ala Asp Asp Asp Lys Gly Trp Thr Leu Asn Ser Ala Gly
450                 455                 460

Tyr Leu Leu Gly Pro His Ala Val Ala Leu Ala Ala Glu Ala Ala
465                 470                 475                 480

Lys Glu Ala Ala Ala Lys Glu Ala Ala Lys Ala Gly Gly Gly
                485                 490                 495

Ser Ala Leu Val Leu Gln Cys Ile Lys Val Asn Asn Trp Asp Leu Phe
            500                 505                 510

Phe Ser Pro Ser Glu Asp Asn Phe Thr Asn Asp Leu Asn Lys Gly Glu
            515                 520                 525

Glu Ile Thr Ser Asp Thr Asn Ile Glu Ala Ala Glu Asn Ile Ser
            530                 535                 540

Leu Asp Leu Ile Gln Gln Tyr Tyr Leu Thr Phe Asn Phe Asp Asn Glu
```

```
              545                 550                 555                 560
Pro Glu Asn Ile Ser Ile Glu Asn Leu Ser Ser Asp Ile Ile Gly Gln
                565                 570                 575

Leu Glu Leu Met Pro Asn Ile Glu Arg Phe Pro Asn Gly Lys Lys Tyr
                580                 585                 590

Glu Leu Asp Lys Tyr Thr Met Phe His Tyr Leu Arg Ala Gln Glu Phe
                595                 600                 605

Glu His Gly Lys Ser Arg Ile Ala Leu Thr Asn Ser Val Asn Glu Ala
                610                 615                 620

Leu Leu Asn Pro Ser Arg Val Tyr Thr Phe Phe Ser Ser Asp Tyr Val
625                 630                 635                 640

Lys Lys Val Asn Lys Ala Thr Glu Ala Ala Met Phe Leu Gly Trp Val
                645                 650                 655

Glu Gln Leu Val Tyr Asp Phe Thr Asp Glu Thr Ser Glu Val Ser Thr
                660                 665                 670

Thr Asp Lys Ile Ala Asp Ile Thr Ile Ile Pro Tyr Ile Gly Pro
                675                 680                 685

Ala Leu Asn Ile Gly Asn Met Leu Tyr Lys Asp Asp Phe Val Gly Ala
                690                 695                 700

Leu Ile Phe Ser Gly Ala Val Ile Leu Leu Glu Phe Ile Pro Glu Ile
705                 710                 715                 720

Ala Ile Pro Val Leu Gly Thr Phe Ala Leu Val Ser Tyr Ile Ala Asn
                725                 730                 735

Lys Val Leu Thr Val Gln Thr Ile Asp Asn Ala Leu Ser Lys Arg Asn
                740                 745                 750

Glu Lys Trp Asp Glu Val Tyr Lys Tyr Ile Val Thr Asn Trp Leu Ala
                755                 760                 765

Lys Val Asn Thr Gln Ile Asp Leu Ile Arg Lys Met Lys Glu Ala
                770                 775                 780

Leu Glu Asn Gln Ala Glu Ala Thr Lys Ala Ile Ile Asn Tyr Gln Tyr
785                 790                 795                 800

Asn Gln Tyr Thr Glu Glu Lys Asn Asn Ile Asn Phe Asn Ile Asp
                805                 810                 815

Asp Leu Ser Ser Lys Leu Asn Glu Ser Ile Asn Lys Ala Met Ile Asn
                820                 825                 830

Ile Asn Lys Phe Leu Asn Gln Cys Ser Val Ser Tyr Leu Met Asn Ser
                835                 840                 845

Met Ile Pro Tyr Gly Val Lys Arg Leu Glu Asp Phe Asp Ala Ser Leu
850                 855                 860

Lys Asp Ala Leu Leu Lys Tyr Ile Tyr Asp Asn Arg Gly Thr Leu Ile
865                 870                 875                 880

Gly Gln Val Asp Arg Leu Lys Asp Lys Val Asn Asn Thr Leu Ser Thr
                885                 890                 895

Asp Ile Pro Phe Gln Leu Ser Lys Tyr Val Asp Asn Gln Arg Leu Leu
                900                 905                 910

Ser Thr Leu Glu Ala Leu Ala Ser Gly His His His His His
                915                 920                 925

<210> SEQ ID NO 40
<211> LENGTH: 916
<212> TYPE: PRT
<213> ORGANISM: Artificial Sequence
<220> FEATURE:
<223> OTHER INFORMATION: Synthetic sequence
```

```
<400> SEQUENCE: 40

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Lys Val Leu Asn Arg Lys Thr
        355                 360                 365

Tyr Leu Asn Phe Asp Lys Ala Val Phe Lys Ile Asn Ile Val Pro Lys
    370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415
```

```
Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Gly Gly Gly
            435                 440                 445

Gly Ser Ala Asp Asp Asp Lys Gly Trp Thr Leu Asn Ser Ala Gly
450                 455                 460

Tyr Leu Leu Gly Pro His Ala Val Ala Leu Ala Ala Glu Ala Ala Ala
465                 470                 475                 480

Lys Glu Ala Ala Ala Lys Glu Ala Ala Ala Lys Ala Gly Gly Gly
                485                 490                 495

Ser Ala Leu Val Leu Gln Cys Ile Lys Val Asn Asn Trp Asp Leu Phe
                500                 505                 510

Phe Ser Pro Ser Glu Asp Asn Phe Thr Asn Asp Leu Asn Lys Gly Glu
            515                 520                 525

Glu Ile Thr Ser Asp Thr Asn Ile Glu Ala Ala Glu Glu Asn Ile Ser
            530                 535                 540

Leu Asp Leu Ile Gln Gln Tyr Tyr Leu Thr Phe Asn Phe Asp Asn Glu
545                 550                 555                 560

Pro Glu Asn Ile Ser Ile Glu Asn Leu Ser Ser Asp Ile Ile Gly Gln
                565                 570                 575

Leu Glu Leu Met Pro Asn Ile Glu Arg Phe Pro Asn Gly Lys Lys Tyr
            580                 585                 590

Glu Leu Asp Lys Tyr Thr Met Phe His Tyr Leu Arg Ala Gln Glu Phe
            595                 600                 605

Glu His Gly Lys Ser Arg Ile Ala Leu Thr Asn Ser Val Asn Glu Ala
            610                 615                 620

Leu Leu Asn Pro Ser Arg Val Tyr Thr Phe Phe Ser Ser Asp Tyr Val
625                 630                 635                 640

Lys Lys Val Asn Lys Ala Thr Glu Ala Ala Met Phe Leu Gly Trp Val
                645                 650                 655

Glu Gln Leu Val Tyr Asp Phe Thr Asp Glu Thr Ser Glu Val Ser Thr
            660                 665                 670

Thr Asp Lys Ile Ala Asp Ile Thr Ile Ile Pro Tyr Ile Gly Pro
            675                 680                 685

Ala Leu Asn Ile Gly Asn Met Leu Tyr Lys Asp Asp Phe Val Gly Ala
            690                 695                 700

Leu Ile Phe Ser Gly Ala Val Ile Leu Leu Glu Phe Ile Pro Glu Ile
705                 710                 715                 720

Ala Ile Pro Val Leu Gly Thr Phe Ala Leu Val Ser Tyr Ile Ala Asn
                725                 730                 735

Lys Val Leu Thr Val Gln Thr Ile Asp Asn Ala Leu Ser Lys Arg Asn
            740                 745                 750

Glu Lys Trp Asp Glu Val Tyr Lys Tyr Ile Val Thr Asn Trp Leu Ala
            755                 760                 765

Lys Val Asn Thr Gln Ile Asp Leu Ile Arg Lys Lys Met Lys Glu Ala
            770                 775                 780

Leu Glu Asn Gln Ala Glu Ala Thr Lys Ala Ile Ile Asn Tyr Gln Tyr
785                 790                 795                 800

Asn Gln Tyr Thr Glu Glu Lys Asn Asn Ile Asn Phe Asn Ile Asp
                805                 810                 815

Asp Leu Ser Ser Lys Leu Asn Glu Ser Ile Asn Lys Ala Met Ile Asn
            820                 825                 830
```

```
Ile Asn Lys Phe Leu Asn Gln Cys Ser Val Ser Tyr Leu Met Asn Ser
            835                 840                 845

Met Ile Pro Tyr Gly Val Lys Arg Leu Glu Asp Phe Asp Ala Ser Leu
850                 855                 860

Lys Asp Ala Leu Leu Lys Tyr Ile Tyr Asp Asn Arg Gly Thr Leu Ile
865                 870                 875                 880

Gly Gln Val Asp Arg Leu Lys Asp Lys Val Asn Asn Thr Leu Ser Thr
                885                 890                 895

Asp Ile Pro Phe Gln Leu Ser Lys Tyr Val Asp Asn Gln Arg Leu Leu
            900                 905                 910

Ser Thr Leu Asp
        915

<210> SEQ ID NO 41
<211> LENGTH: 915
<212> TYPE: PRT
<213> ORGANISM: Artificial Sequence
<220> FEATURE:
<223> OTHER INFORMATION: Synthetic sequence

<400> SEQUENCE: 41

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270
```

```
Asp Ala Lys Phe Ile Asp Ser Leu Gln Glu Asn Glu Phe Arg Leu Tyr
            275                 280                 285

Tyr Tyr Asn Lys Phe Lys Asp Ile Ala Ser Thr Leu Asn Lys Ala Lys
        290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Gly Gly Gly
        435                 440                 445

Gly Ser Ala Asp Asp Asp Lys Gly Trp Thr Leu Asn Ser Ala Gly
        450                 455                 460

Tyr Leu Leu Gly Pro His Ala Val Ala Leu Ala Gly Gly Gly Ser
465                 470                 475                 480

Gly Gly Gly Gly Ser Ala Leu Val Leu Gln Cys Ile Lys Val Asn Asn
                485                 490                 495

Trp Asp Leu Phe Phe Ser Pro Ser Glu Asp Asn Phe Thr Asn Asp Leu
            500                 505                 510

Asn Lys Gly Glu Glu Ile Thr Ser Asp Thr Asn Ile Glu Ala Ala Glu
            515                 520                 525

Glu Asn Ile Ser Leu Asp Leu Ile Gln Gln Tyr Tyr Leu Thr Phe Asn
        530                 535                 540

Phe Asp Asn Glu Pro Glu Asn Ile Ser Ile Glu Asn Leu Ser Ser Asp
545                 550                 555                 560

Ile Ile Gly Gln Leu Glu Leu Met Pro Asn Ile Glu Arg Phe Pro Asn
                565                 570                 575

Gly Lys Lys Tyr Glu Leu Asp Lys Tyr Thr Met Phe His Tyr Leu Arg
            580                 585                 590

Ala Gln Glu Phe Glu His Gly Lys Ser Arg Ile Ala Leu Thr Asn Ser
        595                 600                 605

Val Asn Glu Ala Leu Leu Asn Pro Ser Arg Val Tyr Thr Phe Phe Ser
610                 615                 620

Ser Asp Tyr Val Lys Lys Val Asn Lys Ala Thr Glu Ala Ala Met Phe
625                 630                 635                 640

Leu Gly Trp Val Glu Gln Leu Val Tyr Asp Phe Thr Asp Glu Thr Ser
                645                 650                 655

Glu Val Ser Thr Thr Asp Lys Ile Ala Asp Ile Thr Ile Ile Ile Pro
            660                 665                 670

Tyr Ile Gly Pro Ala Leu Asn Ile Gly Asn Met Leu Tyr Lys Asp Asp
        675                 680                 685

Phe Val Gly Ala Leu Ile Phe Ser Gly Ala Val Ile Leu Leu Glu Phe
```

```
                690                 695                 700
Ile Pro Glu Ile Ala Ile Pro Val Leu Gly Thr Phe Ala Leu Val Ser
705                 710                 715                 720

Tyr Ile Ala Asn Lys Val Leu Thr Val Gln Thr Ile Asp Asn Ala Leu
                725                 730                 735

Ser Lys Arg Asn Glu Lys Trp Asp Glu Val Tyr Lys Tyr Ile Val Thr
            740                 745                 750

Asn Trp Leu Ala Lys Val Asn Thr Gln Ile Asp Leu Ile Arg Lys Lys
        755                 760                 765

Met Lys Glu Ala Leu Glu Asn Gln Ala Glu Ala Thr Lys Ala Ile Ile
    770                 775                 780

Asn Tyr Gln Tyr Asn Gln Tyr Thr Glu Glu Lys Asn Asn Ile Asn
785                 790                 795                 800

Phe Asn Ile Asp Asp Leu Ser Ser Lys Leu Asn Glu Ser Ile Asn Lys
                805                 810                 815

Ala Met Ile Asn Ile Asn Lys Phe Leu Asn Gln Cys Ser Val Ser Tyr
            820                 825                 830

Leu Met Asn Ser Met Ile Pro Tyr Gly Val Lys Arg Leu Glu Asp Phe
        835                 840                 845

Asp Ala Ser Leu Lys Asp Ala Leu Leu Lys Tyr Ile Tyr Asp Asn Arg
    850                 855                 860

Gly Thr Leu Ile Gly Gln Val Asp Arg Leu Lys Asp Lys Val Asn Asn
865                 870                 875                 880

Thr Leu Ser Thr Asp Ile Pro Phe Gln Leu Ser Lys Tyr Val Asp Asn
                885                 890                 895

Gln Arg Leu Leu Ser Thr Leu Glu Ala Leu Ala Ser Gly His His His
            900                 905                 910

His His His
        915

<210> SEQ ID NO 42
<211> LENGTH: 904
<212> TYPE: PRT
<213> ORGANISM: Artificial Sequence
<220> FEATURE:
<223> OTHER INFORMATION: Synthetic sequence

<400> SEQUENCE: 42

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
```

```
                130               135               140
Gly Ser Tyr Arg Ser Glu Glu Leu Asn Leu Val Ile Gly Pro Ser
145                 150               155               160

Ala Asp Ile Ile Gln Phe Glu Cys Lys Ser Phe Gly His Glu Val Leu
                165               170               175

Asn Leu Thr Arg Asn Gly Tyr Gly Ser Thr Gln Tyr Ile Arg Phe Ser
                180               185               190

Pro Asp Phe Thr Phe Gly Phe Glu Glu Ser Leu Glu Val Asp Thr Asn
                195               200               205

Pro Leu Leu Gly Ala Gly Lys Phe Ala Thr Asp Pro Ala Val Thr Leu
                210               215               220

Ala His Glu Leu Ile His Ala Gly His Arg Leu Tyr Gly Ile Ala Ile
225               230               235               240

Asn Pro Asn Arg Val Phe Lys Val Asn Thr Asn Ala Tyr Tyr Glu Met
                245               250               255

Ser Gly Leu Glu Val Ser Phe Glu Glu Leu Arg Thr Phe Gly Gly His
                260               265               270

Asp Ala Lys Phe Ile Asp Ser Leu Gln Glu Asn Glu Phe Arg Leu Tyr
                275               280               285

Tyr Tyr Asn Lys Phe Lys Asp Ile Ala Ser Thr Leu Asn Lys Ala Lys
                290               295               300

Ser Ile Val Gly Thr Thr Ala Ser Leu Gln Tyr Met Lys Asn Val Phe
305               310               315               320

Lys Glu Lys Tyr Leu Leu Ser Glu Asp Thr Ser Gly Lys Phe Ser Val
                325               330               335

Asp Lys Leu Lys Phe Asp Lys Leu Tyr Lys Met Leu Thr Glu Ile Tyr
                340               345               350

Thr Glu Asp Asn Phe Val Lys Phe Phe Lys Val Leu Asn Arg Lys Thr
                355               360               365

Tyr Leu Asn Phe Asp Lys Ala Val Phe Lys Ile Asn Ile Val Pro Lys
                370               375               380

Val Asn Tyr Thr Ile Tyr Asp Gly Phe Asn Leu Arg Asn Thr Asn Leu
385               390               395               400

Ala Ala Asn Phe Asn Gly Gln Asn Thr Glu Ile Asn Asn Met Asn Phe
                405               410               415

Thr Lys Leu Lys Asn Phe Thr Gly Leu Phe Glu Phe Tyr Lys Leu Leu
                420               425               430

Cys Val Asp Gly Gly Gly Ser Gly Gly Gly Ser Gly Gly Gly
                435               440               445

Gly Ser Ala Asp Asp Asp Lys Gly Trp Thr Leu Asn Ser Ala Gly
450                 455               460

Tyr Leu Leu Gly Pro His Ala Val Ala Leu Ala Gly Gly Gly Ser
465                 470               475               480

Gly Gly Gly Gly Ser Ala Leu Val Leu Gln Cys Ile Lys Val Asn Asn
                485               490               495

Trp Asp Leu Phe Phe Ser Pro Ser Glu Asp Asn Phe Thr Asn Asp Leu
                500               505               510

Asn Lys Gly Glu Glu Ile Thr Ser Asp Thr Asn Ile Glu Ala Ala Glu
                515               520               525

Glu Asn Ile Ser Leu Asp Leu Ile Gln Gln Tyr Tyr Leu Thr Phe Asn
                530               535               540

Phe Asp Asn Glu Pro Glu Asn Ile Ser Ile Glu Asn Leu Ser Ser Asp
545               550               555               560
```

Ile Ile Gly Gln Leu Glu Leu Met Pro Asn Ile Glu Arg Phe Pro Asn
                565                 570                 575

Gly Lys Lys Tyr Glu Leu Asp Lys Tyr Thr Met Phe His Tyr Leu Arg
                580                 585                 590

Ala Gln Glu Phe Glu His Gly Lys Ser Arg Ile Ala Leu Thr Asn Ser
                595                 600                 605

Val Asn Glu Ala Leu Leu Asn Pro Ser Arg Val Tyr Thr Phe Phe Ser
            610                 615                 620

Ser Asp Tyr Val Lys Lys Val Asn Lys Ala Thr Glu Ala Ala Met Phe
625                 630                 635                 640

Leu Gly Trp Val Glu Gln Leu Val Tyr Asp Phe Thr Asp Glu Thr Ser
                645                 650                 655

Glu Val Ser Thr Thr Asp Lys Ile Ala Asp Ile Thr Ile Ile Pro
                660                 665                 670

Tyr Ile Gly Pro Ala Leu Asn Ile Gly Asn Met Leu Tyr Lys Asp Asp
                675                 680                 685

Phe Val Gly Ala Leu Ile Phe Ser Gly Ala Val Ile Leu Leu Glu Phe
                690                 695                 700

Ile Pro Glu Ile Ala Ile Pro Val Leu Gly Thr Phe Ala Leu Val Ser
705                 710                 715                 720

Tyr Ile Ala Asn Lys Val Leu Thr Val Gln Thr Ile Asp Asn Ala Leu
                725                 730                 735

Ser Lys Arg Asn Glu Lys Trp Asp Glu Val Tyr Lys Tyr Ile Val Thr
                740                 745                 750

Asn Trp Leu Ala Lys Val Asn Thr Gln Ile Asp Leu Ile Arg Lys Lys
                755                 760                 765

Met Lys Glu Ala Leu Glu Asn Gln Ala Glu Ala Thr Lys Ala Ile Ile
                770                 775                 780

Asn Tyr Gln Tyr Asn Gln Tyr Thr Glu Glu Lys Asn Asn Ile Asn
785                 790                 795                 800

Phe Asn Ile Asp Asp Leu Ser Ser Lys Leu Asn Glu Ser Ile Asn Lys
                805                 810                 815

Ala Met Ile Asn Ile Asn Lys Phe Leu Asn Gln Cys Ser Val Ser Tyr
                820                 825                 830

Leu Met Asn Ser Met Ile Pro Tyr Gly Val Lys Arg Leu Glu Asp Phe
                835                 840                 845

Asp Ala Ser Leu Lys Asp Ala Leu Leu Lys Tyr Ile Tyr Asp Asn Arg
                850                 855                 860

Gly Thr Leu Ile Gly Gln Val Asp Arg Leu Lys Asp Lys Val Asn Asn
865                 870                 875                 880

Thr Leu Ser Thr Asp Ile Pro Phe Gln Leu Ser Lys Tyr Val Asp Asn
                885                 890                 895

Gln Arg Leu Leu Ser Thr Leu Asp
                900

<210> SEQ ID NO 43
<211> LENGTH: 910
<212> TYPE: PRT
<213> ORGANISM: Artificial Sequence
<220> FEATURE:
<223> OTHER INFORMATION: Synthetic sequence

<400> SEQUENCE: 43

Met Gly Ser Met Glu Phe Val Asn Lys Gln Phe Asn Tyr Lys Asp Pro
1               5                   10                  15

```
Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
                100                 105                 110

Ser Ile Val Arg Gly Ile Pro Phe Trp Gly Gly Ser Thr Ile Asp Thr
                115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
                180                 185                 190

Pro Asp Phe Thr Phe Gly Phe Glu Glu Ser Leu Glu Val Asp Thr Asn
                195                 200                 205

Pro Leu Leu Gly Ala Gly Lys Phe Ala Thr Asp Pro Ala Val Thr Leu
                210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
                260                 265                 270

Asp Ala Lys Phe Ile Asp Ser Leu Gln Glu Asn Glu Phe Arg Leu Tyr
                275                 280                 285

Tyr Tyr Asn Lys Phe Lys Asp Ile Ala Ser Thr Leu Asn Lys Ala Lys
            290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
                340                 345                 350

Thr Glu Asp Asn Phe Val Lys Phe Phe Lys Val Leu Asn Arg Lys Thr
                355                 360                 365

Tyr Leu Asn Phe Asp Lys Ala Val Phe Lys Ile Asn Ile Val Pro Lys
                370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
                420                 425                 430
```

-continued

```
Cys Val Asp Gly Gly Gly Gly Ser Gly Gly Gly Ser Gly Gly Gly
            435                 440                 445
Gly Ser Ala Asp Asp Asp Lys Gly Trp Thr Leu Asn Ser Ala Gly
450                 455                 460
Tyr Leu Leu Gly Pro His Ala Val Ala Leu Ala Gly Gly Gly Ser
465                 470                 475                 480
Ala Leu Val Leu Gln Cys Ile Lys Val Asn Asn Trp Asp Leu Phe Phe
            485                 490                 495
Ser Pro Ser Glu Asp Asn Phe Thr Asn Asp Leu Asn Lys Gly Glu Glu
            500                 505                 510
Ile Thr Ser Asp Thr Asn Ile Glu Ala Ala Glu Glu Asn Ile Ser Leu
            515                 520                 525
Asp Leu Ile Gln Gln Tyr Tyr Leu Thr Phe Asn Phe Asp Asn Glu Pro
530                 535                 540
Glu Asn Ile Ser Ile Glu Asn Leu Ser Ser Asp Ile Ile Gly Gln Leu
545                 550                 555                 560
Glu Leu Met Pro Asn Ile Glu Arg Phe Pro Asn Gly Lys Lys Tyr Glu
                565                 570                 575
Leu Asp Lys Tyr Thr Met Phe His Tyr Leu Arg Ala Gln Glu Phe Glu
            580                 585                 590
His Gly Lys Ser Arg Ile Ala Leu Thr Asn Ser Val Asn Glu Ala Leu
            595                 600                 605
Leu Asn Pro Ser Arg Val Tyr Thr Phe Phe Ser Ser Asp Tyr Val Lys
            610                 615                 620
Lys Val Asn Lys Ala Thr Glu Ala Ala Met Phe Leu Gly Trp Val Glu
625                 630                 635                 640
Gln Leu Val Tyr Asp Phe Thr Asp Glu Thr Ser Glu Val Ser Thr Thr
                645                 650                 655
Asp Lys Ile Ala Asp Ile Thr Ile Ile Pro Tyr Ile Gly Pro Ala
                660                 665                 670
Leu Asn Ile Gly Asn Met Leu Tyr Lys Asp Asp Phe Val Gly Ala Leu
            675                 680                 685
Ile Phe Ser Gly Ala Val Ile Leu Leu Glu Phe Ile Pro Glu Ile Ala
            690                 695                 700
Ile Pro Val Leu Gly Thr Phe Ala Leu Val Ser Tyr Ile Ala Asn Lys
705                 710                 715                 720
Val Leu Thr Val Gln Thr Ile Asp Asn Ala Leu Ser Lys Arg Asn Glu
                725                 730                 735
Lys Trp Asp Glu Val Tyr Lys Tyr Ile Val Thr Asn Trp Leu Ala Lys
                740                 745                 750
Val Asn Thr Gln Ile Asp Leu Ile Arg Lys Lys Met Lys Glu Ala Leu
            755                 760                 765
Glu Asn Gln Ala Glu Ala Thr Lys Ala Ile Ile Asn Tyr Gln Tyr Asn
770                 775                 780
Gln Tyr Thr Glu Glu Lys Asn Asn Ile Asn Phe Asn Ile Asp Asp
785                 790                 795                 800
Leu Ser Ser Lys Leu Asn Glu Ser Ile Asn Lys Ala Met Ile Asn Ile
                805                 810                 815
Asn Lys Phe Leu Asn Gln Cys Ser Val Ser Tyr Leu Met Asn Ser Met
            820                 825                 830
Ile Pro Tyr Gly Val Lys Arg Leu Glu Asp Phe Asp Ala Ser Leu Lys
            835                 840                 845
Asp Ala Leu Leu Lys Tyr Ile Tyr Asp Asn Arg Gly Thr Leu Ile Gly
```

850                 855                 860
Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Glu Ala Leu Ala Ser Gly His His His His His
                900                 905                 910

<210> SEQ ID NO 44
<211> LENGTH: 899
<212> TYPE: PRT
<213> ORGANISM: Artificial Sequence
<220> FEATURE:
<223> OTHER INFORMATION: Synthetic sequence

<400> SEQUENCE: 44

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe

```
            305                 310                 315                 320
Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
                340                 345                 350

Thr Glu Asp Asn Phe Val Lys Phe Lys Val Leu Asn Arg Lys Thr
                355                 360                 365

Tyr Leu Asn Phe Asp Lys Ala Val Phe Lys Ile Asn Ile Val Pro Lys
            370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
                420                 425                 430

Cys Val Asp Gly Gly Gly Gly Ser Gly Gly Gly Ser Gly Gly Gly
            435                 440                 445

Gly Ser Ala Asp Asp Asp Lys Gly Trp Thr Leu Asn Ser Ala Gly
        450                 455                 460

Tyr Leu Leu Gly Pro His Ala Val Ala Leu Ala Gly Gly Gly Ser
465                 470                 475                 480

Ala Leu Val Leu Gln Cys Ile Lys Val Asn Asn Trp Asp Leu Phe Phe
                485                 490                 495

Ser Pro Ser Glu Asp Asn Phe Thr Asn Asp Leu Asn Lys Gly Glu Glu
                500                 505                 510

Ile Thr Ser Asp Thr Asn Ile Glu Ala Ala Glu Asn Ile Ser Leu
            515                 520                 525

Asp Leu Ile Gln Gln Tyr Tyr Leu Thr Phe Asn Phe Asp Asn Glu Pro
        530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                565                 570                 575

Leu Asp Lys Tyr Thr Met Phe His Tyr Leu Arg Ala Gln Glu Phe Glu
                580                 585                 590

His Gly Lys Ser Arg Ile Ala Leu Thr Asn Ser Val Asn Glu Ala Leu
            595                 600                 605

Leu Asn Pro Ser Arg Val Tyr Thr Phe Phe Ser Ser Asp Tyr Val Lys
        610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                645                 650                 655

Asp Lys Ile Ala Asp Ile Thr Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
            690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735
```

-continued

```
Lys Trp Asp Glu Val Tyr Lys Tyr Ile Val Thr Asn Trp Leu Ala Lys
            740                 745                 750
Val Asn Thr Gln Ile Asp Leu Ile Arg Lys Lys Met Lys Glu Ala Leu
        755                 760                 765
Glu Asn Gln Ala Glu Ala Thr Lys Ala Ile Ile Asn Tyr Gln Tyr Asn
770                 775                 780
Gln Tyr Thr Glu Glu Lys Asn Asn Ile Asn Phe Asn Ile Asp Asp
785                 790                 795                 800
Leu Ser Ser Lys Leu Asn Glu Ser Ile Asn Lys Ala Met Ile Asn Ile
                805                 810                 815
Asn Lys Phe Leu Asn Gln Cys Ser Val Ser Tyr Leu Met Asn Ser Met
            820                 825                 830
Ile Pro Tyr Gly Val Lys Arg Leu Glu Asp Phe Asp Ala Ser Leu Lys
        835                 840                 845
Asp Ala Leu Leu Lys Tyr Ile Tyr Asp Asn Arg Gly Thr Leu Ile Gly
850                 855                 860
Gln Val Asp Arg Leu Lys Asp Lys Val Asn Asn Thr Leu Ser Thr Asp
865                 870                 875                 880
Ile Pro Phe Gln Leu Ser Lys Tyr Val Asp Asn Gln Arg Leu Leu Ser
                885                 890                 895
Thr Leu Asp

<210> SEQ ID NO 45
<211> LENGTH: 922
<212> TYPE: PRT
<213> ORGANISM: Artificial Sequence
<220> FEATURE:
<223> OTHER INFORMATION: Synthetic sequence

<400> SEQUENCE: 45

Met Gly Ser Met Glu Phe Val Asn Lys Gln Phe Asn Tyr Lys Asp Pro
1               5                   10                  15
Val Asn Gly Val Asp Ile Ala Tyr Ile Lys Ile Pro Asn Ala Gly Gln
                20                  25                  30
Met Gln Pro Val Lys Ala Phe Lys Ile His Asn Lys Ile Trp Val Ile
            35                  40                  45
Pro Glu Arg Asp Thr Phe Thr Asn Pro Glu Glu Gly Asp Leu Asn Pro
        50                  55                  60
Pro Pro Glu Ala Lys Gln Val Pro Val Ser Tyr Tyr Asp Ser Thr Tyr
65                  70                  75                  80
Leu Ser Thr Asp Asn Glu Lys Asp Asn Tyr Leu Lys Gly Val Thr Lys
                85                  90                  95
Leu Phe Glu Arg Ile Tyr Ser Thr Asp Leu Gly Arg Met Leu Leu Thr
            100                 105                 110
Ser Ile Val Arg Gly Ile Pro Phe Trp Gly Gly Ser Thr Ile Asp Thr
        115                 120                 125
Glu Leu Lys Val Ile Asp Thr Asn Cys Ile Asn Val Ile Gln Pro Asp
    130                 135                 140
Gly Ser Tyr Arg Ser Glu Glu Leu Asn Leu Val Ile Ile Gly Pro Ser
145                 150                 155                 160
Ala Asp Ile Ile Gln Phe Glu Cys Lys Ser Phe Gly His Glu Val Leu
                165                 170                 175
Asn Leu Thr Arg Asn Gly Tyr Gly Ser Thr Gln Tyr Ile Arg Phe Ser
            180                 185                 190
```

```
Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
        210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
        290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Lys Val Leu Asn Arg Lys Thr
        355                 360                 365

Tyr Leu Asn Phe Asp Lys Ala Val Phe Lys Ile Asn Ile Val Pro Lys
        370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Ala Asp Asp
        435                 440                 445

Asp Asp Lys Gly Trp Thr Leu Asn Ser Ala Gly Tyr Leu Leu Gly Pro
        450                 455                 460

His Ala Val Ala Leu Ala Ala Glu Ala Ala Lys Glu Ala Ala
465                 470                 475                 480

Lys Glu Ala Ala Ala Lys Ala Gly Gly Gly Ser Ala Leu Val Leu
                485                 490                 495

Gln Cys Ile Lys Val Asn Asn Trp Asp Leu Phe Phe Ser Pro Ser Glu
        500                 505                 510

Asp Asn Phe Thr Asn Asp Leu Asn Lys Gly Glu Glu Ile Thr Ser Asp
        515                 520                 525

Thr Asn Ile Glu Ala Ala Glu Glu Asn Ile Ser Leu Asp Leu Ile Gln
530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
        595                 600                 605

Arg Ile Ala Leu Thr Asn Ser Val Asn Glu Ala Leu Leu Asn Pro Ser
```

```
                    610                 615                 620
Arg Val Tyr Thr Phe Phe Ser Ser Asp Tyr Val Lys Lys Val Asn Lys
625                 630                 635                 640

Ala Thr Glu Ala Ala Met Phe Leu Gly Trp Val Gln Leu Val Tyr
                645                 650                 655

Asp Phe Thr Asp Glu Thr Ser Glu Val Ser Thr Thr Asp Lys Ile Ala
                660                 665                 670

Asp Ile Thr Ile Ile Ile Pro Tyr Ile Gly Pro Ala Leu Asn Ile Gly
                675                 680                 685

Asn Met Leu Tyr Lys Asp Asp Phe Val Gly Ala Leu Ile Phe Ser Gly
            690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
                740                 745                 750

Val Tyr Lys Tyr Ile Val Thr Asn Trp Leu Ala Lys Val Asn Thr Gln
            755                 760                 765

Ile Asp Leu Ile Arg Lys Lys Met Lys Glu Ala Leu Glu Asn Gln Ala
            770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
                820                 825                 830

Asn Gln Cys Ser Val Ser Tyr Leu Met Asn Ser Met Ile Pro Tyr Gly
            835                 840                 845

Val Lys Arg Leu Glu Asp Phe Asp Ala Ser Leu Lys Asp Ala Leu Leu
            850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Glu Ala
                900                 905                 910

Leu Ala Ser Gly His His His His His
            915                 920

<210> SEQ ID NO 46
<211> LENGTH: 911
<212> TYPE: PRT
<213> ORGANISM: Artificial Sequence
<220> FEATURE:
<223> OTHER INFORMATION: Synthetic sequence

<400> SEQUENCE: 46

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
```

-continued

```
             50                  55                  60
Pro Pro Glu Ala Lys Gln Val Pro Val Ser Tyr Tyr Asp Ser Thr Tyr
 65                  70                  75                  80
Leu Ser Thr Asp Asn Glu Lys Asp Asn Tyr Leu Lys Gly Val Thr Lys
                 85                  90                  95
Leu Phe Glu Arg Ile Tyr Ser Thr Asp Leu Gly Arg Met Leu Leu Thr
                100                 105                 110
Ser Ile Val Arg Gly Ile Pro Phe Trp Gly Gly Ser Thr Ile Asp Thr
                115                 120                 125
Glu Leu Lys Val Ile Asp Thr Asn Cys Ile Asn Val Ile Gln Pro Asp
                130                 135                 140
Gly Ser Tyr Arg Ser Glu Glu Leu Asn Leu Val Ile Ile Gly Pro Ser
145                 150                 155                 160
Ala Asp Ile Ile Gln Phe Glu Cys Lys Ser Phe Gly His Glu Val Leu
                165                 170                 175
Asn Leu Thr Arg Asn Gly Tyr Gly Ser Thr Gln Tyr Ile Arg Phe Ser
                180                 185                 190
Pro Asp Phe Thr Phe Gly Phe Glu Glu Ser Leu Glu Val Asp Thr Asn
                195                 200                 205
Pro Leu Leu Gly Ala Gly Lys Phe Ala Thr Asp Pro Ala Val Thr Leu
                210                 215                 220
Ala His Glu Leu Ile His Ala Gly His Arg Leu Tyr Gly Ile Ala Ile
225                 230                 235                 240
Asn Pro Asn Arg Val Phe Lys Val Asn Thr Asn Ala Tyr Tyr Glu Met
                245                 250                 255
Ser Gly Leu Glu Val Ser Phe Glu Glu Leu Arg Thr Phe Gly Gly His
                260                 265                 270
Asp Ala Lys Phe Ile Asp Ser Leu Gln Glu Asn Glu Phe Arg Leu Tyr
                275                 280                 285
Tyr Tyr Asn Lys Phe Lys Asp Ile Ala Ser Thr Leu Asn Lys Ala Lys
                290                 295                 300
Ser Ile Val Gly Thr Thr Ala Ser Leu Gln Tyr Met Lys Asn Val Phe
305                 310                 315                 320
Lys Glu Lys Tyr Leu Leu Ser Glu Asp Thr Ser Gly Lys Phe Ser Val
                325                 330                 335
Asp Lys Leu Lys Phe Asp Lys Leu Tyr Lys Met Leu Thr Glu Ile Tyr
                340                 345                 350
Thr Glu Asp Asn Phe Val Lys Phe Phe Lys Val Leu Asn Arg Lys Thr
                355                 360                 365
Tyr Leu Asn Phe Asp Lys Ala Val Phe Lys Ile Asn Ile Val Pro Lys
                370                 375                 380
Val Asn Tyr Thr Ile Tyr Asp Gly Phe Asn Leu Arg Asn Thr Asn Leu
385                 390                 395                 400
Ala Ala Asn Phe Asn Gly Gln Asn Thr Glu Ile Asn Asn Met Asn Phe
                405                 410                 415
Thr Lys Leu Lys Asn Phe Thr Gly Leu Phe Glu Phe Tyr Lys Leu Leu
                420                 425                 430
Cys Val Asp Gly Gly Gly Ser Gly Gly Gly Ser Ala Asp Asp
                435                 440                 445
Asp Asp Lys Gly Trp Thr Leu Asn Ser Ala Gly Tyr Leu Leu Gly Pro
                450                 455                 460
His Ala Val Ala Leu Ala Ala Glu Ala Ala Lys Glu Ala Ala Ala
465                 470                 475                 480
```

-continued

```
Lys Glu Ala Ala Ala Lys Ala Gly Gly Gly Ser Ala Leu Val Leu
                485             490             495

Gln Cys Ile Lys Val Asn Asn Trp Asp Leu Phe Phe Ser Pro Ser Glu
            500             505             510

Asp Asn Phe Thr Asn Asp Leu Asn Lys Gly Glu Glu Ile Thr Ser Asp
            515             520             525

Thr Asn Ile Glu Ala Ala Glu Glu Asn Ile Ser Leu Asp Leu Ile Gln
        530             535             540

Gln Tyr Tyr Leu Thr Phe Asn Phe Asp Asn Glu Pro Glu Asn Ile Ser
545             550             555             560

Ile Glu Asn Leu Ser Ser Asp Ile Ile Gly Gln Leu Gly Leu Met Pro
                565             570             575

Asn Ile Glu Arg Phe Pro Asn Gly Lys Lys Tyr Glu Leu Asp Lys Tyr
                580             585             590

Thr Met Phe His Tyr Leu Arg Ala Gln Glu Phe Glu His Gly Lys Ser
                595             600             605

Arg Ile Ala Leu Thr Asn Ser Val Asn Glu Ala Leu Leu Asn Pro Ser
            610             615             620

Arg Val Tyr Thr Phe Phe Ser Ser Asp Tyr Val Lys Lys Val Asn Lys
625             630             635             640

Ala Thr Glu Ala Ala Met Phe Leu Gly Trp Val Glu Gln Leu Val Tyr
                645             650             655

Asp Phe Thr Asp Glu Thr Ser Glu Val Ser Thr Thr Asp Lys Ile Ala
                660             665             670

Asp Ile Thr Ile Ile Ile Pro Tyr Ile Gly Pro Ala Leu Asn Ile Gly
            675             680             685

Asn Met Leu Tyr Lys Asp Asp Phe Val Gly Ala Leu Ile Phe Ser Gly
            690             695             700

Ala Val Ile Leu Leu Glu Phe Ile Pro Glu Ile Ala Ile Pro Val Leu
705             710             715             720

Gly Thr Phe Ala Leu Val Ser Tyr Ile Ala Asn Lys Val Leu Thr Val
                725             730             735

Gln Thr Ile Asp Asn Ala Leu Ser Lys Arg Asn Glu Lys Trp Asp Glu
            740             745             750

Val Tyr Lys Tyr Ile Val Thr Asn Trp Leu Ala Lys Val Asn Thr Gln
            755             760             765

Ile Asp Leu Ile Arg Lys Lys Met Lys Glu Ala Leu Glu Asn Gln Ala
770             775             780

Glu Ala Thr Lys Ala Ile Ile Asn Tyr Gln Tyr Asn Gln Tyr Thr Glu
785             790             795             800

Glu Glu Lys Asn Asn Ile Asn Phe Asn Ile Asp Asp Leu Ser Ser Lys
                805             810             815

Leu Asn Glu Ser Ile Asn Lys Ala Met Ile Asn Ile Asn Lys Phe Leu
            820             825             830

Asn Gln Cys Ser Val Ser Tyr Leu Met Asn Ser Met Ile Pro Tyr Gly
            835             840             845

Val Lys Arg Leu Glu Asp Phe Asp Ala Ser Leu Lys Asp Ala Leu Leu
            850             855             860

Lys Tyr Ile Tyr Asp Asn Arg Gly Thr Leu Ile Gly Gln Val Asp Arg
865             870             875             880

Leu Lys Asp Lys Val Asn Asn Thr Leu Ser Thr Asp Ile Pro Phe Gln
                885             890             895
```

```
Leu Ser Lys Tyr Val Asp Asn Gln Arg Leu Leu Ser Thr Leu Asp
            900                 905                 910

<210> SEQ ID NO 47
<211> LENGTH: 910
<212> TYPE: PRT
<213> ORGANISM: Artificial Sequence
<220> FEATURE:
<223> OTHER INFORMATION: Synthetic sequence

<400> SEQUENCE: 47

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
    290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350
```

```
Thr Glu Asp Asn Phe Val Lys Phe Lys Val Leu Asn Arg Lys Thr
            355                 360                 365
Tyr Leu Asn Phe Asp Lys Ala Val Phe Lys Ile Asn Ile Val Pro Lys
370                 375                 380
Val Asn Tyr Thr Ile Tyr Asp Gly Phe Asn Leu Arg Asn Thr Asn Leu
385                 390                 395                 400
Ala Ala Asn Phe Asn Gly Gln Asn Thr Glu Ile Asn Asn Met Asn Phe
                405                 410                 415
Thr Lys Leu Lys Asn Phe Thr Gly Leu Phe Glu Phe Tyr Lys Leu Leu
            420                 425                 430
Cys Val Asp Gly Gly Gly Ser Gly Gly Gly Ser Ala Asp Asp
            435                 440                 445
Asp Asp Lys Gly Trp Thr Leu Asn Ser Ala Gly Tyr Leu Leu Gly Pro
    450                 455                 460
His Ala Val Ala Leu Ala Gly Gly Gly Ser Gly Gly Gly Gly Ser
465                 470                 475                 480
Ala Leu Val Leu Gln Cys Ile Lys Val Asn Asn Trp Asp Leu Phe Phe
                485                 490                 495
Ser Pro Ser Glu Asp Asn Phe Thr Asn Asp Leu Asn Lys Gly Glu Glu
            500                 505                 510
Ile Thr Ser Asp Thr Asn Ile Glu Ala Ala Glu Asn Ile Ser Leu
            515                 520                 525
Asp Leu Ile Gln Gln Tyr Tyr Leu Thr Phe Asn Phe Asp Asn Glu Pro
    530                 535                 540
Glu Asn Ile Ser Ile Glu Asn Leu Ser Ser Asp Ile Ile Gly Gln Leu
545                 550                 555                 560
Glu Leu Met Pro Asn Ile Glu Arg Phe Pro Asn Gly Lys Lys Tyr Glu
                565                 570                 575
Leu Asp Lys Tyr Thr Met Phe His Tyr Leu Arg Ala Gln Glu Phe Glu
            580                 585                 590
His Gly Lys Ser Arg Ile Ala Leu Thr Asn Ser Val Asn Glu Ala Leu
    595                 600                 605
Leu Asn Pro Ser Arg Val Tyr Thr Phe Phe Ser Ser Asp Tyr Val Lys
610                 615                 620
Lys Val Asn Lys Ala Thr Glu Ala Ala Met Phe Leu Gly Trp Val Glu
625                 630                 635                 640
Gln Leu Val Tyr Asp Phe Thr Asp Glu Thr Ser Glu Val Ser Thr Thr
                645                 650                 655
Asp Lys Ile Ala Asp Ile Thr Ile Ile Pro Tyr Ile Gly Pro Ala
            660                 665                 670
Leu Asn Ile Gly Asn Met Leu Tyr Lys Asp Asp Phe Val Gly Ala Leu
    675                 680                 685
Ile Phe Ser Gly Ala Val Ile Leu Leu Glu Phe Ile Pro Glu Ile Ala
690                 695                 700
Ile Pro Val Leu Gly Thr Phe Ala Leu Val Ser Tyr Ile Ala Asn Lys
705                 710                 715                 720
Val Leu Thr Val Gln Thr Ile Asp Asn Ala Leu Ser Lys Arg Asn Glu
                725                 730                 735
Lys Trp Asp Glu Val Tyr Lys Tyr Ile Val Thr Asn Trp Leu Ala Lys
            740                 745                 750
Val Asn Thr Gln Ile Asp Leu Ile Arg Lys Lys Met Lys Glu Ala Leu
    755                 760                 765
Glu Asn Gln Ala Glu Ala Thr Lys Ala Ile Ile Asn Tyr Gln Tyr Asn
```

```
              770                 775                 780
Gln Tyr Thr Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
                820                 825                 830

Ile Pro Tyr Gly Val Lys Arg Leu Glu Asp Phe Asp Ala Ser Leu Lys
                835                 840                 845

Asp Ala Leu Leu Lys Tyr Ile Tyr Asp Asn Arg Gly Thr Leu Ile Gly
                850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Glu Ala Leu Ala Ser Gly His His His His His His
                900                 905                 910

<210> SEQ ID NO 48
<211> LENGTH: 899
<212> TYPE: PRT
<213> ORGANISM: Artificial Sequence
<220> FEATURE:
<223> OTHER INFORMATION: Synthetic sequence

<400> SEQUENCE: 48

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
                20                  25                  30

Met Gln Pro Val Lys Ala Phe Lys Ile His Asn Lys Ile Trp Val Ile
            35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
                100                 105                 110

Ser Ile Val Arg Gly Ile Pro Phe Trp Gly Gly Ser Thr Ile Asp Thr
            115                 120                 125

Glu Leu Lys Val Ile Asp Thr Asn Cys Ile Asn Val Ile Gln Pro Asp
    130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
                180                 185                 190

Pro Asp Phe Thr Phe Gly Phe Glu Glu Ser Leu Glu Val Asp Thr Asn
            195                 200                 205

Pro Leu Leu Gly Ala Gly Lys Phe Ala Thr Asp Pro Ala Val Thr Leu
    210                 215                 220

Ala His Glu Leu Ile His Ala Gly His Arg Leu Tyr Gly Ile Ala Ile
```

```
            225                 230                 235                 240
Asn Pro Asn Arg Val Phe Lys Val Asn Thr Asn Ala Tyr Tyr Glu Met
                    245                 250                 255

Ser Gly Leu Glu Val Ser Phe Glu Glu Leu Arg Thr Phe Gly Gly His
                    260                 265                 270

Asp Ala Lys Phe Ile Asp Ser Leu Gln Glu Asn Glu Phe Arg Leu Tyr
                    275                 280                 285

Tyr Tyr Asn Lys Phe Lys Asp Ile Ala Ser Thr Leu Asn Lys Ala Lys
                290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                    325                 330                 335

Asp Lys Leu Lys Phe Asp Lys Leu Tyr Lys Met Leu Thr Glu Ile Tyr
                    340                 345                 350

Thr Glu Asp Asn Phe Val Lys Phe Phe Lys Val Leu Asn Arg Lys Thr
                355                 360                 365

Tyr Leu Asn Phe Asp Lys Ala Val Phe Lys Ile Asn Ile Val Pro Lys
                370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                    405                 410                 415

Thr Lys Leu Lys Asn Phe Thr Gly Leu Phe Glu Phe Tyr Lys Leu Leu
                    420                 425                 430

Cys Val Asp Gly Gly Gly Ser Gly Gly Gly Ser Ala Asp Asp
                435                 440                 445

Asp Asp Lys Gly Trp Thr Leu Asn Ser Ala Gly Tyr Leu Leu Gly Pro
                450                 455                 460

His Ala Val Ala Leu Ala Gly Gly Gly Ser Gly Gly Gly Ser
465                 470                 475                 480

Ala Leu Val Leu Gln Cys Ile Lys Val Asn Asn Trp Asp Leu Phe Phe
                    485                 490                 495

Ser Pro Ser Glu Asp Asn Phe Thr Asn Asp Leu Asn Lys Gly Glu Glu
                    500                 505                 510

Ile Thr Ser Asp Thr Asn Ile Glu Ala Ala Glu Asn Ile Ser Leu
            515                 520                 525

Asp Leu Ile Gln Gln Tyr Tyr Leu Thr Phe Asn Phe Asp Asn Glu Pro
530                 535                 540

Glu Asn Ile Ser Ile Glu Asn Leu Ser Ser Asp Ile Ile Gly Gln Leu
545                 550                 555                 560

Glu Leu Met Pro Asn Ile Glu Arg Phe Pro Asn Gly Lys Lys Tyr Glu
                    565                 570                 575

Leu Asp Lys Tyr Thr Met Phe His Tyr Leu Arg Ala Gln Glu Phe Glu
                580                 585                 590

His Gly Lys Ser Arg Ile Ala Leu Thr Asn Ser Val Asn Glu Ala Leu
                595                 600                 605

Leu Asn Pro Ser Arg Val Tyr Thr Phe Phe Ser Ser Asp Tyr Val Lys
                610                 615                 620

Lys Val Asn Lys Ala Thr Glu Ala Ala Met Phe Leu Gly Trp Val Glu
625                 630                 635                 640

Gln Leu Val Tyr Asp Phe Thr Asp Glu Thr Ser Glu Val Ser Thr Thr
                    645                 650                 655
```

Asp Lys Ile Ala Asp Ile Thr Ile Ile Pro Tyr Ile Gly Pro Ala
            660                 665                 670

Leu Asn Ile Gly Asn Met Leu Tyr Lys Asp Asp Phe Val Gly Ala Leu
        675                 680                 685

Ile Phe Ser Gly Ala Val Ile Leu Leu Glu Phe Ile Pro Glu Ile Ala
    690                 695                 700

Ile Pro Val Leu Gly Thr Phe Ala Leu Val Ser Tyr Ile Ala Asn Lys
705                 710                 715                 720

Val Leu Thr Val Gln Thr Ile Asp Asn Ala Leu Ser Lys Arg Asn Glu
                725                 730                 735

Lys Trp Asp Glu Val Tyr Lys Tyr Ile Val Thr Asn Trp Leu Ala Lys
                740                 745                 750

Val Asn Thr Gln Ile Asp Leu Ile Arg Lys Lys Met Lys Glu Ala Leu
            755                 760                 765

Glu Asn Gln Ala Glu Ala Thr Lys Ala Ile Ile Asn Tyr Gln Tyr Asn
        770                 775                 780

Gln Tyr Thr Glu Glu Glu Lys Asn Asn Ile Asn Phe Asn Ile Asp Asp
785                 790                 795                 800

Leu Ser Ser Lys Leu Asn Glu Ser Ile Asn Lys Ala Met Ile Asn Ile
                805                 810                 815

Asn Lys Phe Leu Asn Gln Cys Ser Val Ser Tyr Leu Met Asn Ser Met
                820                 825                 830

Ile Pro Tyr Gly Val Lys Arg Leu Glu Asp Phe Asp Ala Ser Leu Lys
            835                 840                 845

Asp Ala Leu Leu Lys Tyr Ile Tyr Asp Asn Arg Gly Thr Leu Ile Gly
        850                 855                 860

Gln Val Asp Arg Leu Lys Asp Lys Val Asn Asn Thr Leu Ser Thr Asp
865                 870                 875                 880

Ile Pro Phe Gln Leu Ser Lys Tyr Val Asp Asn Gln Arg Leu Leu Ser
                885                 890                 895

Thr Leu Asp

<210> SEQ ID NO 49
<211> LENGTH: 905
<212> TYPE: PRT
<213> ORGANISM: Artificial Sequence
<220> FEATURE:
<223> OTHER INFORMATION: Synthetic sequence

<400> SEQUENCE: 49

Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

```
Ser Ile Val Arg Gly Ile Pro Phe Trp Gly Ser Thr Ile Asp Thr
            115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
            290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415

Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Ala Asp Asp
        435                 440                 445

Asp Asp Lys Gly Trp Thr Leu Asn Ser Ala Gly Tyr Leu Leu Gly Pro
450                 455                 460

His Ala Val Ala Leu Ala Gly Gly Gly Ser Ala Leu Val Leu Gln
465                 470                 475                 480

Cys Ile Lys Val Asn Asn Trp Asp Leu Phe Phe Ser Pro Ser Glu Asp
                485                 490                 495

Asn Phe Thr Asn Asp Leu Asn Lys Gly Glu Glu Ile Thr Ser Asp Thr
            500                 505                 510

Asn Ile Glu Ala Ala Glu Glu Asn Ile Ser Leu Asp Leu Ile Gln Gln
        515                 520                 525

Tyr Tyr Leu Thr Phe Asn Phe Asp Asn Glu Pro Glu Asn Ile Ser Ile
```

```
                530                 535                 540
Glu Asn Leu Ser Ser Asp Ile Ile Gly Gln Leu Glu Leu Met Pro Asn
545                 550                 555                 560

Ile Glu Arg Phe Pro Asn Gly Lys Lys Tyr Glu Leu Asp Lys Tyr Thr
                565                 570                 575

Met Phe His Tyr Leu Arg Ala Gln Glu Phe Glu His Gly Lys Ser Arg
            580                 585                 590

Ile Ala Leu Thr Asn Ser Val Asn Glu Ala Leu Leu Asn Pro Ser Arg
        595                 600                 605

Val Tyr Thr Phe Phe Ser Ser Asp Tyr Val Lys Val Asn Lys Ala
    610                 615                 620

Thr Glu Ala Ala Met Phe Leu Gly Trp Val Glu Gln Leu Val Tyr Asp
625                 630                 635                 640

Phe Thr Asp Glu Thr Ser Glu Val Ser Thr Asp Lys Ile Ala Asp
                645                 650                 655

Ile Thr Ile Ile Ile Pro Tyr Ile Gly Pro Ala Leu Asn Ile Gly Asn
                660                 665                 670

Met Leu Tyr Lys Asp Asp Phe Val Gly Ala Leu Ile Phe Ser Gly Ala
            675                 680                 685

Val Ile Leu Leu Glu Phe Ile Pro Glu Ile Ala Ile Pro Val Leu Gly
        690                 695                 700

Thr Phe Ala Leu Val Ser Tyr Ile Ala Asn Lys Val Leu Thr Val Gln
705                 710                 715                 720

Thr Ile Asp Asn Ala Leu Ser Lys Arg Asn Glu Lys Trp Asp Glu Val
                725                 730                 735

Tyr Lys Tyr Ile Val Thr Asn Trp Leu Ala Lys Val Asn Thr Gln Ile
                740                 745                 750

Asp Leu Ile Arg Lys Lys Met Lys Glu Ala Leu Glu Asn Gln Ala Glu
            755                 760                 765

Ala Thr Lys Ala Ile Ile Asn Tyr Gln Tyr Asn Gln Tyr Thr Glu Glu
        770                 775                 780

Glu Lys Asn Asn Ile Asn Phe Asn Ile Asp Asp Leu Ser Ser Lys Leu
785                 790                 795                 800

Asn Glu Ser Ile Asn Lys Ala Met Ile Asn Ile Asn Lys Phe Leu Asn
                805                 810                 815

Gln Cys Ser Val Ser Tyr Leu Met Asn Ser Met Ile Pro Tyr Gly Val
            820                 825                 830

Lys Arg Leu Glu Asp Phe Asp Ala Ser Leu Lys Asp Ala Leu Leu Lys
        835                 840                 845

Tyr Ile Tyr Asp Asn Arg Gly Thr Leu Ile Gly Gln Val Asp Arg Leu
    850                 855                 860

Lys Asp Lys Val Asn Asn Thr Leu Ser Thr Asp Ile Pro Phe Gln Leu
865                 870                 875                 880

Ser Lys Tyr Val Asp Asn Gln Arg Leu Leu Ser Thr Leu Glu Ala Leu
                885                 890                 895

Ala Ser Gly His His His His His His
            900                 905

<210> SEQ ID NO 50
<211> LENGTH: 894
<212> TYPE: PRT
<213> ORGANISM: Artificial Sequence
<220> FEATURE:
<223> OTHER INFORMATION: Synthetic sequence
```

<400> SEQUENCE: 50

```
Met Gly Ser Met Glu Phe Val Asn Lys Gln Phe Asn Tyr Lys Asp Pro
1               5                   10                  15

Val Asn Gly Val Asp Ile Ala Tyr Ile Lys Ile Pro Asn Ala Gly Gln
            20                  25                  30

Met Gln Pro Val Lys Ala Phe Lys Ile His Asn Lys Ile Trp Val Ile
        35                  40                  45

Pro Glu Arg Asp Thr Phe Thr Asn Pro Glu Glu Gly Asp Leu Asn Pro
    50                  55                  60

Pro Pro Glu Ala Lys Gln Val Pro Val Ser Tyr Tyr Asp Ser Thr Tyr
65                  70                  75                  80

Leu Ser Thr Asp Asn Glu Lys Asp Asn Tyr Leu Lys Gly Val Thr Lys
                85                  90                  95

Leu Phe Glu Arg Ile Tyr Ser Thr Asp Leu Gly Arg Met Leu Leu Thr
            100                 105                 110

Ser Ile Val Arg Gly Ile Pro Phe Trp Gly Gly Ser Thr Ile Asp Thr
        115                 120                 125

Glu Leu Lys Val Ile Asp Thr Asn Cys Ile Asn Val Ile Gln Pro Asp
130                 135                 140

Gly Ser Tyr Arg Ser Glu Glu Leu Asn Leu Val Ile Ile Gly Pro Ser
145                 150                 155                 160

Ala Asp Ile Ile Gln Phe Glu Cys Lys Ser Phe Gly His Glu Val Leu
                165                 170                 175

Asn Leu Thr Arg Asn Gly Tyr Gly Ser Thr Gln Tyr Ile Arg Phe Ser
            180                 185                 190

Pro Asp Phe Thr Phe Gly Phe Glu Glu Ser Leu Glu Val Asp Thr Asn
        195                 200                 205

Pro Leu Leu Gly Ala Gly Lys Phe Ala Thr Asp Pro Ala Val Thr Leu
210                 215                 220

Ala His Glu Leu Ile His Ala Gly His Arg Leu Tyr Gly Ile Ala Ile
225                 230                 235                 240

Asn Pro Asn Arg Val Phe Lys Val Asn Thr Asn Ala Tyr Tyr Glu Met
                245                 250                 255

Ser Gly Leu Glu Val Ser Phe Glu Glu Leu Arg Thr Phe Gly Gly His
            260                 265                 270

Asp Ala Lys Phe Ile Asp Ser Leu Gln Glu Asn Glu Phe Arg Leu Tyr
        275                 280                 285

Tyr Tyr Asn Lys Phe Lys Asp Ile Ala Ser Thr Leu Asn Lys Ala Lys
290                 295                 300

Ser Ile Val Gly Thr Thr Ala Ser Leu Gln Tyr Met Lys Asn Val Phe
305                 310                 315                 320

Lys Glu Lys Tyr Leu Leu Ser Glu Asp Thr Ser Gly Lys Phe Ser Val
                325                 330                 335

Asp Lys Leu Lys Phe Asp Lys Leu Tyr Lys Met Leu Thr Glu Ile Tyr
            340                 345                 350

Thr Glu Asp Asn Phe Val Lys Phe Phe Lys Val Leu Asn Arg Lys Thr
        355                 360                 365

Tyr Leu Asn Phe Asp Lys Ala Val Phe Lys Ile Asn Ile Val Pro Lys
370                 375                 380

Val Asn Tyr Thr Ile Tyr Asp Gly Phe Asn Leu Arg Asn Thr Asn Leu
385                 390                 395                 400

Ala Ala Asn Phe Asn Gly Gln Asn Thr Glu Ile Asn Asn Met Asn Phe
                405                 410                 415
```

```
Thr Lys Leu Lys Asn Phe Thr Gly Leu Phe Glu Phe Tyr Lys Leu Leu
            420                 425                 430

Cys Val Asp Gly Gly Gly Ser Gly Gly Gly Ser Ala Asp Asp
            435                 440                 445

Asp Asp Lys Gly Trp Thr Leu Asn Ser Ala Gly Tyr Leu Leu Gly Pro
            450                 455                 460

His Ala Val Ala Leu Ala Gly Gly Gly Ser Ala Leu Val Leu Gln
465                 470                 475                 480

Cys Ile Lys Val Asn Asn Trp Asp Leu Phe Phe Ser Pro Ser Glu Asp
                    485                 490                 495

Asn Phe Thr Asn Asp Leu Asn Lys Gly Glu Ile Thr Ser Asp Thr
                500                 505                 510

Asn Ile Glu Ala Ala Glu Glu Asn Ile Ser Leu Asp Leu Ile Gln Gln
            515                 520                 525

Tyr Tyr Leu Thr Phe Asn Phe Asp Asn Glu Pro Glu Asn Ile Ser Ile
            530                 535                 540

Glu Asn Leu Ser Ser Asp Ile Ile Gly Gln Leu Glu Leu Met Pro Asn
545                 550                 555                 560

Ile Glu Arg Phe Pro Asn Gly Lys Lys Tyr Glu Leu Asp Lys Tyr Thr
                565                 570                 575

Met Phe His Tyr Leu Arg Ala Gln Glu Phe Glu His Gly Lys Ser Arg
            580                 585                 590

Ile Ala Leu Thr Asn Ser Val Asn Glu Ala Leu Leu Asn Pro Ser Arg
            595                 600                 605

Val Tyr Thr Phe Phe Ser Ser Asp Tyr Val Lys Val Asn Lys Ala
            610                 615                 620

Thr Glu Ala Ala Met Phe Leu Gly Trp Val Glu Gln Leu Val Tyr Asp
625                 630                 635                 640

Phe Thr Asp Glu Thr Ser Glu Val Ser Thr Thr Asp Lys Ile Ala Asp
                645                 650                 655

Ile Thr Ile Ile Ile Pro Tyr Ile Gly Pro Ala Leu Asn Ile Gly Asn
                660                 665                 670

Met Leu Tyr Lys Asp Asp Phe Val Gly Ala Leu Ile Phe Ser Gly Ala
            675                 680                 685

Val Ile Leu Leu Glu Phe Ile Pro Glu Ile Ala Ile Pro Val Leu Gly
            690                 695                 700

Thr Phe Ala Leu Val Ser Tyr Ile Ala Asn Lys Val Leu Thr Val Gln
705                 710                 715                 720

Thr Ile Asp Asn Ala Leu Ser Lys Arg Asn Glu Lys Trp Asp Glu Val
                725                 730                 735

Tyr Lys Tyr Ile Val Thr Asn Trp Leu Ala Lys Val Asn Thr Gln Ile
            740                 745                 750

Asp Leu Ile Arg Lys Lys Met Lys Glu Ala Leu Glu Asn Gln Ala Glu
            755                 760                 765

Ala Thr Lys Ala Ile Ile Asn Tyr Gln Tyr Asn Gln Tyr Thr Glu Glu
            770                 775                 780

Glu Lys Asn Asn Ile Asn Phe Asn Ile Asp Asp Leu Ser Ser Lys Leu
785                 790                 795                 800

Asn Glu Ser Ile Asn Lys Ala Met Ile Asn Ile Asn Lys Phe Leu Asn
                805                 810                 815

Gln Cys Ser Val Ser Tyr Leu Met Asn Ser Met Ile Pro Tyr Gly Val
            820                 825                 830
```

```
Lys Arg Leu Glu Asp Phe Asp Ala Ser Leu Lys Asp Ala Leu Leu Lys
            835                 840                 845

Tyr Ile Tyr Asp Asn Arg Gly Thr Leu Ile Gly Gln Val Asp Arg Leu
        850                 855                 860

Lys Asp Lys Val Asn Asn Thr Leu Ser Thr Asp Ile Pro Phe Gln Leu
865                 870                 875                 880

Ser Lys Tyr Val Asp Asn Gln Arg Leu Leu Ser Thr Leu Asp
            885                 890

<210> SEQ ID NO 51
<211> LENGTH: 2889
<212> TYPE: DNA
<213> ORGANISM: Artificial Sequence
<220> FEATURE:
<223> OTHER INFORMATION: Synthetic sequence

<400> SEQUENCE: 51
ggatccttgg tacgagatga cgttgactat caaattttcc gcgactttgc ggaaaataaa      60
ggtaagtttt tcgtcggcgc cacagacctg tccgtcaaaa ataagagagg ccagaacatc     120
ggtaacgcac tgagcaacgt ccctatgatt gattttagtg tagcggacgt taataaacgg     180
attgcaaccg tcgttgatcc gcagtatgct gtcagcgtca acatgctaa agcggaagtt      240 catacgttct attacgggca atataacggc ataacgatg tggctgataa agaaaatgaa      300
tatcgcgtgg tcgagcagaa caattacgaa ccgcacaaag cgtggggcgc gagtaattta     360
ggccgcctgg aggactataa catggcccgt ttcaataaat tcgtgaccga ggtagcaccg     420
atcgccccca cagatgctgg tgggggcctg gatacctaca aagataaaaa ccgcttctct     480
agcttcgtgc gcattggcgc cggtcgtcag ctcgtgtacg agaagggtgt ctatcaccag     540
gaaggtaatg aaaaggggta cgacctccgt gatttgtccc aggcgtatcg ctacgctatt     600
gccggaaccc cgtataaaga tattaatatc gatcaaacca tgaataccga aggcctaatt     660
ggtttcggga atcataataa gcaatatagc gcagaagagc taaagcaggc cctcagccaa     720
gatgcgttaa ccaattacgg agtgttaggc gatagcggca gtccgctgtt tgccttcgat     780
aaacagaaaa atcaatgggt gtttctgggc acttatgatt attgggccgg atatggtaaa     840
aagagctggc aggaatggaa tatttataaa aaggaattcg cagacaaaat caagcagcat     900
gacaacgcag gtacggtgaa ggggaacggc gaacatcact ggaagacgac cggcacgaat     960
agtcatatcg gatcgacggc cgttcgcctg cgcaacaatg agggcgatgc aaacaatggg    1020
caaaacgtga cctttgagga caacggtacc ctggtcctta accagaacat aaatcagggc    1080
gcgggaggct tgttctttaa aggcgactat actgttaagg gagcaaacaa tgacatcacc    1140
tggttagggg ccggtattga cgttgcggat ggaaaaaagg tggtttggca ggttaaaaac    1200
cctaacgggg accggctggc aaaaatcggc aaagggacat ggaaattaa tggtaccggt    1260 gtgaatcagg tcagctgaa agtgggagat gggaccgtga ttctgaacca gaaagcagac    1320
gctgacaaaa aggtgcaagc ctttagccaa gtaggaattg ttagtggtcg tggcacactc    1380
gtcttgaact caagcaacca aataaatccg gataacctgt actttggatt tcgtggcgga    1440
cgcctggatg ctaacgggaa tgatctgacc tttgaacata tccgtaacgt tgacgagggt    1500
gcgcgcatag ttaatcataa tactgaccat gcatcaacta tcaccttgac cgggaaaagt    1560
ctgattacaa acccaaactc tctgtcagta cattccatcc agaatgatta tgatgaagac    1620
gattactcat actattaccg gccgcgtaga ccaattccac aaggtaaaga tctttattac    1680
aaaaattacc gttattacgc attaaaatcc ggagggcggc tgaatgcacc tatgccggaa    1740
```

```
aatggcgtgg ccgaaaacaa tgactggatt tttatgggtt atactcaaga agaggctcgc    1800
aaaaatgcaa tgaaccataa aaataaccga aggatcggtg atttcggcgg attttcgat    1860 gaggaaaatg gtaaaggtca caatggtgcg ctgaatctaa attttaacgg caaaagtgcc    1920
cagaaacgtt tccttctgac tggtggcgct aatctgaatg gtaaaatcag tgtgacgcag    1980
ggtaacgtgc tgctttctgg ccggccaact ccgcatgcac gtgattttgt aaataaatcg    2040
agcgctcgta aagatgcgca ttttctaaa ataacgagg tcgtgtttga agatgactgg    2100
ataaatcgca cctttaaagc ggcagaaatc gcggttaatc agagtgcgag cttttcatcg    2160
ggtaggaatg tatctgatat tacagcaaac attacagcca ctgataatgc gaaggtcaac    2220
ctgggttata aaacggtga tgaagtttgt gttcgatcgg attacacggg ctatgttacc    2280
tgcaacactg gcaatctgtc tgataaagcg cttaactctt ttgacgccac gcgcattaac    2340
gggaatgtga acctgaacca aaacgctgcc ttggtacttg gtaaggccgc gttgtggggt    2400
aaaattcagg gccagggcaa ctcccgtgtg tctctgaacc agcactcgaa gtggcacctg    2460
acgggggact cgcaggtgca caacttgtcc ctggccgata gccatattca ccttaacaat    2520
gcgtccgatg cccagtcagc taataaatat catacgatca aaatcaatca cctctctggc    2580
aacggtcact ttcactactt aacggattta gcaaaaaact taggggataa agtcctggta    2640
aaagaatcag cgagcggaca ttatcagtta catgtacaga acaaaacagg cgagccaaat    2700
caggaaggcc ttgacttatt tgatgcttca tcggtacaag atcgttccag actgttcgtt    2760
tcactcgcga atcactacgt tgatctgggt gcgctgcgct atactataaa gacggaaaat    2820
ggcataacac gcctctataa tccctatgcc ggtaacggcc gtccggtgaa acctgctccc    2880
tgcgtcgac                                                            2889

<210> SEQ ID NO 52
<211> LENGTH: 4284
<212> TYPE: DNA
<213> ORGANISM: Artificial Sequence
<220> FEATURE:
<223> OTHER INFORMATION: Synthetic sequence

<400> SEQUENCE: 52
ggatccttgg tacgagatga cgttgactat caaattttcc gcgactttgc ggaaaataaa      60
ggtaagtttt tcgtcggcgc cacagacctg tccgtcaaaa ataagagagg ccagaacatc     120
ggtaacgcac tgagcaacgt ccctatgatt gattttagtg tagcggacgt taataaacgg     180
attgcaaccg tcgttgatcc gcagtatgct gtcagcgtca acatgctaa agcggaagtt     240 catacgttct attacgggca atataacggc cataacgatg tggctgataa agaaaatgaa     300
tatcgcgtgg tcgagcagaa caattacgaa ccgcacaaag cgtggggcgc gagtaattta     360
ggccgcctgg aggactataa catggcccgt ttcaataaat tcgtgaccga ggtagcaccg     420
atcgccccca cagatgctgg tggggcctg gatacctaca agataaaaa ccgcttctct     480 agcttcgtgc gcattggcgc cggtcgtcag ctcgtgtacg agaagggtgt ctatcaccag     540
gaaggtaatg aaaaggggta cgacctccgt gatttgtccc aggcgtatcg ctacgctatt     600
gccggaaccc cgtataaaga tattaatatc gatcaaacca tgaataccga aggcctaatt     660
ggtttcggga atcataataa gcaatatagc gcagaagagc taaagcaggc cctcagccaa     720
gatgcgttaa ccaattacgg agtgttaggc gatagcggca gtccgctgtt tgccttcgat     780
aaacagaaaa atcaatgggt gtttctgggc acttatgatt attgggccgg atatggtaaa     840
```

```
aagagctggc aggaatggaa tatttataaa aaggaattcg cagacaaaat caagcagcat    900
gacaacgcag gtacggtgaa ggggaacggc gaacatcact ggaagacgac cggcacgaat    960
agtcatatcg gatcgacggc cgttcgcctg gcgaacaatg agggcgatgc aaacaatggg   1020
caaaacgtga cctttgagga caacggtacc ctggtcctta accagaacat aaatcagggc   1080
gcgggaggct tgttctttaa aggcgactat actgttaagg gagcaaacaa tgacatcacc   1140
tggttagggg ccggtattga cgttgcggat ggaaaaaagg tggtttggca ggttaaaaac   1200
cctaacgggg accggctggc aaaaatcggc aaagggacat tggaaattaa tggtaccggt   1260
gtgaatcagg gtcagctgaa agtgggagat gggaccgtga ttctgaacca gaaagcagac   1320
gctgacaaaa aggtgcaagc ctttagccaa gtaggaattg ttagtggtcg tggcacactc   1380
gtcttgaact caagcaacca aataaatccg gataacctgt actttggatt tcgtggcgga   1440
cgcctggatg ctaacgggaa tgatctgacc tttgaacata tccgtaacgt tgacgagggt   1500
gcgcgcatag ttaatcataa tactgaccat gcatcaacta tcaccttgac cgggaaaagt   1560
ctgattacaa acccaaactc tctgtcagta cattccatcc agaatgatta tgatgaagac   1620
gattactcat actattaccg gccgcgtaga ccaattccac aaggtaaaga tctttattac   1680
aaaaattacc gttattacgc attaaaatcc ggagggcggc tgaatgcacc tatgccggaa   1740
aatggcgtgg ccgaaaacaa tgactggatt tttatgggtt atactcaaga agaggctcgc   1800
aaaaatgcaa tgaaccataa aaataaccga aggatcggtg atttcggcgg atttttcgat   1860
gaggaaaatg gtaaaggtca caatggtgcg ctgaatctaa attttaacgg caaaagtgcc   1920
cagaaacgtt tccttctgac tggtggcgct aatctgaatg gtaaaatcag tgtgacgcag   1980
ggtaacgtgc tgctttctgg ccggccaact ccgcatgcac gtgattttgt aaataaatcg   2040
agcgctcgta aagatgcgca tttttctaaa aataacgagg tcgtgtttga agatgactgg   2100
ataaatcgca cctttaaagc ggcagaaatc gcggttaatc agagtgcgag cttttcatcg   2160
ggtaggaatg tatctgatat tacagcaaac attacagcca ctgataatgc gaaggtcaac   2220
ctgggttata aaaacggtga tgaagtttgt gttcgatcgg attacacggg ctatgttacc   2280
tgcaacactg gcaatctgtc tgataaagcg cttaactctt ttgacgccac gcgcattaac   2340
gggaatgtga acctgaacca aaacgctgcc ttggtacttg gtaaggccgc gttgtggggt   2400
aaaattcagg gccagggcaa ctcccgtgtg tctctgaacc agcactcgaa gtggcacctg   2460
acgggggact cgcaggtgca caacttgtcc ctggccgata gccatattca ccttaacaat   2520
gcgtccgatg cccagtcagc taataaatat catacgatca aaatcaatca cctctctggc   2580
aacggtcact ttcactactt aacggattta gcaaaaaact tagggataaa agtcctggta   2640
aaagaatcag cgagcggaca ttatcagtta catgtacaga acaaaacagg cgagccaaat   2700
caggaaggcc ttgacttatt tgatgcttca tcggtacaag atcgttccag actgttcgtt   2760
tcactcgcga atcactacgt tgatctgggt gcgctgcgct atactataaa gacggaaaat   2820
ggcataacac gcctctataa tccctatgcc ggtaacggcc gtccggtgaa acctgctccc   2880
tgcgtcgacg gcggtggcgg tagcgcagac gatgacgata aaggttggac cctgaactct   2940
gctggttacc tgctgggtcc gcacgctgtt gcgctagcgg gcggtggcgg tagcggcggt   3000
ggcggtagcg gcggtggcgg tagcgcacta gtgctgcagt gtatcaaggt taacaactgg   3060
gatttattct tcagcccgag tgaagacaac ttcaccaacg acctgaacaa aggtgaagaa   3120
atcacctcag atactaacat cgaagcagcc gaagaaaaca tctcgctgga cctgatccag   3180
cagtactacc tgacctttaa tttcgacaac gagccggaaa acatttctat cgaaaacctg   3240
```

```
agctctgata tcatcggcca gctggaactg atgccgaaca tcgaacgttt cccaaacggt    3300
aaaaagtacg agctggacaa atataccatg ttccactacc tgcgcgcgca ggaatttgaa    3360
cacggcaaat cccgtatcgc actgactaac tccgttaacg aagctctgct caacccgtcc    3420
cgtgtataca ccttcttctc tagcgactac gtgaaaaagg tcaacaaagc gactgaagct    3480
gcaatgttct tgggttgggt tgaacagctt gtttatgatt ttaccgacga cgtccgaa     3540 gtatctacta ccgacaaaat tgcggatatc actatcatca tcccgtacat cggtccggct    3600
ctgaacattg caacatgct gtacaaagac gacttcgttg gcgcactgat cttctccggt    3660
gcggtgatcc tgctggagtt catcccggaa atcgccatcc cggtactggg caccttttgct   3720 ctggtttctt acattgcaaa caaggttctg actgtacaaa ccatcgacaa cgcgctgagc    3780
aaacgtaacg aaaaatggga tgaagtttac aaatatatcg tgaccaactg gctggctaag    3840
gttaatactc agatcgacct catccgcaaa aaaatgaaag aagcactgga aaaccaggcg    3900
gaagctacca aggcaatcat taactaccag tacaaccagt acaccgagga agaaaaaaac    3960
aacatcaact tcaacatcga cgatctgtcc tctaaactga cgaatccat caacaaagct    4020 atgatcaaca tcaacaagtt cctgaaccag tgctctgtaa gctatctgat gaactccatg    4080
atcccgtacg gtgttaaacg tctggaggac ttcgatgcgt ctctgaaaga cgccctgctg    4140
aaatacattt acgacaaccg tggcactctg atcggtcagg ttgatcgtct gaaggacaaa    4200
gtgaacaata ccttatcgac cgacatccct tttcagctca gtaaatatgt cgataaccaa    4260
cgccttttgt ccactctaga ctag                                           4284
```

<210> SEQ ID NO 53
<211> LENGTH: 1427
<212> TYPE: PRT
<213> ORGANISM: Artificial Sequence
<220> FEATURE:
<223> OTHER INFORMATION: Synthetic sequence

<400> SEQUENCE: 53

```
Gly Ser Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
                20                  25                  30

Lys Asn Lys Arg Gly Gln Asn Ile Gly Asn Ala Leu Ser Asn Val Pro
            35                  40                  45

Met Ile Asp Phe Ser Val Ala Asp Val Asn Lys Arg Ile Ala Thr Val
        50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
                85                  90                  95

Lys Glu Asn Glu Tyr Arg Val Val Glu Gln Asn Asn Tyr Glu Pro His
            100                 105                 110

Lys Ala Trp Gly Ala Ser Asn Leu Gly Arg Leu Glu Asp Tyr Asn Met
        115                 120                 125

Ala Arg Phe Asn Lys Phe Val Thr Glu Val Ala Pro Ile Ala Pro Thr
    130                 135                 140

Asp Ala Gly Gly Gly Leu Asp Thr Tyr Lys Asp Lys Asn Arg Phe Ser
145                 150                 155                 160

Ser Phe Val Arg Ile Gly Ala Gly Arg Gln Leu Val Tyr Glu Lys Gly
                165                 170                 175
```

```
Val Tyr His Gln Glu Gly Asn Glu Lys Gly Tyr Asp Leu Arg Asp Leu
            180                 185                 190

Ser Gln Ala Tyr Arg Tyr Ala Ile Ala Gly Thr Pro Tyr Lys Asp Ile
            195                 200                 205

Asn Ile Asp Gln Thr Met Asn Thr Glu Gly Leu Ile Gly Phe Gly Asn
210                 215                 220

His Asn Lys Gln Tyr Ser Ala Glu Glu Leu Lys Gln Ala Leu Ser Gln
225                 230                 235                 240

Asp Ala Leu Thr Asn Tyr Gly Val Leu Gly Asp Ser Gly Ser Pro Leu
            245                 250                 255

Phe Ala Phe Asp Lys Gln Lys Asn Gln Trp Val Phe Leu Gly Thr Tyr
            260                 265                 270

Asp Tyr Trp Ala Gly Tyr Gly Lys Lys Ser Trp Gln Glu Trp Asn Ile
            275                 280                 285

Tyr Lys Lys Glu Phe Ala Asp Lys Ile Lys Gln His Asp Asn Ala Gly
            290                 295                 300

Thr Val Lys Gly Asn Gly Glu His His Trp Lys Thr Thr Gly Thr Asn
305                 310                 315                 320

Ser His Ile Gly Ser Thr Ala Val Arg Leu Ala Asn Asn Glu Gly Asp
            325                 330                 335

Ala Asn Asn Gly Gln Asn Val Thr Phe Glu Asp Asn Gly Thr Leu Val
            340                 345                 350

Leu Asn Gln Asn Ile Asn Gln Gly Ala Gly Gly Leu Phe Phe Lys Gly
            355                 360                 365

Asp Tyr Thr Val Lys Gly Ala Asn Asn Asp Ile Thr Trp Leu Gly Ala
            370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
            405                 410                 415

Asn Gly Thr Gly Val Asn Gln Gly Gln Leu Lys Val Gly Asp Gly Thr
            420                 425                 430

Val Ile Leu Asn Gln Lys Ala Asp Ala Asp Lys Lys Val Gln Ala Phe
            435                 440                 445

Ser Gln Val Gly Ile Val Ser Gly Arg Gly Thr Leu Val Leu Asn Ser
450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
            485                 490                 495

Val Asp Glu Gly Ala Arg Ile Val Asn His Asn Thr Asp His Ala Ser
            500                 505                 510

Thr Ile Thr Leu Thr Gly Lys Ser Leu Ile Thr Asn Pro Asn Ser Leu
            515                 520                 525

Ser Val His Ser Ile Gln Asn Asp Tyr Asp Glu Asp Asp Tyr Ser Tyr
            530                 535                 540

Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
            565                 570                 575

Pro Met Pro Glu Asn Gly Val Ala Glu Asn Asn Asp Trp Ile Phe Met
            580                 585                 590
```

```
Gly Tyr Thr Gln Glu Glu Ala Arg Lys Asn Ala Met Asn His Lys Asn
            595                 600                 605

Asn Arg Arg Ile Gly Asp Phe Gly Gly Phe Phe Asp Glu Glu Asn Gly
610                 615                 620

Lys Gly His Asn Gly Ala Leu Asn Leu Asn Phe Asn Gly Lys Ser Ala
625                 630                 635                 640

Gln Lys Arg Phe Leu Leu Thr Gly Gly Ala Asn Leu Asn Gly Lys Ile
                645                 650                 655

Ser Val Thr Gln Gly Asn Val Leu Leu Ser Gly Arg Pro Thr Pro His
                660                 665                 670

Ala Arg Asp Phe Val Asn Lys Ser Ser Ala Arg Lys Asp Ala His Phe
            675                 680                 685

Ser Lys Asn Asn Glu Val Val Phe Glu Asp Asp Trp Ile Asn Arg Thr
690                 695                 700

Phe Lys Ala Ala Glu Ile Ala Val Asn Gln Ser Ala Ser Phe Ser Ser
705                 710                 715                 720

Gly Arg Asn Val Ser Asp Ile Thr Ala Asn Ile Thr Ala Thr Asp Asn
                725                 730                 735

Ala Lys Val Asn Leu Gly Tyr Lys Asn Gly Asp Glu Val Cys Val Arg
            740                 745                 750

Ser Asp Tyr Thr Gly Tyr Val Thr Cys Asn Thr Gly Asn Leu Ser Asp
            755                 760                 765

Lys Ala Leu Asn Ser Phe Asp Ala Thr Arg Ile Asn Gly Asn Val Asn
770                 775                 780

Leu Asn Gln Asn Ala Ala Leu Val Leu Gly Lys Ala Ala Leu Trp Gly
785                 790                 795                 800

Lys Ile Gln Gly Gln Gly Asn Ser Arg Val Ser Leu Asn Gln His Ser
                805                 810                 815

Lys Trp His Leu Thr Gly Asp Ser Gln Val His Asn Leu Ser Leu Ala
                820                 825                 830

Asp Ser His Ile His Leu Asn Asn Ala Ser Asp Ala Gln Ser Ala Asn
            835                 840                 845

Lys Tyr His Thr Ile Lys Ile Asn His Leu Ser Gly Asn Gly His Phe
            850                 855                 860

His Tyr Leu Thr Asp Leu Ala Lys Asn Leu Gly Asp Lys Val Leu Val
865                 870                 875                 880

Lys Glu Ser Ala Ser Gly His Tyr Gln Leu His Val Gln Asn Lys Thr
                885                 890                 895

Gly Glu Pro Asn Gln Glu Gly Leu Asp Leu Phe Asp Ala Ser Ser Val
            900                 905                 910

Gln Asp Arg Ser Arg Leu Phe Val Ser Leu Ala Asn His Tyr Val Asp
            915                 920                 925

Leu Gly Ala Leu Arg Tyr Thr Ile Lys Thr Glu Asn Gly Ile Thr Arg
930                 935                 940

Leu Tyr Asn Pro Tyr Ala Gly Asn Gly Arg Pro Val Lys Pro Ala Pro
945                 950                 955                 960

Cys Val Asp Gly Gly Gly Ser Ala Asp Asp Asp Lys Gly Trp
                965                 970                 975

Thr Leu Asn Ser Ala Gly Tyr Leu Leu Gly Pro His Ala Val Ala Leu
                980                 985                 990

Ala Gly Gly Gly Gly Ser Gly Gly Gly Ser Gly Gly Gly Gly Ser
            995                 1000                1005

Ala Leu Val Leu Gln Cys Ile Lys Val Asn Asn Trp Asp Leu Phe
```

```
                    1010                1015                1020

Phe Ser Pro Ser Glu Asp Asn Phe Thr Asn Asp Leu Asn Lys Gly
    1025                1030                1035

Glu Glu Ile Thr Ser Asp Thr Asn Ile Glu Ala Ala Glu Glu Asn
    1040                1045                1050

Ile Ser Leu Asp Leu Ile Gln Gln Tyr Tyr Leu Thr Phe Asn Phe
    1055                1060                1065

Asp Asn Glu Pro Glu Asn Ile Ser Ile Glu Asn Leu Ser Ser Asp
    1070                1075                1080

Ile Ile Gly Gln Leu Glu Leu Met Pro Asn Ile Glu Arg Phe Pro
    1085                1090                1095

Asn Gly Lys Lys Tyr Glu Leu Asp Lys Tyr Thr Met Phe His Tyr
    1100                1105                1110

Leu Arg Ala Gln Glu Phe Glu His Gly Lys Ser Arg Ile Ala Leu
    1115                1120                1125

Thr Asn Ser Val Asn Glu Ala Leu Leu Asn Pro Ser Arg Val Tyr
    1130                1135                1140

Thr Phe Phe Ser Ser Asp Tyr Val Lys Lys Val Asn Lys Ala Thr
    1145                1150                1155

Glu Ala Ala Met Phe Leu Gly Trp Val Glu Gln Leu Val Tyr Asp
    1160                1165                1170

Phe Thr Asp Glu Thr Ser Glu Val Ser Thr Thr Asp Lys Ile Ala
    1175                1180                1185

Asp Ile Thr Ile Ile Pro Tyr Ile Gly Pro Ala Leu Asn Ile
    1190                1195                1200

Gly Asn Met Leu Tyr Lys Asp Asp Phe Val Gly Ala Leu Ile Phe
    1205                1210                1215

Ser Gly Ala Val Ile Leu Leu Glu Phe Ile Pro Glu Ile Ala Ile
    1220                1225                1230

Pro Val Leu Gly Thr Phe Ala Leu Val Ser Tyr Ile Ala Asn Lys
    1235                1240                1245

Val Leu Thr Val Gln Thr Ile Asp Asn Ala Leu Ser Lys Arg Asn
    1250                1255                1260

Glu Lys Trp Asp Glu Val Tyr Lys Tyr Ile Val Thr Asn Trp Leu
    1265                1270                1275

Ala Lys Val Asn Thr Gln Ile Asp Leu Ile Arg Lys Lys Met Lys
    1280                1285                1290

Glu Ala Leu Glu Asn Gln Ala Glu Ala Thr Lys Ala Ile Ile Asn
    1295                1300                1305

Tyr Gln Tyr Asn Gln Tyr Thr Glu Glu Glu Lys Asn Asn Ile Asn
    1310                1315                1320

Phe Asn Ile Asp Asp Leu Ser Ser Lys Leu Asn Glu Ser Ile Asn
    1325                1330                1335

Lys Ala Met Ile Asn Ile Asn Lys Phe Leu Asn Gln Cys Ser Val
    1340                1345                1350

Ser Tyr Leu Met Asn Ser Met Ile Pro Tyr Gly Val Lys Arg Leu
    1355                1360                1365

Glu Asp Phe Asp Ala Ser Leu Lys Asp Ala Leu Leu Lys Tyr Ile
    1370                1375                1380

Tyr Asp Asn Arg Gly Thr Leu Ile Gly Gln Val Asp Arg Leu Lys
    1385                1390                1395

Asp Lys Val Asn Asn Thr Leu Ser Thr Asp Ile Pro Phe Gln Leu
    1400                1405                1410
```

```
Ser Lys Tyr Val Asp Asn Gln Arg Leu Leu Ser Thr Leu Asp
    1415                1420                1425
```

<210> SEQ ID NO 54
<211> LENGTH: 558
<212> TYPE: DNA
<213> ORGANISM: Artificial Sequence
<220> FEATURE:
<223> OTHER INFORMATION: Synthetic sequence

<400> SEQUENCE: 54

```
ctgcagtgta tcaatctgga ttgggacgta atccgtgata agaccaaaac aaaaatcgag    60
tctttgaaag aacacggccc gatcaaaaat aagatgtctg aatcacccaa taaaactgtt   120
tcggaggaaa aagcgaaaca gtatttggaa gagtttcatc aaaccgcgct tgaacatccg   180
gagctcagtg aactgaaaac agtgacggga acgaatcctg tttttgcagg cgcaaactat   240
gcggcttggg ccgtgaatgt tgcccaagta attgatagtg agaccgcaga caacctggaa   300
aagacgaccg cagcgttaag catttttaccg gggattggtt ccgtgatggg tatagcggat   360
ggagcggtcc accataacac tgaggaaatt gtcgcccagt caatcgctct gagttccctg   420
atggttgcac aggctatccc actcgtgggg gaactggttg acataggttt cgccgcctac   480
aacttcgtag aaagcattat taatcttttt caggtggtgc ataacagcta caaccgccct   540
ctagaatgat aaaagctt                                                  558
```

<210> SEQ ID NO 55
<211> LENGTH: 2010
<212> TYPE: DNA
<213> ORGANISM: Artificial Sequence
<220> FEATURE:
<223> OTHER INFORMATION: Synthetic sequence

<400> SEQUENCE: 55

```
catatgggat ccatggagtt cgttaacaaa cagttcaact ataaagaccc agttaacggt    60
gttgacattg cttacatcaa atcccgaac gctggccaga tgcagccggt aaaggcattc   120
aaaatccaca acaaaatctg ggttatcccg aacgtgata cctttactaa cccggaagaa   180
ggtgacctga acccgccacc ggaagcgaaa caggtgccgg tatcttacta tgactccacc   240
tacctgtcta ccgataacga aaggacaac tacctgaaag gtgttactaa actgttcgag   300
cgtatttact ccaccgacct gggccgtatg ctgctgacta gcatcgttcg cggtatcccg   360
ttctggggcg ttctaccat cgataccgaa ctgaaagtaa tcgacactaa ctgcatcaac   420
gttattcagc cggacggttc ctatcgttcc gaagaactga acctggtgat catcggcccg   480
tctgctgata tcatccagtt cgagtgtaag agctttggtc acgaagttct gaacctcacc   540
cgtaacggct acggttccac tcagtacatc cgtttctctc cggacttcac cttcggtttt   600
gaagaatccc tggaagtaga cacgaaccca ctgctgggcg ctggtaaatt cgcaactgat   660
cctgcggtta ccctggctca cgaactgatt catgcaggcc accgcctgta cggtatcgcc   720
atcaatccga accgtgtctt caaagttaac accaacgcgt attacgagat gtccggtctg   780
gaagttagct cgaagaact gcgtactttt ggcggtcacg acgctaaatt catcgactct   840
ctgcaagaaa acgagttccg tctgtactac tataacaagt tcaaagatat cgcatccacc   900
ctgaacaaag cgaaatccat cgtgggtacc actgcttctc tccagtacat gaagaacgtt   960
tttaaagaaa ataccctgct cagcgaagac acctccggca aattctctgt agacaagttg  1020
aaattcgata aactttacaa aatgctgact gaaatttaca ccgaagacaa cttcgttaag  1080
```

-continued

```
ttctttaaag ttctgaaccg caaaacctat ctgaacttcg acaaggcagt attcaaaatc      1140
aacatcgtgc cgaaagttaa ctacactatc tacgatggtt tcaacctgcg taacaccaac      1200
ctggctgcta attttaacgg ccagaacacg gaaatcaaca acatgaactt cacaaaactg      1260
aaaaacttca ctggtctgtt cgagttttac aagctgctgt gcgtcgacgg cggtggcggt      1320
agcgcagacg atgacgataa aggttggacc ctgaactctg ctggttacct gctgggtccg      1380
cacgctgttg cgctagcggg cggtggcggt agcggcggtg gcggtagcgg cggtggcggt      1440
agcgcactag tgctgcagtg tatcaatctg gattgggacg taatccgtga taagaccaaa      1500
acaaaaatcg agtctttgaa agaacacggc ccgatcaaaa ataagatgtc tgaatcaccc      1560
aataaaactg tttcggagga aaaagcgaaa cagtatttgg aagagtttca tcaaaccgcg      1620
cttgaacatc cggagctcag tgaactgaaa acagtgacgg gaacgaatcc tgttttttgca     1680 ggcgcaaact atgcggcttg ggccgtgaat gttgcccaag taattgatag tgagaccgca      1740
gacaacctgg aaaagacgac cgcagcgtta agcattttac cggggattgg ttccgtgatg      1800
ggtatagcgg atggagcggt ccaccataac actgaggaaa ttgtcgccca gtcaatcgct      1860
ctgagttccc tgatggttgc acaggctatc ccactcgtgg gggaactggt tgacataggt      1920
ttcgccgcct acaacttcgt agaaagcatt attaatcttt tcaggtggt gcataacagc       1980 tacaaccgcc ctctagaatg ataaaagctt                                      2010
```

<210> SEQ ID NO 56
<211> LENGTH: 666
<212> TYPE: PRT
<213> ORGANISM: Artificial Sequence
<220> FEATURE:
<223> OTHER INFORMATION: Synthetic sequence

<400> SEQUENCE: 56

```
His Met Gly Ser Met Glu Phe Val Asn Lys Gln Phe Asn Tyr Lys Asp
1               5                   10                  15

Pro Val Asn Gly Val Asp Ile Ala Tyr Ile Lys Ile Pro Asn Ala Gly
            20                  25                  30

Gln Met Gln Pro Val Lys Ala Phe Lys Ile His Asn Lys Ile Trp Val
        35                  40                  45

Ile Pro Glu Arg Asp Thr Phe Thr Asn Pro Glu Glu Gly Asp Leu Asn
    50                  55                  60

Pro Pro Pro Glu Ala Lys Gln Val Pro Val Ser Tyr Tyr Asp Ser Thr
65                  70                  75                  80

Tyr Leu Ser Thr Asp Asn Glu Lys Asp Asn Tyr Leu Lys Gly Val Thr
                85                  90                  95

Lys Leu Phe Glu Arg Ile Tyr Ser Thr Asp Leu Gly Arg Met Leu Leu
            100                 105                 110

Thr Ser Ile Val Arg Gly Ile Pro Phe Trp Gly Gly Ser Thr Ile Asp
        115                 120                 125

Thr Glu Leu Lys Val Ile Asp Thr Asn Cys Ile Asn Val Ile Gln Pro
    130                 135                 140

Asp Gly Ser Tyr Arg Ser Glu Glu Leu Asn Leu Val Ile Ile Gly Pro
145                 150                 155                 160

Ser Ala Asp Ile Ile Gln Phe Glu Cys Lys Ser Phe Gly His Glu Val
                165                 170                 175

Leu Asn Leu Thr Arg Asn Gly Tyr Gly Ser Thr Gln Tyr Ile Arg Phe
            180                 185                 190
```

-continued

```
Ser Pro Asp Phe Thr Phe Gly Phe Glu Glu Ser Leu Glu Val Asp Thr
            195                 200                 205

Asn Pro Leu Leu Gly Ala Gly Lys Phe Ala Thr Asp Pro Ala Val Thr
210                 215                 220

Leu Ala His Glu Leu Ile His Ala Gly His Arg Leu Tyr Gly Ile Ala
225                 230                 235                 240

Ile Asn Pro Asn Arg Val Phe Lys Val Asn Thr Asn Ala Tyr Tyr Glu
                245                 250                 255

Met Ser Gly Leu Glu Val Ser Phe Glu Leu Arg Thr Phe Gly Gly
            260                 265                 270

His Asp Ala Lys Phe Ile Asp Ser Leu Gln Glu Asn Glu Phe Arg Leu
            275                 280                 285

Tyr Tyr Tyr Asn Lys Phe Lys Asp Ile Ala Ser Thr Leu Asn Lys Ala
290                 295                 300

Lys Ser Ile Val Gly Thr Thr Ala Ser Leu Gln Tyr Met Lys Asn Val
305                 310                 315                 320

Phe Lys Glu Lys Tyr Leu Leu Ser Glu Asp Thr Ser Gly Lys Phe Ser
                325                 330                 335

Val Asp Lys Leu Lys Phe Asp Lys Leu Tyr Lys Met Leu Thr Glu Ile
            340                 345                 350

Tyr Thr Glu Asp Asn Phe Val Lys Phe Phe Lys Val Leu Asn Arg Lys
            355                 360                 365

Thr Tyr Leu Asn Phe Asp Lys Ala Val Phe Lys Ile Asn Ile Val Pro
            370                 375                 380

Lys Val Asn Tyr Thr Ile Tyr Asp Gly Phe Asn Leu Arg Asn Thr Asn
385                 390                 395                 400

Leu Ala Ala Asn Phe Asn Gly Gln Asn Thr Glu Ile Asn Asn Met Asn
                405                 410                 415

Phe Thr Lys Leu Lys Asn Phe Thr Gly Leu Phe Glu Phe Tyr Lys Leu
            420                 425                 430

Leu Cys Val Asp Gly Gly Gly Ser Ala Asp Asp Asp Lys Gly
            435                 440                 445

Trp Thr Leu Asn Ser Ala Gly Tyr Leu Leu Gly Pro His Ala Val Ala
            450                 455                 460

Leu Ala Gly Gly Gly Gly Ser Gly Gly Gly Gly Ser Gly Gly Gly Gly
465                 470                 475                 480

Ser Ala Leu Val Leu Gln Cys Ile Asn Leu Asp Trp Asp Val Ile Arg
                485                 490                 495

Asp Lys Thr Lys Thr Lys Ile Glu Ser Leu Lys Glu His Gly Pro Ile
            500                 505                 510

Lys Asn Lys Met Ser Glu Ser Pro Asn Lys Thr Val Ser Glu Glu Lys
            515                 520                 525

Ala Lys Gln Tyr Leu Glu Glu Phe His Gln Thr Ala Leu Glu His Pro
            530                 535                 540

Glu Leu Ser Glu Leu Lys Thr Val Thr Gly Thr Asn Pro Val Phe Ala
545                 550                 555                 560

Gly Ala Asn Tyr Ala Ala Trp Ala Val Asn Val Ala Gln Val Ile Asp
                565                 570                 575

Ser Glu Thr Ala Asp Asn Leu Glu Lys Thr Thr Ala Ala Leu Ser Ile
            580                 585                 590

Leu Pro Gly Ile Gly Ser Val Met Gly Ile Ala Asp Gly Ala Val His
            595                 600                 605

His Asn Thr Glu Glu Ile Val Ala Gln Ser Ile Ala Leu Ser Ser Leu
```

```
              610                615                620
    Met Val Ala Gln Ala Ile Pro Leu Val Gly Glu Leu Val Asp Ile Gly
    625                 630                635                640

Phe Ala Ala Tyr Asn Phe Val Glu Ser Ile Ile Asn Leu Phe Gln Val
                    645                 650                655

Val His Asn Ser Tyr Asn Arg Pro Leu Glu
                660                 665

<210> SEQ ID NO 57
<211> LENGTH: 1329
<212> TYPE: DNA
<213> ORGANISM: Artificial Sequence
<220> FEATURE:
<223> OTHER INFORMATION: Synthetic sequence

<400> SEQUENCE: 57
ggatccatgc ctattactat taacaatttt cgttatagcg atcccgtcaa caatgacacc      60
attatcatga tggaaccgcc atattgcaaa ggactggaca tttactataa agccttcaag     120
attactgacc gcatttggat tgttccagag cgttacgagt tcgggacgaa accagaagat     180
tttaacccgc cttcatcgct gatcgaagga gcatcagagt attacgatcc gaactatctg     240
cgtacggaca gcgataaaga ccgcttctta cagaccatgg tcaaactttt taaccgtatt     300
aagaacaatg tggccggaga agcactcttg gataagatta tcaacgcgat tccatacctg     360
ggcaattctt acagcctgct ggataaattt gacacaaata gtaattcagt cagctttaac     420
ctgttagaac aagatccgag tggcgcaacc acgaagtctg ccatgctgac aaatctgatc     480
atttttggtc aggtcctgt actgaataaa aatgaagtac gcggcatcgt tctccgcgtg     540
gacaataaga actactttcc atgccgtgac ggcttcggtt cgatcatgca gatggctttc     600
tgtccggagt acgttccgac gtttgataat gttattgaga atatcacgag tttaacaatc     660
ggtaagtcaa atatttttca agatccggcc cttctcctta tgcatgaact gattcacgtg     720
ctgcacggct tatatggtat gcaagtgtcc tcgcatgaaa tcattccgtc caaacaggaa     780
atttatatgc agcataccta cccgatttca gctgaagagt tgtttacgtt tggtggccag     840
gacgcgaatt tgatctccat cgacatcaaa acgatctgt atgagaaaac attaaatgac     900
tataaagcga ttcgaacaa actgtctcag gtgactagct gcaacgatcc taacattgat     960
attgattcct acaaacaaat ttatcaacag aaataccagt tcgataaaga cagcaatggt    1020
cagtatatcg taaacgaaga taaatttcag atcctgtata acagcattat gtatggcttt    1080
accgaaattg agttggggaa gaaatttaac attaaaaccc gtctgtctta ttttagtatg    1140
aaccatgatc cggtgaaaat ccccaatctg cttgatgata ccatttataa tgataccgaa    1200
gggttcaaca ttgaatctaa ggatctgaaa tccgaataca aaggccaaaa tatgcgtgtt    1260
aatactaacg ctttccgtaa tgttgatggt agtggactcg tctcgaaact gattggggtg    1320
tgtgtcgac                                                            1329

<210> SEQ ID NO 58
<211> LENGTH: 2772
<212> TYPE: DNA
<213> ORGANISM: Artificial Sequence
<220> FEATURE:
<223> OTHER INFORMATION: Synthetic sequence

<400> SEQUENCE: 58
catatgggat ccatgcctat tactattaac aattttcgtt atagcgatcc cgtcaacaat      60
```

```
gacaccatta tcatgatgga accgccatat tgcaaaggac tggacattta ctataaagcc    120
ttcaagatta ctgaccgcat ttggattgtt ccagagcgtt acgagttcgg gacgaaacca    180
gaagatttta acccgccttc atcgctgatc gaaggagcat cagagtatta cgatccgaac    240
tatctgcgta cggacagcga taaagaccgc ttcttacaga ccatggtcaa acttttaac    300 cgtattaaga acaatgtggc cggagaagca ctcttggata agattatcaa cgcgattcca    360
tacctgggca attcttacag cctgctggat aaatttgaca caaatagtaa ttcagtcagc    420
tttaacctgt tagaacaaga tccgagtggc gcaaccacga agtctgccat gctgacaaat    480
ctgatcattt ttggtccagg tcctgtactg aataaaaatg aagtacgcgg catcgttctc    540
cgcgtggaca ataagaacta cttcccatgc cgtgacggct tcggttcgat catgcagatg    600
gctttctgtc cggagtacgt tccgacgttt gataatgtta ttgagaatat cacgagttta    660
acaatcggta agtcaaaata ttttcaagat ccggcccttc tccttatgca tgaactgatt    720
cacgtgctgc acggcttata tggtatgcaa gtgtcctcgc atgaaatcat tccgtccaaa    780
caggaaattt atatgcagca tacctacccg atttcagctg aagagttgtt tacgtttggt    840
ggccaggacg cgaatttgat ctccatcgac atcaaaaacg atctgtatga gaaacatta    900 aatgactata aagcgattgc gaacaaactg tctcaggtga ctagctgcaa cgatcctaac    960
attgatattg attcctacaa acaaatttat caacagaaat accagttcga taaagacagc   1020
aatggtcagt atatcgtaaa cgaagataaa tttcagatcc tgtataacag cattatgtat   1080
ggctttaccg aaattgagtt ggggaagaaa tttaacatta aaacccgtct gtcttatttt   1140
agtatgaacc atgatccggt gaaaatcccc aatctgcttg atgataccat ttataatgat   1200
accgaagggt tcaacattga atctaaggat ctgaaatccg aatacaaagg ccaaaatatg   1260
cgtgttaata ctaacgcttt ccgtaatgtt gatggtagtg gactcgtctc gaaactgatt   1320
gggttgtgtg tcgacggcgg tggcggtagc gcagacgatg acgataaagg ttggaccctg   1380
aactctgctg gttacctgct gggtccgcac gctgttgcgc tagcgggcgg tggcggtagc   1440
ggcggtggcg gtagcggcgg tggcggtagc gcactagtgc tgcagtgtat caaggttaac   1500
aactgggatt tattcttcag cccgagtgaa gacaacttca ccaacgacct gaacaaaggt   1560
gaagaaatca cctcagatac taacatcgaa gcagccgaag aaaacatctc gctggacctg   1620
atccagcagt actacctgac ctttaatttc gacaacgagc cggaaaacat ttctatcgaa   1680
aacctgagct ctgatatcat cggccagctg gaactgatgc cgaacatcga acgtttccca   1740
aacggtaaaa agtacgagct ggacaaatat accatgttcc actacctgcg cgcgcaggaa   1800
tttgaacacg gcaaatcccg tatcgcactg actaactccg ttaacgaagc tctgctcaac   1860
ccgtcccgtg tatacacctt cttctctagc gactacgtga aaaaggtcaa caaagcgact   1920
gaagctgcaa tgttcttggg ttgggttgaa cagcttgttt atgattttac cgacgagacg   1980
tccgaagtat ctactaccga caaaattgcg gatatcacta tcatcatccc gtacatcggt   2040
ccggctctga acattggcaa catgctgtac aaagacgact tcgttggcgc actgatcttc   2100
tccggtgcgg tgatcctgct ggagttcatc ccggaaatcg ccatcccggt actgggcacc   2160
tttgctctgg tttcttacat tgcaaacaag gttctgactg tacaaaccat cgacaacgcg   2220
ctgagcaaac gtaacgaaaa atgggatgaa gtttacaaat atatcgtgac caactggctg   2280
gctaaggtta atactcagat cgacctcatc cgcaaaaaaa tgaaagaagc actggaaaac   2340
caggcggaag ctaccaaggc aatcattaac taccagtaca accagtacac cgaggaagaa   2400
aaaaacaaca tcaacttcaa catcgacgat ctgtcctcta aactgaacga atccatcaac   2460
```

-continued

```
aaagctatga tcaacatcaa caagttcctg aaccagtgct ctgtaagcta tctgatgaac    2520
tccatgatcc cgtacggtgt taaacgtctg gaggacttcg atgcgtctct gaaagacgcc    2580
ctgctgaaat acatttacga caaccgtggc actctgatcg gtcaggttga tcgtctgaag    2640
gacaaagtga acaataccct atcgaccgac atcccttttc agctcagtaa atatgtcgat    2700
aaccaacgcc ttttgtccac tctagaagca ctagcgagtg gcaccatca ccatcaccat     2760 taatgaaagc tt                                                        2772
```

<210> SEQ ID NO 59
<211> LENGTH: 920
<212> TYPE: PRT
<213> ORGANISM: Artificial Sequence
<220> FEATURE:
<223> OTHER INFORMATION: Synthetic sequence

<400> SEQUENCE: 59

```
His Met Gly Ser Met Pro Ile Thr Ile Asn Asn Phe Arg Tyr Ser Asp
1               5                   10                  15

Pro Val Asn Asn Asp Thr Ile Ile Met Met Glu Pro Pro Tyr Cys Lys
            20                  25                  30

Gly Leu Asp Ile Tyr Tyr Lys Ala Phe Lys Ile Thr Asp Arg Ile Trp
        35                  40                  45

Ile Val Pro Glu Arg Tyr Glu Phe Gly Thr Lys Pro Glu Asp Phe Asn
    50                  55                  60

Pro Pro Ser Ser Leu Ile Glu Gly Ala Ser Glu Tyr Tyr Asp Pro Asn
65                  70                  75                  80

Tyr Leu Arg Thr Asp Ser Asp Lys Asp Arg Phe Leu Gln Thr Met Val
                85                  90                  95

Lys Leu Phe Asn Arg Ile Lys Asn Asn Val Ala Gly Glu Ala Leu Leu
            100                 105                 110

Asp Lys Ile Ile Asn Ala Ile Pro Tyr Leu Gly Asn Ser Tyr Ser Leu
        115                 120                 125

Leu Asp Lys Phe Asp Thr Asn Ser Asn Ser Val Ser Phe Asn Leu Leu
    130                 135                 140

Glu Gln Asp Pro Ser Gly Ala Thr Thr Lys Ser Ala Met Leu Thr Asn
145                 150                 155                 160

Leu Ile Ile Phe Gly Pro Gly Pro Val Leu Asn Lys Asn Glu Val Arg
                165                 170                 175

Gly Ile Val Leu Arg Val Asp Asn Lys Asn Tyr Phe Pro Cys Arg Asp
            180                 185                 190

Gly Phe Gly Ser Ile Met Gln Met Ala Phe Cys Pro Glu Tyr Val Pro
        195                 200                 205

Thr Phe Asp Asn Val Ile Glu Asn Ile Thr Ser Leu Thr Ile Gly Lys
    210                 215                 220

Ser Lys Tyr Phe Gln Asp Pro Ala Leu Leu Leu Met His Glu Leu Ile
225                 230                 235                 240

His Val Leu His Gly Leu Tyr Gly Met Gln Val Ser Ser His Glu Ile
                245                 250                 255

Ile Pro Ser Lys Gln Glu Ile Tyr Met Gln His Thr Tyr Pro Ile Ser
            260                 265                 270

Ala Glu Glu Leu Phe Thr Phe Gly Gly Gln Asp Ala Asn Leu Ile Ser
        275                 280                 285

Ile Asp Ile Lys Asn Asp Leu Tyr Glu Lys Thr Leu Asn Asp Tyr Lys
    290                 295                 300
```

```
Ala Ile Ala Asn Lys Leu Ser Gln Val Thr Ser Cys Asn Asp Pro Asn
305                 310                 315                 320

Ile Asp Ile Asp Ser Tyr Lys Gln Ile Tyr Gln Gln Lys Tyr Gln Phe
                325                 330                 335

Asp Lys Asp Ser Asn Gly Gln Tyr Ile Val Asn Glu Asp Lys Phe Gln
            340                 345                 350

Ile Leu Tyr Asn Ser Ile Met Tyr Gly Phe Thr Glu Ile Glu Leu Gly
                355                 360                 365

Lys Lys Phe Asn Ile Lys Thr Arg Leu Ser Tyr Phe Ser Met Asn His
370                 375                 380

Asp Pro Val Lys Ile Pro Asn Leu Leu Asp Thr Ile Tyr Asn Asp
385                 390                 395                 400

Thr Glu Gly Phe Asn Ile Glu Ser Lys Asp Leu Lys Ser Glu Tyr Lys
                405                 410                 415

Gly Gln Asn Met Arg Val Asn Thr Asn Ala Phe Arg Asn Val Asp Gly
                420                 425                 430

Ser Gly Leu Val Ser Lys Leu Ile Gly Leu Cys Val Asp Gly Gly Gly
            435                 440                 445

Gly Ser Ala Asp Asp Asp Lys Gly Trp Thr Leu Asn Ser Ala Gly
450                 455                 460

Tyr Leu Leu Gly Pro His Ala Val Ala Leu Ala Gly Gly Gly Ser
465                 470                 475                 480

Gly Gly Gly Gly Ser Gly Gly Gly Ser Ala Leu Val Leu Gln Cys
                485                 490                 495

Ile Lys Val Asn Asn Trp Asp Leu Phe Phe Ser Pro Ser Glu Asp Asn
                500                 505                 510

Phe Thr Asn Asp Leu Asn Lys Gly Glu Glu Ile Thr Ser Asp Thr Asn
                515                 520                 525

Ile Glu Ala Ala Glu Asn Ile Ser Leu Asp Leu Ile Gln Gln Tyr
                530                 535                 540

Tyr Leu Thr Phe Asn Phe Asp Asn Glu Pro Glu Asn Ile Ser Ile Glu
545                 550                 555                 560

Asn Leu Ser Ser Asp Ile Ile Gly Gln Leu Glu Leu Met Pro Asn Ile
                565                 570                 575

Glu Arg Phe Pro Asn Gly Lys Lys Tyr Glu Leu Asp Lys Tyr Thr Met
                580                 585                 590

Phe His Tyr Leu Arg Ala Gln Glu Phe Glu His Gly Lys Ser Arg Ile
                595                 600                 605

Ala Leu Thr Asn Ser Val Asn Glu Ala Leu Leu Asn Pro Ser Arg Val
                610                 615                 620

Tyr Thr Phe Phe Ser Ser Asp Tyr Val Lys Lys Val Asn Lys Ala Thr
625                 630                 635                 640

Glu Ala Ala Met Phe Leu Gly Trp Val Glu Gln Leu Val Tyr Asp Phe
                645                 650                 655

Thr Asp Glu Thr Ser Glu Val Ser Thr Thr Asp Lys Ile Ala Asp Ile
                660                 665                 670

Thr Ile Ile Ile Pro Tyr Ile Gly Pro Ala Leu Asn Ile Gly Asn Met
                675                 680                 685

Leu Tyr Lys Asp Asp Phe Val Gly Ala Leu Ile Phe Ser Gly Ala Val
                690                 695                 700

Ile Leu Leu Glu Phe Ile Pro Glu Ile Ala Ile Pro Val Leu Gly Thr
705                 710                 715                 720
```

```
Phe Ala Leu Val Ser Tyr Ile Ala Asn Lys Val Leu Thr Val Gln Thr
                725                 730                 735

Ile Asp Asn Ala Leu Ser Lys Arg Asn Glu Lys Trp Asp Glu Val Tyr
            740                 745                 750

Lys Tyr Ile Val Thr Asn Trp Leu Ala Lys Val Asn Thr Gln Ile Asp
        755                 760                 765

Leu Ile Arg Lys Lys Met Lys Glu Ala Leu Glu Asn Gln Ala Glu Ala
    770                 775                 780

Thr Lys Ala Ile Ile Asn Tyr Gln Tyr Asn Gln Tyr Thr Glu Glu Glu
785                 790                 795                 800

Lys Asn Asn Ile Asn Phe Asn Ile Asp Asp Leu Ser Ser Lys Leu Asn
                805                 810                 815

Glu Ser Ile Asn Lys Ala Met Ile Asn Ile Asn Lys Phe Leu Asn Gln
            820                 825                 830

Cys Ser Val Ser Tyr Leu Met Asn Ser Met Ile Pro Tyr Gly Val Lys
        835                 840                 845

Arg Leu Glu Asp Phe Asp Ala Ser Leu Lys Asp Ala Leu Leu Lys Tyr
    850                 855                 860

Ile Tyr Asp Asn Arg Gly Thr Leu Ile Gly Gln Val Asp Arg Leu Lys
865                 870                 875                 880

Asp Lys Val Asn Asn Thr Leu Ser Thr Asp Ile Pro Phe Gln Leu Ser
                885                 890                 895

Lys Tyr Val Asp Asn Gln Arg Leu Leu Ser Thr Leu Glu Ala Leu Ala
            900                 905                 910

Ser Gly His His His His His His
        915                 920

<210> SEQ ID NO 60
<211> LENGTH: 5
<212> TYPE: PRT
<213> ORGANISM: Unknown
<220> FEATURE:
<223> OTHER INFORMATION: Description of Unknown:
      Enterokinase sequence

<400> SEQUENCE: 60

Asp Asp Asp Asp Lys
1               5

<210> SEQ ID NO 61
<211> LENGTH: 4
<212> TYPE: PRT
<213> ORGANISM: Unknown
<220> FEATURE:
<223> OTHER INFORMATION: Description of Unknown:
      Factor Xa sequence

<400> SEQUENCE: 61

Ile Glu Gly Arg
1

<210> SEQ ID NO 62
<211> LENGTH: 4
<212> TYPE: PRT
<213> ORGANISM: Unknown
<220> FEATURE:
<223> OTHER INFORMATION: Description of Unknown:
      Factor Xa sequence

<400> SEQUENCE: 62

Ile Asp Gly Arg
```

```
<210> SEQ ID NO 63
<211> LENGTH: 7
<212> TYPE: PRT
<213> ORGANISM: Tabacco Etch virus

<400> SEQUENCE: 63

Glu Asn Leu Tyr Phe Gln Gly
1               5

<210> SEQ ID NO 64
<211> LENGTH: 6
<212> TYPE: PRT
<213> ORGANISM: Unknown
<220> FEATURE:
<223> OTHER INFORMATION: Description of Unknown:
      Thrombin sequence

<400> SEQUENCE: 64

Leu Val Pro Arg Gly Ser
1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Val Leu Phe Gln Gly Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Gly Gly Ser Ala
1               5

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Gly Gly Gly Ser Gly Gly Gly Gly Ser Ala
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68
```

```
Ala Leu Ala Gly Gly Gly Ser Gly Gly Gly Gly Ser Ala Leu Val
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gly Gly Gly Ser Gly Gly Gly Ser Gly Gly Gly Gly Ser Ala
1               5                   10                  15

<210> SEQ ID NO 70
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ala Leu Ala Gly Gly Gly Ser Gly Gly Gly Ser Gly Gly Gly
1               5                   10                  15

Gly Ser Ala Leu Val
            20

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Gly Gly Gly Gly Ser Gly Gly Gly Ser Gly Gly Gly Gly Ser
1               5                   10                  15

Ala Ala Ala

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ser Gly Gly Gly Gly Ser Gly Gly Gly Ser Gly Gly Gly Gly
1               5                   10                  15

Ser Gly Gly Gly Gly Ser Ala Ala Ala
            20                  25

<210> SEQ ID NO 73
<211> LENGTH: 6
<212> TYPE: PRT
<213> ORGANISM: Clostridium botulinum

<400> SEQUENCE: 73

Gly Ile Ile Thr Ser Lys
1               5
```

```
<210> SEQ ID NO 74
<211> LENGTH: 5
<212> TYPE: PRT
<213> ORGANISM: Clostridium botulinum

<400> SEQUENCE: 74

Ala Ile Asp Gly Arg
1               5

<210> SEQ ID NO 75
<211> LENGTH: 5
<212> TYPE: PRT
<213> ORGANISM: Clostridium botulinum

<400> SEQUENCE: 75

Ile Val Ser Val Lys
1               5

<210> SEQ ID NO 76
<211> LENGTH: 4
<212> TYPE: PRT
<213> ORGANISM: Clostridium botulinum

<400> SEQUENCE: 76

Val Ile Pro Arg
1

<210> SEQ ID NO 77
<211> LENGTH: 4
<212> TYPE: PRT
<213> ORGANISM: Clostridium botulinum

<400> SEQUENCE: 77

Val Met Tyr Lys
1

<210> SEQ ID NO 78
<211> LENGTH: 10
<212> TYPE: PRT
<213> ORGANISM: Clostridium tetani

<400> SEQUENCE: 78

Ile Ile Pro Pro Thr Asn Ile Arg Glu Asn
1               5                   10

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Leu Ala Ala Glu Ala Ala Lys Glu Ala Ala Lys Glu Ala
1               5                   10                  15

Ala Ala Lys Ala Gly Gly Gly Gly Ser Ala Leu Val
            20                  25

<210> SEQ ID NO 80
<211> LENGTH: 25
<212> TYPE: PRT
<213> ORGANISM: Clostridium botulinum

<400> SEQUENCE: 80
```

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 81
<211> LENGTH: 25
<212> TYPE: PRT
<213> ORGANISM: Clostridium botulinum

<400> SEQUENCE: 81

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 82
<211> LENGTH: 10
<212> TYPE: PRT
<213> ORGANISM: Clostridium botulinum

<400> SEQUENCE: 82

Cys Lys Ser Val Lys Ala Pro Gly Ile Cys
1               5                   10

<210> SEQ ID NO 83
<211> LENGTH: 17
<212> TYPE: PRT
<213> ORGANISM: Clostridium botulinum

<400> SEQUENCE: 83

Cys His Lys Ala Ile Asp Gly Arg Ser Leu Tyr Asn Lys Thr Leu Asp
1               5                   10                  15

Cys

<210> SEQ ID NO 84
<211> LENGTH: 14
<212> TYPE: PRT
<213> ORGANISM: Clostridium botulinum

<400> SEQUENCE: 84

Cys Leu Arg Leu Thr Lys Asn Ser Arg Asp Asp Ser Thr Cys
1               5                   10

<210> SEQ ID NO 85
<211> LENGTH: 15
<212> TYPE: PRT
<213> ORGANISM: Clostridium botulinum

<400> SEQUENCE: 85

Cys Lys Asn Ile Val Ser Val Lys Gly Ile Arg Lys Ser Ile Cys
1               5                   10                  15

<210> SEQ ID NO 86
<211> LENGTH: 17
<212> TYPE: PRT
<213> ORGANISM: Clostridium botulinum

<400> SEQUENCE: 86

Cys Lys Ser Val Ile Pro Arg Lys Gly Thr Lys Ala Pro Pro Arg Leu
1               5                   10                  15

Cys

```
<210> SEQ ID NO 87
<211> LENGTH: 15
<212> TYPE: PRT
<213> ORGANISM: Clostridium botulinum

<400> SEQUENCE: 87

Cys Lys Pro Val Met Tyr Lys Asn Thr Gly Lys Ser Glu Gln Cys
1               5                   10                  15

<210> SEQ ID NO 88
<211> LENGTH: 29
<212> TYPE: PRT
<213> ORGANISM: Clostridium tetani

<400> SEQUENCE: 88

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
                20                  25

<210> SEQ ID NO 89
<211> LENGTH: 23
<212> TYPE: PRT
<213> ORGANISM: Influenza A virus

<400> SEQUENCE: 89

Gly Leu Phe Gly Ala Ile Ala Gly Phe Ile Glu Asn Gly Trp Glu Gly
1               5                   10                  15

Met Ile Asp Gly Trp Tyr Gly
                20
```

FUSION PROTEINS COMPRISING A NON-CYTOTOXIC PROTEASE, A TRANSLOCATION DOMAIN, AND A TARGETING MOIETY THAT BINDS A GALANIN RECEPTOR AND METHODS FOR TREATING, PREVENTING OR AMELIORATING PAIN USING SUCH FUSION PROTEINS

This application is a continuation of U.S. application Ser. No. 15/661,433, filed Jul. 27, 2017, which in turn is a continuation of U.S. application Ser. No. 14/422,574, filed Feb. 19, 2015, which is a national stage of International Patent Application No. PCT/GB2013/052243, filed Aug. 27, 2013, which is a continuation-in-part of U.S. application Ser. No. 13/595,927, filed Aug. 27, 2012.

The instant application contains a Sequence Listing that has been submitted electronically in ASCII format and is hereby incorporated by reference in its entirety. The ASCII copy was created on Aug. 3, 2021, is named 79708-295559 SL.txt and is 360,443 bytes in size.

This invention relates to non-cytotoxic fusion proteins, and to the therapeutic application thereof as analgesic molecules.

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins have attracted much interest in the design of "magic bullets" (e.g. immunoconjugates, which comprise a cytotoxic toxin component and an antibody that binds to a specific marker on a target cell) for the treatment of cellular disorders and conditions such as cancer. Cytotoxic toxins typically kill their target cells by inhibiting the cellular process of protein synthesis.

The second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. Non-cytotoxic toxins are produced by a variety of plants, and by a variety of microorganisms such as *Clostridium* sp. and *Neisseria* sp.

Clostridial neurotoxins are proteins that typically have a molecular mass of the order of 150 kDa. They are produced by various species of bacteria, especially of the genus *Clostridium*, most importantly *C. tetani* and several strains of *C. botulinum, C. butyricum* and *C. argentinense*. There are at present eight different classes of the clostridial neurotoxin, namely: tetanus toxin, and botulinum neurotoxin in its serotypes A, B, C1, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain), which has a molecular mass of approximately 100 kDa, and the light chain (L-chain or LC), which has a molecular mass of approximately 50 kDa.

L-chains possess a protease function (zinc-dependent endopeptidase activity) and exhibit a high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

*Neisseria* sp., most importantly from the species *N. gonorrhoeae*, produce functionally similar non-cytotoxic proteases. An example of such a protease is IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

The above-mentioned TM replacement may be effected by conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press. Alternatively, recombinant techniques may be employed, such as those described in WO98/07864. All of the above cited references are incorporated by reference herein.

Pain-sensing cells possess a wide range of receptor types. However, not all receptor types are suited (least of all desirable) for receptor-mediated endocytosis. Similarly, binding properties can vary widely between different TMs for the same receptor, and even more so between different TMs and different receptors.

There is therefore a need to develop modified non-cytotoxic fusion proteins that address one or more of the above problems. Of particular interest is the development of an alternative/improved non-cytotoxic fusion protein for use in treating pain.

The present invention seeks to address one or more of the above problems by providing unique fusion proteins.

The present invention addresses one or more of the above-mentioned problems by providing a single chain, polypeptide fusion protein, comprising:

a. a non-cytotoxic protease which protease cleaves a protein of the exocytic fusion apparatus of a nociceptive sensory afferent;
  b. a galanin Targeting Moiety that binds to a Binding Site on the nociceptive sensory afferent, which Binding Site endocytoses to be incorporated into an endosome within the nociceptive sensory afferent;
  c. a protease cleavage site at which site the fusion protein is cleavable by a protease, wherein the protease cleavage site is located between the non-cytotoxic protease and the galanin Targeting Moiety;
  d. a translocation domain that translocates the protease from within an endosome, across the endosomal membrane and into the cytosol of the nociceptive sensory afferent, wherein the Targeting Moiety is located between the protease cleavage site and the translocation domain;

e. a first spacer located between the non-cytotoxic and the protease cleavage site, wherein said first spacer comprises an amino acid sequence of from 4 to 25 amino acid residues;

f. a second spacer located between the galanin Targeting Moiety and the translocation domain, wherein said second spacer comprises an amino acid sequence of from 4 to 35 amino acid residues.

The non-cytotoxic protease component of the present invention is a non-cytotoxic protease, which protease is capable of cleaving different but specific peptide bonds in one of three substrate proteins, namely synaptobrevin, syntaxin or SNAP-25, of the exocytic fusion apparatus in a nociceptive sensory afferent. These substrates are important components of the neurosecretory machinery. The non-cytotoxic protease component of the present invention is preferably a neisserial IgA protease or a clostridial neurotoxin L-chain. The term non-cytotoxic protease embraces functionally equivalent fragments and derivatives of said non-cytotoxic protease(s). A particularly preferred non-cytotoxic protease component is a botulinum neurotoxin (BoNT) L-chain.

The translocation component of the present invention enables translocation of the non-cytotoxic protease (or fragment thereof) into the target cell such that functional expression of protease activity occurs within the cytosol of the target cell. The translocation component is preferably capable of forming ion-permeable pores in lipid membranes under conditions of low pH. Preferably it has been found to use only those portions of the protein molecule capable of pore-formation within the endosomal membrane. The translocation component may be obtained from a microbial protein source, in particular from a bacterial or viral protein source. Hence, in one embodiment, the translocation component is a translocating domain of an enzyme, such as a bacterial toxin or viral protein. The translocation component of the present invention is preferably a clostridial neurotoxin H-chain or a fragment thereof. Most preferably it is the $H_N$ domain (or a functional component thereof), wherein $H_N$ means a portion or fragment of the H-chain of a clostridial neurotoxin approximately equivalent to the amino-terminal half of the H-chain, or the domain corresponding to that fragment in the intact H-chain.

The galanin TM component of the present invention is responsible for binding the fusion protein of the present invention to a Binding Site on a target cell. Thus, the galanin TM component is a ligand through which the fusion proteins of the present invention bind to a selected target cell.

In the context of the present invention, the target cell is a nociceptive sensory afferent, preferably a primary nociceptive afferent (e.g. an A-fibre such as an Aδ-fibre or a C-fibre). Thus, the fusion proteins of the present invention are capable of inhibiting neurotransmitter or neuromodulator [e.g. glutamate, substance P, calcitonin-gene related peptide (CGRP), and/or neuropeptide Y] release from discrete populations of nociceptive sensory afferent neurons. In use, the fusion proteins reduce or prevent the transmission of sensory afferent signals (e.g. neurotransmitters or neuromodulators) from peripheral to central pain fibres, and therefore have application as therapeutic molecules for the treatment of pain, in particular chronic pain.

It is routine to confirm that a TM binds to a nociceptive sensory afferent. For example, a simple radioactive displacement experiment may be employed in which tissue or cells representative of the nociceptive sensory afferent (for example DRGs) are exposed to labelled (e.g. tritiated) ligand in the presence of an excess of unlabeled ligand. In such an experiment, the relative proportions of non-specific and specific binding may be assessed, thereby allowing confirmation that the ligand binds to the nociceptive sensory afferent target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

The fusion proteins of the present invention generally demonstrate a reduced binding affinity (in the region of up to 10-fold) for the galanin receptor (e.g. GALR1) when compared with the corresponding 'free' TM (e.g. gal16). However, despite this observation, the fusion proteins of the present invention surprisingly demonstrate good efficacy. This can be attributed to two principal features. First, the non-cytotoxic protease component is catalytic—thus, the therapeutic effect of a few such molecules is rapidly amplified. Secondly, the galanin receptors present on the nociceptive sensory afferents need only act as a gateway for entry of the therapeutic, and need not necessarily be stimulated to a level required in order to achieve a ligand-receptor mediated pharmacological response. Accordingly, the fusion proteins of the present invention may be administered at a dosage that is much lower that would be employed for other types of analgesic molecules such as NSAIDS, morphine, and gabapentin. The latter molecules are typically administered at high microgram to milligram (even up to hundreds of milligram) quantities, whereas the fusion proteins of the present invention may be administered at much lower dosages, typically at least 10-fold lower, and more typically at 100-fold lower.

The galanin TM of the invention can also be a molecule that acts as an "agonist" at one or more of the galanin receptors present on a nociceptive sensory afferent, more particularly on a primary nociceptive afferent. Conventionally, an agonist has been considered any molecule that can either increase or decrease activities within a cell, namely any molecule that simply causes an alteration of cell activity. For example, the conventional meaning of an agonist would include a chemical substance capable of combining with a receptor on a cell and initiating a reaction or activity, or a drug that induces an active response by activating receptors, whether the response is an increase or decrease in cellular activity.

However, for the purposes of this invention, an agonist is more specifically defined as a molecule that is capable of stimulating the process of exocytic fusion in a target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists. For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

In one embodiment, the fusion proteins according to the present invention demonstrate preferential receptor binding and/or internalisation properties. This, in turn, may result in more efficient delivery of the protease component to a pain-sensing target cell.

Use of an agonist as a TM is self-limiting with respect to side-effects. In more detail, binding of an agonist TM to a pain-sensing target cell increases exocytic fusion, which may exacerbate the sensation of pain. However, the exocytic process that is stimulated by agonist binding is subsequently reduced or inhibited by the protease component of the fusion protein.

The agonist properties of a TM that binds to a receptor on a nociceptive afferent can be confirmed using the methods described in Example 9.

The Targeting Moiety of the present invention comprises or consists of galanin and/or derivatives of galanin. Galanin receptors (e.g. GALR1, GALR2 and GALR3) are found pre- and post-synaptically in DRGs (Liu & Hokfelt, (2002), Trends Pharm. Sci., 23(10), 468-74), and are enhanced in expression during neuropathic pain states. Xu et al., (2000) Neuropeptides, 34 (3&4), 137-147 provides further information in relation to galanin. All of the above cited references are incorporated by reference herein.

In one embodiment of the invention, the target for the galanin TM is the GALR1, GALR2 and/or the GALR3 receptor. These receptors are members of the G-protein-coupled class of receptors, and have a seven transmembrane domain structure.

In one embodiment, the galanin TM is a molecule that binds (preferably that specifically binds) to the GALR1, GALR2 and/or the GALR3 receptor. More preferably, the galanin TM is an "agonist" of the GALR1, GALR2 and/or the GALR3 receptor. The term "agonist" in this context is defined as above.

Wild-type human galanin peptide is a 30 amino acid peptide, abbreviated herein as "GA30" (represented by SEQ ID NO: 7). In one embodiment, the galanin TM comprises or consists of SEQ ID NO: 7.

The invention also encompasses fragments, variants, and derivatives of the galanin TM described above. These fragments, variants, and derivatives substantially retain the properties that are ascribed to said galanin TM (i.e. are functionally equivalent). For example, the fragments, variants, and derivatives may retain the ability to bind to the GALR1, GALR2 and/or GALR3 receptor. In one embodiment, the galanin TM of the invention comprises or consists of a 16 amino acid fragment of full-length galanin peptide and is referred to herein as GA16 (represented by SEQ ID NO: 8).

In one embodiment, the galanin TM comprises or consists of an amino acid sequence having at least 70%, preferably at least 80% (such as at least 82, 84, 85, 86, 88 or 89%), more preferably at least 90% (such as at least 91, 92, 93 or 94%), and most preferably at least 95% (such as at least 96, 97, 98, 99 or 100%) amino acid sequence acid identity to SEQ ID NO: 7 or SEQ ID NO: 8.

In one embodiment the galanin TM comprises or consists of an amino acid sequence having at least 70% (such as at least 80, 82, 84, 85, 86, 88 or 89%), more preferably at least 90% (such as at least 91, 92, 93 or 94%), and most preferably at least 95% (such as at least 96, 97, 98, 99 or 100%) amino acid sequence acid identity to full-length amino acid sequence of SEQ ID NO: 7 or SEQ ID NO: 8, or a fragment of SEQ ID NO: 7 or SEQ ID NO: 8 comprising or consisting of at least 10 (such as at least 11, 12, 13, 14, 15, 16, 17, 18, 19, 20, 21, 22, 23, 24, 25, 26, 27, 28 or 29) contiguous amino acid residues thereof.

In one embodiment, the galanin Targeting Moiety comprises or consists of an amino acid sequence according to SEQ ID NO. 7 or a fragment comprising or consisting of at least 16 (such as at least 10, 11, 12, 13, 14 or 15) contiguous amino acid residues thereof, or a variant amino acid sequence of said SEQ ID NO: 7 or said fragment having a maximum of 6 (such as a maximum of 5, 4, 3, 2 or 1) conservative amino acid substitutions.

The protease cleavage site of the present invention allows cleavage (preferably controlled cleavage) of the fusion protein at a position between the non-cytotoxic protease component and the TM component. It is this cleavage reaction that converts the fusion protein from a single chain polypeptide into a disulphide-linked, di-chain polypeptide.

According to a preferred embodiment of the present invention, the galanin TM binds via a domain or amino acid sequence that is located away from the C-terminus of the galanin TM. For example, the relevant binding domain may include an intra domain or an amino acid sequence located towards the middle (i.e. of the linear peptide sequence) of the TM. Preferably, the relevant binding domain is located towards the N-terminus of the galanin TM, more preferably at or near to the N-terminus.

In one embodiment, the single chain polypeptide fusion may include more than one proteolytic cleavage site. However, where two or more such sites exist, they are different, thereby substantially preventing the occurrence of multiple cleavage events in the presence of a single protease. In another embodiment, it is preferred that the single chain polypeptide fusion has a single protease cleavage site.

The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed, the followingg are preferred:

| | |
|---|---|
| Enterokinase | (DDDDK↓; SEQ ID NO: 60) |
| Factor Xa | (IEGR↓; SEQ ID NO: 61/IDGR↓; SEQ ID NO: 62) |
| TEV (Tobacco Etch virus) | (ENLYFQ↓G; SEQ ID NO: 63) |
| Thrombin | (LVPR↓GS; SEQ ID NO: 64) |
| PreScission | (LEVLFQ↓GP; SEQ ID NO: 65). |

In one embodiment, the protease cleavage site is an enterokinase cleavage site (DDDDKI↓; SEquidD NO: 60). In one embodiment, enterokinase protease is used to cleave the enterokinase cleavage site and activate the fusion protein.

Also embraced by the term protease cleavage site is an intein, which is a self-cleaving sequence. The self-splicing reaction is controllable, for example by varying the concentration of reducing agent present.

In use, the protease cleavage site is cleaved and the N-terminal region (preferably the N-terminus) of the TM becomes exposed. The resulting polypeptide has a TM with an N-terminal domain or an intra domain that is substantially free from the remainder of the fusion protein. This arrangement ensures that the N-terminal component (or intra domain) of the TM may interact directly with a Binding Site on a target cell.

In one embodiment, the TM and the protease cleavage site are distanced apart in the fusion protein by at most 10 amino acid residues, more preferably by at most 5 amino acid residues, and most preferably by zero amino acid residues. In one embodiment, the TM and the protease cleavage site are distanced apart in the fusion protein by 0-10 (such as 0-9, 0-8, 0-7, 0-6, 0-5, 0-4, 0-3, 0-2) and preferably 0-1 amino acid residues Thus, following cleavage of the protease cleavage site, a fusion is provided with a TM that has an N-terminal domain that is substantially free from the remainder of the fusion. This arrangement ensures that the N-terminal component of the Targeting Moiety may interact directly with a Binding Site on a target cell.

One advantage associated with the above-mentioned activation step is that the TM only becomes susceptible to N-terminal degradation once proteolytic cleavage of the fusion protein has occurred. In addition, the selection of a specific protease cleavage site permits selective activation of the polypeptide fusion into a di-chain conformation.

Construction of the single-chain polypeptide fusion of the present invention places the protease cleavage site between the TM and the non-cytotoxic protease component.

It is preferred that, in the single-chain fusion, the TM is located between the protease cleavage site and the translocation component. This ensures that the TM is attached to the translocation domain (i.e. as occurs with native clostridial holotoxin), though in the case of the present invention the order of the two components is reversed vis-à-vis native holotoxin. A further advantage with this arrangement is that the TM is located in an exposed loop region of the fusion protein, which has minimal structural effects on the conformation of the fusion protein. In this regard, said loop is variously referred to as the linker, the activation loop, the inter-domain linker, or just the surface exposed loop (Schiavo et al 2000, Phys. Rev., 80, 717-766; Turton et al., 2002, Trends Biochem. Sci., 27, 552-558).

The single chain fusion protein of the present invention comprises a first spacer located between the non-cytotoxic protease and the protease cleavage site, wherein said first spacer comprises (or consists of) an amino acid sequence of from 4 to 25 (such as from 6 to 25, 8 to 25, 10 to 25, 15 to 25 or from 4 to 21, 4 to 20, 4 to 18, 4 to 15, 4 to 12 or 4 to 10) amino acid residues. In one embodiment, the first spacer comprises (or consists of) an amino acid sequence of at least 4 (such as at least 5, 6, 7, 8, 9, 10, 11, 12, 13, 14, 15) amino acid residues. In one embodiment, the first spacer comprises (or consists of) an amino acid sequence of at most 25 (such as at most 24, 23, 22, 21, 20, 19, 18, 17, 16, 15, 14, 13, 12, 10) amino acid residues. Said first spacer enables cleavage of the fusion protein at the protease cleavage site.

Without a first spacer of the present invention, protease cleavage and activation of the fusion protein is markedly poor. Without wishing to be bound by theory, it is hypothesised that the galanin Targeting Moiety may sterically block or interact with the protease cleavage site resulting in poor activation of fusion proteins lacking a first spacer of the present invention. The present inventors believe that it is the flexibility afforded by the first spacer which provides for the enhanced/improved activation properties of the presently claimed fusion proteins. Rigid linkers such as alpha-helical linkers do not afford the necessary flexibility. This is also true for galanin fusion proteins having 'natural' spacer sequences containing a protease cleavage site, which may replicate undesirable rigid alpha-helical linker structures. Flexibility and mobility of polypeptide domains can be ascertained by a number of methods including determining the X-ray crystallographic B-factor (see e.g. Smith et al., 2003 *Protein Science*, 12:1060-1072; incorporated by reference herein). The specifically selected spacer sequences of the present invention provide for enhanced activation over and above any 'natural' spacer sequences. Activation in this context means that said first spacer enables cleavage of the fusion protein at the protease cleavage site. Particularly preferred amino acid residues for use in the first spacer include glycine, threonine, arginine, serine, alanine, asparagine, glutamine, aspartic acid, proline, glutamic acid and/or lysine. The aforementioned amino acids are considered to be the most flexible amino acids—see Smith et al. 2003 Protein Science 2003; 12:1060-1072.

In one embodiment, the amino acid residues of the first spacer are selected from the group consisting of glycine, threonine, arginine, serine, asparagine, glutamine, alanine, aspartic acid, proline, glutamic acid, lysine, leucine and/or valine. In one embodiment, the amino acid residues of the first spacer are selected from the group consisting of glycine, serine, alanine, leucine and/or valine. In one embodiment, the amino acid residues of the first spacer are selected from the group consisting of glycine, serine and/or alanine. Glycine and serine are particularly preferred. In one embodiment, the first spacer comprises or consists of one or more pentapeptides having glycine, serine, and or threonine residues. One way of assessing whether the first spacer possesses the requisite flexibility in the presently claimed fusion proteins is by performing a simple protease cleavage assay. It would be routine for a person skilled in the art to assess cleavage/activation of a fusion protein—standard methodology is described, for example, in Example 1.

In one embodiment, the first spacer may be selected from a GS5, GS10, GS15, GS18, GS20, FL3 and/or FL4 spacers. The sequence of said spacers is provided in Table 1, below.

TABLE 1

| Spacer | Sequence |
|--------|----------|
| GS5 | GGGGSA (SEQ ID NO: 66) |
| GS10 | GGGGSGGGGSA (SEQ ID NO: 67) |
| GS15 | ALAGGGGSGGGGSALV (SEQ ID NO: 68) |
| GS18 | GGGGSGGGGSGGGGSA (SEQ ID NO: 69) |
| GS20 | ALAGGGGSGGGGSGGGGSALV (SEQ ID NO: 70) |
| FL3 | LGGGGSGGGGSGGGGSAAA (SEQ ID NO: 71) |
| FL4 | LSGGGGSGGGGSGGGGSGGGGSAAA (SEQ ID NO: 72) |

In one embodiment, the First spacer enables at least 45% (such as at least 50, 55, 60, 65, 70, 75, 80, 90, 95, 98, 99 or 100%) activation of the fusion protein by protease cleavage. In one embodiment, the first spacer enables at least 70% activation of the fusion protein by protease cleavage.

In one embodiment, the first spacer is not a naturally-occurring spacer sequence. In one embodiment, the first spacer does not comprise or consist of an amino acid sequence native to the natural (i.e. wild-type) clostridial neurotoxin, such as botulinum neurotoxin. In other words, the first spacer may be a non-clostridial sequence (i.e. not found in the native clostridial neurotoxin). In one embodiment, the fusion protein does not comprise or consist of the amino acid sequence GIITSH (SEQ ID NO: 73) (BoNT/A);

VK (BoNT B); AIDGR (SEQ NO: 74) (BoNT/C); LTK (BoNT/D); ICSVK (SEQ ID NO: 75) (BoNT/E); VIPR SEQ ID NO: 75). (BONT/F); VMYK (SEQ ID NO: 77) (BoNT/G) and/or IIPPTNIREN (SEQ ID NO: 78) (TeNT) AS the first spacer.

In one embodiment, the first spacer begins on the third amino acid residue following the conserved cysteine residue in the clostridial neurotoxin L-chain (see Table 3 below). In one embodiment, the first spacer begins after the VD amino acid residues of a non-cytotoxic protease clostridial L-chain engineered with a sal1 site following the conserved cysteine residue. In one embodiment, the first spacer ends with the amino acid residue marking the beginning of the protease cleavage sites mentioned above.

In one embodiment, the single chain fusion protein comprises a second spacer, which is located between the galanin Targeting Moiety and the translocation domain. Said second spacer may comprise (or consist of) an amino acid sequence of from 4 to 35 (such as from 6 to 35, 10 to 35, 15 to 35, 20 to 35 or from 4 to 28, 4 to 25, 4 to 20 or 4 to 10) amino acid residues. The present inventors have unexpectedly found that the fusion proteins of the present invention may demonstrate an improved binding activity when the size of the second spacer is selected so that (in use) the C-terminus of the TM and the N-terminus of the translocation component are separated from one another by 40-105 angstroms, preferably by 50-100 angstroms, and more preferably by 50-90 angstroms.

Suitable second spacers may be routinely identified and obtained according to Crasto, C. J. and Feng, J. A. (2000) May, 13(5), pp. 309-312 In one embodiment, the second spacer is selected from a GS5, GS10, GS15, GS18, GS20 or HX27 spacer. The sequence of said spacers is provided in Table 2, below.

TABLE 2

| Spacer | Sequence |
| --- | --- |
| GS5 | GGGGSA (SEQ ID NO: 66) |
| GS10 | GGGGSGGGGSA (SEQ ID NO: 67) |
| GS15 | ALAGGGGSGGGGSALV (SEQ ID NO: 68) |
| GS18 | GGGGSGGGGSGGGGSA (SEQ ID NO: 69) |
| GS20 | ALAGGGGSGGGGSGGGGSALV (SEQ ID NO: 70) |
| HX27 | ALAAEAAAKEAAAKEAAAKAGGGGSALV (SEQ ID NO: 79) |

The Inventors have surprisingly found, that the presently claimed fusion proteins having said first and second spacer features display enhanced activation properties and increased yield during recombinant expression. In addition, the presently claimed fusion proteins display enhanced potency compared to fusion proteins wherein the galanin TM is C-terminal of the translocation domain component.

In one embodiment, the invention provides a single-chain polypeptide fusion protein comprising (or consisting of) an amino acid sequence having at least 80% (such as at least 85, 90, 92, 94, 95, 96, 97, 98, 99 or 100%) sequence identity to the amino acid sequence of SEQ ID NOs: 10, 11, 13, 14, 16, 17, 19, 20, 22, 23, 25, 26, 28, 29, 31, 32, 33, 34, 35, 36, 37, 38, 39, 40, 41, 42, 43, 44, 45, 46, 47, 48, 49, 50, 53, 56 and/or 59.

In one embodiment, the invention provides a single-chain polypeptide fusion protein comprising (or consisting of) an amino acid sequence having at least 80% (such as at least 85, 90, 92, 94, 95, 96, 97, 98, 99 or 100%) sequence identity to the full-length amino acid sequence of SEQ ID NOs: 10, 11, 13, 14, 16, 17, 19, 20, 22, 23, 25, 26, 28, 29, 31, 32, 33, 34, 35, 36, 37, 38, 39, 40, 41, 42, 43, 44, 45, 46, 47, 48, 49, 50, 53, 56 and/or 59.

In one embodiment, in the single chain polypeptide, the non-cytotoxic protease component and the translocation component are linked together by a disulphide bond. Thus, following cleavage of the protease cleavage site, the polypeptide assumes a di-chain conformation, wherein the protease and translocation components remain linked together by the disulphide bond. To this end, it is preferred that the protease and translocation components are distanced apart from one another in the single chain fusion protein by a maximum of 100 amino acid residues, more preferably a maximum of 80 amino acid residues, particularly preferably by a maximum of 60 amino acid residues, and most preferably by a maximum of 50 amino acid residues.

In one embodiment, the non-cytotoxic protease component forms a disulphide bond with the translocation component of the fusion protein. For example, the amino acid residue of the protease component that forms the disulphide bond is located within the last 20, preferably within the last 10 C-terminal amino acid residues of the protease component. Similarly, the amino acid residue within the translocation component that forms the second part of the disulphide bond may be located within the first 20, preferably within the first 10 N-terminal amino acid residues of the translocation component.

Alternatively, in the single chain polypeptide, the non-cytotoxic protease component and the TM may be linked together by a disulphide bond. In this regard, the amino acid residue of the TM that forms the disulphide bond is preferably located away from the N-terminus of the TM, more preferably towards to C-terminus of the TM.

In one embodiment, the non-cytotoxic protease component forms a disulphide bond with the TM component of the fusion protein. In this regard, the amino acid residue of the protease component that forms the disulphide bond is preferably located within the last 20, more preferably within the last 10 C-terminal amino acid residues of the protease component. Similarly, the amino acid residue within the TM component that forms the second part of the disulphide bond is preferably located within the last 20, more preferably within the last 10 C-terminal amino acid residues of the TM.

The above disulphide bond arrangements have the advantage that the protease and translocation components are arranged in a manner similar to that for native clostridial neurotoxin. By way of comparison, referring to the primary amino acid sequence for native clostridial neurotoxin, the respective cysteine amino acid residues are distanced apart by between 8 and 27 amino acid residues taken from Popoff, M R & Marvaud, J-C, 1999, Structural & genomic features of clostridial neurotoxins, Chapter 9, in The Comprehensive Sourcebook of Bacterial Protein Toxins. Ed. Alouf & Freer:

TABLE 3

| Serotype[1] | Sequence | 'Native' length between C-C |
|---|---|---|
| BoNT/A1 | CVRGIITSKTKS----LDKGYNKALNDLC (SEQ ID NO: 80) | 23 |
| BoNT/A2 | CVRGIIPFKTKS----LDEGYNKALNDLC (SEQ ID NO: 81) | 23 |
| BoNT/B | CKSVKAPG------------------IC (SEQ ID NO: 82) | 8 |
| BoNT/C | CHKAIDGRS----------LYNKTLDC (SEQ ID NO: 83) | 15 |
| BoNT/D | CLRLTK--------------NSRDDSTC (SEQ ID NO: 84) | 12 |
| BoNT/E | CKN-IVSVK----------GIRK---SIC (SEQ ID NO: 85) | 13 |
| BoNT/F | CKS-VIPRK----------GTKAPP-RLC (SEQ ID NO: 86) | 15 |
| BoNT/G | CKPVMYKNT----------GKSE----QC (SEQ ID NO: 87) | 13 |
| TeNT | CKKIIPPTNIRENLYNRTASLTDLGGELC (SEQ ID NO: 88) | 27 |

[1]Information from proteolytic strains only

The fusion protein may comprise one or more purification tags, which are located N-terminal to the protease component and/or C-terminal to the translocation component.

Whilst any purification tag may be employed, the following are preferred:

His-tag (e.g. 6× histidine), preferably as a C-terminal and/or N-terminal tag

MBP-tag (maltose binding protein), preferably as an N-terminal tag

GST-tag (glutathione-S-transferase), preferably as an N-terminal tag

His-MBP-tag, preferably as an N-terminal tag

GST-MBP-tag, preferably as an N-terminal tag

Thioredoxin-tag, preferably as an N-terminal tag

CBD-tag (Chitin Binding Domain), preferably as an N-terminal tag.

According to a further embodiment of the present invention, one or more additional peptide spacer molecules may be included in the fusion protein. For example, a peptide spacer may be employed between a purification tag and the rest of the fusion protein molecule (e.g. between an N-terminal purification tag and a protease component of the present invention; and/or between a C-terminal purification tag and a translocation component of the present invention.

In accordance with a second aspect of the present invention, there is provided a DNA sequence that encodes the above-mentioned single chain polypeptide. In a preferred aspect of the present invention, the DNA sequence is prepared as part of a DNA vector, wherein the vector comprises a promoter and terminator.

In a preferred embodiment, the vector has a promoter selected from:

| Promoter | Induction Agent | Typical Induction Condition |
|---|---|---|
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

The DNA construct of the present invention is preferably designed in silico, and then synthesised by conventional DNA synthesis techniques.

The above-mentioned DNA sequence information is optionally modified for codon-biasing according to the ultimate host cell (e.g. E. coli) expression system that is to be employed.

The DNA backbone is preferably screened for any inherent nucleic acid sequence, which when transcribed and translated would produce an amino acid sequence corresponding to the protease cleave site encoded by the second peptide-coding sequence. This screening may be performed manually or with the assistance of computer software (e.g. the MapDraw program by DNASTAR, Inc.).

According to a further embodiment of the present invention, there is provided a method of preparing a non-cytotoxic agent, comprising:

a. contacting a single-chain polypeptide fusion protein of the invention with a protease capable of cleaving the protease cleavage site;

b. cleaving the protease cleavage site, and thereby forming a di-chain fusion protein.

This aspect provides a di-chain polypeptide, which generally mimics the structure of clostridial holotoxin. In more detail, the resulting di-chain polypeptide typically has a structure wherein:

a. the first chain comprises the non-cytotoxic protease, which protease is capable of cleaving a protein of the exocytic fusion apparatus of a nociceptive sensory afferent;

b. the second chain comprises the galanin TM and the translocation domain that is capable of translocating the protease from within an endosome, across the endosomal membrane and into the cytosol of the nociceptive sensory afferent; and the first and second chains are disulphide linked together.

In one aspect of the invention, the single chain or dichchain polypeptide of the invention is for use as medicament/therapeutic molecule.

In use, the single chain or di-chain polypeptide of the invention treat, prevent or ameliorate pain.

In use, a therapeutically effective amount of a single chain or di-chain polypeptide of the invention is administered to a patient.

According to a further aspect of the present invention, there is provided use of a single chain or di-chain polypeptide of the invention, for the manufacture of a medicament for treating, preventing or ameliorating pain.

According to a related aspect, there is provided a method of treating, preventing or ameliorating pain in a subject, comprising administering to said patient a therapeutically effective amount of a single chain or di-chain polypeptide of the invention.

The compounds described here may be used to treat a patient suffering from one or more types of chronic pain including neuropathic pain, inflammatory pain, headache pain, somatic pain, visceral pain, and referred pain.

To "treat," as used here, means to deal with medically. It includes, for example, administering a compound of the invention to prevent pain or to lessen its severity.

The term "pain," as used here, means any unpleasant sensory experience, usually associated with a physical disorder. The physical disorder may or may not be apparent to a clinician. Pain is of two types: chronic and acute. An "acute pain" is a pain of short duration having a sudden onset. One type of acute pain, for example, is cutaneous pain felt on injury to the skin or other superficial tissues, such as caused by a cut or a burn. Cutaneous nociceptors terminate just below the skin, and due to the high concentration of nerve endings, produce a well-defined, localized pain of short duration. "Chronic pain" is a pain other than an acute pain. Chronic pain includes neuropathic pain, inflammatory pain, headache pain, somatic pain visceral pain and referred pain.

I. Neuropathic Pain

The compounds of the invention may be used to treat pain caused by or otherwise associated with any of the following neuropathic pain conditions.

"Neuropathic pain" means abnormal sensory input, resulting in discomfort, from the peripheral nervous system, central nervous systems, or both.

A. Symptoms of Neuropathic Pain

Symptoms of neuropathic pain can involve persistent, spontaneous pain, as well as allodynia (a painful response to a stimulus that normally is not painful), hyperalgesia (an accentuated response to a painful stimulus that usually causes only a mild discomfort, such as a pin prick), or hyperpathia (where a short discomfort becomes a prolonged severe pain).

B. Causes of Neuropathic Pain

Neuropathic pain may be caused by any of the following.

1. A traumatic insult, such as, for example, a nerve compression injury (e.g., a nerve crush, a nerve stretch, a nerve entrapment or an incomplete nerve transection); a spinal cord injury (e.g., a hemisection of the spinal cord); a limb amputation; a contusion; an inflammation (e.g., an inflammation of the spinal cord); or a surgical procedure.

2. An ischemic event, including, for example, a stroke and heart attack.

3. An infectious agent

4. Exposure to a toxic agent, including, for example, a drug, an alcohol, a heavy metal (e.g., lead, arsenic, mercury), an industrial agent (e.g., a solvent, fumes from a glue) or nitrous oxide.

5. A disease, including, for example, an inflammatory disorder, a neoplastic tumor, an acquired immune deficiency syndrome (AIDS), Lymes disease, a leprosy, a metabolic disease, a peripheral nerve disorder, like neuroma, a mononeuropathy or a polyneuropathy.

C. Types of Neuropathic Pain

1. Neuralgia.

A neuralgia is a pain that radiates along the course of one or more specific nerves usually without any demonstrable pathological change in the nerve structure. The causes of neuralgia are varied. Chemical irritation, inflammation, trauma (including surgery), compression by nearby structures (for instance, tumors), and infections may all lead to neuralgia. In many cases, however, the cause is unknown or unidentifiable. Neuralgia is most common in elderly persons, but it may occur at any age. A neuralgia, includes, without limitation, a trigeminal neuralgia, a post-herpetic neuralgia, a postherpetic neuralgia, a glossopharyngeal neuralgia, a sciatica and an atypical facial pain.

Neuralgia is pain in the distribution of a nerve or nerves. Examples are trigeminal neuralgia, atypical facial pain, and postherpetic neuralgia (caused by shingles or herpes). The affected nerves are responsible for sensing touch, temperature and pressure in the facial area from the jaw to the forehead. The disorder generally causes short episodes of excruciating pain, usually for less than two minutes and on only one side of the face. The pain can be described in a variety of ways such as "stabbing," "sharp," "like lightning," "burning," and even "itchy". In the atypical form of TN, the pain can also present as severe or merely aching and last for extended periods. The pain associated with TN is recognized as one the most excruciating pains that can be experienced.

Simple stimuli such as eating, talking, washing the face, or any light touch or sensation can trigger an attack (even the sensation of a gentle breeze). The attacks can occur in clusters or as an isolated attack.

Symptoms include sharp, stabbing pain or constant, burning pain located anywhere, usually on or near the surface of the body, in the same location for each episode; pain along the path of a specific nerve; impaired function of affected body part due to pain, or muscle weakness due to concomitant motor nerve damage; increased sensitivity of the skin or numbness of the affected skin area (feeling similar to a local anesthetic such as a Novocaine shot); and any touch or pressure is interpreted as pain. Movement may also be painful.

Trigeminal neuralgia is the most common form of neuralgia. It affects the main sensory nerve of the face, the trigeminal nerve ("trigeminal" literally means "three origins", referring to the division of the nerve into 3 branches). This condition involves sudden and short attacks of severe pain on the side of the face, along the area supplied by the trigeminal nerve on that side. The pain attacks may be severe enough to cause a facial grimace, which is classically referred to as a painful tic (tic douloureux). Sometimes, the cause of trigeminal neuralgia is a blood vessel or small tumor pressing on the nerve. Disorders such as multiple sclerosis (an inflammatory disease affecting the brain and spinal cord), certain forms of arthritis, and diabetes (high blood sugar) may also cause trigeminal neuralgia, but a cause is not always identified. In this condition, certain movements such as chewing, talking, swallowing, or touching an area of the face may trigger a spasm of excruciating pain.

A related but rather uncommon neuralgia affects the glosso-pharyngeal nerve, which provides sensation to the throat. Symptoms of this neuralgia are short, shock-like episodes of pain located in the throat.

Neuralgia may occur after infections such as shingles, which is caused by the varicella-zoster virus, a type of herpesvirus. This neuralgia produces a constant burning pain after the shingles rash has healed. The pain is worsened by movement of or contact with the affected area. Not all of those diagnosed with shingles go on to experience postherpetic neuralgia, which can be more painful than shingles. The pain and sensitivity can last for months or even years. The pain is usually in the form of an intolerable sensitivity to any touch but especially light touch. Postherpetic neuralgia is not restricted to the face; it can occur anywhere on the body but usually occurs at the location of the shingles rash. Depression is not uncommon due to the pain and social isolation during the illness.

Postherpetic neuralgia may be debilitating long after signs of the original herpes infection have disappeared. Other infectious diseases that may cause neuralgia are syphilis and Lyme disease.

Diabetes is another common cause of neuralgia. This very common medical problem affects almost 1 out of every 20 Americans during adulthood. Diabetes damages the tiny arteries that supply circulation to the nerves, resulting in nerve fiber malfunction and sometimes nerve loss. Diabetes can produce almost any neuralgia, including trigeminal neuralgia, carpal tunnel syndrome (pain and numbness of the hand and wrist), and meralgia paresthetica (numbness and pain in the thigh due to damage to the lateral femoral cutaneous nerve). Strict control of blood sugar may prevent diabetic nerve damage and may accelerate recovery in patients who do develop neuralgia.

Other medical conditions that may be associated with neuralgias are chronic renal insufficiency and porphyria—a hereditary disease in which the body cannot rid itself of certain substances produced after the normal breakdown of blood in the body. Certain drugs may also cause this problem.

2. Deafferentation.

Deafferentation indicates a loss of the sensory input from a portion of the body, and can be caused by interruption of either peripheral sensory fibres or nerves from the central nervous system. A deafferentation pain syndrome, includes, without limitation, an injury to the brain or spinal cord, a post-stroke pain, a phantom pain, a paraplegia, a brachial plexus avulsion injuries, lumbar radiculopathies.

3. Complex Regional Pain Syndromes (CRPSs)

CRPS is a chronic pain syndrome resulting from sympathetically-maintained pain, and presents in two forms. CRPS 1 currently replaces the term "reflex sympathetic dystrophy syndrome". It is a chronic nerve disorder that occurs most often in the arms or legs after a minor or major injury. CRPS 1 is associated with severe pain; changes in the nails, bone, and skin; and an increased sensitivity to touch in the affected limb. CRPS 2 replaces the term causalgia, and results from an identified injury to the nerve. A CRPS, includes, without limitation, a CRPS Type I (reflex sympathetic dystrophy) and a CRPS Type II (causalgia).

4. Neuropathy.

A neuropathy is a functional or pathological change in a nerve and is characterized clinically by sensory or motor neuron abnormalities.

Central neuropathy is a functional or pathological change in the central nervous system.

Peripheral neuropathy is a functional or pathological change in one or more peripheral nerves. The peripheral nerves relay information from your central nervous system (brain and spinal cord) to muscles and other organs and from your skin, joints, and other organs back to your brain. Peripheral neuropathy occurs when these nerves fail to carry information to and from the brain and spinal cord, resulting in pain, loss of sensation, or inability to control muscles. In some cases, the failure of nerves that control blood vessels, intestines, and other organs results in abnormal blood pressure, digestion problems, and loss of other basic body processes. Risk factors for neuropathy include diabetes, heavy alcohol use, and exposure to certain chemicals and drugs. Some people have a hereditary predisposition for neuropathy. Prolonged pressure on a nerve is another risk for developing a nerve injury. Pressure injury may be caused by prolonged immobility (such as a long surgical procedure or lengthy illness) or compression of a nerve by casts, splints, braces, crutches, or other devices. Polyneuropathy implies a widespread process that usually affects both sides of the body equally. The symptoms depend on which type of nerve is affected. The three main types of nerves are sensory, motor, and autonomic. Neuropathy can affect any one or a combination of all three types of nerves. Symptoms also depend on whether the condition affects the whole body or just one nerve (as from an injury). The cause of chronic inflammatory polyneuropathy is an abnormal immune response. The specific antigens, immune processes, and triggering factors are variable and in many cases are unknown. It may occur in association with other conditions such as HIV, inflammatory bowel disease, lupus erythematosis, chronic active hepatitis, and blood cell abnormalities.

Peripheral neuropathy may involve a function or pathological change to a single nerve or nerve group (monneuropathy) or a function or pathological change affecting multiple nerves (polyneuropathy).

Peripheral Neuropathies
Hereditary disorders
   Charcot-Marie-Tooth disease
   Friedreich's ataxia
Systemic or metabolic disorders
   Diabetes (diabetic neuropathy)
   Dietary deficiencies (especially vitamin B-12)
   Excessive alcohol use (alcoholic neuropathy)
   Uremia (from kidney failure)
   Cancer
Infectious or inflammatory conditions
   AIDS
   Hepatitis
   Colorado tick fever
   diphtheria
   Guillain-Barre syndrome
   HIV infection without development of AIDS
   leprosy
   Lyme
   polyarteritis nodosa
   rheumatoid arthritis
   sarcoidosis
   Sjogren syndrome
   syphilis
   systemic lupus erythematosus
   amyloid
Exposure to toxic compounds
   sniffing glue or other toxic compounds
   nitrous oxide
   industrial agents—especially solvents
   heavy metals (lead, arsenic, mercury, etc.)
   Neuropathy secondary to drugs like analgesic nephropathy
Miscellaneous causes
   ischemia (decreased oxygen/decreased blood flow)
   prolonged exposure to cold temperature
   a. Polyneuropathy
   Polyneuropathy is a peripheral neuropathy involving the loss of movement or sensation to an area caused by damage or destruction to multiple peripheral nerves. Polyneuropathic pain, includes, without limitation, post-polio syndrome, postmastectomy syndrome, diabetic neuropathy, alcohol neuropathy, amyloid, toxins, AIDS, hypothyroidism, uremia, vitamin deficiencies, chemotherapy-induced pain, 2',3'-didexoycytidine (ddC) treatment, Guillain-Barré syndrome or Fabry's disease.
   b. Mononeuropathy
   Mononeuropathy is a peripheral neuropathy involving loss of movement or sensation to an area caused by damage or destruction to a single peripheral nerve or nerve group. Mononeuropathy is most often caused by damage to a local area resulting from injury or trauma, although occasionally systemic disorders may cause isolated nerve damage (as with mononeuritis multiplex). The usual causes are direct trauma, prolonged pressure on the nerve, and compression of the nerve by swelling or injury to nearby body structures. The damage includes destruction of the myelin sheath (covering) of the nerve or of part of the nerve cell (the axon). This damage slows or prevents conduction of impulses through the nerve. Mononeuropathy may involve any part of the body. Mononeuropathic pain, includes, without limitation, a sciatic nerve dysfunction, a common peroneal nerve dysfunction. a radial nerve dysfunction, an ulnar nerve dysfunction, a cranial mononeuropathy VI, a cranial mononeuropathy VII, a cranial mononeuropathy III (compression type), a cranial mononeuropathy III (diabetic type), an axillary nerve dysfunction, a carpal tunnel syndrome, a femoral nerve dysfunction, a tibial nerve dysfunction, a Bell's palsy, a thoracic outlet syndrome, a carpal tunnel syndrome and a sixth (abducent) nerve palsy c. Generalized peripheral neuropathies Generalized peripheral neuropathies are symmetrical, and usually due to various systematic illnesses and disease processes that affect the peripheral nervous system in its entirety. They are further subdivided into several categories:

i. Distal axonopathies are the result of some metabolic or toxic derangement of neurons. They may be caused by metabolic diseases such as diabetes, renal failure, deficiency syndromes such as malnutrition and alcoholism, or the effects of toxins or drugs. Distal axonopathy (aka dying back neuropathy) is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy.

ii. Myelinopathies are due to a primary attack on myelin causing an acute failure of impulse conduction. The most common cause is acute inflammatory demyelinating polyneuropathy (AIDP; aka Guillain-Barré syndrome), though other causes include chronic inflammatory demyelinating syndrome (CIDP), genetic metabolic disorders (e.g., leukodystrophy), or toxins. Myelinopathy is due to primary destruction of myelin or the myelinating Schwann cells, which leaves the axon intact, but causes an acute failure of impulse conduction. This demyelination slows down or completely blocks the conduction of electrical impulses through the nerve. The most common cause is acute inflammatory demyelinating polyneuropathy (AIDP, better known as Guillain-Barré syndrome), though other causes include chronic inflammatory demyelinating polyneuropathy (CIDP), genetic metabolic disorders (e.g., leukodystrophy or Charcot-Marie-Tooth disease), or toxins.

iii. Neuronopathies are the result of destruction of peripheral nervous system (PNS) neurons. They may be caused by motor neurone diseases, sensory neuronopathies (e.g., Herpes zoster), toxins or autonomic dysfunction. Neurotoxins may cause neuronopathies, such as the chemotherapy agent vincristine. Neuronopathy is dysfunction due to damage to neurons of the peripheral nervous system (PNS), resulting in a peripheral neuropathy. It may be caused by motor neurone diseases, sensory neuronopathies (e.g., Herpes zoster), toxic substances or autonomic dysfunction. A person with neuronopathy may present in different ways, depending on the cause, the way it affects the nerve cells, and the type of nerve cell that is most affected.

iv. Focal entrapment neuropathies (e.g., carpal tunnel syndrome).

II. Inflammatory Pain

The compounds of the invention may be used to treat pain caused by or otherwise associated with any of the following inflammatory conditions A. Arthritic Disorder Arthritic disorders include, for example, a rheumatoid arthritis; a juvenile rheumatoid arthritis; a systemic lupus erythematosus (SLE); a gouty arthritis; a scleroderma; an osteoarthritis; a psoriatic arthritis; an ankylosing spondylitis; a Reiter's syndrome (reactive arthritis); an adult Still's disease; an arthritis from a viral infection; an arthritis from a bacterial infection, such as, e.g., a gonococcal arthritis and a non-gonococcal bacterial arthritis (septic arthritis); a Tertiary Lyme disease; a tuberculous arthritis; and an arthritis from a fungal infection, such as, e,g. a blastomycosis B. Autoimmune Diseases Autoimmune diseases include, for example, a Guillain-Barré syndrome, a Hashimoto's thyroiditis, a pernicious anemia, an Addison's disease, a type I diabetes, a systemic lupus erythematosus, a dermatomyositis, a Sjogren's syndrome, a lupus erythematosus, a multiple sclerosis, a myasthenia gravis, a Reiter's syndrome and a Grave's disease.

C. Connective Tissue Disorder

Connective tissue disorders include, for example, a spondyloarthritis a dermatomyositis, and a fibromyalgia.

D. Injury

Inflammation caused by injury, including, for example, a crush, puncture, stretch of a tissue or joint, may cause chronic inflammatory pain.

E. Infection

Inflammation caused by infection, including, for example, a tuberculosis or an interstitial keratitis may cause chronic inflammatory pain.

F. Neuritis

Neuritis is an inflammatory process affecting a nerve or group of nerves. Symptoms depend on the nerves involved, but may include pain, paresthesias, paresis, or hypesthesia (numbness).

Examples include:

a. Brachial neuritis b. Retrobulbar neuropathy, an inflammatory process affecting the part of the optic nerve lying immediately behind the eyeball.

c. Optic neuropathy, an inflammatory process affecting the optic nerve causing sudden, reduced vision in the affected eye. The cause of optic neuritis is unknown. The sudden inflammation of the optic nerve (the nerve connecting the eye and the brain) leads to swelling and destruction of the myelin sheath. The inflammation may occasionally be the result of a viral infection, or it may be caused by autoimmune diseases such as multiple sclerosis. Risk factors are related to the possible causes.

d. Vestibular neuritis, a viral infection causing an inflammatory process affecting the vestibular nerve.

G. Joint Inflammation

Inflammation of the joint, such as that caused by bursitis or tendonitis, for example, may cause chronic inflammatory pain.

III. Headache Pain

The compounds of the invention may be used to treat pain caused by or otherwise associated with any of the following headache conditions. A headache (medically known as cephalgia) is a condition of mild to severe pain in the head; sometimes neck or upper back pain may also be interpreted as a headache. It may indicate an underlying local or systemic disease or be a disorder in itself.

A. Muscular/Myogenic Headache

Muscular/myogenic headaches appear to involve the tightening or tensing of facial and neck muscles; they may radiate to the forehead. Tension headache is the most common form of myogenic headache.

A tension headache is a condition involving pain or discomfort in the head, scalp, or neck, usually associated with muscle tightness in these areas. Tension headaches result from the contraction of neck and scalp muscles. One cause of this muscle contraction is a response to stress, depression or anxiety. Any activity that causes the head to be held in one position for a long time without moving can cause a headache. Such activities include typing or use of computers, fine work with the hands, and use of a microscope. Sleeping in a cold room or sleeping with the neck in an abnormal position may also trigger this type of headache. A tension-type headache, includes, without limitation, an episodic tension headache and a chronic tension headache.

B. Vascular Headache

The most common type of vascular headache is migraine. Other kinds of vascular headaches include cluster headaches, which cause repeated episodes of intense pain, and headaches resulting from high blood pressure 1. Migraine A migraine is a heterogeneous disorder that generally involves recurring headaches. Migraines are different from other headaches because they occur with other symptoms, such as, e.g., nausea, vomiting, or sensitivity to light. In most people, a throbbing pain is felt only on one side of the head. Clinical features such as type of aura symptoms, presence of prodromes, or associated symptoms such as vertigo, may be seen in subgroups of patients with different underlying pathophysiological and genetic mechanisms. A migraine headache, includes, without limitation, a migraine without aura (common migraine), a migraine with aura (classic migraine), a menstrual migraine, a migraine equivalent (acephalic headache), a complicated migraine, an abdominal migraine and a mixed tension migraine.

2. Cluster headache

Cluster headaches affect one side of the head (unilateral) and may be associated with tearing of the eyes and nasal congestion. They occurs in clusters, happening repeatedly every day at the same time for several weeks and then remitting.

D. High Blood Pressure Headache

E. Traction and Inflammatory Headache

Traction and inflammatory headaches are usually symptoms of other disorders, ranging from stroke to sinus infection.

F. Hormone Headache

G. Rebound Headache

Rebound headaches, also known as medication overuse headaches, occur when medication is taken too frequently to relieve headache. Rebound headaches frequently occur daily and can be very painful.

H. Chronic Sinusitis Headache

Sinusitis is inflammation, either bacterial, fungal, viral, allergic or autoimmune, of the paranasal sinuses. Chronic sinusitis is one of the most common complications of the common cold. Symptoms include: Nasal congestion; facial pain; headache; fever; general malaise; thick green or yellow discharge; feeling of facial 'fullness' worsening on bending over. In a small number of cases, chronic maxillary sinusitis can also be brought on by the spreading of bacteria from a dental infection. Chronic hyperplastic eosinophilic sinusitis is a noninfective form of chronic sinusitis.

I. An Organic Headache

J. Ictal Headaches

Ital headaches are headaches associated with seizure activity.

IV. Somatic Pain

The compounds of the invention may be used to treat pain caused by or otherwise associated with any of the following somatic pain conditions. Somatic pain originates from ligaments, tendons, bones, blood vessels, and even nerves themselves. It is detected with somatic nociceptors. The scarcity of pain receptors in these areas produces a dull, poorly-localized pain of longer duration than cutaneous pain; examples include sprains and broken bones. Additional examples include the following.

A. Excessive Muscle Tension

Excessive muscle tension can be caused, for example, by a sprain or a strain.

B. Repetitive Motion Disorders

Repetitive motion disorders can result from overuse of the hands, wrists, elbows, shoulders, neck, back, hips, knees, feet, legs, or ankles.

C. Muscle Disorders

Muscle disorders causing somatic pain include, for example, a polymyositis, a dermatomyositis, a lupus, a fibromyalgia, a polymyalgia rheumatica, and a rhabdomyolysis.

D. Myalgia

Myalgia is muscle pain and is a symptom of many diseases and disorders. The most common cause for myalgia is either overuse or over-stretching of a muscle or group of muscles. Myalgia without a traumatic history is often due to viral infections. Longer-term myalgias may be indicative of a metabolic myopathy, some nutritional deficiencies or chronic fatigue syndrome.

E. Infection

Infection can cause somatic pain. Examples of such infection include, for example, an abscess in the muscle, a trichinosis, an influenza, a Lyme disease, a malaria, a Rocky Mountain spotted fever, Avian influenza, the common cold, community-acquired pneumonia, meningitis, monkeypox, Severe Acute Respiratory Syndrome, toxic shock syndrome, trichinosis, typhoid fever, and upper respiratory tract infection.

F. Drugs

Drugs can cause somatic pain. Such drugs include, for example, cocaine, a statin for lowering cholesterol (such as atorvastatin, simvastatin, and lovastatin), and an ACE inhibitor for lowering blood pressure (such as enalapril and captopril)

V. Visceral Pain

The compounds of the invention may be used to treat pain caused by or otherwise associated with any of the following visceral pain conditions. Visceral pain originates from body's viscera, or organs. Visceral nociceptors are located within body organs and internal cavities. The even greater scarcity of nociceptors in these areas produces pain that is usually more aching and of a longer duration than somatic pain. Visceral pain is extremely difficult to localise, and several injuries to visceral tissue exhibit "referred" pain, where the sensation is localised to an area completely unrelated to the site of injury. Examples of visceral pain include the following.

A. Functional Visceral Pain

Functional visceral pain includes, for example, an irritable bowel syndrome and a chronic functional abdominal pain (CFAP), a functional constipation and a functional dyspepsia, a non-cardiac chest pain (NCCP) and a chronic abdominal pain.

B. Chronic Gastrointestinal Inflammation

Chronic gastrointestinal inflammation includes, for example, a gastritis, an inflammatory bowel disease, like, e.g., a Crohn's disease, an ulcerative colitis, a microscopic colitis, a diverticulitis and a gastroenteritis; an interstitial cystitis; an intestinal ischaemia; a cholecystitis; an appendicitis; a gastroesophageal reflux; an ulcer, a nephrolithiasis, an urinary tract infection, a pancreatitis and a hernia.

C. Autoimmune Pain

Autoimmune pain includes, for example, a sarcoidosis and a vasculitis.

D. Organic Visceral Pain

Organic visceral pain includes, for example, pain resulting from a traumatic, inflammatory or degenerative lesion of the gut or produced by a tumor impinging on sensory innervation.

E. Treatment-Induced Visceral Pain

Treatment-induced visceral pain includes, for example, a pain attendant to chemotherapy therapy or a pain attendant to radiation therapy.

VI. Referred Pain

The compounds of the invention may be used to treat pain caused by or otherwise associated with any of the following referred pain conditions.

Referred pain arises from pain localized to an area separate from the site of pain stimulation. Often, referred pain arises when a nerve is compressed or damaged at or near its origin. In this circumstance, the sensation of pain will generally be felt in the territory that the nerve serves, even though the damage originates elsewhere. A common example occurs in intervertebral disc herniation, in which a nerve root arising from the spinal cord is compressed by adjacent disc material. Although pain may arise from the damaged disc itself, pain will also be felt in the region served by the compressed nerve (for example, the thigh, knee, or foot). Relieving the pressure on the nerve root may ameliorate the referred pain, provided that permanent nerve damage has not occurred. Myocardial ischaemia (the loss of blood flow to a part of the heart muscle tissue) is possibly the best known example of referred pain; the sensation can occur in the upper chest as a restricted feeling, or as an ache in the left shoulder, arm or even hand.

The present invention addresses a wide range of pain conditions, in particular chronic pain conditions. Preferred conditions include cancerous and non-cancerous pain, inflammatory pain and neuropathic pain. The opioid-fusions of the present application are particularly suited to addressing inflammatory pain, though may be less suited to addressing neuropathic pain. The galanin-fusions are more suited to addressing neuropathic pain.

In use, the polypeptides of the present invention are typically employed in the form of a pharmaceutical composition in association with a pharmaceutical carrier, diluent and/or excipient, although the exact form of the composition may be tailored to the mode of administration. Administration is preferably to a mammal, more preferably to a human.

The polypeptides may, for example, be employed in the form of a sterile solution for intra-articular administration or intra-cranial administration. Spinal injection (e.g. epidural or intrathecal) is preferred.

The dosage ranges for administration of the polypeptides of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein as the 1× dose. In this regard, preferred dosages are in the range 1×-100× (i.e. 2.5-250 ng). This dosage range is significantly lower (i.e. at least 10-fold, typically 100-fold lower) than would be employed with other types of analgesic molecules such as NSAIDS, morphine, and gabapentin. Moreover, the above-mentioned difference is considerably magnified when the same comparison is made on a molar basis—this is because the fusion proteins of the present invention have a considerably greater Mw than do conventional 'small' molecule therapeutics.

Wide variations in the required dosage, however, are to be expected depending on the precise nature of the components, and the differing efficiencies of various routes of administration.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle. The active ingredients, depending on the vehicle and concentration used, can be either dissolved or suspended in the vehicle.

In preparing administrable solutions, the polypeptides can be dissolved in a vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the polypeptides and other ingredients may be dissolved in an aqueous vehicle, the solution is sterilized by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

Definitions Section

Targeting Moiety (TM) means any chemical structure associated with an agent that functionally interacts with a Binding Site to cause a physical association between the agent and the surface of a target cell. In the context of the present invention, the target cell is a nociceptive sensory afferent. The term TM embraces any molecule (i.e. a naturally occurring molecule, or a chemically/physically modified variant thereof) that is capable of binding to a Binding Site on the target cell, which Binding Site is capable of internalisation (e.g. endosome formation)—also referred to as receptor-mediated endocytosis. The TM may possess an endosomal membrane translocation function, in which case separate TM and Translocation Domain components need not be present in an agent of the present invention.

The TM of the present invention binds (preferably specifically binds) to a nociceptive sensory afferent (e.g. a primary nociceptive afferent). In this regard, specifically binds means that the TM binds to a nociceptive sensory afferent (e.g. a primary nociceptive afferent) with a greater affinity than it binds to other neurons such as non-nociceptive afferents, and/or to motor neurons (i.e. the natural target for clostridial neurotoxin holotoxin). The term "specifically binding" can also mean that a given TM binds to a given receptor, for example galanin receptors, such as GALR1, GALR2 and/or GALR3 receptors, with a binding affinity (Ka) of $10^6$ $M^{-1}$ or greater, preferably $10^7$ $M^{-1}$ or greater, more preferably $10^8$ $M^{-1}$ or greater, and most preferably, $10^9$ $M^{-1}$ or greater.

For the purposes of this invention, an agonist is defined as a molecule that is capable of stimulating the process of exocytic fusion in a target cell, which process is susceptible to inhibition by a protease capable of cleaving a protein of the exocytic fusion apparatus in said target cell.

Accordingly, the particular agonist definition of the present invention would exclude many molecules that would be conventionally considered as agonists.

For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

The term "fragment", when used in relation to a protein, means a peptide having at least thirty-five, preferably at least twenty-five, more preferably at least twenty, and most preferably at least 19, 18, 17, 16, 15, 14, 13, 12, 11, 10, 9, 8, 7, 6 or 5 amino acid residues of the protein in question.

The term "variant", when used in relation to a protein, means a peptide or peptide fragment of the protein that contains one or more analogues of an amino acid (e.g. an unnatural amino acid), or a substituted linkage.

The term "derivative", when used in relation to a protein, means a protein that comprises the protein in question, and a further peptide sequence. The further peptide sequence should preferably not interfere with the basic folding and thus conformational structure of the original protein. Two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polypeptide components may be included.

The term non-cytotoxic means that the protease molecule in question does not kill the target cell to which it has been re-targeted.

The protease of the present invention embraces all naturally-occurring non-cytotoxic proteases that are capable of cleaving one or more proteins of the exocytic fusion apparatus in eukaryotic cells.

The non-cytotoxic protease of the present invention is preferably a bacterial protease. In one embodiment, the non-cytotoxic protease is selected from the genera *Clostridium* or *Neisseria* (e.g. a clostridial L-chain, or a neisserial IgA protease preferably from *N. gonorrhoeae*). The term protease embraces functionally equivalent fragments and molecules thereof.

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain or LC fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of K⁺ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. It is preferred that the H-chain substantially lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is preferably incapable of binding to the Binding Site on a target cell to which native clostridial neurotoxin (i.e. holotoxin) binds.

In one embodiment, the translocation domain is a $H_N$ domain (or a fragment thereof) of a clostridial neurotoxin. Examples of suitable clostridial Translocation Domains include:

Botulinum type A neurotoxin—amino acid residues (449-871)

Botulinum type B neurotoxin—amino acid residues (441-858)

Botulinum type C neurotoxin—amino acid residues (442-866)

Botulinum type D neurotoxin—amino acid residues (446-862)

Botulinum type E neurotoxin—amino acid residues (423-845)

Botulinum type F neurotoxin—amino acid residues (440-864)

Botulinum type G neurotoxin—amino acid residues (442-863)

Tetanus neurotoxin—amino acid residues (458-879)

For further details on the genetic basis of toxin production in *Clostridium botulinum* and *C. tetani*, we refer to Henderson et al (1997) in The Clostridia: Molecular Biology and Pathogenesis, Academic press.

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see Table 4). Examples of non-clostridial Translocation Domain origins include, but are not restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) Biochem. Biophys. Acta., 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) PNAS, 89, pp. 7934-7938], and amphiphilic peptides [Murata et al (1992) Biochem., 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the Translocation Domains listed in Table (below) includes use of sequence variants thereof. A variant may comprise one or more conservative nucleic acid substitutions and/or nucleic acid deletions or insertions, with the proviso that the die variant possesses the requisite translocating function. A variant may also comprise one or more amino acid substitutions and/or amino acid deletions or insertions, so long as the variant possesses the requisite translocating function.

| Translocation domain source | Amino acid residues | References |
|---|---|---|
| Diphtheria toxin | 194-380 | Silverman et al., 1994, J. Biol. Chem. 269, 22524-22532<br>London E., 1992, Biochem. Biophys. Acta., 1113, 25-51 |
| Domain II of *pseudomonas* exotoxin | 405-613 | Prior et al., 1992, Biochemistry 31, 3555-3559<br>Kihara & Pastan, 1994, Bioconj Chem. 5, 532-538 |
| Influenza virus haemagglutinin | GLFGAIAGFIENGWE GMIDGWYG (SEQ ID NO: 89), and Variants thereof | Plank et al., 1994, J. Biol. Chem. 269, 12918-12924<br>Wagner et al., 1992, PNAS, 89, 7934-7938<br>Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

"CPGA16" refers to centrally-presented galanin GA16.
"CPGA30" refers to centrally-presented galanin GA30.
"EN" refers to an enterokinase cleavage site.
"HT" refers to a His-tag.

There now follows a brief description of the Figures, which illustrate aspects and/or embodiments of the present invention.

FIG. 1—Purification of a LC/A-spacer-galanin-spacer-$H_N$/A fusion protein

Using the methodology outlined in Example 3, a LC/A-GS18-galanin-GS20-$H_N$/A fusion protein was purified from *E. coli* BL21 cells. Briefly, the soluble products obtained following cell disruption were applied to a nickel-charged affinity capture column. Bound proteins were eluted with 100 mM imidazole, treated with enterokinase to activate the fusion protein and treated with factor Xa to remove the maltose-binding protein (MBP) tag. Activated fusion protein was then re-applied to a second nickel-charged affinity capture column. Samples from the purification procedure were assessed by SDS-PAGE (Panel A) and Western blotting (Panel B). Anti-galanin antisera (obtained from Abcam) and Anti-histag antisera (obtained from Qiagen) were used as the primary antibody for Western blotting. The final purified material in the absence and presence of reducing agent is identified in the lanes of Panel A marked [−] and [+] respectively. Panel A, Lane 1=Benchmark ladder; 2=soluble fraction; 3=$1^{st}$ His product; 4=activated purified protein; 5=second His product; 6=final purified protein 5 µl; 7=final purified protein 10 µl; 8=final purified protein 20 µl; 9=final purified protein 5 µl+DTT; 10=final purified protein 10 µl+DTT. Panel B Lane 1=Benchmark ladder; 2=soluble fraction; 3=$1^{st}$ His product; 4=activated purified protein; 5=second His product; 6=final purified protein 2 µl; 7=final purified protein 5 µl; 8=final purified protein 10 µl; 9=final purified protein 2 µl+DTT; 10=final purified protein 5 µl+DTT.

Figure 2:
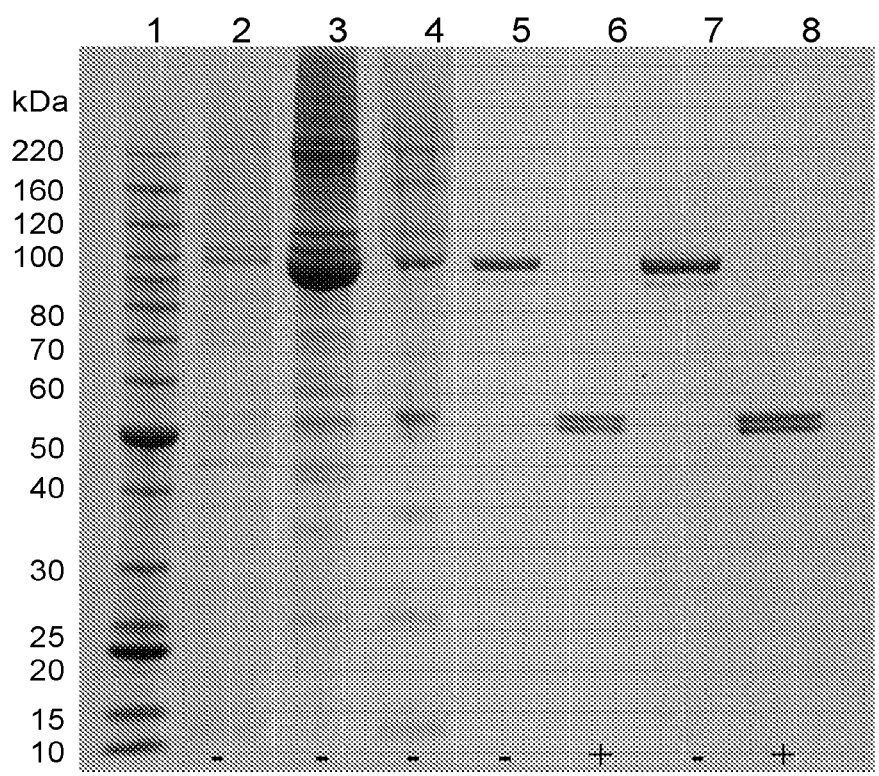
Figure 2:
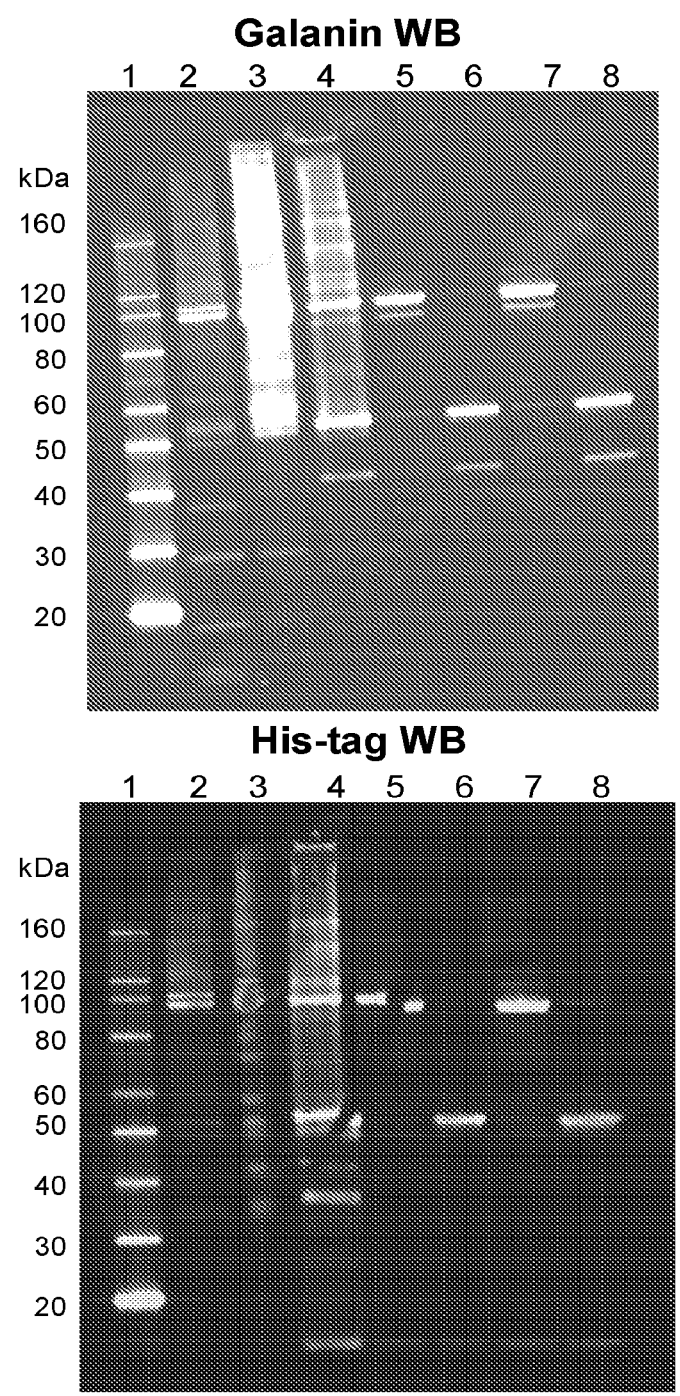

FIG. 2—Purification of a LC/C-spacer-galanin-spacer-$H_N$/C fusion protein

Using the methodology outlined in Example 3, an LC/C-galanin-$H_N$/C fusion protein was purified from *E. coli* BL21 cells. Briefly, the soluble products obtained following cell disruption were applied to a nickel-charged affinity capture column. Bound proteins were eluted with 100 mM imidazole, treated with enterokinase to activate the fusion protein, then re-applied to a second nickel-charged affinity capture column. Samples from the purification procedure were assessed by SDS-PAGE (Panel A) and Western blotting (Panel B). Anti-galanin antisera (obtained from Abcam) and Anti-histag antisera (obtained from Qiagen) were used as the primary antibody for Western blotting. The final purified material in the absence and presence of reducing agent in Panel A is identified in the lanes marked [−] and [+] respectively. Panel A, Lane 1=Benchmark ladder; 2=soluble fraction; 3=product $1^{st}$ column; 4=enterokinase activated protein; 5=final product 0.1 mg/ml (5 µl); 6=final product 0.1 mg/ml+DTT (5 µl); 7=final product 0.1 mg/ml (10 µl); 8=final product 0.1 mg/ml+DTT (10 µl). Panel B, Lane 1=Magic mark; 2=soluble fraction; 3=product $1^{st}$ His-tag column; 4=activated fusion; 5=purified @ 0.1 mg/ml (5 µl); 6=purified @ 0.1 mg/ml+DTT (5 µl); 7 purified @ 0.1 mg/ml+100 mm DTT (10 µl); 8=purified @ 0.1 mg/ml+100 mm DTT (10 µl)+DTT.

Figure 3:
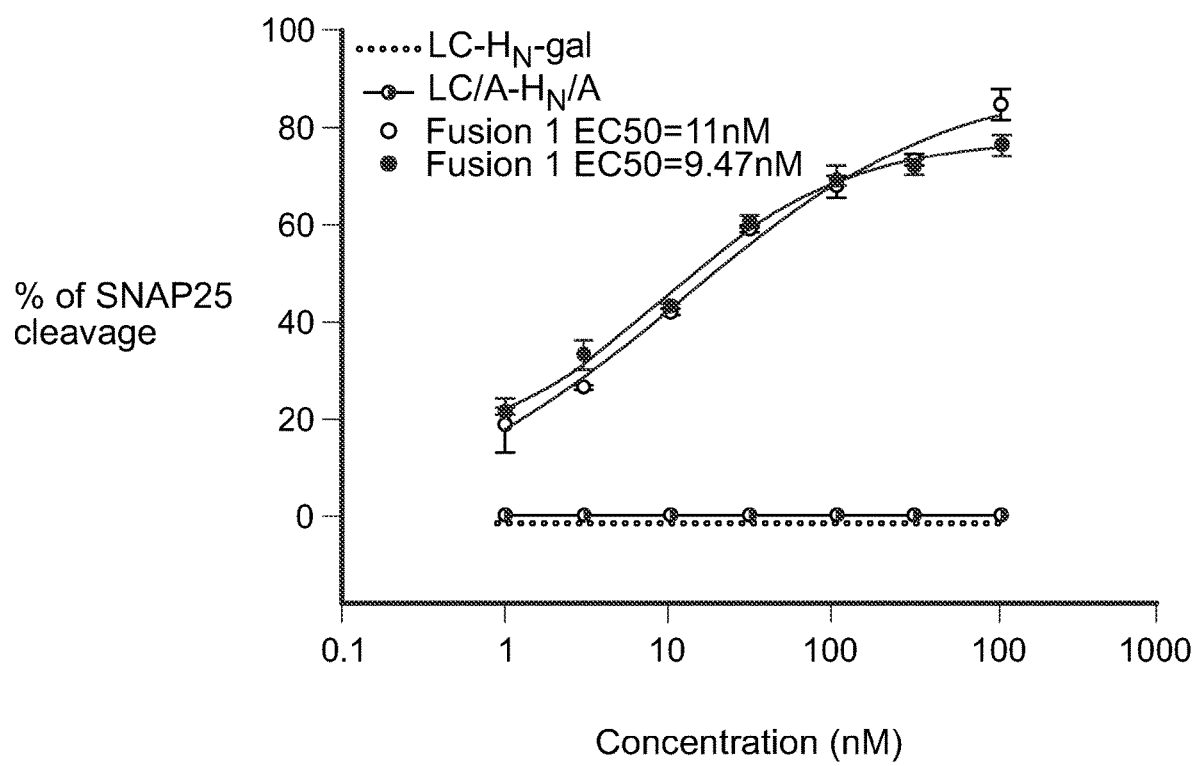
Figure 3:
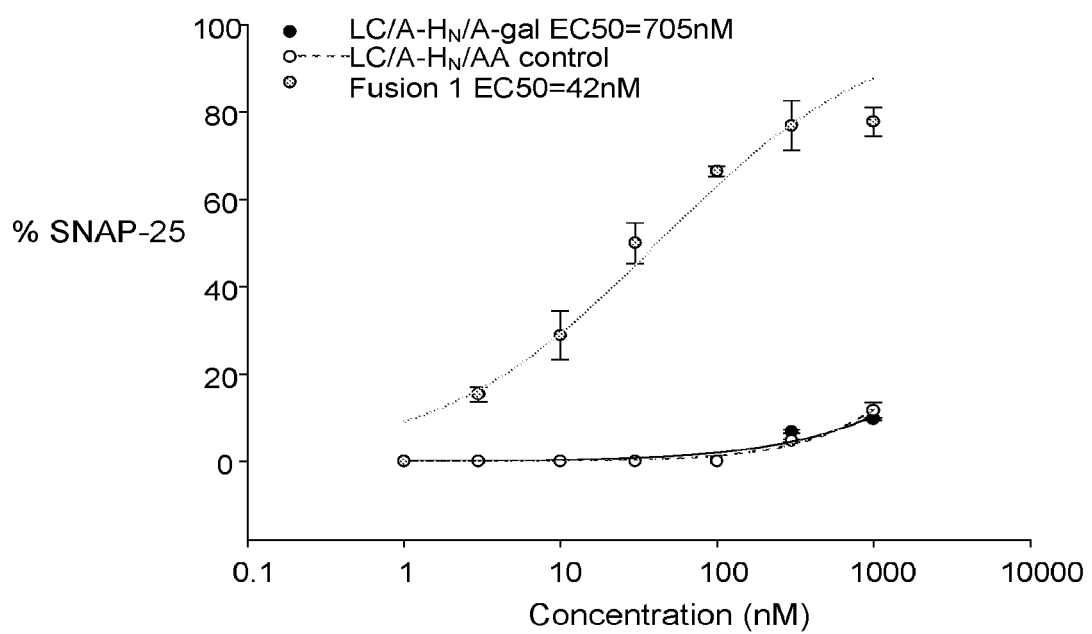

FIG. 3—Comparison of SNARE cleavage efficacy of a LC/A-spacer-galanin-spacer-$H_N$ A fusion protein and a LC-$H_N$-galanin fusion protein.

Panels A & B: The ability of galanin fusions to cleave SNAP-25 in a CHO GALR1 SNAP25 cells was assessed. Chinese hamster ovary (CHO) cells were transfected so that they express the GALR1 receptor. Said cells were further transfected to express a SNARE protein (SNAP-25). The transfected cells were exposed to varying concentrations of different galanin fusion proteins for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. it is clear from the data that the LC/A-spacer-galanin-spacer-$H_N$ A fusion (Fusion 1) is more potent than the LC/A-$H_N$ A-galanin fusion and the unliganded LC/A-$H_N$/A control molecule.

Figure 4:
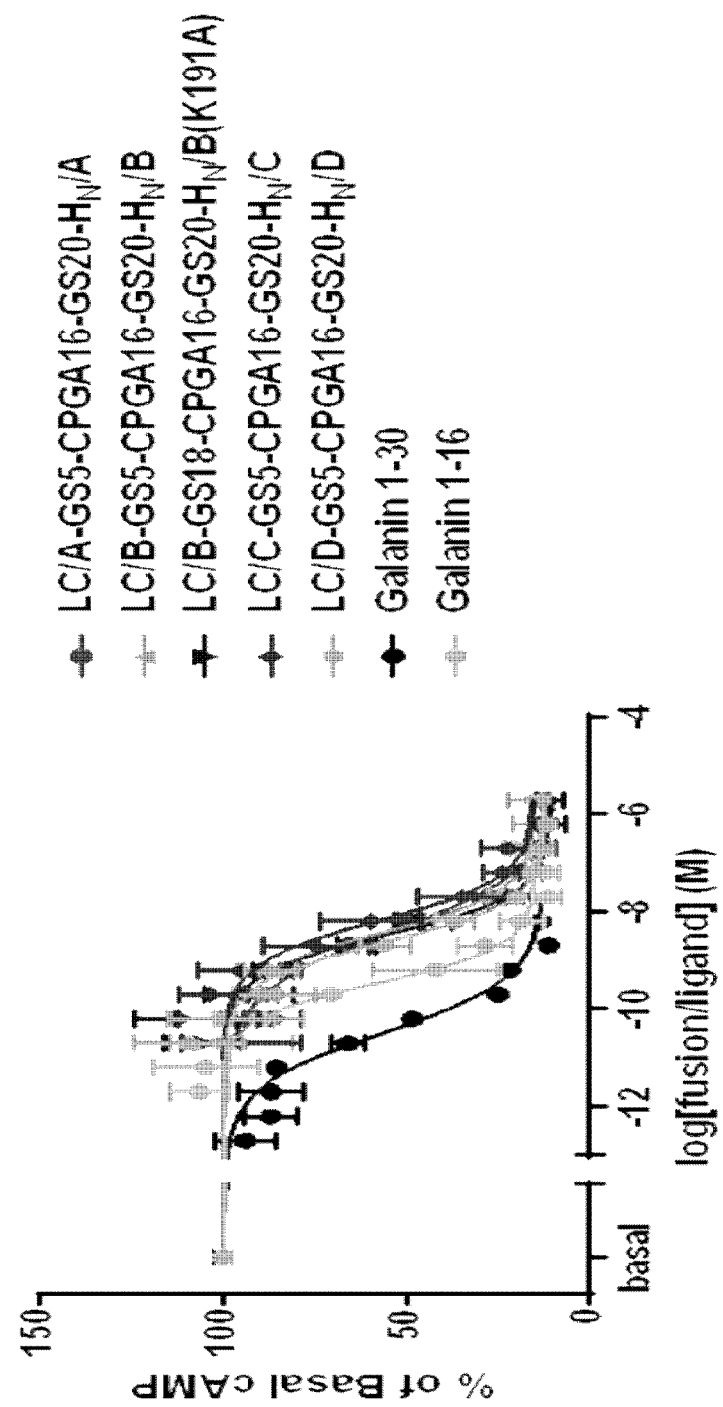

FIG. 4—GALR1 receptor activation studies in the CHO-GALCHO-GALR1 SNAP-25 cleavage assay with galanin fusion proteins of the present invention having different serotype backbones Chinese hamster ovary (CHO) cells were transfected so that they express the GALR1 receptor and SNAP-25. Said cells were used to measure cAMP deletion that occurs when the receptor is activated with a galanin ligand, using a FRET-based cAMP kit (LANCE kit from Perkin Elmer). The transfected cells were exposed to varying concentrations of galanin (GA16) fusion proteins having different serotype backbones (i.e. botulinum neurotoxin serotypes A, B, C and D) for 2 hours. cAMP levels were then detected by addition of a detection mix containing a fluorescently labelled cAMP tracer (Europium-streptavadi/biotin-cAMP) and fluorescently (Alexa) labelled anti-cAMP antibody and incubating at room temperature for 24 hours. Then samples are excited at 320 nM and emitted light measured at 665 nM to determine cAMP levels. The data demonstrate that galanin fusion proteins of the present invention having different serotype backbones activated the GALR1 receptor.

FIG. 5—Cleavage of SNARE protein by galanin (GA16 and GA30) fusion proteins in CHO-GALR1 SNAP-25 cleavage assay Chinese hamster ovary (CHO) cells were transfected so that they express the GALR1 receptor. Said cells were further transfected to express a SNARE protein (SNAP-25). The transfected cells were exposed to varying concentrations of different galanin fusion proteins for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The data demonstrate that galanin fusion proteins having galanin-16 and galanin-30 ligands cleave SNARE protein. In addition, the data confirm that galanin fusion proteins having GS5, GS10 and GS18 spacers between the non-cytotoxic protease component and the protease cleavage site are functional.

FIG. 6—Results of in vivo paw guarding assay employing galanin fusion proteins

The nociceptive flexion reflex (also known as paw guarding assay) is a rapid withdrawal movement that constitutes a protective mechanism against possible limb damage. It can be quantified by assessment of electromyography (EMG) response in anesthetized rat as a result of low dose capsaicin, electrical stimulation or the capsaicin-sensitized electrical response. Intraplantar pretreatment (24 hour) of fusion proteins of the present invention into 300-380 g male Sprague-Dawley rats. Induction of paw guarding was achieved by 0.006% capsaicin, 10 µl in PBS (7.5% DMSO), injected in 10 seconds. This produced a robust reflex response from biceps feroris muscle. A reduction/inhibition of the nociceptive flexion reflex indicates that the test substance demonstrates an antinociceptive effect. The data demonstrated the antinociceptive effect of the galanin fusion proteins of the present invention.

Figure 7:
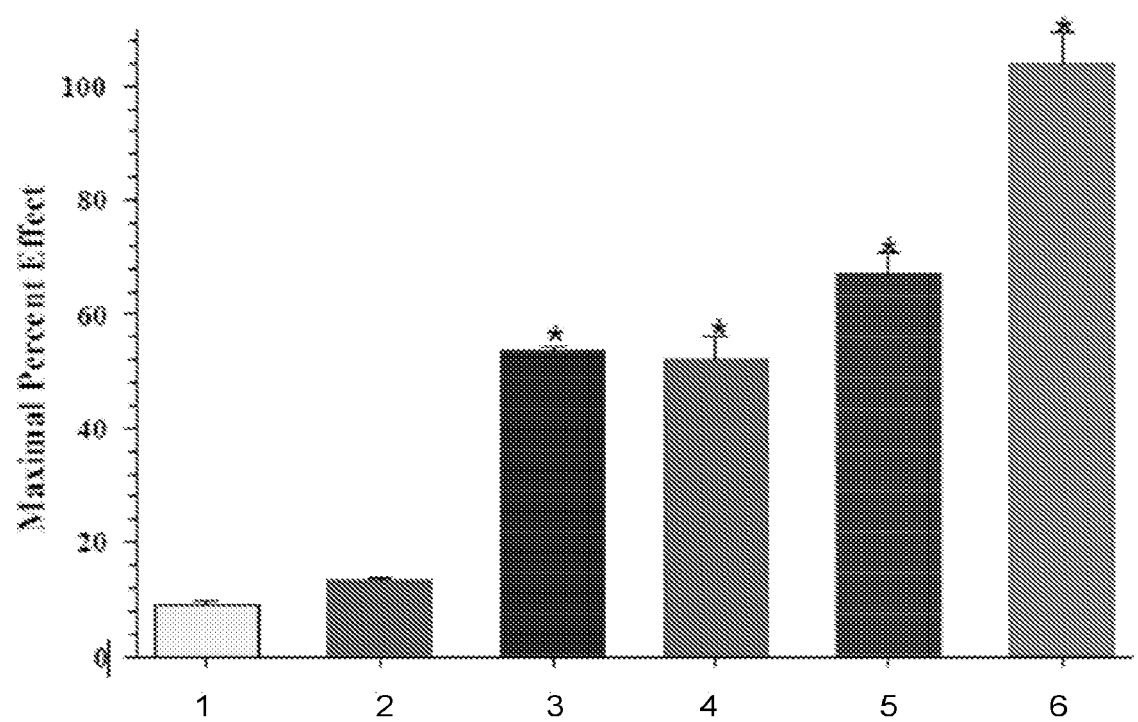

FIG. 7—Galanin fusion protein efficacy in capsaicin-induced thermal hyperalgesia assay The ability of different galanin fusion proteins of the invention to inhibit capsaicin-induced thermal hyperalgesia was evaluated. Intraplantar pretreatment of fusion proteins into Sprague-Dawley rats and 24 hours later 0.3% capsaicin was injected and rats were put on 25° C. glass plate (rats contained in acrylic boxes, on 25° C. glass plate). Light beam (adjustable light Intensity) focused on the hind paw. Sensors detected movement of paw, stopping timer. Paw Withdrawal Latency is time to remove paw from heat source (Cut-off of 20.48 seconds). A reduction/inhibition of the paw withdrawal latency indicates that the test substance demonstrates an antinociceptive effect. No. 1=LC_$H_N$-GA16; No. 2=LC-$H_N$-GA30; No. 3=LC-GS5-EN-CPGA16-GS20-$H_N$-HT; No. 4=LC-GS18-EN-CPGA16-GS20-$H_N$-HT; No. 5=BOTOX; No. 6=morphine. The data demonstrated the enhanced antinociceptive effect of the galanin fusion proteins of the present invention compared to fusion proteins with a C-terminally presented ligand.

FIG. 8—Galanin fusion protein efficacy in capsaicin-induced thermal hyperalgesia assay The ability of different galanin fusion proteins of the invention to inhibit capsaicin-induced thermal hyperalgesia was evaluated. Intraplantar pretreatment of fusion proteins into Sprague-Dawley rats and 24 hours later 0.3% capsaicin was injected and rats were put on 25° C. glass plate (rats contained in acrylic boxes, on 25° C. glass plate). Light beam (adjustable light Intensity) focused on the hind paw. Sensors detected movement of paw, stopping timer. Paw Withdrawal Latency is time to remove paw from heat source (Cut-off of 20.48 seconds). A reduction/inhibition of the paw withdrawal latency indicates that the test substance demonstrates an antinociceptive effect. The data demonstrated the antinociceptive effect of the galanin fusion proteins of the present invention having different serotype backbones (i.e. A, B, C and D).

Figure 9:
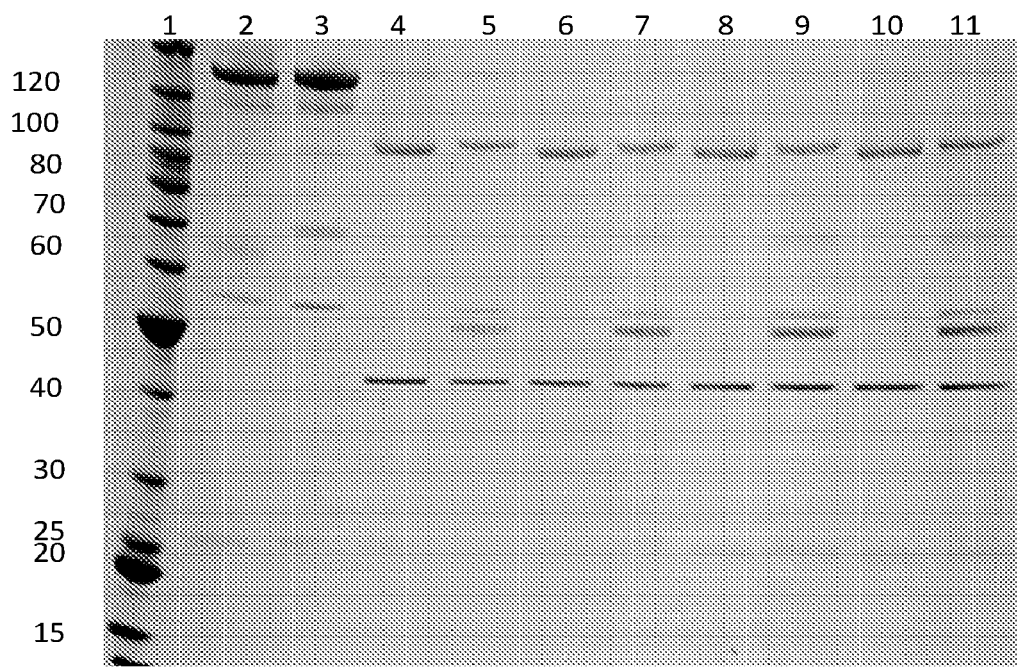
Figure 9:
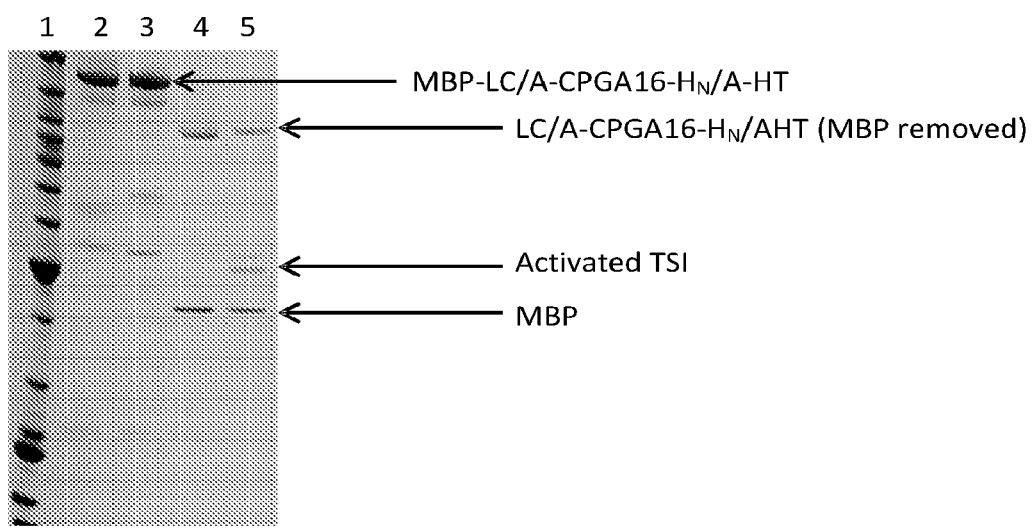
Figure 9:
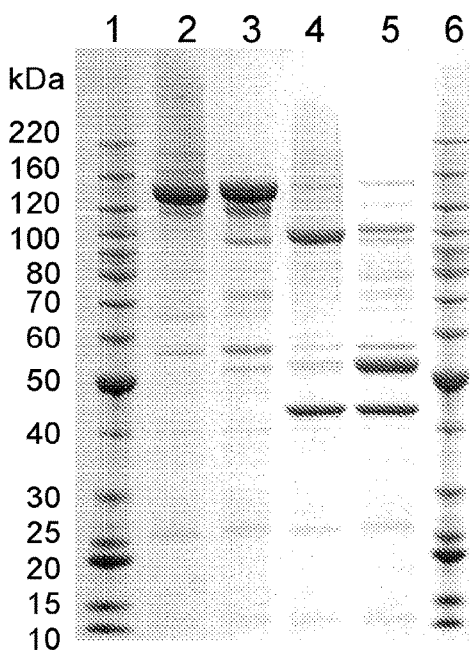
Figure 9:
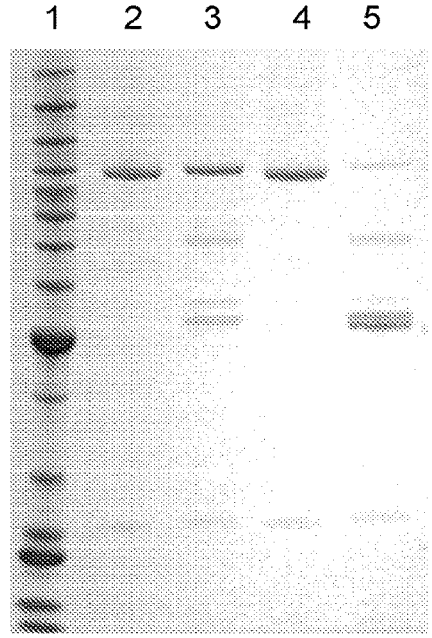
Figure 9:
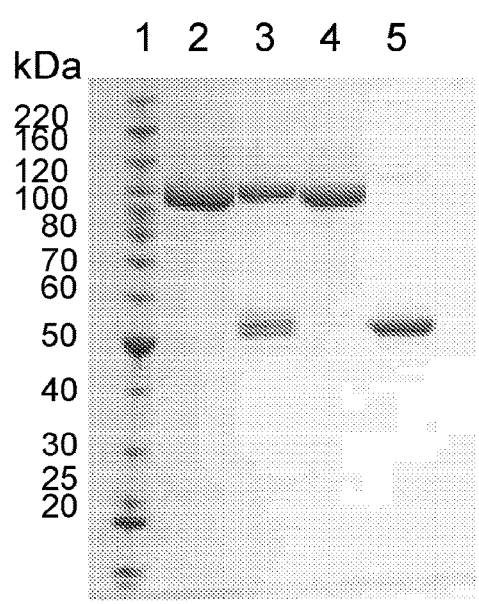
Figure 9:
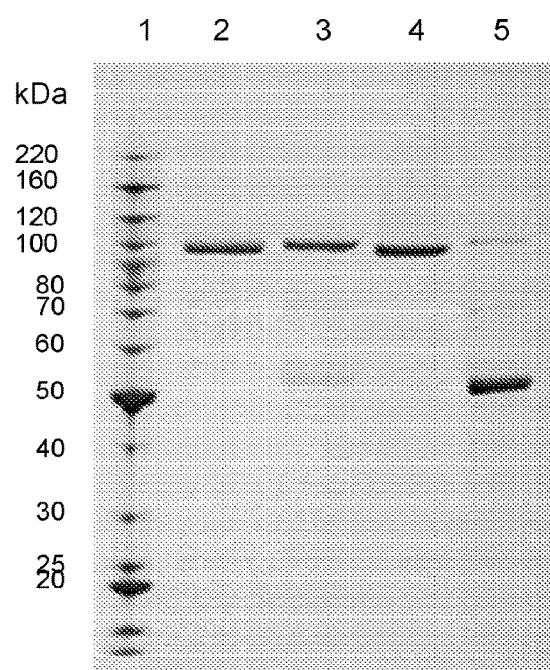

FIG. 9—Activation of galanin fusion proteins with single and double-spacers

Galanin fusion protein lacking a first spacer (spacer 1) of the present invention located between the non-cytotoxic protease component and the Targeting Moiety component (LC/A-EN-CPGA16-HX27-$H_N$/A) showed poor activation with protease (Panels A and B). Panel C demonstrates the enhanced activation of galanin fusion proteins of the present invention haviri 0-both first (spacer 1) and second (spacer 2) spacers (LC/A-GS5-EN-CPGA16-HX27 $H_N$/A). Panels A&B: 1) Benchmark ladder; 2) Unactivated control; 3) Unactivated control+DTT; 4) Protease activated protein+0.0 mM ZnCl2; 5) Protease activated protein+0.0 mM ZnCl2+DTT; 6) Protease activated protein+0.2 mM ZnCl2; 7) Protease activated protein+0.2 mM ZnCl2+DTT; 8) Protease activated protein+0.4 mM ZnCl2; 9) Protease activated protein+0.4 mM ZnCl2+DTT; 10) Protease activated protein+0.8 mM ZnCl2; 11) Protease activated protein+0.8 mM ZnCl2+DTT, Panel C: 1) Benchmark ladder; 2) Unactivated control 25° C.; 3) Unactivated control 25° C.+DTT; 4) Protease activated protein 25° C.; 5) Protease activated protein 25° C.+DTT; 6) Benchmark ladder.

SEQ ID NOS

Where an initial Met amino acid residue or a corresponding initial codon is indicated in any of the following SEQ ID NOs, said residue/codon is optional.

| | |
|---|---|
| SEQ ID NO 1 | DNA sequence of the LC/A |
| SEQ ID NO 2 | DNA sequence of the $H_N$/A |
| SEQ ID NO 3 | DNA sequence of the LC/B |
| SEQ ID NO 4 | DNA sequence of the $H_N$/B |
| SEQ ID NO 5 | DNA sequence of the LC/C |
| SEQ ID NO 6 | DNA sequence of the $H_N$/C |
| SEQ ID NO 7 | Protein sequence of galanin GA30 |
| SEQ ID NO 8 | Protein sequence of galanin GA16 |

-continued

| | |
|---|---|
| SEQ ID NO 9 | DNA sequence of LC/A-GS18-EN-CPGA16-GS20-$H_N$/A-HT |
| SEQ ID NO 10 | Protein sequence of LC/A-GS18-EN-CPGA16-GS20-$H_N$/A-HT |
| SEQ ID NO 11 | Protein sequence of LC/A-GS18-EN-CPGA16-GS20-$H_N$/A |
| SEQ ID NO 12 | DNA sequence of LC/A-GS5-EN-CPGA16-GS20-$H_N$/A-HT |
| SEQ ID NO 13 | Protein sequence of LC/A-GS5-EN-CPGA16-GS20-$H_N$/A-HT |
| SEQ ID NO 14 | Protein sequence of LC/A-GS5-EN-CPGA16-$H_N$/A-GS20 |
| SEQ ID NO 15 | DNA sequence of LC/A-GS5-EN-CPGA30-GS20-$H_N$/A-HT |
| SEQ ID NO 16 | Protein sequence of LC/A-GS5-EN-CPGA30-GS20-$H_N$/A-HT |
| SEQ ID NO 17 | Protein sequence of LC/A-GS5-EN-CPGA30-GS20-$H_N$/A |
| SEQ ID NO 18 | DNA sequence of LC/B-GS5-EN-CPGA16-GS20-$H_N$/B(K191A)-HT |
| SEQ ID NO 19 | Protein sequence of LC/B-GS5-EN-CPGA16-GS20-$H_N$/B(K191A)-HT |
| SEQ ID NO 20 | Protein sequence of LC/B-GS5-EN-CPGA16-GS20-$H_N$/B(K191A) |
| SEQ ID NO 21 | DNA sequence of LC/B-GS5-EN-CPGA16-GS20-$H_N$/B-HT |
| SEQ ID NO 22 | Protein sequence of LC/B-GS5-EN-CPGA16-GS20-$H_N$/B-HT |
| SEQ ID NO 23 | Protein sequence of LC/B-GS5-EN-CPGA16-GS20-$H_N$/B |
| SEQ ID NO 24 | DNA sequence of LC/C-GS5-EN-CPGA16-GS20-$H_N$/C-HT |
| SEQ ID NO 25 | Protein sequence of LC/C-GS5-EN-CPGA16-GS20-$H_N$/C-HT |
| SEQ ID NO 26 | Protein sequence of LC/C-GS5-EN-CPGA16-GS20-$H_N$/C |
| SEQ ID NO 27 | DNA sequence of LC/D-GS5-EN-CPGA16-GS20-$H_N$/D-HT |
| SEQ ID NO 28 | Protein sequence of LC/D-GS5-EN-CPGA16-GS20-$H_N$/D-HT |
| SEQ ID NO 29 | Protein sequence of LC/D-GS5-EN-CPGA16-$H_N$/D-GS20 |
| SEQ ID NO 30 | DNA sequence of LC/A-GS5-EN-CPGA16-HX27-$H_N$/A-HT |
| SEQ ID NO 31 | Protein sequence of LC/A-GS5-EN-CPGA16-HX27-$H_N$/A-HT |
| SEQ ID NO 32 | Protein sequence of LC/A-GS5-EN-CPGA16-HX27-$H_N$/A- |
| SEQ ID NO 33 | Protein sequence of LC/A-GS10-EN-CPGA16-$H_N$/A-GS20-HT |
| SEQ ID NO 34 | Protein sequence of LC/A-GS10-EN-CPGA16-GS20-$H_N$/A |
| SEQ ID NO 35 | Protein sequence of LC/A-GS5-EN-CPGA16-GS15-$H_N$/A-HT |
| SEQ ID NO 36 | Protein sequence of LC/A-GS5-EN-CPGA16-GS15-$H_N$/A |
| SEQ ID NO 37 | Protein sequence of LC/A-GS5-EN-CPGA16-GS10-$H_N$/A-HT |
| SEQ ID NO 38 | Protein sequence of LC/A-GS5-EN-CPGA16-GS10-$H_N$/A |
| SEQ ID NO 39 | Protein sequence of LC/A-GS18-EN-CPGA16-HX27-$H_N$/A-HT |
| SEQ ID NO 40 | Protein sequence of LC/A-GS18-EN-CPGA16-HX27-$H_N$/A |
| SEQ ID NO 41 | Protein sequence of LC/A-GS18-EN-CPGA16-GS15-$H_N$/A-HT |
| SEQ ID NO 42 | Protein sequence of LC/A-GS18-EN-CPGA16-GS15 |
| SEQ ID NO 43 | Protein sequence of LC/A-GS18-EN-CPGA16-GS10-HT |
| SEQ ID NO 44 | Protein sequence of LC/A-GS18-EN-CPGA16-GS10 |
| SEQ ID NO 45 | Protein sequence of LC/A-GS10-EN-CPGA16-HX27-HT |
| SEQ ID NO 46 | Protein sequence of LC/A-GS10-EN-CPGA16-HX27 |
| SEQ ID NO 47 | Protein sequence of LC/A-GS10-EN-CPGA16-GS15-$H_N$/A-HT |
| SEQ ID NO 48 | Protein sequence of LC/A-GS10-EN-CPGA16-GS15-$H_N$/A |
| SEQ ID NO 49 | Protein sequence of LC/A-GS10-EN-CPGA16-GS10-$H_N$/A-HT |
| SEQ ID NO 50 | Protein sequence of LC/A-GS10-EN-CPGA16-GS10-$H_N$/A |
| SEQ ID NO 51 | DNA sequence of the IgA protease |
| SEQ ID NO 52 | DNA sequence of the IgA-GS5-CPGA16-GS20-$H_N$/A fusion |
| SEQ ID NO 53 | Protein sequence of the IgA-GS5-CPGA16-GS20-$H_N$/A fusion |
| SEQ ID NO 54 | DNA sequence of DT translocation domain |
| SEQ ID NO 55 | DNA sequence of LC/A-GS5-GA16-GS20-DT |
| SEQ ID NO 56 | Protein sequence of LC/A-GS5-GA16-GS20-DT |
| SEQ ID NO 57 | DNA sequence of TeNT LC |
| SEQ ID NO 58 | DNA sequence of TeNT LC-GS5--CPGA16-GS20-$H_N$/A |
| SEQ ID NO 59 | Protein sequence of TeNT LC-GS5-EN-CPGA16-GS20-$H_N$/A |

EXAMPLES

Example 1—Construction and Activation of Galanin Fusion Proteins

Preparation of a LC/A and $H_N$/A Backbone Clones

The following procedure creates the LC and $H_N$ fragments for use as the component backbone for multidomain fusion expression. This example is based on preparation of a serotype A based clone (SEQ ID NO1 and SEQ ID NO2), though the procedures and methods are equally applicable to the other serotypes (i.e. A, B, C, D and E serotypes) as illustrated by the sequence listing for serotype B (SEQ ID NO3 and SEQ ID NO4) and serotype C (SEQ ID NO5 and SEQ ID NO6)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO1) is created by one of two ways:

The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of *Clostridium* target DNA, one oligonucleotide for each of the two DNA strands. To generate a PCR product the pair of short oligonucleotide primers specific for the *Clostridium* DNA sequence are mixed with the *Clostridium* DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis [for example, using Quickchange (Stratagene Inc.)].

Preparation of Translocation (e.g. $H_N$) Insert

The $H_N$/A (SEQ ID NO2) is created by one of two ways:

The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best *E. coli* reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Preparation of LC/A-GS18-EN-CPGA16-GS20-$H_N$/A Fusion

In order to create the LC/A-GS18-EN-CPGA16-GS20-$H_N$/A construct, an A serotype linker with the addition of an Enterokinase site for activation, arranged as BamHI-SalI-GS18-protease site-GS20-PstI-XbaI-stop codon-HindIII is synthesised. The pCR 4 vector encoding the linker is cleaved with BamHI+SalI restriction enzymes. This cleaved vector then serves as the recipient for insertion and ligation of the LC/A DNA (SEQ ID NO1) also cleaved with BamHI+SalI. This construct is then cleaved with BamHI+HindIII and inserted into an expression vector such as the pMAL plasmid (NEB) or pET based plasmid (Novagen). The resulting plasmid DNA is then cleaved with PstI+XbaI restriction enzymes and the $H_N$/A DNA (SEQ ID NO2) is then cleaved with PstI+XbaI restriction enzymes and inserted into the a similarly cleaved pMAL vector to create pMAL-LC/A-GS18-EN-CPGA16-GS20-$H_N$/A-XbaI-His-tag-stop codon-HindIII. The final construct contains the GS18-EN-CPGA16-GS20 spacer ORF for expression as a protein of the sequence illustrated in SEQ ID NO10.

Activation Assay

NuPAGE 4-12% Bis-Tris gels (10, 12 and 15 well prepoured gel) were used to analyze activation of fusion proteins after treatment with protease. Protein samples were prepared with NuPAGE 4×LDS sample buffer, typically to a final volume of 100 μl. Samples were either diluted or made up neat (75 μl of sample, 25 μl of sample buffer) depending on protesin concentration. The samples were mixed and then heated in the heat block at 95° C. for 5 min before loading onto the gel. 5-20 μl of sample was loaded along with 5 μl of the protein marker (Benchmark™ protein marker from Invitrogen). The gels were typically run for 50 min at 200 V. The gel was immersed in $dH_2O$ and microwaved for 2 min on full power. The gel was rinsed and the microwave step was repeated. The gel was transferred to a staining box and immersed in Simply Blue SafeStain (Invitrogen). It was microwaved for 1 minute on full power and left for 0.5-2 h to stain. The gel was then destained by pouring off the Safestain and rinsing the gel with $dH_2O$. The gels were left in $dH_2O$ to destain overnight and an image was taken on a GeneGnome (Syngene) imager. Total activated protein was calculated by comparing the density of the band that corresponded to full-length fusion protein (after protease treatment) in non-reduced and reduced conditions.

Example 2—Preparation of an LC/A-GS18-EN-CPGA16-GS20-$H_N$/A Fusion Protein Family with Variable Spacer Length Using the same strategy as employed in Example 1, a range of DNA linkers were prepared that encoded galanin16 and variable spacer content. Using one of a variety of reverse translation software tools [for example EditSeq best

*E. coli* reverse translation (DNASTAR Inc.), or Backtranslation tool v2.0 (Entelechon)], the DNA sequence encoding the Spacer 1-Protease site—ligand-spacer 2 region is determined. Restriction sites are then incorporated into the DNA sequence and can be arranged as BamHI-SalI-Spacer 1-protease site-CPGA16-NheI-spacer 2-SpeI-PstI-XbaI-stop codon-HindIII. It is important to ensure the correct reading frame is maintained for the spacer, GA16 and restriction sequences and that the XbaI sequence is not preceded by the bases, TC which would result on DAM methylation. The DNA sequence is screened for restriction sequence incorporation and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacer-linkers that were created included:

| Spacer 1 - protease site-GA16 - Spacer 2 | SEQ ID NO of the linker |
|---|---|
| GS5-EN-CPGA16-GS20 | 12, 13, 14, 18, 19, 20, 21, 22, 23, 24, 25, 26, 27, 28, 29 |
| GS10-EN-CPGA16-GS20 | 33, 34 |
| GS5-EN-CPGA16-HX27 | 30, 31, 32 |
| GS5-EN-CPGA16-GS15 | 35, 36 |
| GS5-EN-CPGA16-GS10 | 37, 38 |
| GS18-EN-CPGA16-HX27 | 39, 40 |
| GS18-EN-CPGA16-GS15 | 41, 42 |
| GS18-EN-CPGA16-GS10 | 43, 44 |
| GS10-EN-CPGA16-HX27 | 45, 46 |
| GS10-EN-CPGA16-GS15 | 47, 48 |
| GS10-EN-CPGA16-GS10 | 49, 50 |

By way of example, in order to create the LC/A-GS5-EN-CPGA16-GS20-H$_N$/A fusion construct (SEQ ID NO12), the pCR 4 vector encoding BamHI-SalI-GS5-protease site-GS20-PstI-XbaI-stop codon-HindIII the linker is cleaved with BamHI+SalI restriction enzymes. This cleaved vector then serves as the recipient vector for insertion and ligation of the LC/A DNA (SEQ ID NO1) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB) or the pET vector (Novagen). The $H_N$/A DNA (SEQ ID NO2) is then cleaved with PstI+HindIII restriction enzymes and inserted into the similarly cleaved pMAL-LC/A-linker construct. The final construct contains the LC/A-GS5-EN-CPGA16-GS20-$H_N$/A ORF for expression as a protein of the sequence illustrated in SEQ ID NO13.

Example 3—Purification Method for Galanin Fusion Protein

Defrost falcon tube containing 25 ml 50 mM HEPES pH 7.2, 200 mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M $NiSO_4$ charged Chelating column (20-30 ml column is sufficient) equilibrated with 50 mM HEPES pH 7.2, 200 mM NaCl. Using a step gradient of 10 and 40 mM imidazole, wash away the non-specific bound protein and elute the fusion protein with 100 mM imidazole. Dialyse the eluted fusion protein against 5 L of 50 mM HEPES pH 7.2, 200 mM NaCl at 4° C. overnight and measure the OD of the dialysed fusion protein. Add 1 μg of enterokinase (1 mg/ml) per 100 μg of purified fusion protein and 10 μl of factor Xa per mg of purified fusion protein if the fusion protesin contains a maltose binding protein. Incubate at 25° C. static overnight. Load onto a 0.1 M $NiSO_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazole, wash away the non-specific bound protein and elute the fusion protein with 100 mM imidazole. Dialyses the eluted fusion protein against 5 L of 50 mM HEPES pH 7.2, 200 mM NaCl at 4° C. overnight and concentrate the fusion to about 2 mg/ml, aliquot sample and freeze at −20° C.

Example 4—Preparation of a LC/C-GA16-$H_N$/IC Fusion Protein with a Serotype A Activation Sequence Following the methods used in Examples 1 and 2, the LC/C (SEQ ID NO5) and $H_N$/C (SEQ ID NO6) are created and inserted into the A serotype linker arranged as BamHI-SalI-Spacer 1-protease site-GA16-NheI-spacer 2-SpeI-PstI-XbaI-stop codon-HindIII. The final construct contains the LC-spacer 1-GA16-spacer 2-$H_N$ ORF for expression as a protein of the sequence illustrated in SEQ ID NO25.

Example 5—Preparation of an IgA Protease-GA16-$H_N$/A Fusion Protein

The IgA protease amino acid sequence was obtained from freely available database sources such as GenBank (accession number P09790). Information regarding the structure of the *N. gonorrhoeae* IgA protease gene is available in the literature (Pohlner et al., Gene structure and extracellular secretion of *Neisseria gonorrhoeae* IgA protease, *Nature,* 1987, 325(6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID NO51) containing the IgA open reading frame (ORF) is then commercially synthesized.

The IgA (SEQ ID NO51) is inserted into the LC-GS5-CPGA16-GS20-$H_N$ ORF using BamHI and SalI restriction enzymes to replace the LC with the IgA protease DNA. The final construct contains the IgA-GS5-CPGA16-GS20-H$_N$ ORF for expression as a protein of the sequence illustrated in SEQ ID NO53.

Example 6—Preparation of a Galanin Targeted Endopeptidase Fusion Protein Containing a LC Domain Derived from Tetanus The DNA sequence is designed by back translation of the tetanus toxin LC amino acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID NO57). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (invitrogen). The pCR 4 vector encoding the TeNT LC is cleaved with BamHI and SalI. The BamHI-SalI fragment is then inserted into the LC/A-GA16-$H_N$/A vector that has also been cleaved by BamHI and SalI. The final construct contains the TeNT LC-GS5-GA16-GS20-$H_N$ ORF sequences for expression as a protein of the sequence illustrated in SEQ ID NO58.

Example 7—Construction of CHO-K1 GALR1 & GALR2 Receptor Activation Assay and SNAP-25 Cleavage Assay Cell-Line Creation CHO-K1 cells stably expressing either the human galanin 1 receptor (CHO-K1-Gal-1R; product number ES-510-C) or human galanin 2 receptor (CHO-K1-Gal-2R; product number ES-511-C) were purchased from Perkin-Elmer (Bucks, UK). Where required, cells were transfected with SNAP-25 DNA using Lipofectamine™ 2000 and incubated for 4 hours before media replacement. After 24 hours, cells were transferred to a T175 flask. 100 ug/ml Zeocin was added after a further 24 hours to begin selection of SNAP-25 expressing cells, and 5 ug/ml Blasticidin added to maintain selective pressure for the receptor. Cells were maintained in media containing selection agents for two weeks, passaging cells every two to three days to maintain 30-70% confluence. Cells were then diluted in selective media to achieve 0.5 cell per well in a 96 well microplate. After a few days, the plates were examined under a microscope, and those containing single colonies were marked. Media in these wells was changed weekly. As cells became confluent in the wells, they were transferred to T25 flasks. When they had expanded sufficiently each clone was seeded to 24 wells of a 96 well plate, plus a frozen stock vial created. Galanin fusion proteins of the invention and LC/A-$H_N$A were applied to the cells for 24 hours, and then western blots performed to detect SNAP-25 cleavage. Clones from which SNAP-25 bands were strong and cleavage levels were high with fusion were maintained for further investigation. Full dose curves were run on these, and the clone with the highest differential between galanin fusion protein and LC/A-$H_N$A cleavage levels was selected.

GALR1 Receptor Activation Assay

The GALR1 receptor activation assay measures the potency and intrinsic efficacy of ligands at the GALR1 receptor in transfected CHO-K1 cells by quantifying the reduction of forskolin-stimulated intracellular cAMP using a FRET-based cAMP (Perkin Elmer LANCE cAMP kit). After stimulation, a fluorescently labelled cAMP tracer (Europium-streptavadin/biotin-cAMP) and fluorescently (Alexa) labelled anti-cAMP antibody are added to the cells in a lysis buffer. cAMP from the cells competes with the cAMP tracer for antibody binding sites. When read, a light pulse at 320 nm excites the fluorescent portion (Europium) of the cAMP tracer. The energy emitted from the europium is transferred to the Alexa fluor-labelled antibodies bound to the tracer, generating a TR-FRET signal at 665 nm (Time-resolved fluorescence resonance energy transfer is based on the proximity of the donor label, europium, and the acceptor label, Alexa fluor, which have been brought together by a specific binding reaction). Residual energy from the europium produces light at 615 nm. In agonist treated cells there will be less cAMP to compete with the tracer so a dose dependent increase in signal at 665 nm will be observed compared with samples treated with forskolin alone. The signal at 665 nm signal is converted to cAMP concentration by interpolation to a cAMP standard curve which is included in each experiment.

Using Gilson pipettes and Sigmacoted or lo-bind tips, test materials and standards were diluted to the appropriate concentrations in the wells of the first two columns of an eppendorf 500 µl deep-well lo-bind plate, in assay buffer containing 10 µM forskolin. The chosen concentrations in columns one and two were half a log unit apart. From these, serial 1:10 dilutions were made across the plate (using an electronic eight channel pipette with sigmacote or lo-bind tips) until eleven concentrations at half log intervals had been created. In the twelfth column, assay buffer only was added as a 'basal'. Using a 12 channel digital pipette, 10 µl of sample from the lo-bind plate was transferred to the optiplate 96 well microplate.

To wells containing the standard curve, 10 ul of assay buffer was added using a multichannel digital pipette. To wells containing the test materials, 10 ul of cells in assay buffer at the appropriate concentration were added. Plates were sealed and incubated for 120 min at room temperature, for the first hour on an IKA MTS 2/4 orbital shaker set to maximum speed.

LANCE Eu-W8044 labelled streptavidin (Eu-SA) and Biotin-cAMP (b-cAMP) were diluted in cAMP Detection Buffer (both from Perkin Elmer LANCE cAMP kit) to create sub-stocks, at dilution ratios of 1:17 and 1:5, respectively. The final detection mix was prepared by diluting from the two sub stocks into detection buffer at a ratio of 1:125. The mixture was incubated for 15-30 min at room temperature before addition of 1:200 Alexa Fluor® 647-anti cAMP Antibody (Alexa-Fluor Ab). After briefly vortex mixing, 20 µl was immediately added to each well using a digital multichannel pipette. Microplate sealers were applied and plates incubated for 24 h at room temperature (for the first hour on an IKA MTS 2/4 orbital shaker set to maximum speed). Plate sealers were removed prior to reading on the Envision.

GALR2 Receptor Activation Assay The GALR2 receptor activation assay measures the potency and intrinsic efficacy of ligands at GALR2 receptor in transfected CHO-K1 cells by measuring the calcium mobilisation that occurs when the receptor is activated. The transfected cells are pre-loaded with a calcium sensitive dye (FLIPR) before treatment. When read using Flexstation 3 microplate reader (Molecular devices) a light pulse at 485 nm excites the fluorescent dye and causes an emission at 525 nm. This provides real-time fluorescence data from changes in intracellular calcium. In agonist treated cells there will be activation of the receptor, leading to an increase in calcium mobilisation. This will be measured as an increase in the relative fluorescence units (RFU) at 525 nM.

Culture of Cells for Receptor Activation Assay:

Cells were seeded and cultured in T175 flasks containing Ham F12 with Glutamax, 10% Foetal bovine serum, 5 µg ml-1 Blasticidin and 100 µg ml-1 Zeocin. The flasks were incubated at 37° C. in a humidified environment containing 5% $CO_2$ until 60-80% confluent. On the day of harvest the media was removed and the cells washed twice with 25 ml PBS. The cells were removed from the flask by addition of 10 ml of Tryple Express, and incubation at 37° C. for 10 min followed by gentle tapping of the flask. The dislodged cells were transferred to a 50 ml centrifuge tube and the flask washed twice with 10 ml media which was added to the cell suspension. The tube was centrifuged at 1300×g for 3 min and the supernatant removed. Cells were gently re-suspended in 10 ml media (if freezing cells) or assay buffer (if using 'fresh' cells in assay), and a sample was removed for counting using a nucleocounter (ChemoMetec). Cells for use 'fresh' in an assay were diluted further in assay buffer to the appropriate concentration. Cells harvested for freezing were re-centrifuged (1300×g; 3 min), the supernatant removed and cells re-suspended in Synth-a-freeze at 4° C. to 3×106 cells/ml. Cryovials containing 1 ml suspension each were placed in a chilled Nalgene Mr Frosty freezing container (−1° C./minute cooling rate), and left overnight in a −80° C. freezer. The following day vials were transferred to the vapour phase of a liquid nitrogen storage tank.

FIG. 4 demonstrates that galanin fusion proteins of the present invention having different galanin ligands (i.e. galanin-16 and galanin-30) and different serotype backbones (i.e. LC/A-$H_N$/A, LC/B-$H_N$/B, LC/C-$H_N$/C and LC/D-$H_N$/D) activate GALR1 receptors.

CHO-K1 GALR1 SNAP-25 Cleavage Assays

Cultures of cells were exposed to varying concentrations of galanin fusion protein for 24 hours. Cellular proteins were separated by SDS-PAGE and western blotted with anti-SNAP-25 antibody to facilitate assessment of SNAP-25 cleavage. SNAP-25 cleavage calculated by densitometric analysis (Syngene).

Plating Cells

Prepare cells at 2×10e5 cells/ml and seed 125 μl per well of 96 well plate. Use the following media: 500 ml Gibco Ham F12 with Glutamax (product code 31765068), 50 ml FBS, 5 ug/ml Blasticidin (250 μl aliquot from box in freezer, G13) (Calbiochem #203351, 10 ml at 10 mg/ml), 100 ug/ml Zeocin (500 μl from box in freezer, G35). (Invitrogen from Fisher, 1 g in 8×1.25 ml tubes at 100 mg/ml product code VXR25001). Allow cells to grow for 24 hrs (37° C., 5% $CO_2$, humidified atmosphere).

Cell Treatment

Prepare dilutions of test protein for a dose range of each test proteins (make up double (2×) the desired final concentrations because 125 μl will be applied directly onto 125 μl of media already in each well). Filter sterilize CHO GALR1 feeding medium (20 ml syringe, 0.2 μm syringe filter) to make the dilutions. Add the filtered medium into 5 labelled bijoux's (7 ml tubes), 0.9 ml each using a Gilson pipette or multi-stepper. Dilute the stock test protein to 2000 nM (working stock solution 1) and 600 nM (working stock solution 2). Using a Gilson pipette prepare 10-fold serial dilutions of each working stock, by adding 100 μl to the next concentration in the series. Pipette up and down to mix thoroughly. Repeat to obtain 4 serial dilutions for solution 1, and 3 serial dilutions for solution 2. A 0 nM control (filtered feeding medium only) should also be prepared as a negative control for each plate. Repeat the above for each test protein. In each experiment a 'standard' batch of material must be included as control/reference material, this is unliganded LC/A-$H_N$/A.

Apply Diluted Sample to CHO GALR1 Plates

Apply 125 μl of test sample (double concentration) per well. Each test sample should be applied to triplicate wells and each dose range should include a 0 nM control. Incubate for 24 hrs (37° C., 5% $CO_2$, humidified atmosphere).

Cell Lysis

Prepare fresh lysis buffer (20 mls per plate) with 25% (4×) NuPAGE LDS sample buffer, 65% $dH_2O$ and 10% 1 M DTT. Remove medium from the CHO GALR1 plate by inverting over a waste receptacle. Drain the remaining media from each well using a fine-tipped pipette. Lyse the cells by adding 125 μl of lysis buffer per well using a multi-stepper pipette. After a minimum of 20 mins, remove the buffer from each well to a 1.5 ml microcentrifuge tube. Tubes must be numbered to allowing tracking of the CHO GALR1 treatments throughout the blotting procedure. A1-A3 down to H1-H3 numbered 1-24, A4-A6 down to H4-H6 numbered 25-48, A7-A9 down to H7-H93 numbered 49-72, A10-A12 down to H10-H12 numbered 73-96. Vortex each sample and heat at 90° C. for 5-10 mins in a prewarmed heat block. Store at −20° C. or use on the same day on an SDS gel.

Gel Electrophoresis

If the sample has been stored o/n or longer, put in a heat block prewarmed to 90° C. for 5-10 mins. Set up SDS page gels, use 1 gel per 12 samples, prepare running buffer (1×, Invitrogen NuPAGE MOPS SDS Running Buffer (20×) (NP0001))≈800 ml/gel tank. Add 500 μl of NuPAGE antioxidant to the upper buffer chamber. Load 15 ul samples onto gel lanes from left to right as and load 2.5 ul of Invitrogen Magic Marker XP and 5 ul Invitrogen See Blue Plus 2 pre-stained standard and 15 ul of non-treated control. It is important to maximize the resolution of separation during SDS_PAGE. This can be achieved by running 12% bis-tris gels at 200 V for 1 hour and 25 minutes (until the pink (17 kDa) marker reaches the bottom of the tank).

Western Blotting

Complete a Semi-dry transfer: using an Invitrogen iBlot (use iBlot Programme 3 for 6 minutes). Put the nitrocellulose membranes in individual small trays. Incubate the membranes with blocking buffer solution (5 g Marvel milk powder per 100 ml 0.1% PBS/Tween) at room temperature, on a rocker, for 1 hour. Apply primary antibody (Anti-SNAP-25 1:1000 dilution) and incubate the membranes with primary antibody (diluted in blocking buffer) for 1 hour on a rocker at room temperature. Wash the membranes by rinsing 3 times with PBS/Tween (0.1%). Then apply the secondary (Anti-Rabbit-HRP conjugate diluted 1:1000) and incubate the membranes with secondary antibody (diluted in blocking buffer) at room temperature, on a rocker, for 1 hour. Wash the membranes by rinsing 3 times with PBS/Tween (0.1%), leave membrane a minimum of 20 mins for the last wash. Detect the bound antibody using Syngene: Drain blots of PBS/Tween, mix WestDura reagents 1:1 and add to blots for 5 minutes. Ensure enough solution is added to the membranes to completely cover them. Place membrane in Syngene tray, set up Syngene software for 5 min expose time.

FIGS. 3 and 5 demonstrate that galanin fusion proteins of the invention effectively cleave SNAP-25.

Example 8—Assessment of In Vivo Efficacy of a Galanin Fusion

The nociceptive flexion reflex (also known as paw guarding assay) is a rapid withdrawal movement that constitutes a protective mechanism against possible limb damage. It can be quantified by assessment of electromyography (EMG) response in anesthetized rat as a result of low dose capsaicin, electrical stimulation or the capsaicin-sensitized electrical response. Intraplantar pretreatment (24 hour) of fusion proteins of the present invention into 300-380 g male Sprague-Dawley rats. Induction of paw guarding was achieved by 0.006% capsaicin, 10 μl in PBS (7.5% DMSO), injected in 10 seconds. This produced a robust reflex response from biceps feroris muscle. A reduction/inhibition of the nociceptive flexion reflex indicates that the test substance demonstrates an antinociceptive effect. The data demonstrated the antinociceptive effect of the galanin fusion proteins of the present invention as a percentage (FIG. 6)

The ability of different galanin fusion proteins of the invention to inhibit capsaicin-induced thermal hyperalgesia was evaluated (FIGS. 7 and 8). Intraplantar pretreatment of fusion proteins into Sprague-Dawley rats and 24 hours later 0.3% capsaicin was injected and rats were put on 25° C. glass plate (rats contained in acrylic boxes, on 25° C. glass plate). Light beam (adjustable light Intensity) focused on the hind paw. Sensors detected movement of paw, stopping timer. Paw Withdrawal Latency is time to remove paw from heat source (Cut-off of 20.48 seconds). A reduction/inhibition of the paw withdrawal latency indicates that the test substance demonstrates an antinociceptive effect. The data demonstrated the enhanced antinociceptive effect of the galanin fusion proteins of the present invention compared to fusion proteins with a C-terminally presented ligand.

Example 9—Confirmation of TM Agonist Activity by Measuring Release of Substance P from Neuronal Cell Cultures Materials Substance P EIA is obtained from R&D Systems, UK.

Methods

Primary neuronal cultures of eDRG are established as described previously (Duggan et al., 2002). Substance P release from the cultures is assessed by EIA, essentially as described previously (Duggan et al., 2002). The TM of interest is added to the neuronal cultures (established for at least 2 weeks prior to treatment); control cultures are performed in parallel by addition of vehicle in place of TM. Stimulated (100 mM KCl) and basal release, together with total cell lysate content, of substance P are obtained for both control and TM treated cultures. Substance P immunoreactivity is measured using Substance P Enzyme Immunoassay Kits (Cayman Chemical Company, USA or R&D Systems, UK) according to manufacturers' instructions.

The amount of Substance P released by the neuronal cells in the presence of the TM of interest is compared to the release obtained in the presence and absence of 100 mM KCl. Stimulation of Substance P release by the TM of interest above the basal release, establishes that the TM of interest is an "agonist ligand" as defined in this specification. If desired the stimulation of Substance P release by the TM of interest can be compared to a standard Substance P release-curve produced using the natural ORL-1 receptor ligand, nociceptin (Tocris).

Example 10

A method of treating, preventing or ameliorating pain in a subject, comprising administration to said patient a therapeutic effective amount of fusion protein, wherein said pain is selected from the group consisting of: chronic pain arising from malignant disease, chronic pain not caused by malignant disease (peripheral neuropathies).

Patient A

A 73 year old woman suffering from severe pain caused by posthepatic neuralgia is treated by a peripheral injection with fusion protein to reduce neurotransmitter release at the synapse of nerve terminals to reduce the pain. The patient experiences good analgesic effect within 2 hours of said injection.

Patient B

A 32 year old male suffering from phantom limb pain after having his left arm amputated following a car accident is treated by peripheral injection with fusion protein to reduce the pain. The patient experiences good analgesic effect within 1 hour of said injection.

Patient C

A 55 year male suffering from diabetic neuropathy is treated by a peripheral injection with fusion protein to reduce neurotransmitter release at the synapse of nerve terminals to reduce the pain. The patient experiences good analgesic effect within 4 hours of said injection.

Patient D

A 63 year old woman suffering from cancer pain is treated by a peripheral injection with fusion protein to reduce neurotransmitter release at the synapse of nerve terminals to reduce the pain. The patient experiences good analgesic effect within 4 hours of said injection.

All documents, books, manuals, papers, patents, published patent applications, guides, abstracts and other reference materials cited herein are incorporated by reference in their entirety. While the foregoing specification teaches the principles of the present invention, with examples provided for the purpose of illustration, it will be appreciated by one skilled in the art from reading this disclosure that various changes in form and detail can be made without departing from the true scope of the invention.

The invention claimed is:

1. A fusion protein comprising an analgesic, non-cytotoxic single chain polypeptide, the polypeptide comprising:
   a non-cytotoxic protease capable of cleaving a protein of the exocytic fusion apparatus of a nociceptive sensory afferent;
   a targeting moiety that binds to a binding site on the nociceptive sensory afferent, wherein the binding site is capable of being incorporated into an endosome within the nociceptive sensory afferent;
   a protease cleavage site;
   a translocation domain capable of translocating the protease from within the endosome, across the endosomal membrane, and into the cytosol of the nociceptive sensory afferent;
   a first spacer located between the non-cytotoxic protease and the protease cleavage site, the first spacer comprising an amino acid sequence of from 4 to 25 amino acid residues; and
   a second spacer located between the targeting moiety and the translocation domain, the second spacer comprising an amino acid sequence of from 4 to 35 amino acid residues;
   wherein:
   the protease cleavage site is located between the non-cytotoxic protease and the targeting moiety;
   the targeting moiety is located between the protease cleavage site and the translocation domain; and
   the analgesic, single-chain polypeptide has at least 99% sequence identity to SEQ ID NO: 32.

2. The fusion protein of claim 1, wherein the first spacer consists of an amino acid sequence of from 6 to 16 amino acid residues.

3. The fusion protein of claim 1, wherein the first spacer comprises amino acid residues selected from the group consisting of: glycine, threonine, arginine, serine, alanine, asparagine, glutamine, aspartic acid, proline, glutamic acid, and lysine.

4. The fusion protein of claim 1, wherein the first spacer comprises amino acid residues selected from the group consisting of: glycine, serine, and alanine.

5. The fusion protein of claim 1, wherein the first spacer is a GS5 spacer.

6. The fusion protein of claim 1, wherein the targeting moiety comprises an amino acid sequence having at least 70% sequence identity to SEQ ID NO: 8.

7. The fusion protein of claim 1 consisting of an analgesic, single-chain polypeptide having at least 99% sequence identity with the sequence of SEQ ID NO: 32.

8. The fusion protein of claim 1 comprising the analgesic, single-chain polypeptide of SEQ ID NO: 32.

9. The fusion protein of claim 1 consisting of the analgesic, single-chain polypeptide of SEQ ID NO: 32.

* * * * *